United States Patent
Kovach et al.

(10) Patent No.: US 12,168,008 B2
(45) Date of Patent: Dec. 17, 2024

(54) OXABICYCLOHEPTANES FOR MODULATION OF IMMUNE RESPONSE

(71) Applicants: LIXTE BIOTECHNOLOGY, INC., Pasadena, CA (US); THE UNITED STATES OF AMERICA, as Represented by the Secretary, Bethesda, MD (US)

(72) Inventors: John S. Kovach, Pasadena, CA (US); Zhengping Zhuang, Bethesda, MD (US); Sze Chun Winson Ho, Bethesda, MD (US); Herui Wang, Bethesda, MD (US); Rongze Lu, Sunnyvale, CA (US)

(73) Assignees: Lixte Biotechnology, Inc., Pasadena, CA (US); The United States of America, as Represented by the Secretary Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/467,721

(22) PCT Filed: Dec. 8, 2017

(86) PCT No.: PCT/US2017/065270
§ 371 (c)(1),
(2) Date: Jun. 7, 2019

(87) PCT Pub. No.: WO2018/107004
PCT Pub. Date: Jun. 14, 2018

(65) Prior Publication Data
US 2020/0069680 A1    Mar. 5, 2020

Related U.S. Application Data

(60) Provisional application No. 62/545,373, filed on Aug. 14, 2017, provisional application No. 62/465,001, filed on Feb. 28, 2017, provisional application No. 62/497,949, filed on Dec. 8, 2016.

(51) Int. Cl.
*A61K 39/395*  (2006.01)
*A61K 9/00*  (2006.01)
*A61K 31/496*  (2006.01)
*A61P 35/00*  (2006.01)
*A61K 39/00*  (2006.01)

(52) U.S. Cl.
CPC .......... *A61K 31/496* (2013.01); *A61K 9/0019* (2013.01); *A61K 39/3955* (2013.01); *A61P 35/00* (2018.01); *A61K 2039/54* (2013.01); *A61K 2039/545* (2013.01)

(58) Field of Classification Search
None
See application file for complete search history.

(56) References Cited

U.S. PATENT DOCUMENTS

| | | |
|---|---|---|
| 2,957,906 A | 10/1960 | Erickson et al. |
| 3,227,473 A | 1/1966 | Halbern |
| 3,954,913 A | 5/1976 | Uebele et al. |
| 3,980,674 A | 9/1976 | Kubela et al. |
| 4,143,054 A | 3/1979 | Sprague |
| 4,218,478 A | 8/1980 | Omura et al. |
| 4,298,752 A | 11/1981 | Dauben et al. |
| 4,463,015 A | 7/1984 | Haslanger et al. |
| 4,518,696 A | 5/1985 | Gehrman et al. |
| 4,524,151 A | 6/1985 | Das et al. |
| 4,614,825 A | 9/1986 | Snitman et al. |
| 4,654,355 A | 3/1987 | Nakane et al. |
| 4,690,918 A | 9/1987 | Beppu et al. |
| 4,760,067 A | 7/1988 | Firestone |
| 4,816,579 A | 3/1989 | Thottathil |
| 4,851,423 A | 7/1989 | Girijavallabhan et al. |
| 4,851,553 A | 7/1989 | Thottathil |
| 5,206,386 A | 4/1993 | Narayanan et al. |
| 5,266,710 A | 11/1993 | Patel et al. |
| 5,326,898 A | 7/1994 | Chandraratna |
| 5,565,435 A | 10/1996 | Yoneyama et al. |
| 5,580,856 A | 12/1996 | Prestrelski et al. |
| 5,580,858 A | 12/1996 | Ippolito et al. |
| 5,763,647 A | 6/1998 | Ohtani et al. |
| 5,770,382 A | 6/1998 | Hwang et al. |
| 5,925,651 A | 7/1999 | Hutchinson |
| 5,968,965 A | 10/1999 | Dinsmore et al. |
| 6,222,055 B1 | 4/2001 | Wolter et al. |
| 6,262,116 B1 | 7/2001 | Pandolfi et al. |
| 6,632,823 B1 | 10/2003 | Vernier et al. |
| 6,696,483 B2 | 2/2004 | Singh |
| 6,706,762 B1 | 3/2004 | Evans et al. |
| 6,777,217 B1 | 8/2004 | Schreiber et al. |

(Continued)

FOREIGN PATENT DOCUMENTS

| | | |
|---|---|---|
| CN | 1586500 A | 3/2005 |
| CN | 1687072 A | 10/2005 |

(Continued)

OTHER PUBLICATIONS

Champiat et al., Journal of Thoracic Oncology, vol. 9, No. 2, p. 144-153 (Year: 2014).*
Apostolidis et al., "Phosphatase PP2A is requisite for the function of regulatory T cells," Nat Immunol, 17(5):556-64 (May 2016).
Bai et al., "Inhibition of protein phosphatase 2A enhances cytotoxicity and accessibility of chemotherapeutic drugs to hepatocellular carcinomas," *Mol Cancer Ther*, 13:2062-72 (Aug. 2014).
Bai et al., Inhibition of protein phosphatase 2A sensitizes pancreatic cancer to chemotherapy by increasing drug perfusion via HIF-1α-VEGF mediated angiogenesis, Cancer Lett, 355(2):281-287 (Dec. 2014).
Baroja et al., "Inhibition of CTLA-4 Function by the Regulatory Subunit of Serine/Threonine Phosphatase 2A," J Immunol, 168(10):5070-5078 (May 2002).

(Continued)

*Primary Examiner* — Yunsoo Kim
(74) *Attorney, Agent, or Firm* — Banner & Witcoff, Ltd.

(57) ABSTRACT

The present invention provides a method of treating a subject afflicted with cancer comprising administering to the subject an effective amount of a PP2A inhibitor.

35 Claims, 49 Drawing Sheets

(56) References Cited

U.S. PATENT DOCUMENTS

| | | |
|---|---|---|
| 6,905,669 B2 | 6/2005 | DiMartino |
| 6,949,624 B1 | 9/2005 | Liu et al. |
| 7,067,551 B2 | 6/2006 | Remiszewski et al. |
| 7,154,002 B1 | 12/2006 | Bressi et al. |
| 7,154,022 B2 | 12/2006 | Howe et al. |
| 7,834,019 B2 | 11/2010 | Sagara et al. |
| 7,893,096 B2 | 2/2011 | Valiante, Jr. |
| 7,943,743 B2 | 5/2011 | Korman et al. |
| 7,998,957 B2 | 8/2011 | Kovach et al. |
| 8,008,449 B2 | 8/2011 | Korman et al. |
| 8,058,268 B2 | 11/2011 | Kovach |
| 8,143,445 B2 | 3/2012 | Kovach et al. |
| 8,227,473 B2 | 7/2012 | Kovach et al. |
| 8,329,719 B2 | 12/2012 | Kovach |
| 8,354,509 B2 | 1/2013 | Carven et al. |
| 8,413,445 B2 | 4/2013 | Poyyapakkam |
| 8,426,444 B2 | 4/2013 | Kovach et al. |
| 8,455,668 B2 | 6/2013 | Fu et al. |
| 8,455,688 B2 | 6/2013 | Kovach et al. |
| 8,541,458 B2 | 9/2013 | Kovach et al. |
| 8,609,089 B2 | 12/2013 | Langermann et al. |
| 8,685,436 B2 | 4/2014 | Ley et al. |
| 8,697,845 B2 | 4/2014 | Ward et al. |
| 8,822,461 B2 | 9/2014 | Kovach et al. |
| 8,840,924 B2 | 9/2014 | Tengler et al. |
| 9,079,917 B2 * | 7/2015 | Kovach ............. A61P 35/02 |
| 9,526,915 B2 | 12/2016 | Kovach |
| 9,833,450 B2 | 12/2017 | Kovach et al. |
| 9,988,394 B2 | 6/2018 | Kovach et al. |
| 9,994,584 B2 | 6/2018 | Piotrowski et al. |
| 10,023,587 B2 | 7/2018 | Kovach et al. |
| 10,071,092 B2 | 9/2018 | Jayaraman et al. |
| 10,071,094 B2 | 9/2018 | List et al. |
| 10,149,847 B2 | 12/2018 | Kovach |
| 10,364,252 B2 | 7/2019 | Kovach et al. |
| 10,399,993 B2 * | 9/2019 | Kovach ............. A61K 31/496 |
| 10,413,541 B2 | 9/2019 | Kovach et al. |
| 10,434,100 B2 | 10/2019 | List et al. |
| 10,532,050 B2 | 1/2020 | Kovach et al. |
| 10,618,908 B2 | 4/2020 | Kovach et al. |
| 10,668,062 B2 | 6/2020 | Kovach |
| 11,236,102 B2 | 2/2022 | Kovach et al. |
| 11,866,444 B2 | 1/2024 | Kovach et al. |
| 11,931,354 B2 | 3/2024 | Kovach et al. |
| 2002/0115826 A1 | 8/2002 | Delorme et al. |
| 2002/0147345 A1 | 10/2002 | El Tayer et al. |
| 2002/0177692 A1 | 11/2002 | Bartel |
| 2003/0162186 A1 | 8/2003 | Bejanin et al. |
| 2003/0171329 A1 | 9/2003 | Jones et al. |
| 2004/0010045 A1 | 1/2004 | Yi |
| 2004/0053996 A1 | 3/2004 | Gesing et al. |
| 2004/0087531 A1 | 5/2004 | Telerman et al. |
| 2004/0087657 A1 | 5/2004 | Richon et al. |
| 2004/0106141 A1 | 6/2004 | Mischel et al. |
| 2004/0116366 A1 | 6/2004 | Monia et al. |
| 2004/0122101 A1 | 6/2004 | Miller et al. |
| 2004/0161475 A1 | 8/2004 | Ellison et al. |
| 2004/0197888 A1 | 10/2004 | Armour et al. |
| 2004/0209934 A1 | 10/2004 | McCluskey et al. |
| 2004/0253637 A1 | 12/2004 | Buechler et al. |
| 2005/0014839 A1 | 1/2005 | Kozikowski et al. |
| 2005/0020831 A1 | 1/2005 | Inman et al. |
| 2005/0054626 A1 | 3/2005 | Carter et al. |
| 2005/0119229 A1 | 6/2005 | Ammermann et al. |
| 2005/0136090 A1 | 6/2005 | Falotico et al. |
| 2005/0171202 A1 | 8/2005 | Graupner |
| 2005/0203082 A1 | 9/2005 | Hsu et al. |
| 2005/0215526 A1 | 9/2005 | Hulme et al. |
| 2005/0220831 A1 | 10/2005 | Jorsal |
| 2005/0222013 A1 | 10/2005 | Jung et al. |
| 2005/0272644 A1 | 12/2005 | Chung |
| 2005/0277583 A1 | 12/2005 | Yoshida et al. |
| 2005/0282893 A1 | 12/2005 | Au et al. |
| 2006/0030616 A1 | 2/2006 | McCluskey et al. |
| 2006/0117994 A1 | 6/2006 | Ryu et al. |
| 2006/0134682 A1 | 6/2006 | Roberts et al. |
| 2006/0167103 A1 | 7/2006 | Bacopoulos et al. |
| 2006/0235231 A1 | 10/2006 | Joel et al. |
| 2006/0264415 A1 | 11/2006 | Leit De Moradei et al. |
| 2007/0004771 A1 | 1/2007 | Lee et al. |
| 2007/0010669 A1 | 1/2007 | Breslow et al. |
| 2007/0049476 A1 | 3/2007 | Belcastro et al. |
| 2007/0049576 A1 | 3/2007 | Barlow et al. |
| 2007/0110669 A1 | 5/2007 | Driehuys et al. |
| 2007/0135365 A1 | 6/2007 | Tanizawa et al. |
| 2007/0135433 A1 | 6/2007 | Dean et al. |
| 2007/0155751 A1 | 7/2007 | Paruch et al. |
| 2007/0197550 A1 | 8/2007 | Georgopapadakou et al. |
| 2007/0208166 A1 | 9/2007 | Baly et al. |
| 2007/0213330 A1 | 9/2007 | Delorme et al. |
| 2007/0280918 A1 | 12/2007 | Schwartz et al. |
| 2008/0097561 A1 | 4/2008 | Melsky et al. |
| 2008/0132503 A1 | 6/2008 | Moradei et al. |
| 2008/0214569 A1 | 9/2008 | Zhuang et al. |
| 2008/0267947 A1 | 10/2008 | Cirrito et al. |
| 2009/0012066 A1 | 1/2009 | Izumo et al. |
| 2009/0018142 A9 | 1/2009 | Zhuang et al. |
| 2009/0035292 A1 | 2/2009 | Kovach et al. |
| 2009/0036309 A1 | 2/2009 | Kovach et al. |
| 2009/0143445 A1 | 6/2009 | Kovach et al. |
| 2010/0016235 A1 | 1/2010 | Kroemer et al. |
| 2010/0028330 A1 | 2/2010 | Collins et al. |
| 2010/0029484 A1 | 2/2010 | Kovach et al. |
| 2010/0029640 A1 | 2/2010 | Kovach |
| 2010/0029683 A1 | 2/2010 | Kovach et al. |
| 2010/0137294 A1 | 6/2010 | Gasser et al. |
| 2011/0287537 A1 | 11/2011 | Kovach |
| 2012/0039906 A1 | 2/2012 | Olive |
| 2012/0114649 A1 | 5/2012 | Langermann et al. |
| 2012/0135522 A1 | 5/2012 | Kovach |
| 2012/0178783 A1 | 7/2012 | Kovach et al. |
| 2012/0264764 A1 | 10/2012 | Kovach et al. |
| 2012/0270736 A1 | 10/2012 | Kovach et al. |
| 2012/0316081 A1 | 12/2012 | List et al. |
| 2013/0280210 A1 | 10/2013 | Kovach |
| 2013/0302402 A1 | 11/2013 | Kovach et al. |
| 2014/0235649 A1 | 8/2014 | Kovach et al. |
| 2014/0343071 A1 | 11/2014 | Shumway et al. |
| 2015/0045373 A1 | 2/2015 | Kovach et al. |
| 2015/0141661 A1 | 5/2015 | He et al. |
| 2015/0141669 A1 | 5/2015 | Hashihayata et al. |
| 2015/0148353 A1 | 5/2015 | Kovach |
| 2015/0174123 A1 | 6/2015 | Kovach |
| 2015/0210769 A1 | 7/2015 | Freeman et al. |
| 2015/0224083 A1 | 8/2015 | Cirrito et al. |
| 2016/0008336 A1 | 1/2016 | Kovach |
| 2016/0051544 A1 | 2/2016 | Kovach et al. |
| 2016/0074390 A1 | 3/2016 | Kovach |
| 2016/0264593 A1 | 9/2016 | Kovach et al. |
| 2016/0303115 A1 | 10/2016 | Kovach et al. |
| 2016/0333024 A1 | 11/2016 | Kovach et al. |
| 2017/0136008 A1 | 5/2017 | Kovach et al. |
| 2017/0209434 A1 | 7/2017 | List et al. |
| 2017/0240558 A1 | 8/2017 | Kovach et al. |
| 2017/0259081 A1 | 9/2017 | Kovach |
| 2017/0305925 A1 | 10/2017 | Piotrowski et al. |
| 2017/0340628 A1 | 11/2017 | List et al. |
| 2017/0369503 A1 | 12/2017 | Kovach et al. |
| 2018/0244690 A1 | 8/2018 | Kovach et al. |
| 2018/0256565 A1 | 9/2018 | Kovach et al. |
| 2018/0370983 A1 | 12/2018 | Kovach et al. |
| 2019/0046525 A1 | 2/2019 | List et al. |
| 2019/0111053 A1 | 4/2019 | List et al. |
| 2019/0167671 A1 | 6/2019 | Kovach |
| 2019/0359627 A1 | 11/2019 | Kovach et al. |
| 2020/0179375 A1 | 6/2020 | Kovach et al. |
| 2020/0325151 A1 | 10/2020 | Kovach et al. |
| 2021/0275521 A1 | 9/2021 | Kovach |
| 2021/0379106 A1 | 12/2021 | Kovach et al. |
| 2022/0184066 A1 | 6/2022 | List et al. |
| 2022/0235066 A1 | 7/2022 | Kovach et al. |
| 2022/0323433 A2 | 10/2022 | List et al. |

(56) References Cited

U.S. PATENT DOCUMENTS

| | | |
|---|---|---|
| 2023/0065158 A1 | 3/2023 | Kovach et al. |
| 2023/0310418 A1 | 10/2023 | Kovach et al. |
| 2024/0041864 A1 | 2/2024 | Kovach |

FOREIGN PATENT DOCUMENTS

| | | |
|---|---|---|
| CN | 101662939 A | 3/2010 |
| CN | 103788108 A | 5/2014 |
| DE | 19600707 A1 | 7/1997 |
| EP | 1443967 A1 | 8/2004 |
| EP | 1443967 B1 | 1/2007 |
| FR | 2872704 A1 | 1/2006 |
| IE | 912486 A1 | 1/1992 |
| JP | 5069091 | 6/1975 |
| JP | S5069091 A | 6/1975 |
| JP | S5132733 A | 3/1976 |
| JP | 5188631 | 8/1976 |
| JP | S5188631 A | 8/1976 |
| JP | S5198755 A | 8/1976 |
| JP | H02256650 A | 10/1990 |
| JP | 2001329061 A | 11/2001 |
| JP | 2004531500 A | 10/2004 |
| JP | 2005507852 A | 3/2005 |
| JP | 2006507271 A | 3/2006 |
| JP | 2006519609 A | 8/2006 |
| JP | 2007511528 A | 5/2007 |
| JP | 2007514665 A | 6/2007 |
| RU | 2015980 C1 | 7/1994 |
| RU | 201598 U1 | 12/2020 |
| SU | 1553533 A1 | 3/1990 |
| WO | WO-9118891 A1 | 12/1991 |
| WO | WO-9604792 A1 | 2/1996 |
| WO | WO-0004023 A1 | 1/2000 |
| WO | WO-0162242 A1 | 8/2001 |
| WO | WO-0209680 A2 | 2/2002 |
| WO | WO-0228387 A1 | 4/2002 |
| WO | WO-0242310 A2 | 5/2002 |
| WO | WO-2002066045 | 8/2002 |
| WO | WO-02076989 A1 | 10/2002 |
| WO | WO-03045898 A1 | 6/2003 |
| WO | WO-03092616 A2 | 11/2003 |
| WO | WO-03092719 A2 | 11/2003 |
| WO | WO-2004035064 A1 | 4/2004 |
| WO | WO-2004080416 A2 | 9/2004 |
| WO | WO-2004087153 A2 | 10/2004 |
| WO | WO-2005018673 A1 | 3/2005 |
| WO | WO-2005049084 A2 | 6/2005 |
| WO | WO-2005054257 A1 | 6/2005 |
| WO | WO-2005058280 A2 | 6/2005 |
| WO | WO-2005074941 A1 | 8/2005 |
| WO | WO-2006016062 A1 | 2/2006 |
| WO | WO-2006023603 A2 | 3/2006 |
| WO | WO-2006052842 A2 | 5/2006 |
| WO | WO-2006121168 A1 | 11/2006 |
| WO | WO-2006129105 A1 | 12/2006 |
| WO | WO-2007005874 A2 | 1/2007 |
| WO | WO-2007014029 A2 | 2/2007 |
| WO | WO-2007021682 A1 | 2/2007 |
| WO | WO-2007092414 A2 | 8/2007 |
| WO | WO-2007118137 A1 | 10/2007 |
| WO | WO-2008028965 A2 | 3/2008 |
| WO | WO-2008030617 A2 | 3/2008 |
| WO | WO-2008058342 | 5/2008 |
| WO | WO-2008097561 A1 | 8/2008 |
| WO | WO-2009020565 A1 | 2/2009 |
| WO | WO-2009045440 A1 | 4/2009 |
| WO | WO-2009101611 A1 | 8/2009 |
| WO | WO-2009114335 A2 | 9/2009 |
| WO | WO-2010014141 A1 | 2/2010 |
| WO | WO-2010014220 A1 | 2/2010 |
| WO | WO-2010014254 | 2/2010 |
| WO | WO-2010014254 A1 | 2/2010 |
| WO | WO-2010027827 A2 | 3/2010 |
| WO | WO-2010077634 A1 | 7/2010 |
| WO | WO-2010147612 A1 | 12/2010 |
| WO | WO-2011066342 A2 | 6/2011 |
| WO | WO-2011132171 A1 | 10/2011 |
| WO | WO-2011143147 A1 | 11/2011 |
| WO | WO-2012162535 A1 | 11/2012 |
| WO | WO-2013056211 A2 | 4/2013 |
| WO | WO-2013180271 A1 | 12/2013 |
| WO | WO-2014005080 | 1/2014 |
| WO | WO-2014005084 | 1/2014 |
| WO | WO-2014005084 A1 | 1/2014 |
| WO | WO-2014089279 A1 | 6/2014 |
| WO | WO-2014137741 A1 | 9/2014 |
| WO | WO-2014149494 A1 | 9/2014 |
| WO | WO-2014168941 | 10/2014 |
| WO | WO-2015073802 A1 | 5/2015 |
| WO | WO-2015196073 A1 | 12/2015 |
| WO | WO-2016014778 A1 | 1/2016 |
| WO | WO-2016014783 A1 | 1/2016 |
| WO | WO-2016040877 | 3/2016 |
| WO | WO-2016061193 A1 | 4/2016 |
| WO | WO-2016134257 A1 | 8/2016 |
| WO | WO-2016168716 A1 | 10/2016 |
| WO | WO-2016186963 A1 | 11/2016 |
| WO | WO-2017049166 A1 | 3/2017 |
| WO | WO-2017132445 A1 | 8/2017 |
| WO | WO-2017176289 A1 | 10/2017 |
| WO | WO-2018107004 A1 | 6/2018 |
| WO | WO-2019113155 A1 | 6/2019 |
| WO | WO-2019241536 A1 | 12/2019 |
| WO | WO-2022159150 A1 | 7/2022 |
| WO | WO-2023133371 A2 | 7/2023 |

OTHER PUBLICATIONS

Berge et al., "Pharmaceutical salts," J Pharm Sci, 66(1):1-19 (1977).
Bertini et al., "Structural Basis of Serine/Threonine Phosphatase Inhibition by the Archetypal Small Molecules Cantharidin and Norcantharidin," *J. Med. Chem*, 52(15):4838-4843 (Aug. 2009).
Bian et al., "Synthetic genetic array screen identifies PP2A as a therapeutic target in Mad2-overexpressing tumors," *Proc Natl Acad Sci U S A*, 111(4):1628-1633 (2014).
Brahmer et al., "Phase I study of single-agent anti-programmed death-1 (MDX-1106) in refractory solid tumors: safety, clinical activity, pharmacodynamics, and immunologic correlates," *J Clin Oncol*, 28(19):3167-3175 (Jul. 2010).
Brunet et al., "A new member of the immunoglobulin superfamily CTLA-4," Nature, 328(6127):267-270 (Jul. 1987).
Carreno et al., "CTLA-4 (CD152) can inhibit T cell activation by two different mechanisms depending on its level of cell surface expression," J Immunol, 165(3):1352-1356 (Aug. 2000).
Chang et al., "The Protein Phosphatase 2A Inhibitor LB-100 Sensitizes Ovarian Carcinoma Cells to Cisplatin-Mediated Cytotoxicity," *Mol Cancer Ther*, 14(1):90-100 (Jan. 2015).
Chapman et al., "mTOR signaling, Tregs and immune modulation," *Immunotherapy*, 6(12):1295-1311 (2014).
Chen et al., "Oncology meets immunology: the cancer-immunity cycle," *Immunity*, 39(1):1-10 (Jul. 2013).
Chuang et al., "The CD28 and CTLA-4 Receptors Associate with the Serine/Threonine Phosphatase PP2A," Immunity, 13(3):313-322 (Sep. 2000).
Chung et al., "Safety, Tolerability, and Preliminary Activity of LB-100, an Inhibitor of Protein Phosphatase 2A, in Patients with Relapsed Solid Tumors: An Open-Label, Dose Escalation, First-in-Human, Phase I Trial," Clin Cancer Res, 23(13):3277-3284 (Jul. 2017).
ClinicalTrials.gov identifier NCT01837667, "Phase I study of LB-100 with docetaxel in solid tumors," https://clinicaltrials.gov/ct2/show/NCT01837667 (8 pages) (2013).
Delgoffe et al., "The kinase mTOR regulates the differentiation of helper T cells through the selective activation of signaling by mTORC1 and mTORC2," *Nat Immunol*, 12(4):295-303 (Apr. 2011).
Delgoffe, "PP2A's restraint of mTOR is critical for T(reg) cell activity," *Nat Immunol*, 17(5):478-479 (May 2016).
Ebert et al., "MAP Kinase Inhibition Promotes T Cell and Anti-tumor Activity in Combination with PD-L1 Checkpoint Blockade," *Immunity*, 44:609-621 (Mar. 2016).

(56) References Cited

OTHER PUBLICATIONS

Efferth et al., "Activity of drugs from traditional Chinese medicine toward sensitive and MDR1- or MRP1-overexpressing multidrug-resistant human CCRF-CEM leukemia cells," Blood Cells Mol Dis, 28(2):160-8 (Mar.-Apr. 2002).
Efferth et al., "Molecular modes of action of cantharidin in tumor cells," Biochem Pharmacol, 69(5):811-8 (Mar. 2005).
Eil et al., "Ionic immune suppression within the tumour microenvironment limits T cell effector function," Nature, 537:539-543 (Sep. 2016).
Falconer et al., "Preliminary evidence for in vivo tumour initiation by oral administration of extracts of the blue-green alga cylindrospermopsis raciborskii containing the toxin cylindrospermopsin," Environ Toxicol, 16(2):192-195 (2001).
Gehringer, "Microcystin-LR and okadaic acid-induced cellular effects: a dualistic response," FEBS Lett, 557:1-8 (Jan. 2004).
Gordon et al., "Protein Phosphatase 2A Inhibition with LB100 Enhances Radiation-Induced Mitotic Catastrophe and Tumor Growth Delay in Glioblastoma," Mol Cancer Ther, 14:1540-47 (Jul. 2015).
Grosso et al., "CTLA-4 blockade in tumor models: an overview of preclinical and translational research," Cancer Immun, 13:5 (2013) (14 pp.).
Haxhinasto et al., "The AKT-mTOR axis regulates de novo differentiation of CD4+Foxp3+ cells," J Exp Med, 205:565-574 (2008).
Hein et al., "PR55α Subunit of Protein Phosphatase 2A Supports the Tumorigenic and Metastatic Potential of Pancreatic Cancer Cells by Sustaining Hyperactive Oncogenic Signaling," Cancer Res, 76(8):2243-53 (2016).
Ho et al., "PP2A inhibition with LB100 enhances cisplatin cytotoxicity and overcomes cisplatin resistance in medulloblastoma cells," Oncotarget, 7:12447-63 (2016).
Hodi et al., "Improved Survival with Ipilimumab in Patients with Metastatic Melanoma," N Engl J Med, 363(8):711-723 (2010).
Holmgaard et al., "Indoleamine 2,3-dioxygenase is a critical resistance mechanism in antitumor T cell immunotherapy targeting CTLA-4," J Exp Med, 210:1389-1402 (2013).
Hong et al., "LB100, a Small Molecule Inhibitor of PP2A with Potent Chemo- and Radio-sensitizing Potential," Cancer Biol Ther, 16:821-33 (2015).
International Search Report and Written Opinion issued by the United States Patent and Trademark Office as International Searching Authority for International Patent Application No. PCT/US2017/065270 mailed Apr. 13, 2018 (12 pages).
Intlekofer et al., "At the bench: preclinical rationale for CTLA-4 and PD-1 blockade as cancer immunotherapy," J Leukoc Biol, 94(1):25-39 (2013).
Janssens et al., "PP2A holoenzyme assembly: in cauda venenum (the sting is in the tail)," Trends Biochem Sci, 33:113-121 (2008).
Janssens et al., The Role and Therapeutic Potential of Ser/Thr Phosphatase PP2A in Apoptotic Signalling Networks in Human Cancer Cells, Curr Mol Med, 12:268-287 (2012).
Johansson et al., "Immune checkpoint therapy for pancreatic cancer," World J Gastroenterol, 22(43):9457-9476 (2016).
Keytruda® Prescribing Information, Merck Sharp & Dohme Corp. (2014), FDA Approved Labeling (Reference ID:3621876), Retrieved from the Internet: <URL: www.accessdata.fda.gov/drugsatfda_docs/label/2014/125514lbl.pdf> (16 pages).
Kiely et al., "PP2A: The Wolf in Sheep's Clothing?," Cancers (Basel), 7:648-669 (2015).
Kingwell, "Cancer: Live screening of immunotherapy targets," Nat Rev Drug Discov, 13:258 (2014).
Larkin et al., "Combined Nivolumab and Ipilimumab or Monotherapy in Untreated Melanoma," N Engl J Med, 373:23-24 (2015).
Lê et al., "Phase I and pharmacokinetic study of fostriecin given as an intravenous bolus daily for five consecutive days," Invest New Drugs, 22:159-167 (2004).
Lecca et al., "Rescue of GABAB and GIRK function in the lateral habenula by protein phosphatase 2A inhibition ameliorates depression-like phenotypes in mice," Nat Med, 22:254-261 (2016).

Lu et al., "Inhibition of serine/threonine phosphatase PP2A enhances cancer chemotherapy by blocking DNA damage induced defense mechanisms," Proc Natl Acad Sci U S A, 106(28):11697-702 (2009).
Lv et al., "Inhibition of protein phosphatase 2A with a small molecule LB-100 radiosensitizes nasopharyngeal carcinoma xenografts by inducing mitotic catastrophe and blocking DNA damage repair," Oncotarget, 5:7512-7524 (2014).
Martiniova et al., "Pharmacologic modulation of serine/threonine phosphorylation highly sensitizes PHEO in a MPC cell and mouse model to conventional chemotherapy," PLoS One, 6(2):e14678 (2011).
Melero et al., "T-cell and NK-cell infiltration into solid tumors: a key limiting factor for efficacious cancer immunotherapy," Cancer Discov, 4:522-526 (2014).
Mumby, "PP2A: unveiling a reluctant tumor suppressor," Cell, 130:21-4 (2007).
Ngiow et al., "A Threshold Level of Intratumor CD8+ T-cell PD1 Expression Dictates Therapeutic Response to Anti-PD1," Cancer Res, 75:3800-3811 (2015).
Opdivo® Prescribing Information, Bristol-Myers Squibb Company (2014), FDA Approved Labeling (Reference ID:3677021), Retrieved from the Internet: <URL: www.accessdata.fda.gov/drugsatfda_docs/label/2014/125554lbl.pdf> (20 pages).
Parry et al., "CTLA-4 and PD-1 Receptors Inhibit T-Cell Activation by Distinct Mechanisms," Molecular and Cellular Biology, 25(21):9543-9553 (2005).
Perrotti et al., "Targeting A Tumor Suppressor To Suppress Tumor Growth: News and Views on Protein Phosphatase 2A (PP2A) as a Target for Anti-cancer Therapy," Lancet Oncol, 14:e229-e238 (2013).
Pico De Coana et al., "Checkpoint blockade for cancer therapy: revitalizing a suppressed immune system," Trends Mol Med 21(8):482-91 (2015).
Quang et al., "LC-MS/MS Method Development and Validation for the Quantification of LB-100 and Endothall Metabolite in Biological Matrices," Poster MP 158, 64th American Society for Mass Spectrometry Conference on Mass Spectrometry and Allied Topics, Jun. 6, 2016, San Antonio, TX.
Robert et al., "Nivolumab in previously untreated melanoma without BRAF mutation," N Engl J Med, 372:320-330 (2015).
Rossini et al, "The toxic responses induced by okadaic acid involve processing of multiple caspase isoforms," Toxicon 39:763-770 (2001).
Sagiv-Barfi et al., "Therapeutic antitumor immunity by checkpoint blockade is enhanced by ibrutinib, an inhibitor of both BTK and ITK," Proc Natl Acad Sci U S A, 112:E966-972 (2015).
Sallman et al., "PP2A: the Achilles heal in MDS with 5q deletion," Front Oncol, 4:264 (2014) (7 pp.).
Sangodkar et al., "All roads lead to PP2A: exploiting the therapeutic potential of this phosphatase," FEBS J, 283:1004-24 (2016).
Schvartzman et al., "Mad2 Is a Critical Mediator of the Chromosome Instability Observed upon Rb and p53 Pathway Inhibition," Cancer Cell, 19:701-714 (2011).
Seshacharyulu et al., "Phosphatase: PP2A structural importance, regulation and its aberrant expression in cancer," Cancer Lett, 335:9-118 (2013).
Shi, "Serine/Threonine Phosphatases: Mechanism through Structure," Cell, 139: 468-484 (2009).
Snyder et al., "Genetic Basis for Clinical Response to CTLA-4 Blockade in Melanoma," N Engl J Med, 371(23):2189-2199 (2014).
Sukari et al., "Cancer Immunology and Immunotherapy," Anticancer Res, 36:5593-5606 (2016).
Swart et al., "Combination Approaches with Immune-Checkpoint Blockade in Cancer Therapy," Frontiers in Oncology, 6:233 (2016) (16 pp.).
Taffs et al., "Modulation of cytolytic T lymphocyte functions by an inhibitor of serine/threonine Phosphatase, okadaic acid. Enhancement of cytolytic T lymphocyte-mediated cytotoxicity," J Immunol, 147:722-728 (1991).
Tecentriq® Prescribing Information, Genentech Inc. (2016), FDA Approved Labeling (Reference ID:4000525), Retrieved from the Internet: <URL: www.accessdata.fda.gov/drugsatfda_docs/label/2016/761041lbl.pdf > (23 pages).

(56) References Cited

OTHER PUBLICATIONS

Teft et al., "A molecular perspective of CTLA-4 function," *Annu Rev Immunol*, 24:65-97 (2006).
Teft et al., "Structure-Function analysis of the CTLA-4 interaction with PP2A," *BMC Immunology*, 10:23 (2009) (10 pp.).
Topalian et al., "Immune Checkpoint Blockage: A Common Denominator Approach to Cancer Therapy," Cancer Cell, 27:450-461 (2015).
Tsiatas et al., Future perspective in cancer immunotherapy, Ann Transl Med, 4(14):273 (2016) (7 pp.).
Wang et al., "In vitro characterization of the anti-PD-1 antibody nivolumab, BMS-936558, and in vivo toxicology in non-human primates," *Cancer Immunol Res*, 2:846-856 (2014).
Wang, "Medical uses of mylabris in ancient China and recent studies," *J Ethnopharmacol*, 26(2):147-62 (1989).
Wei et al., "Inhibition of protein phosphatase 2A radiosensitizes pancreatic cancers by modulating CDC25C/CDK1 and homologous recombination repair," Clin Cancer Res, 19(16):4422-32 (2013).
Westermarck et al., Multiple pathways regulated by the tumor suppressor PP2A in transformation, *Trends Mol Med*, 14:152-160 (2008).
Wolchok et al., "Nivolumab plus ipilimumab in advanced melanoma," N Engl J Med, 369(2):122-33 (2013).
Yatsunami et al., "Hyperphosphorylation of cytokeratins by okadaic acid class tumor promoters in primary human keratinocytes," *Cancer Res*, 53:992-996 (1993).
Yervoy® Prescribing Information, Bristol-Myers Squibb Company (2015), FDA Approved Labeling (Reference ID: 3839653), Retrieved from the Internet: <URL: www.accessdata.fda.gov/drugsatfda_docs/label/2015/125377s073lbl.pdf> (32 pages).
Zhang et al., "A synthetic cantharidin analog for the enhancement of doxorubicin suppression of stem cell-derived aggressive sarcoma," Biomaterials, 31(36):9535-43 (2010).
Zhang et al., "Viewing serine/threonine protein phosphatases through the eyes of drug designers," *FEBS J*, 280:4739-4760 (2013).
Zhou et al., "In vivo Discovery of Immunotherapy Targets in the Tumor Microenvironment," *Nature*, 506:52-57 (2014).
Zhuang et al., "Enhancement of cancer chemotherapy by simultaneously altering cell cycle progression and DNA-damage defenses through global modification of the serine/threonine phosphoproteome," *Cell Cycle*, 8:3303-6 (2009).
Ho et al., "Pharmacologic inhibition of protein phosphatase-2A achieves durable immune-mediated antitumor activity when combined with PD-1 blockade," Nature Communications. 2018; 9(1):2018.
Hill, T. A. et al., "Heterocyclic substituted cantharidin and norcantharidin analogues—synthesis, protein phosphatase (1 and 2A) inhibition, and anti-cancer activity," Bioorganic & Medicinal Chemistry Letters, 17(12):3392-3397 (2007).
Maggio, D. et al., "Inhibition of protein phosphatase-2A with LB-100 enhances antitumor immunity against glioblastoma," J. Neurooncol. 148(2):231-244 (Jun. 2020) and Supplementary Material.
Yen, Y-T et al., "Protein phosphatase 2A inactivation induces microsatellite instability, neoantigen production and immune response," Nature Communications, 12, 7297 (2021).
Ho, W. S. et al., "Abstract LB-193: Protein phosphatase 2A inhibition, with a novel small molecule inhibitor, LB-100, achieves durable immune-mediated antitumor activity when combined with PD1 blockade in a preclinical model," Poster Presentations, Cancer Res (Jul. 2017) 77 (13_Supplement): LB-193, 2 pages.
Hofstetter C.P., et al., "Protein Phosphatase 2A Mediates Dormancy of Glioblastoma Multiforme-Derived Tumor Stem-like Cells During Hypoxia," Public Library of Science One, Jan. 2012, vol. 7 (1), pp. 1-11.
Lu, J. et al., "The effect of a PP2A inhibitor on the nuclear receptor corepressor pathway in glioma," J Neurosurg, vol. 113, No. 2, pp. 225-233 (Aug. 2010).
Mirzapoiazova, T. et al., "Protein Phosphatase 2A as a Therapeutic Target in Small Cell Lung Cancer," Molecular Cancer Therapeutics, 2021, 20(10):1820-1835.

Ronk, H. et al., "Targeting PP2A for cancer therapeutic modulation," Cancer Biol Med., vol. 19, No. 10, Oct. 2022, pp. 1428-1439; doi: 10.20892/j.issn.2095-3941.2022.0330, 12 pages.
Stanford, S. M. et al., "Targeting protein phosphatases in cancer immunotherapy and autoimmune disorders," Nature Reviews Drug Discovery, (Jan. 2023), https://doi.org/10.1038/s41573-022-00618-w, 22 pages.
Aarts, M. et al. (2012). Forced mitotic entry of S-phase cells as a therapeutic strategy induced by inhibition of WEE1. Cancer Discovery, 2(6), 524-539. https://doi.org/10.1158/2159-8290.CD-11-0320.
Abbas, A. A., "Synthesis of mixed-donor azaoxathia macrocyclic tetraamides, acyclic polyether di/and tetraamides and their C-pivot lariat derivatives," Journal of Heterocyclic Chemistry, vol. 44, Issue 3, May/Jun. 2007, pp. 651-661.
Abdel-Rahman, W. M. et al., "Spectral karyotyping suggests additional subsets of colorectal cancers characterized by pattern of chromosome rearrangement," Proc Natl Acad Sci USA, Feb. 2001;98(5):2538-43. doi: 10.1073/pnas.041603298. Epub Feb. 20, 2001.
Abel et al., "Epigenetic targets of HDAC inhibition in neurodegenerative and psychiatric disorders," Current Opinion in Pharmacology, vol. 8, No. 1, Feb. 2008 (pp. 57-64).
Abraham, D. et al., Raf-1-associated protein phosphatase 2A as a positive regulator of kinase activation. J Biol Chem 275(29):22300-22304 (Jul. 2000).
Acharya et al., "Rational development of histone deacetylase inhibitors as anticancer agents: a review," Molecular Pharmacology, vol. 68, No. 4, Oct. 2005 (pp. 917-932).
Adams, J. M. et al., The Bcl-2 protein family: arbiters of cell survival. Science 281:1322-1326 (Aug. 1998).
Adams, J. M. et al., Transgenic models of lymphoid neoplasia and development of a pan-hematopoietic vector. Oncogene 18:5268-5277 (1999).
Adcock, I.M. "HDAC inhibitors as anti-inflammatory agents", Br J Pharmacol. (2007), 150(7): 829-831.
Agata Y., et al., "Expression of the PD-1 antigen on the surface of stimulated mouse T and B lymphocytes," International Immunology, May 1996, vol. 8 (5), pp. 765-772.
Agoston. A. T. et al., "Retinoblastoma Pathway Dysregulation Causes DNA Methyltransferase 1 Overexpression in Cancer via MAD2-Mediated Inhibition of the Anaphase-Promoting Complex," The American Journal of Pathology, vol. 170, No. 5, pp. 1585-1593 (May 2007).
Ajay, A. K. et al., Cdk5 phosphorylates non-genotoxically overexpressed p53 following inhibition of PP2A to induce cell cycle arrest/apoptosis and inhibits tumor progression. Mol Cancer 9:204 (2010), 15 pages.
Albert, "Changing the trajectory of cognitive decline," New England Journal of Medicine, vol. 357, No. 5, Aug. 2007 (pp. 502-503).
Ambrogio, C. et al., In vivo oncogenic conflict triggered by co-existing KRAS and EGFR activating mutations in lung adenocarcinoma. Oncogene. Apr. 2017, 36(16):2309-2318.
Anderson, A.C. (2003) "The Process of Structure-Based Drug Design" Chem Biol, 10(9):787-797.
Andrabi et al., "Protein phosphatase 2A regulates life and death decisions via Akt in a context-dependent manner," Proceedings of the National Academy of Sciences U.S.A., vol. 104, No. 48, Nov. 2007 (pp. 19011-19016).
Andreatta, M. et al. (2021), "UCell: Robust and scalable single-cell gene signature scoring," Comput Struct Biotechnol J., vol. 19, pp. 3796-3798. 10.1016/j.csbj.2021.06.043.
Arakawa, T. et al., "The Mechanism of Action of Na Glutamate, Lysine HCI, and Piperazine-N,N'-bis(2-Ethanesulfonie Acid) in The Stabilization of Tubulin and Microtubule Formation*," The Journal of Biological Chemistry, Apr. 25, 1984, vol. 239, No. 8, pp. 4979-4986.
Arnold, C. P. et al., MicroRNA programs in normal and aberrant stem and progenitor cells. Genome Res. 21:798-810 (2011).
Arnold, H. K. et al., "A tumor suppressor role for PP2A-B56(alpha) through negative regulation of c-Myc and other key oncoproteins," Cancer Metastasis Review, vol. 27, No. 2, Jun. 2008, pp. 147-158.

(56) References Cited

OTHER PUBLICATIONS

Asquith, C. R. M. et al. (Mar. 2020). "PKMYT1: a forgotten member of the WEE1 family. Nature reviews." Nat. Rev. Drug Discov. 19(3):157. https://doi.org/10.1038/d41573-019-00202-9, 1 page.

Avila, J. et al. (Jan. 2006), "Tau Phosphorylation, Aggregation, and Cell Toxicity," Journal of Biomedicine and Biotechnology, vol. 2006, 5 pages.

Ayaydin et al., "Inhibition of serine/threonine-specific protein phosphatases causes premature activation of cdc2MsF kinase at G2/M transition and early mitotic microtubule organisation in alfalfa," The Plant Journal, vol. 23, No. 1, Jul. 2000 (pp. 85-96).

Baki, L. et al., "PS1 activates PI3K thus inhibiting GSK-3 activity and tau overphosphorylation: effects of FAD mutations," The EMBO Journal, vol. 23, No. 13, Jul. 2004, pp. 2586-2596.

Baki, L. et al., "Wild-Type But Not FAD Mutant Presenilin-1 Prevents Neuronal Degeneration by Promoting Phosphatidylinositol 3-Kinase Neuroprotective Signaling," The Journal of Neuroscience, vol. 28, No. 2, pp. 483-490 (Jan. 2008).

Balar, A. V. et al., "Atezolizumab as first-line treatment in cisplatin-ineligible patients with locally advanced and metastatic urothelial carcinoma: a single-arm, multicentre, phase 2 trial," Lancet, 2017;389(10064):67-76.

Bankhead, P. et al., QuPath: Open source software for digital pathology image analysis. Sci Rep 7, 16878 (2017), 7 pages.

Baskin, et al., "Inhibitors of protein kinases and phosphatases alter root morphology and disorganize cortical microtubules," Plant Physiology, vol. 113, No. 2, Feb. 1997, pp. 493-502.

Bastein, J. et al., "Nuclear Retinoid Receptors and The Transcription of Retinoid-target Genes," Gene, 2004, vol. 328, pp. 1-16.

Becht, E. et al. (Jan. 2019), "Dimensionality reduction for visualizing single-cell data using UMAP," Nature Biotechnology, vol. 37, No. 1, pp. 38-47.

Beck, H. et al. (2012). Cyclin-Dependent Kinase Suppression by WEE1 Kinase Protects the Genome through Control of Replication Initiation and Nucleotide Consumption. Molecular and Cellular Biology, 32(20), 4226-4236. https://doi.org/10.1128/mcb.00412-12.

Beglopoulos et al., "Regulation of CRE-dependent transcription by presenilins: prospects for therapy of Alzheimer's disease," Trends in Pharmacological Sciences, vol. 27, No. 1, Jan. 2006 (pp. 33-40).

Bengtsson, A. et al. (2020). The actual 5-year survivors of pancreatic ductal adenocarcinoma based on real-world data. Scientific Reports, 10(1):16425. https://doi.org/10.1038/s41598-020-73525-y, 9 pages.

Benito, A. et al., Apoptosis of human myeloid leukemia cells induced by an inhibitor of protein phosphatases (okadaic acid) is prevented by Bcl-2 and Bcl-X(L). Leukemia 11:940-944 (1997).

Bermudez, O. et al. (May 2010), "The dual-specificity MAP kinase phosphatases: critical roles in development and cancer," Am J Physiol Cell Physiol., vol. 299, pp. C189-C202.

Bernards, R., "Unconventional approaches to the treatment of cancer," PowerPoint Slides presented at the Dana-Farber Cancer Institute, AACR Annual Meeting (Apr. 2022), 16 pages.

Berry, L. D. et al., Chapter 10: Regulation of Cdc2 activity by phosphorylation at T14/Y15. Progress in Cell Cycle Research, Plenum Press, New York, 2:99-105 (1996).

Berthold et al., "Myeloablative megatherapy with autologous stem-cell rescue versus oral maintenance chemotherapy as consolidation treatment in patients with high-risk neuroblastoma: a randomised controlled trial," The Lancet Biology, vol. 6, No. 9, Sep. 2005 (pp. 649-658).

Blaheta et al., "Valproate and valproate-analogues: potent tools to fight against cancer," Current Medicinal Chemistry, vol. 9, No. 15, Aug. 2002 (pp. 1417-1433).

Blaskovich et al., "Recent discovery and development of protein tyrosince phosphatase inhibitors," Expert Opinion on Therapeutic Patents, vol. 12, No. 6, Jun. 2002 (pp. 871-905).

Bochner, B. R. et al., "Assay of the multiple energy-producing pathways of mammalian cells," PLoS One, vol. 6, Issue 3, e18147 (Mar. 2011), 8 pages.

Bodor, C. et al., "Elevated expression of Cu, Zn-SOD and Mn-SOD mRNA in inflamed dental pulp tissue," International Endodontic Journal, vol. 40, No. 2, pp. 128-132 (Feb. 2007).

Bollen, M. et al. (2010). The extended PP1 toolkit: Designed to create specificity. Trends in Biochemical Sciences, vol. 35, Issue 8, pp. 450-458. https://doi.org/10.1016/j.tibs.2010.03.002.

Bommer et al., "The translationally controlled tumor protein TCTP," International Journal of Biochemistry and Cell Biology, vol. 36, No. 3, Mar. 2004 (pp. 379-385).

Bonness, K. et al., Cantharidin-induced mitotic arrest is associated with the formation of aberrant mitotic spindles and lagging chromosomes resulting, in part, from the suppression of PP2Aalpha. Mol. Cancer Ther. 5(11):2727-2736 (2006).

Bononi, A. et al., Review Article: Protein kinases and phosphatases in the control of cell fate. Enzyme Res., vol. 2011, Article ID 329098 (2011), 26 pages.

Boschert, V. et al., "The Influence of Met Receptor Level on HGF-Induced Glycolytic Reprogramming in Head and Neck Squamous Cell Carcinoma," Int J Mol Sci 21:471 (2020), 17 pages.

Boudreau, R. T.M. et al., Apoptosis induced by protein phosphatase 2A (PP2A) inhibition in T leukemia cells is negatively regulated by PP2A-associated p38 mitogen-activated protein kinase. Cell Signal 19:139-151 (2007).

Bouscary, D. et al., Fas/Apo-1 (CD95) expression and apoptosis in patients with myelodysplastic syndromes. Leukemia 11:839-845 (1997).

Brazil et al., "Advances in protein kinase B signalling AKTion on multiple fronts," Trends in Biochemical Sciences, vol. 29, No. 5, May 2004 (pp. 233-242).

Bukhari, A. B. et al. (Mar. 2019), "Inhibiting Wee1 and ATR kinases produces tumor-selective synthetic lethality and suppresses metastasis," Journal of Clinical Investigation, vol. 129, No. 3, pp. 1329-1344.

Bundgaard H., "Novel Chemical Approaches In Prodrug Design", Drugs Of The Future, Es, Prous Science, 1991, vol. 16, No. 5, p. 443-458.

Bunn, P. A. Jr. et al., "A phase I study of carboplatin and paclitaxel in non-small cell lung cancer: a University of Colorado Cancer Center study," Semin Oncol., 1995;22(4 Suppl 9):2-6.

Bunn, P. A. Jr., Review of therapeutic trials of carboplatin in lung cancer. Semin Oncol. 1989;16(2 Suppl 5):27-33.

Burgess, A. et al., Loss of human Greatwall results in G2 arrest and multiple mitotic defects due to deregulation of the cyclin B-Cdc2/PP2A balance. Proc Acad Sci USA 107(28):12564-12569 (Jul. 2010).

Burke, "Inhibition of mitogen-activated protein kinase and stimulation of Akt kinase signaling pathways: Two approaches with therapeutic potential in the treatment of neurodegenerative disease," Pharmacology & Therapeutics, vol. 114, No. 3, Jun. 2007 (pp. 261-277).

Cañadas, I. et al., Targeting epithelial-to-mesenchymal transition with Met inhibitors reverts chemoresistance in small cell lung cancer. Clin Cancer Res 20, 938-950 (2014).

Camphausen et al., "Influence of in vivo growth on human glioma cell line gene expression: convergent profiles under orthotopic conditions," Proceedings of the National Academy of Sciences U.S.A., vol. 102, No. 23, Jun. 2005 (pp. 8287-8292).

Caplus AN 1962:73368, Yur'ev, Y K. et al., "Furan Series. XVII. Synthesis of amino alcohols of the 3, 6-endoxocyclohexane series," Zhurnal Obshchei Khimii, (1961), 31, 2898-902, 2 pages.

Carter, L. L., et al., "PD-1: PD-L inhibitory pathway affects both CD4+ and CD8+ T cells and is overcome by IL-2", European Journal of Immunology (2002); 32(3): 634-643.

Castedo et al., "Cell death by mitotic catastrophe: a molecular definition," Oncogene, vol. 23, No. 16, Apr. 2004 (pp. 2825-2837).

Cazzola, M. et al., "The genetic basis of myelodysplasia and its clinical relevance," Blood, vol. 122, No. 25, pp. 4021-4034 (Dec. 2013).

Chan, L. N. et al. (Jul. 2020), "Signalling input from divergent pathways subverts B cell transformation," Nature, vol. 583, 31 pages. https://doi.org/10.1038/s41586-020-2513-4.

(56) References Cited

OTHER PUBLICATIONS

Chang et al., "All-trans-retinoic acid induces cell growth arrest in a human medullablastoma cell line," Journal of Neuro-Oncology, vol. 84, No. 3, Sep. 2007 (pp. 263-267).
Chen et al., "Mcl-1 Down-regulation Potentiates ABT-737 Lethality by Cooperatively Inducing Bak Activation and Bax Translocation," Cancer Research, vol. 67, No. 2, Jan. 2007 (pp. 782-791).
Chen, J. et al., Leukemogenesis: more than mutant genes. Nature Reviews Cancer, 10(1):23-36 (Jan. 2010).
Chen, J. T. et al., HGF increases cisplatin resistance via down-regulation of AIF in lung cancer cells. Am J Respir Cell Mol Biol 38, 559-565 (2008).
Chen, S. H. et al., "A knockout mouse approach reveals that TCTP functions as an essential factor for cell proliferation and survival in a tissue- or cell type-specific manner," Molecular Biology of the Cell, vol. 18, No. 7, Jul. 2007, pp. 2525-2532.
Chen, W. et al., "Identification of specific PP2A complexes involved in human cell transformation," Cancer Cell, vol. 5, No. 2, pp. 127-136 (Feb. 2004).
Chen, X. et al., The microtubule depolymerizing agent CYT997 effectively kills acute myeloid leukemia cells via activation of caspases and inhibition of PI3K/Akt/mTOR pathway proteins. Exp Ther Med 6:299-304 (2013).
Chen, Y-N et al., Effector mechanisms of norcantharidin-induced mitotic arrest and apoptosis in human hepatoma cells. Int J Cancer 100:158-165 (2002).
Cheson, B. D. et al., "Clinical application and proposal for modification of the International Working Group (IWG) response criteria in myelodysplasia," Blood, vol. 108, No. 2, pp. 419-425 (Jul. 2006).
Cho et al., "Crystal structure of a protein phosphatase 2A heterotrimeric holoenzyme," Nature, vol. 445, No. 7123, Jan. 2007 (pp. 53-57).
Choi, J-W et al., "High expression of spindle assembly checkpoint proteins CDC20 and MAD2 is associated with poor prognosis in urothelial bladder cancer," Virchows Archiv., vol. 463, No. 5, Nov. 2013, pp. 681-687.
Chou et al., "Quantitative analysis of dose-effect relationships: the combined effects of multiple drugs or enzyme inhibitors", Advances in Enzyme Regulation, vol. 22, p. 27-55 (1984).
Chu, P-M et al., Review: Deregulated microRNAs identified in isolated glioblastoma stem cells: an overview. Cell Transplantation, 22:741-753 (2013).
Chung, V. M. et al., "A phase 1 study of a novel inhibitor of protein phosphatase 2A alone and with docetaxel," Meeting Abstract, 2014 ASCO Annual Meeting, Abstract TPS2636 (2014), 2 pages.
Ciccone, M. et al. (Feb. 2015). From the biology of PP2A to the PADs for therapy of hematologic malignancies. Frontiers in Oncology, vol. 5, Article 21, https://doi.org/10.3389/fonc.2015.00021, 10 pages.
Cogle, C. et al., Incidence of the myelodysplastic syndromes using a novel claims-based algorithm: high number of uncaptured cases by cancer registries. Blood 117(26):7121-7125 (2011).
Cohen, M. V. et al., "Is it time to translate ischemic preconditioning's mechanism of cardioprotection into clinical practice?" Journal of Cardiovascular Pharmacology and Therapeutics, vol. 16, No. 3-4, Sep.-Dec. 2011, pp. 273-280.
Cohen, P., "The Structure and Regulation of Protein Phosphatases," Annual Review of Biochemistry, 1989, vol. 58, pp. 453-508.
Coleman, T. R. et al., Cdc2 regulatory factors. Curr. Opin. Cell Biol., 6:877-882 (1994).
Coles, G. L. et al., "Unbiased Proteomic Profiling Uncovers a Targetable GNAS/PKA/PP2A Axis in Small Cell Lung Cancer Stem Cells," Cancer Cell, 38:129-143 (Jul. 2020), pp. 129-143.
Colic, M. et al. (Aug. 2019), "Identifying chemogenetic interactions from CRISPR screens with drugZ," Genome Medicine, vol. 11, No. 52, 12 pages.
Crafts, "Herbicides," Annual Review of Plant Physiology, vol. 4, Jun. 1953 (pp. 253-282).
Craig, "MCL1 provides a window on the role of the BCL2 family in cell proliferation, differentiation and tumorigenesis," Leukemia, vol. 16, No. 4, Apr. 2002 (pp. 444-454).

David et al., "Histone deacetylase associated with mSin3A mediates repression by the acute promyelocytic leukemia-associated PLZF protein," Oncogene, vol. 16, No. 19, May 1998 (pp. 2549-2556).
Davis, R. E. et al., Bcl-2 expression by myeloid precursors in myelodysplastic syndromes: relation to disease progression. Leuk Res 22:767-777 (1998).
De Luca, A. et al., "The RAS/RAF/MEK/ERK and the PI3K/AKT signalling pathways: role in cancer pathogenesis and implications for therapeutic approaches," Expert Opin Ther Targets 16(Suppl 2), S17-S27 (2012).
De Witt Hamer, P. C. et al. (2011). WEE1 kinase targeting combined with DNA-damaging cancer therapy catalyzes mitotic catastrophe. Clinical Cancer Research, vol. 17, Issue 13, pp. 4200-4207. https://doi.org/10.1158/1078-0432.CCR-10-2537.
Di Fagagna, F., "Living on a break: cellular senescence as a DNA-damage response," Nature Reviews Cancer, vol. 8, No. 7, Jul. 2008, pp. 512-522.
Dias, M. H. et al. (2019). Fibroblast Growth Factor 2 lethally sensitizes cancer cells to stress-targeted therapeutic inhibitors. Molecular Oncology, 13(2), 290-306. https://doi.org/10.1002/1878-0261.12402.
Dias, M. H. et al., "Paradoxical activation of oncogenic signaling as a cancer treatment strategy," Feb. 2023, bioRxiv preprint doi: https://doi.org/10.1101/2023.02.06.527335, 79 pages.
Dias, M. H. et al., "Playing cancer at its own game: activating mitogenic signaling as a paradoxical intervention," Mol Oncol. Aug. 2021;15(8):1975-1985.
DiFeo, T. J., "Drug Product Development: A Technical Review of Chemistry, Manufacturing, and Controls Information for The Support of Pharmaceutical Compound Licensing Activities," Drug Development and Industrial Pharmacy, Aug. 2003, vol. 29, No. 9, pp. 939-958.
Dreesen et al., "Signaling pathways in cancer and embryonic stem cells," Stem Cell Review, vol. 3, No. 1, Jan. 2007 (pp. 7-17).
Drewinko et al., "Combination chemotherapy in vitro with adriamycin. Observations of additive, antagonistic, and synergistic effects when used in two-drug combinations on cultured human lymphoma cells," Cancer Biochemistry Biophysics, vol. 1, No. 4, May 1976 (pp. 187-195).
Duda, H. et al. (Dec. 2016), "A Mechanism for Controlled Breakage of Under-replicated Chromosomes during Mitosis," Developmental Cell, vol. 39, pp. 740-755. http://dx.doi.org/10.1016/j.devcel.2016.11.017.
Duong, F. H. et al., Hepatitis C virus inhibits interferon signaling through up-regulation of protein phosphatase 2A. Gastroenterology 126, 263-277 (2004).
Duong, F. H. et al., Protein phosphatase 2A promotes hepatocellular carcinogenesis in the diethylnitrosamine mouse model through inhibition of p53. Carcinogenesis 35, 114-122 (2014).
Durusu, I. Z. et al., "Anti-Cancer Effect of Clofazimine as a Single Agent and in Combination with Cisplatin On U266 Multiple Myeloma Cell Line," Leukemia Research, Apr. 2017, vol. 55, pp. 33-40.
Ebert, B. L. et al., "Identification of RPS14 as a 5q-syndrome gene by RNA interference screen," Nature, vol. 451, No. 7176, pp. 335-339 (Jan. 2008).
Eckardt, J. R. et al., "Open-label, multicenter, randomized, phase III study comparing oral topotecan/cisplatin versus etoposide/cisplatin as treatment for chemotherapy-naive patients with extensive-disease small-cell lung cancer," J Clin Oncol. 2006;24(13):2044-2051.
Ecker, V. et al. (Jun. 2021), "Targeted PI3K/AKT-hyperactivation induces cell death in chronic lymphocytic leukemia," Nature Communications, vol. 12, No. 3526, 17 pages. https://doi.org/10.1038/s41467-021-23752-2.
Eichhorn, P. J.A. et al., Review: Protein phosphatase 2A regulatory subunits and cancer. Biochim Biophys Acta 1795:1-15 (2009).
Elbaek, C. R. et al. (2022). WEE1 kinase protects the stability of stalled DNA replication forks by limiting CDK2 activity. Cell Reports, 38(3). https://doi.org/10.1016/j.celrep.2021.110261, 14 pages.
Engel, T. et al., "Full Reversal of Alzheimer's Disease-Like Phenotype in a Mouse Model with Conditional Overexpression of Glycogen Synthase Kinase-3," The Journal of Neuroscience, vol. 26, No. 19 (May 2006), pp. 5083-5090.

(56) References Cited

OTHER PUBLICATIONS

Erdodi, F. et al. (Nov. 1995), "Endothall thianhydride inhibits protein phosphatases-1 and -2A in vivo," American Journal of Physiology, vol. 269, No. 5 Pt 1, pp. C1176-C1184.

Essers et al., "Synthesis of the first fluorinated cantharidin analogues," Tetrahedron Letters, vol. 42, No. 32, Aug. 2001 (pp. 5429-5433).

Fabel et al., "Long-term stabilization in patients with malignant glioma after treatment with liposomal doxorubicin," Cancer, vol. 92, No. 7, Oct. 2001 (pp. 1936-1942).

Fang, Y. et al. (Jun. 2019), "Sequential Therapy with PARP and WEE1 Inhibitors Minimizes Toxicity while Maintaining Efficacy," Cancer Cell, vol. 35, pp. 851-867. https://doi.org/10.1016/j.ccell.2019.05.001.

Fang, Z. et al. (Nov. 2022), "GSEApy: a comprehensive package for performing gene set enrichment analysis in Python," Bioinformatics, vol. 39, No. 1, 3 pages. https://doi.org/10.1093/bioinformatics/btac757.

Fanghanel, E. et al. (Oct. 1994), "Cycloaddition Reactions of [1,]Dithiolo[1,2]dithiole Derivatives with Dimethyl Acetylenedicarboxylate: Formation of New Bi-, Tri- and Tetracyclic Thiopyran Derivatives," Synthesis, vol. 10, pp. 1067-1071.

Faoro, L. et al., EphA2 mutation in lung squamous cell carcinoma promotes increased cell survival, cell invasion, focal adhesions, and mammalian target of rapamycin activation. J Biol Chem 285, 18575-18585 (2010).

Federal Register Online via the Government Publishing Office, Federal Register, vol. 66, No. 4, Jan. 2001, 19 pages.

Fehrenbacher, L. et al., "Atezolizumab versus docetaxel for patients with previously treated non-small-cell lung cancer (POPLAR): a multicentre, open-label, phase 2 randomised controlled trial," Lancet, Apr. 2016;387(10030):1837-1846.

Ferron, P-J et al., Comparative analysis of the cytotoxic effects of okadaic acid-group toxins on human intestinal cell lines. Mar. Drugs 12:4616-4634 (2014).

Finger, E. C. et al., "Hypoxia, inflammation, and the tumor microenvironment in metastatic disease," Cancer Metastasis Rev., vol. 29, pp. 285-293 (2010).

Finnin, M. S. et al., "Structures of a histone deacetylase homologue bound to the TSA and SAHA inhibitors," Nature (Sep. 1999), vol. 401, pp. 188-193.

Fischer et al., "Recovery of learning and memory is associated with chromatin remodelling," Nature, vol. 447, No. 7141, May 2007 (pp. 178-182).

Flicker et al., "Tyrosine kinase signaling pathways control the expression of retinoic acid receptor-alpha in SK-BR-3 breast cancer cells," Cancer Letters, vol. 115, No. 1, May 1997 (pp. 63-72).

Forester, C. M. et al., "Control of mitotic exit by PP2A regulation of Cdc25C and Cdk1," Proceedings of the National Academy of Sciences U.S.A., vol. 104, No. 50, Dec. 2007, pp. 19867-19872.

Francia, G. et al., Identification by differential display of a protein phosphatase-2A regulatory subunit preferentially expressed in malignant melanoma cells. Int J Cancer 82:709-713 (1999).

Frasor, J. et al., "Estrogen down-regulation of the Corepressor N-CoR: Mechanism and implications for estrogen derepression of N-CoR-Regulated Genes," Proceedings of the National Academy of Sciences of the United States of America, vol. 102, No. 37, (Sep. 2005), pp. 13153-13157.

Freeman, G. J., et al., "Engagement of the PD-1 immunoinhibitory receptor by a novel B7 family member leads to negative regulation of lymphocyte activation", The Journal of Experimental Medicine (2000); 192(7): 1027-1034.

Fung, M. K.-L. et al., "MAD2 expression and its significance in mitotic checkpoint control in testicular germ cell tumour," Biochimica et Biophysica Acta, vol. 1773, No. 6, Jun. 2007, pp. 821-832.

Furumai, R. et al., "Potent histone deacetylase inhibitors built from trichostatin A and cyclic tetrapeptide antibiotics including trapoxin", Proc Natl Acad Sci U S A. (2001), 98(1): 87-92.

Gachet et al., "The growth-related, translationally controlled protein P23 has properties of a tubulin binding protein and associates transiently with microtubules during the cell cycle," Journal of Cell Science, vol. 112, pt. 8, Apr. 1999 (pp. 1257-1271).

Gallo, D. et al. (2022). CCNE1 amplification is synthetic lethal with PKMYT1 kinase inhibition. Nature, vol. 604, No. 7907, pp. 749-756. https://doi.org/10.1038/s41586-022-04638-9.

Gandino, L. et al., Phosphorylation of serine 985 negatively regulates the hepatocyte growth factor receptor kinase. J Biol Chem 269, 1815-1820 (1994).

Garcia-Echeverria et al., "Drug discovery approaches targeting the PI3K/Akt pathway in cancer," Oncogene, vol. 27, No. 41, Sep. 2008 (pp. 5511-5526).

Gatzemeier, U. et al., "Phase II and III studies with carboplatin in small cell lung cancer," Semin Oncol., Feb. 1992, vol. 19, No. 1, Suppl. 2, pp. 28-36.

Ge, X. Q. et al. (2007). Dormant origins licensed by excess Mcm2-7 are required for human cells to survive replicative stress. Genes and Development, vol. 21, No. 24, pp. 3331-3341. https://doi.org/10.1101/gad.457807.

Gendron, S. et al., Integrin alpha2beta1 inhibits Fas-mediated apoptosis in T lymphocytes by protein phosphatase 2A-dependent activation of the MAPK/ERK pathway. J Biol Chem 278(49):48633-48643 (Dec. 2003).

Germain, P-L et al. (Sep. 2021), "Doublet identification in single-cell sequencing data using scDblFinder [version 1; peer review: 1 approved, 1 approved with reservations]," F1000Research, vol. 10, No. 979, 23 pages. https://doi.org/10.12688/f1000research.73600.1.

Giagounidis, A. et al., "Clinical, morphological, cytogenetic, and prognostic features of patients with myelodysplastic syndromes and del(5q) including band q31," Leukemia, vol. 18, No. 1, pp. 113-119 (Jan. 2004).

Giannini, R. et al., "Expression Analysis of a Subset of Coregulators and Three Nuclear Receptors in Human Colorectal Carcinoma," Anticancer Research, vol. 25, No. 6B, Nov. 2005, pp. 4287-4292.

Godlewski, J. et al., microRNA-451: A conditional switch controlling glioma cell proliferation and migration. Cell Cycle, 9(14):2814-2820 (Jul. 2010).

Godlewski, J. et al., microRNA-451 regulates LKB1/AMPK signaling and allows adaptation to metabolic stress in glioma cells. Mol Cell 37:620-632 (Mar. 2010).

Godlewski, J. et al., MicroRNAs and glioblastoma; the stem cell connection. Cell Death and Differentiation, 17:221-228 (2010).

Gong, C.-X. al., "Post-translational modifications of tau protein in Alzheimer's disease," J. Neural Transmission, vol. 112, (2005), pp. 813-838.

Gorecki, L. et al. (Feb. 2021), Clinical candidates targeting the ATR-CHK1-WEE1 axis in cancer, Cancers, vol. 13, Issue 4, pp. 1-22. Published online Feb. 14, 2021. doi: 10.3390/cancers13040795.

Gottlicher et al., "Valproic acid defines a novel class of HDAC inhibitors inducing differentiation of transformed cells," EMBO Journal, vol. 20, No. 24, Dec. 2001 (pp. 6969-6978).

Graziano, M. J. et al., "Comparison of the acute toxicity of endothal and cantharidic acid on mouse liver in vivo," Toxicology Letters, vol. 37, No. 2, Jul. 1987, pp. 143-148.

Greenberg, P. et al., "International scoring system for evaluating prognosis in myelodysplastic syndromes," Blood, vol. 89, No. 6, pp. 2079-2088 (Mar. 1997) with Erratum.

Greenberg, P. L. et al., "Myelodysplastic syndromes: clinical practice guidelines in oncology," J. Natl. Compr. Canc. Netw., vol. 11, No. 7, pp. 838-874 (Jul. 2013).

Greenberg, P. L. et al., "Revised International Prognostic Scoring System for Myelodysplastic Syndromes," Blood, vol. 120, No. 12, pp. 2454-2465 (Sep. 2012).

Grimes, C. A. et al., "The multifaceted roles of glycogen synthase kinase 3(beta) in cellular signaling," Progress In Neurobiology, vol. 65, Issue 4, Nov. 2001, pp. 391-426.

Groenendijk, F. H. et al. (2014). Drug resistance to targeted therapies: déjà vu all over again. Molecular Oncology, 8(6):1067-1083. https://doi.org/10.1016/j.molonc.2014.05.004.

Gumireddy et al., "All-trans-retinoic acid-induced apoptosis in human medulloblastoma: activation of caspase-3/poly (ADP-ribose) polymerase 1 pathway," Clinical Cancer Research, vol. 9, No. 11, Sep. 2003 (pp. 4052-4059).

(56) References Cited

OTHER PUBLICATIONS

Gwinn, D. et al., "The Phosphatase PP2A Links Glutamine to the Tumor Suppressor p53," Molecular Cell, vol. 50, No. 2, Apr. 2013, pp. 157-158.
Haase, D. et al., "New insights into the prognostic impact of the karyotype in MDS and correlation with subtypes: evidence from a core dataset of 2124 patients," Blood, vol. 110, No. 13, pp. 4385-4395 (Dec. 2007).
Hanahan, D. et al. (Jan. 2000). The Hallmarks of Cancer. Review. Cell, 100(1):57-70. https://doi.org/10.1007/s00262-010-0968-0.
Hardy-Werbin, M. et al., "MET Inhibitors in Small Cell Lung Cancer: From the Bench to the Bedside," Cancers, 11:1404 (2019), 14 pages.
Hart, M.E., et al., "Modified norcantharidins: synthesis, protein phosphatases 1 and 2A inhibition, and anticancer activity," Bioorganic & Medicinal Chemistry Letters, vol. 14, No. 8, pp. 1969-1973 (Apr. 2004).
Hashigasako, A. et al., Bidirectional regulation of Ser-985 phosphorylation of c-met via protein kinase C and protein phosphatase 2A involves c-Met activation and cellular responsiveness to hepatocyte growth factor. J Biol Chem 279, 26445-26452 (2004).
Havrilesky L.J., et al., "Relationship Between Expression of Coactivators and Corepressors of Hormone Receptors and Resistance of Ovarian Cancers to Growth Regulation By Steroid Hormones," Journal of the Society of the Gynecologic Investigation, Mar./Apr. 2001, vol. 8 (2), pp. 104-113.
Hawkins C.E., et al., "Molecular Genetic Approaches and Potential New Therapeutic Strategies for Pediatric Diffuse Intrinsic Pontine Glioma," Journal of Clinical Oncology, Oct. 2011, vol. 29 (30), pp. 3956-3957.
He, L. et al., MicroRNAs: small RNAs with a big role in gene regulation. Nat. Rev. Genet., 5:522-531 (Jul. 2004).
Hermanson, O. et al., "N-CoR Controls Differentiation of Neural Stem Cells into Astrocytes," Nature, Oct. 31, 2002, vol. 419, pp. 934-939.
Hildmann et al., "Histone-deacetylases—an important class of cellular regulators with a variety of functions," Applied Microbiology and Biotechnology, vol. 75, No. 3, Jun. 2007 (pp. 487-497).
Hirose et al., "Akt activation suppresses Chk2-mediated methylating agent-induced G2 arrest and protects from temozolomide-induced mitotic catastrophe and cellular senescence," Cancer Research, vol. 65, No. 11, Jun. 2005 (pp. 4861-4869).
Hisaoka, M. et al., "Aberrant MAD2 expression in soft-tissue sarcoma," Pathology International, vol. 58, No. 6, Jun. 2008, pp. 329-333.
Holford, N. H.G. et al., Understanding the dose-effect relationship: clinical application of pharmacokinetic-pharmacodynamic models. Clin. Pharmacokinet, 6(6):429-453 (Nov.-Dec. 1981).
Hong, C., et al., "Norcantharidin-induced post-G2/M Apoptosis is Dependent on Wild-Type p53 Gene," Biochem. Biophys. Res. Comm., vol. 276, No. 1, pp. 278-285 (Sep. 2000).
Honkanen, R. E., "Cantharidin, Another Natural Toxin That Inhibits the Activity of Serine/threonine Protein Phosphatases Types 1 and 2A," The Federation of European Biochemical Societies (FEBS) Letters, vol. 330, No. 3, Sep. 1993, pp. 283-286.
Honkanen, R. E. et al., "Regulators of Serine/Threonine Protein Phosphatases at the Dawn of a Clinical Era?" Curr. Med. Chem, vol. 9, No. 22, (2002), pp. 2055-2075.
Horn, L. et al., First-Line Atezolizumab plus Chemotherapy in Extensive-Stage Small-Cell Lung Cancer. N Engl J Med. 2018;379(23):2220-2229.
Hoshikawa et al., "Trichostatin A induces morphological changes and gelsolin expression by inhibiting histone deacetylase in human carcinoma cell lines," Experimental Cell Research, vol. 214, No. 1, Sep. 1994 (pp. 189-197).
Hu, C. et al., "PP2A inhibition from LB100 therapy enhances daunorubicin cytotoxicity in secondary acute myeloid leukemia via miR-181b-1 upregulation," Scientific Reports, 7(1):2894 (Jun. 2017), 14 pages.
Huan, S. K-H et al., Cantharidin-induced cytotoxicity and cyclooxygenase 2 expression in human bladder carcinoma cell line. Toxicology 223:136-143 (2006).
Huang, B. et al., Metabolic control of Ca2+/calmodulin-dependent protein kinase II (CaMKII)-mediated caspase-2 suppression by the B55beta/protein phosphatase 2A (PP2A). J Biol Chem 289(52):35882-35890 (Dec. 2014).
Huang, D. C. S. et al., BH3-Only proteins—essential initiators of apoptotic cell death. Cell, 103:839-842 (Dec. 2000).
Huang, "Targeting histone deacetylases for the treatment of cancer and inflammatory diseases," Journal of Cell Physiology, vol. 209, No. 3, Dec. 2006 (pp. 611-616).
Huang, W-W et al., Cantharidin induces G2/M phase arrest and apoptosis in human colorectal cancer colo 205 cells through inhibition of CDK1 activity and caspase-dependent signaling pathways. Int J Oncol 38:1067-1073 (2011).
Hughes et al., "Ciliary neurotrophic factor induces type-2 astrocyte differentiation in culture," Nature, vol. 335, No. 6185, Sep. 1988 (pp. 70-73).
Ianzini et al., "Delayed DNA damage associated with mitotic catastrophe following X-irradiation of HeLa S3 cells," Mutagenesis, vol. 13, No. 4, Jul. 1998 (pp. 337-344).
Ibarra, A. et al. (2008). Excess MCM proteins protect human cells from replicative stress by licensing backup origins of replication. Proceedings of the National Academy of Sciences of the United States of America, 105(26):8956-8961. https://doi.org/10.1073/pnas.0803978105.
International Preliminary Report on Patentability for International Application No. PCT/US2008/001549, mailed Aug. 11, 2009, 6 pages.
International Preliminary Report on Patentability for International Application No. PCT/US2009/004108, dated Feb. 1, 2011, 6 pages.
International Preliminary Report on Patentability for International Application No. PCT/US2014/033317, mailed Oct. 22, 2015, 14 pages.
International Preliminary Report on Patentability for International Application No. PCT/US2015/041709, mailed Feb. 2, 2017, 7 pages.
International Preliminary Report on Patentability for International Application No. PCT/US2015/041714, mailed Feb. 2, 2017, 8 pages.
International Preliminary Report on Patentability for International Application No. PCT/US2018/063980, mailed Jun. 18, 2020, 7 pages.
International Preliminary Report on Patentability for International Application No. PCT/US2019/037015, mailed Dec. 24, 2020, 7 pages.
International Preliminary Report on Patentability for International Application No. PCT/US2021/051647 dated Aug. 3, 2023, 6 pages.
International Search Report and Written Opinion for International Application No. PCT/US2008/001549, mailed May 16, 2008, 7 pages.
International Search Report and Written Opinion for International Application No. PCT/US2014/033317, mailed Aug. 25, 2014, 16 pages.
International Search Report and Written Opinion for International Application No. PCT/US2014/065669, mailed Jan. 29, 2015, 18 pages.
International Search Report and Written Opinion for International Application No. PCT/US2015/036693, mailed Oct. 16, 2015, 9 pages.
International Search Report and Written Opinion for International Application No. PCT/US2015/041709, mailed Oct. 23, 2015, 9 pages.
International Search Report and Written Opinion for International Application No. PCT/US2015/041714, mailed Oct. 30, 2015, 10 pages.
International Search Report and Written Opinion for International Application No. PCT/US2016/032123, mailed Oct. 17, 2016, 12 pages.
International Search Report and Written Opinion for International Application No. PCT/US2017/015237, mailed Apr. 5, 2017, 10 pages.

(56) References Cited

OTHER PUBLICATIONS

International Search Report and Written Opinion for International Application No. PCT/US2018/063980, mailed Feb. 14, 2019, 9 pages.
International Search Report and Written Opinion for International Application No. PCT/US2019/037015, mailed Oct. 1, 2019, 10 pages.
International Search Report and Written Opinion for International Application No. PCT/US2021/051647, mailed Dec. 13, 2021, 7 pages.
International Search Report and Written Opinion for International Application No. PCT/US2023/060033 mailed Jul. 7, 2023, 17 pages.
Invitation to Pay Additional Fees for International Application PCT/US2023/060033, mailed Mar. 30, 2023, 2 pages.
Isfort, C. S. et al., "Helical Complexes Containing Diamide-Bridged Benzene-o-dithiolato/Catecholato Ligands," Chemistry—A European Journal, vol. 13, Issue 8, Mar. 2007, pp. 2344-2357.
Ishida, Y. et al., Treatment of myeloid leukemic cells with the phosphatase inhibitor okadaic acid induces cell cycle arrest at either G1/S or G2/M depending on dose. J Cell Physiol 150:484-492 (1992).
Ito, T. et al. (2021). Paralog knockout profiling identifies DUSP4 and DUSP6 as a digenic dependence in MAPK pathway-driven cancers. Nature Genetics, 53(12):1664-1672. https://doi.org/10.1038/s41588-021-00967-z.
Jain, G. et al., "Theory and Practice of Physical Pharmacy," Elsevier India, 1st Ed. E-Book, Jan. 2013, pp. 150-154, ISBN: 9788131232651.
Janssens, V. et al., Review Article: Protein phosphatase 2A: a highly regulated family of serine/threonine phosphatases implicated in cell growth and signalling. Biochem. J., 353(Pt 3):417-439 (Feb. 2001).
Jia, D. et al., "Elucidating the Metabolic Plasticity of Cancer: Mitochondrial Reprogramming and Hybrid Metabolic States," Cells, 7, 21 (2018), 19 pages.
Jin, H. et al.,. EGFR activation limits the response of liver cancer to lenvatinib. Nature. Jul. 2021, 595(7869):730-734.
Jin, N. et al., "Identification of metabolic vulnerabilities of receptor tyrosine kinases-driven cancer," Nature Communications, 10:2701 (2019), 15 pages.
Johnson et al., Plk1 activation by Ste20-like kinase (Slk) phosphorylation and polo-box phosphopeptide binding assayed with the substrate translationally controlled tumor protein (TCTP), Biochemistry, vol. 47, No. 12, Mar. 2008 (pp. 3688-3696).
Johnstone, R. W. et al., Apoptosis: a link between cancer genetics and chemotherapy. Cell, 108:153-164 (Jan. 2002).
Joshi et al., "Retinoic acid receptors and tissue-transglutaminase mediate short-term effect of retinoic acid on migration and invasion of neuroblastoma SH-SY5Y cells," Oncogene, vol. 25, No. 2, Jan. 2006 (pp. 240-247).
Junttila, M. R. et al., "CIP2A inhibits PP2A in human malignancies," Cell, vol. 130, No. 1, Jul. 2007, pp. 51-62.
Kalev, P. et al., "Loss of PPP2R2A inhibits homologous recombination DNA repair and predicts tumor sensitivity to PARP inhibition," Cancer Research, vol. 72, No. 24, Dec. 2012, pp. 6414-6424.
Kamat, P. K. et al., Molecular and cellular mechanism of okadaic acid (OKA)-induced neurotoxicity: a novel tool for Alzheimer's disease therapeutic application. Mol. Neurobiol 50:852-865 (2014).
Kamitani et al., "Histone acetylation may suppress human glioma cell proliferation when p21 WAF/Cip1 and gelsolin are induced," Neuro-Oncology, vol. 4, No. 2, Apr. 2002 (pp. 95-101).
Kang, D. E. et al., "Preseniliins mediate phosphatidylinositol 3-kinase/AKT and ERK activation via select signaling receptors," The Journal of Biological Chemistry, vol. 280, No. 36, Sep. 2005, pp. 31537-31547.
Kantarjian, H. et al., "Proposal for a new risk model in myelodysplastic syndrome that accounts for events not considered in the original International Prognostic Scoring System," Cancer, 113(6):1351-1361 (Sep. 2008).
Kanteti, R. et al., "MET and PI3K/mTOR as a potential combinatorial therapeutic target in malignant pleural mesothelioma," PLoS One, 9(9):e105919 (2014), 16 pages.
Karras, D. J. et al., Poisoning from "Spanish Fly" (Cantharidin). Am J Emerg Med 14:478-483 (1996).
Kato, T. et al., "Overexpression of MAD2 predicts clinical outcome in primary lung cancer patients," Lung Cancer, vol. 4, No. 1, Oct. 2011, pp. 124-131.
Katsushima, K. et al., Non-coding RNAs as epigenetic regulator of glioma stem-like cell differentiation. Frontiers in Genetics, vol. 5, Article 14, (Feb. 2014), 8 pages.
Kauko, O. et al., Non-genomic mechanisms of protein phosphatase 2A (PP2A) regulation in cancer. Int J Biochem Cell Biol 96, 157-164 (2018).
Kawada, I. et al., Paxillin mutations affect focal adhesions and lead to altered mitochondrial dynamics: relevance to lung cancer. Cancer Biol Ther 14, 679-691 (2013).
Kawamura et al., "Endothall thioanhydride: structural aspects of unusually high mouse toxicity and specific binding site in liver," Chemical Research in Toxicology, vol. 3, No. 4, Jul. 1990 (pp. 318-324).
Kayser et al., "Metal hydride reductions of unsymmetrical cyclic anhydrides. The importance of the antiperiplanar effect on the regioselectivity of these reactions," Canadian Journal of Chemistry, vol. 60, No. 10, May 1982 (pp. 1192-1198).
Kayser et al., "On the regioselectivity of Wittig reactions with unsymmetrically substituted succinic anhydrides," Canadian Journal of Chemistry, vol. 67, No. 9, Sep. 1989 (pp. 1401-1410).
Kaytor, M. D. et al., "The GSK3B signaling cascade and neurodegenerative disease," vol. 12, (2002), pp. 275-278.
Kazi, A. et al. (2018), "GSK3 suppression upregulates β-catenin and c-Myc to abrogate KRas-dependent tumors," Nature Communications, vol. 9, No. 1, 9 pages.
Kelland, L., "The resurgence of platinum-based cancer chemotherapy," Nature Reviews Cancer, Aug. 2007, vol. 7, No. 8, pp. 573-584.
Kelly, W.K., et al., "Drug insight: Histone deacetylase inhibitors—development of the new targeted anticancer agent suberoylanilide hydroxamic acid", Nat ClinPract Oncol. (2005), 2(3): 150-157.
Kent, L. N. et al. (Jun. 2019), "The broken cycle: E2F dysfunction in cancer," Nat Rev Cancer, vol. 19, pp. 326-338. https://doi.org/10.1038/s41568-019-0143-7.
Kijima, M., et al., "Trapoxin, an antitumor cyclic tetrapeptide, is an irreversible inhibitor of mammalian histone deacetylase," Journal of Biological Chemistry, vol. 268, No. 30, Oct. 1993 (pp. 22429-22435).
Kilari, D. et al., Role of copper transporters in platinum resistance. World J Clin Oncol 7, 106-113 (2016).
Kim et al., "Selective Induction of cyclin-Dependent Kinase Inhibitors and Their Roles in Cell Cycle Arrest Caused by Trichostatin A, an Inhibitor of Histone Deacetylase," Annals of the New York Academy of Sciences, vol. 886, Dec. 1999 (pp. 200-203).
Kim et al., "Susceptibility and radiosensitization of human glioblastoma cells to trichostatin A, a histone deacetylase inhibitor," International Journal of Radiation Oncology, Biology, Physics, vol. 59, No. 4, Jul. 2004 (pp. 1174-1180).
Kim, H. Y. et al., "Molecularly Targeted Therapies for Hepatocellular Carcinoma: Sorafenib as a Stepping Stone," Digestive Diseases, vol. 29, No. 3, Aug. 2011, pp. 303-309.
Kim, Y. et al., "MAD2 and CDC20 are upregulated in high-grade squamous intraepithelial lesions and squamous cell carcinomas of the uterine cervix," International Journal of Gynecological Pathology, vol. 33, No. 5, Sep. 2014, pp. 517-523.
King, F. D. et al., "Bioisosteres, Conformational Restriction and Pro-drugs—Case History: An Example of a Conformational Restriction Approach," Medicinal Chemistry: Principles and Practice, vol. 1994, Chapter 14, pp. 206-209.
Kirsch, D. G. et al., Tumor-suppressor p53: implications for tumor development and prognosis. J Clin Oncol 16:3158-3168 (1998).
Kitamura, K. et al. (Mar. 2000), "Histone deacetylase inhibitor but not arsenic trioxide differentiates acute promyelocytic leukemia cells with t(11;17) in combination with all-trans retinoic acid," British Journal of Haematology, vol. 108, No. 4, pp. 696-702.

(56) References Cited

OTHER PUBLICATIONS

Kok, S-H et al., "Norcantharidin-induced apoptosis in oral cancer cells is associated with an increase of proapoptotic to antiapoptotic protein ratio," Cancer Letters, vol. 217, No. 1, Jan. 2005, pp. 43-52.
Komrokji, R. S. et al., "Role of Lenalidomide in the Treatment of Myelodysplastic Syndromes," Seminars in Oncology, Oct. 2011, vol. 38, No. 5, pp. 648-657.
Kong, A. et al., "WEE1 Inhibitor: Clinical Development," Curr Oncol Rep., 23(9):107, Jul. 2021, 8 pages. doi: 10.1007/s11912-021-01098-8.
Kopetz, S.et al. (2019). Encorafenib, Binimetinib, and Cetuximab in BRAF V600E-Mutated Colorectal Cancer . New England Journal of Medicine, 381(17):1632-1643. https://doi.org/10.1056/nejmoa1908075.
Korotkevich, G. et al. (Jun. 2016), "Fast gene set enrichment analysis," Version 3, doi: https://doi.org/10.1101/060012, 40 pages.
Korzus et al., "CBP histone acetyltransferase activity is a critical component of memory consolidation," Neruon, vol. 42, No. 6, Jun. 2004 (pp. 961-972).
Kotsantis, P. et al. (May 2018), "Mechanisms of oncogene-induced replication stress: Jigsaw falling into place," Cancer Discov., vol. 8, No. 5, pp. 537-555. doi: 10.1158/2159-8290.CD-17-1461.
Koukourakis, M. I. et al.,"Concurrent twice-a-week docetaxel and radiotherapy a dose escalation trial with immunological toxicity evaluation," International Journal of Radiation Oncology, Biology, Physics, vol. 43, No. 1, Jan. 1999, pp. 107-114.
Kouno, T. et al., "Standardization of the body surface area (BSA) formula to calculate the dose of anticancer agents in Japan," Jpn J. Clin. Oncol., Jun. 2003, vol. 33, No. 6, pp. 309-313.
Kovach et al., "Enhancement of the antiproliferative activity of human interferon by polyamine depletion," Cancer Treatment Reports, vol. 69, No. 1, Jan. 1985 (pp. 97-103).
Kovalchuk, O. et al., Involvement of microRNA-451 in resistance of the MCF-7 breast cancer cells to chemotherapeutic drug doxorubicin. Mol. Cancer Ther., 7:2152-2159 (2008).
Kozikowski et al., "Functional differences in epigenetic modulators—superiority of mercaptoacetamide-based histone deacetylase inhibitors relative to hydroxamates in cortical neuron neuroprotection studies," Journal of Medicinal Chemistry, vol. 50, No. 13, Jun. 2007 (pp. 3054-3061).
Krasinska, L. et al. (2011). Protein phosphatase 2A controls the order and dynamics of cell-cycle transitions. Molecular Cell, 44(3):437-450. https://doi.org/10.1016/j.molcel.2011.10.007.
Kreickmann, T. et al., "Metallosupramolecular Chemistry with Bis (benzene-o-dithiolato) Ligands," J. Am. Chem. Soc., vol. 128, No. 36, 2006, pp. 11808-11819.
Kulasekararaj, A. G. et al., "TP53 mutations in myelodysplastic syndrome are strongly correlated with aberrations of chromosome 5, and correlate with adverse prognosis," Br J Haematol, vol. 160, No. 5, pp. 660-672 (Jan. 2013).
Kumar, M. S. et al., "Coordinate loss of a microRNA and protein-coding gene cooperate in the pathogenesis of 5q-syndrome," Blood, vol. 118, No. 17, pp. 4666-4673 (Oct. 2011).
Kuo, J-H et al., "Cantharidin induces apoptosis in human bladder cancer TSGH 8301 cells through mitochondria-dependent signal pathways," Int. J. Oncol., (2010) vol. 37, pp. 1243-1250.
Kurebayashi et al., "Expression levels of estrogen receptor-alpha, estrogen receptor-beta, coactivators, and corepressors in breast cancer," Clinical Cancer Research, vol. 6, No. 2, Feb. 2000 (pp. 512-518).
Kwon, H.J., et al., "Depudecin induces morphological reversion of transformed fibroblasts via the inhibition of histone deacetylase," Proceedings of the National Academy of Sciences U.S.A., vol. 95, No. 7, Mar. 1998 (pp. 3356-3361).
Langley et al., "Pulse inhibition of histone deacetylases induces complete resistance to oxidative death in cortical neurons without toxicity and reveals a role for cytoplasmic p21(wafl/cipl) in cell cycle-independent neuroprotection," Journal of Neuroscience, vol. 28, No. 1, Jan. 2008 (pp. 163-176).
Larive, S. et al., "Carboplatin-etoposide combination in small cell lung cancer patients older than 70 years: a phase II trial," Lung Cancer, 2002;35(1):1-7.
Latchman, Y., et al., "PD-L2 is a second ligand for PD-1 and inhibits T cell activation", Nature Immunology (2001); 2(3): 261-268.
Lavinsky et al., "Diverse signaling pathways modulate nuclear receptor recruitment of N-CoR and SMRT complexes," Proceedings of the National Academy of Sciences U.S.A., vol. 95, No. 6, Mar. 1998 (pp. 2920-2925).
Lecarpentier, Y. et al. (Nov. 2019), "Multiple Targets of the Canonical WNT/β-Catenin Signaling in Cancers," Frontiers in Oncology, vol. 9, Article 1248, 7 pages. https://doi.org/10.3389/fonc.2019.01248.
Lee, M-O et al., Role of Coactivators and Corepressors in the Induction of the RARbeta gene in human colon cancer cells Biological and Pharmaceutical Bulletin, vol. 25, No. 10, (2002), pp. 1298-1302.
Lee, Y. S. et al., MicroRNAs in cancer. Annu. Rev. Pathol. Mech. Dis., 4:199-227 (2009).
Lei et al., "Plk1 depletion in nontransformed diploid cells activates the DNA-damage checkpoint," Oncogene, vol. 27, No. 28, Jun. 2008 (pp. 3935-3943).
Lerga, A. et al., Apoptosis and mitotic arrest are two independent effects of the protein phosphatases inhibitor okadaic acid in K562 leukemia cells. Biochem Biophys Res Commun 260:256-264 (1999).
Levenson et al., "Regulation of histone acetylation during memory formation in the hippocampus," Journal of Biological Chemistry, vol. 279, No. 39, Sep. 2004 (pp. 40545-40559).
Levesque, D., "Reduction of L-DOPA-induced dyskinesias by retinoid agonists: a new way to improve Parkinson's disease treatment," The Parkinson Alliance, 2004 Pilot Study Grants (abstract), 6 pages.
Li et al., "Valproic acid induces growth arrest, apoptosis, and senescence in medulloblastomas by increasing histone hyperacetylation and regulating expression of p21Cip1, CDK4, and CMYC," Molecular Cancer Therapeutics, vol. 4, No. 12, Dec. 2005 (pp. 1912-1922).
Li, F. et al., "CHK1 Inhibitor Blocks Phosphorylation of FAM122A and Promotes Replication Stress," Molecular Cell, vol. 80, Nov. 2020, with Supplemental Information, 35 pages.
Li, L. et al., "Combination analysis of Bub1 and Mad2 expression in endometrial cancer: act as a prognostic factor in endometrial cancer," Archives of Gynecology and Obstetrics, vol. 288, No. 1, Jul. 2013 pp. 155-165.
Li, W. et al., Cantharidin, a potent and selective PP2A inhibitor, induces an oxidative stress-independent growth inhibition of pancreatic cancer cells through G2/M cell-cycle arrest and apoptosis. Cancer Sci. 101:1226-1233 (2010).
Li, Y-M et al., "Cantharidin-binding protein: identification as protein phosphatase 2A," Proc Natl Acad Sci USA, vol. 89, No. 24, pp. 11867-11870 (Dec. 1992).
Li Y-M., et al., "Protein Phosphatase 2A and its [3H]Cantharidin/ [3H]Endothall Thioanhydride Binding Site, Inhibitor Specificity of Cantharidin and ATP Analogues," Biochemical Pharmacology, Oct. 1993, vol. 46 (8), pp. 1435-1443.
Li, Z. et al., Up-regulation of a HOXA-PBX3 homeobox-gene signature following down-regulation of miR-181 is associated with adverse prognosis in patients with cytogenetically abnormal AML. Blood, 119(10):2314-2324 (Mar. 2012).
Lim, K-H. et al., "Tumour maintenance is mediated by eNOS," Nature, vol. 452, Apr. 2008, pp. 646-649.
Lim, Z. et al., "Allogeneic Hematopoietic Stem-Cell Transplantation for Patients 50 Years or Older with Myelodysplastic Syndromes or Secondary Acute Myeloid Leukemia," Journal of Clinical Oncology, vol. 28, No. 3, pp. 405-411 (Jan. 2010).
Lin et al., "Role of the histone deacetylase complex in acute promyelocytic leukaemia," Nature, vol. 391, No. 6669, Feb. 1998 (pp. 811-814).
Lindqvist, A. et al. (2009). The decision to enter mitosis: feedback and redundancy in the mitotic entry network. Journal of Cell Biology, vol. 185, Issue 2, pp. 193-202. https://doi.org/10.1083/jcb.200812045.
List, A. et al., "Efficacy of lenalidomide in myelodysplastic syndromes," N Engl J Med, vol. 352, No. 6, pp. 549-557 (Feb. 2005).

(56) References Cited

OTHER PUBLICATIONS

List, A. et al., "Lenalidomide in The Myelodysplastic Syndrome with Chromosome 5q Deletion," The New England Journal of Medicine, Oct. 2006, vol. 355, No. 14, pp. 1456-1465.

List, A. F. et al., "Extended survival and reduced risk of AML progression in erythroid-responsive lenalidomide-treated patients with lower-risk del(5q) MDS," Leukemia, vol. 28, No. 5, pp. 1033-1040 (May 2014).

List, A. F. et al., "Lenalidomide (CC-5013; Revlimid(R)) Promotes Erythropoiesis in Myelodysplastic Syndromes (MDS) by CD45 Protein Tyrosine Phosphatase (PTP) Inhibition," ASH Annual Meeting Abstracts, Blood, 108:1360 (2006) (Abstract), 2 pages.

List, A. F. et al., "Lenalidomide: targeted anemia therapy for myelodysplastic syndromes," Cancer Control, vol. 13, Supplement, pp. 4-11 (Dec. 2006).

Littler, S. et al. (Jul. 2019), "Oncogenic MYC amplifies mitotic perturbations," Open Biol. vol. 9:190136, 20 pages. http://dx.doi.org/10.1098/rsob.190136.

Liu, C-Y et al., Tamoxifen induces apoptosis through cancerous inhibitor of protein phosphatase 2A-dependent phospho-Akt inactivation in estrogen receptor-negative human breast cancer cells. Breast Cancer Research 16:431 (2014), 15 pages.

Liu, D. et al., "The effects of cantharidin and cantharidin derivates on tumour cells," Anti-Cancer Agents in Medicinal Chemistry, vol. 9, No. May 2009, pp. 392-396.

Liu et al., "Normal cells, but not cancer cells, survive severe Plk1 depletion," Molecular and Cellular Biology, vol. 26, No. 6, Mar. 2006 (pp. 2093-2108).

Liu et al., "Stabilization and enhancement of the antiapoptic activity of Mcl-1 by TCTP," Molecular and Cellular Biology, vol. 25, No. 8, Apr. 2005 (pp. 3117-3126).

Liu, F. et al., "The inhibition of glycogen synthase kinase 3β by a metabotropic glutamate receptor 5 mediated pathway confers neuroprotection to Aβ peptides," Journal of Neurochemistry, vol. 95, No. 5, (2005) pp. 1363-1372.

Liu, G. P. et al., Silencing PP2A inhibitor by lenti-shRNA interference ameliorates neuropathologies and memory deficits in tg2576 mice. Mol Ther. 2013;21(12):2247-2257.

Liu, L. et al., Inhibition of Protein Phosphatase 2A Sensitizes Mucoepidermoid Carcinoma to Chemotherapy via the PI3K-AKT Pathway in Response to Insulin Stimulus. Cell Physiol Biochem 50, 317-331 (2018).

Llovet et al. "Sorafenib in advanced hepatocellular carcinoma", N Engl J Med 2008; 359:378-90.

Longacre, L. S. et al., "New Horizons in Cardioprotection. Recommendations From the 2010 National Heart, Lung, and Blood Institute Workshop," Circulation, vol. 124, No. 10, Sep. 2011, pp. 1172-1179.

Lopez-Pajares et al., "Phosphorylation of MDMX mediated by Akt leads to stabilization and induces 14-3-3 binding," Journal of Biological Chemistry, vol. 283, No. 20, May 2008 (pp. 13707-13713).

Love, M. I. et al. (2014), "Moderated estimation of fold change and dispersion for RNA-seq data with DESeq2," Genome Biology, vol. 15:550, 21 pages. DOI 10.1186/s13059-014-0550-8.

Lu, F. et al., "miR-181b increases drug sensitivity in acute myeloid leukemia via targeting HMGB1 and Mcl-1," Int J Oncol. 2014; 45(1):383-392.

Lu, J. et al. (May 2008), "LB-1, an inhibitor of serine-threonine protein phosphatase PP2A, suppresses the growth of glioblastoma cells in vitro and in vivo," Cancer Research, vol. 68, Issue 9 Supplement, Abstract 5693, 99th AACR Annual Meeting, Apr. 12-16, 2008; San Diego, CA, 4 pages.

Lu, S., et al., "Aqueous ring-opening metathesis polymerization and copolymerization of 2,3-dicarboxylic acid anhydride, 2,3-bis(methoxymethyl) and 2,3-dicarboxylic acid monomethyl ester derivatives of 7-oxanorbornene," European Polymer Journal, vol. 29, No. 2-3, Feb.-Mar. 1993 (pp. 269-279).

Lu, S., et al., "Aqueous ring-opening metathesis polymerization of 7-oxanorbornene derivatives with oxygen-containing functionalities," Macromolecular Chemistry and Physics, vol. 195, No. 4, Apr. 1994 (pp. 1273-1288).

Luchenko, V. L. et al., "Schedule-dependent synergy of histone deacetylase inhibitors with DNA damaging agents in small cell lung cancer," Cell Cycle, vol. 10, No. 18, (2011) pp. 3119-3128.

Luo, J. et al. (2009). Principles of Cancer Therapy: Oncogene and Non-oncogene Addiction The Current State of Cancer Research. Cell, 136(5):823-837. https://doi.org/10.1016/j.cell.2009.02.024.

Luserna di Rorà, A. G. et al. (2020). A WEE1 family business: Regulation of mitosis, cancer progression, and therapeutic target. Journal of Hematology and Oncology, vol. 13, Issue 1, 17 pages. https://doi.org/10.1186/s13045-020-00959-2.

Ma, L. et al., "Metabolic Symbiosis in Chemoresistance: Refocusing the Role of Aerobic Glycolysis," Front Oncol., vol. 10, Article 5 (Jan. 2020), 8 pages.

Ma, P. C. et al., Expression and mutational analysis of MET in human solid cancers. Genes Chromosomes Cancer 47, 1025-1037 (2008).

Maghfoor, I. et al., "Lung cancer," Ann Saudi Med. 2005;25(1):1-12.

Maillet, M. et al. (2008). DUSP6 (MKP3) null mice show enhanced ERK1/2 Phosphorylation at baseline and increased myocyte proliferation in the heart affecting disease susceptibility. Journal of Biological Chemistry, 283(45):31246-31255. https://doi.org/10.1074/jbc.M806085200.

Mallo, M. et al., "Impact of adjunct cytogenetic abnormalities for prognostic stratification in patients with myelodysplastic syndrome and deletion 5q," Leukemia, vol. 25, No. 1, pp. 110-120 (Jan. 2011).

Mangan et al, "Turning Back the Clock on Neurodegeneration," Cell, vol. 129, No. 5, Jun. 2007 (pp. 851-853).

Manka, J.T., et al., "Retro Diels-Alder Reactions of 5,6-Disbustituted-7-oxabicyclo[2.2.1]hept-2-enes: Experimental and Density Functional Theory Studies," Journal of Organic Chemistry, vol. 65, No. 17, Aug. 2000 (pp. 5202-5206).

Marcucci, G. et al., MicroRNA expression in cytogenetically normal acute myeloid leukemia. N Engl J Med 358:1919-1928 (2008).

Marcucci, G. et al., Phase 1 and pharmacodynamic studies of G3139, a Bcl-2 antisense oligonucleotide, in combination with chemotherapy in refractory or relapsed acute leukemia. Blood, 101:425-432 (2003).

Marcucci, G. et al., Prognostic significance of, and gene and microRNA expression signatures associated with, CEBPA mutations in cytogenetically normal acute myeloid leukemia with high-risk molecular features: a Cancer and Leukemia Group B Study. J. Clin. Oncol. 26(31):5078-5087 (Nov. 2008).

Mardor et al., "Monitoring response to convection-enhances taxol delivery in brain tumor patients using diffusion-weighted magnetic resonance imaging," Cancer Research, vol. 61, No. 13, Jul. 2001 (pp. 4971-4973).

Marks et al., "Histone deacetylases," Current Opinion in Pharmacology, vol. 3, No. 4, Aug. 2003 (pp. 344-351).

Martinou, J-C et al., Breaking the mitochondrial barrier. Nat Rev Mol Cell Biol 2:63-67 (Jan. 2001).

Matsuzawa et al., "Endothal and cantharidin analogs: relation of structure to herbicidal activity and mammalian toxicity," Journal of Agricultural and Food Chemistry, vol. 35, No. 5, Sep. 1987 (pp. 823-829).

Matthay et al., "Treatment of High-Risk Neuroblastoma and Intensive Chemotherapy, Radiotherapy, Autologous Bone Marrow Transplantation, and 13-cis-Retinoic Acid," New England Journal of Medicine, vol. 341, Oct. 1999 (pp. 1165-1173).

Mazhar, S. et al., "Targeting PP2A in cancer: Combination therapies," Biochim. Biophys Acta Mol Cell Res. Jan. 2019;1866(1):51-63.

McCluskey, A. et al., "Anhydride modified cantharidin analogues. Is ring opening important in the inhibition of protein phosphatase 2A?," European Journal of Medicinal Chemistry, vol. 35, No. 10, Oct. 2000, pp. 957-964.

McCluskey, A. et al., "Anhydride modified cantharidin analogues: synthesis, inhibition of protein phosphatases 1 and 2A and antican-

(56) References Cited

OTHER PUBLICATIONS cer activity," Bioorganic & Medicinal Chemistry Letters, vol. 10, No. 15, Aug. 2000, pp. 1687-1690.
McCluskey, A. et al., "Inhibition of Protein Phosphatase 2A by Cantharidin Analogues," Bioorganic and Medicinal Chemistry Letters, vol. 6, No. 9, May 1996, pp. 1025-1028.
McDaniel, J. M. et al., "Reversal of T-cell Tolerance in Myelodysplastic Syndrome through Lenalidomide Immune Modulation," Leukemia, Jun. 2012, vol. 26, No. 6, pp. 1425-1429.
McDaniel, J. M., "Lenalidomide Targets the T-Cell Co-Stimulatory Pathway to Mediate Immune Modulation," Graduate Thesis and Dissertations, University of South Florida, Scholar Commons, Jan. 2012, 191 pages.
McGraw, K. L. et al., "Lenalidomide induces lipid raft assembly to enhance erythropoietin receptor signaling in myelodysplastic syndrome progenitors," PloS One, 9(12):e114249 (Dec. 2014), 18 pages.
Mehta, R. S., "Dose-Dense and/or Metronomic Schedules of Specific Chemotherapies Consolidate the Chemosensitivity of Triple-Negative Breast Cancer: A Step Toward Reversing Triple-Negative Paradox," Journal of Clinical Oncology, vol. 26, No. 19, Jul. 2008, pp. 3286-3288.
Meng, F. et al., "EGFL9 promotes breast cancer metastasis by inducing cMET activation and metabolic reprogramming," Nature Communications, 10:5033 (2019), 17 pages.
Meske, V. et al., "Coupling of Mammalian Target of Rapamycin with Phosphoinositide 3-Kinase Signaling Pathway Regulates Protein Phosphatase 2A- and Glycogen Synthase Kinase-3beta-dependent Phosphorylation of Tau," vol. 283, No. 1, Jan. 2008, pp. 100-109.
Mi, S. et al., MicroRNA expression signatures accurately discriminate acute lymphoblastic leukemia from acute myeloid leukemia. Proc Natl Acad Sci USA, 104(50):19971-19976 (Dec. 2007).
Mielnicki et al., "Epigenetic regulation of gelsolin expression in human breast cancer cells," Experimental Cell Research, vol. 249, No. 1, May 1999 (pp. 161-176).
Millar, J. et al., cdc25 M-phase inducer. Cold Spring Harbor Symposia on Quantitative Biology, 56:577-584 (1991).
Millward, T. A. et al., Regulation of protein kinase cascades by protein phosphatase 2A. Trends Biochem Sci. 24:186-191 (May 1999).
Mirzaei, H. R. et al., "Chimeric Antigen Receptors T Cell Therapy in Solid Tumor: Challenges and Clinical Applications," Front Immunol, Dec. 2017, vol. 8 Article 1850, 13 pages.
Mirzapoiazova, T. et al., HABP2 is a Novel Regulator of Hyaluronan-Mediated Human Lung Cancer Progression. Front Oncol., vol. 5, Article 164 (Jul. 2015), 12 pages.
Momparler, R. L. (1980), "In vitro systems for evaluation of combination chemotherapy," Pharmacol. Ther., vol. 8, No. 1, pp. 21-35.
Moore, C. D. et al., "Immunotherapy in Cancer Treatment: A Review of Checkpoint Inhibitors," U.S. Pharmacist, 2018, vol. 43, No. 2, pp. 27-31.
Morse et al., "Docetaxel induces cell death through mitotic catastrophe in human breast cancer cells," Molecular Cancer Therapeutics, vol. 4, No. 10, Oct. 2005 (pp. 1495-1504).
Munster, P. N. et al., "Phase I trial of vorinostat and doxorubicin in solid tumors: histone deacetylase 2 expression as a predictive marker," British Journal of Cancer, vol. 101, (2009) pp. 1044-1050.
Musacchio, A. et al., "The spindle-assembly checkpoint in space and time," Nature Reviews, Molecular Cell Biology, vol. 8, No. 5, May 2007, pp. 379-393.
Muzny, D. M. et al. (2012). Comprehensive molecular characterization of human colon and rectal cancer. Nature, 487(7407):330-337. https://doi.org/10.1038/nature11252.
Myers, E. et al., "Associations and Interactions between Ets-1 and Ets-2 and Coregulatory Proteins, SRC-1, AIB1, and NCoR in Breast Cancer," Clinical Cancer Research, vol. 11, Mar. 2005, pp. 2111-2122.

Nair and Jacob, "A Simple Practice Guide for Dose Conversion Between Animals and Human," Journal of Basic and Clinical Pharmacy, vol. 7, Issue 2, Mar.-May 2016, pp. 27-31.
Nakano, Y. et al., "Mitotic arrest deficiency 2 induces carcinogenesis in mucinous ovarian tumors," Oncology Letters, vol. 3, No. 2, Feb. 2012, pp. 281-286.
National Library of Medicine—Medical Subject Headings, 2009 MeSH, MeSH Descriptor Data, Phosphoric Monoester Hydrolases, Phosphatases (2009), 2 pages.
Neviani et al., "FTY720, a new alternative for treating blast crisis chronic myelogenous leukemia and Philadelphia chromosome-positive acute lymphocytic leukemia," Journal of Clinical Investigation, vol. 117, No. 9, Sep. 2007 (pp. 2408-2421).
Ngan et al., "Oxaliplatin induces mitotic catastrophe and apoptosis in esophageal cancer cells," Cancer Science, vol. 99, No. 1, Jan. 2008 (pp. 129-139).
Niell, H. B. et al., Carboplatin/etoposide/paclitaxel in the treatment of patients with extensive small-cell lung cancer. Clin Lung Cancer. 2001;2(3):204-209.
Niell, H. B. et al., Randomized phase III intergroup trial of etoposide and cisplatin with or without paclitaxel and granulocyte colony-stimulating factor in patients with extensive-stage small-cell lung cancer: Cancer and Leukemia Group B Trial 9732. J Clin Oncol. 2005;23(16):3752-3759.
Nieto, P. et al., A Braf kinase-inactive mutant induces lung adenocarcinoma. Nature. Aug. 2017, 548(7666):239-243.
Nifoussi, S. K. et al., "Inhibition of Protein Phosphatase 2A (PP2A) Prevents Mc1-1 Protein Dephosphorylation and the Thr-163/Ser-159 Phosphodegron, Dramatically Reducing Expression in Mc1-1-amplified Lymphoma Cells," The Journal of Biological Chemistry, Aug. 2014, vol. 289, No. 32, pp. 21950-21959.
Nikaki, A. et al., "Role of microRNAs in gliomagenesis: targeting miRNAs in glioblastoma multiforme therapy," Expert Opin Investig Drugs, 21(10):1475-1488 (Oct. 2012).
Nimer, S. D., "Myelodysplastic Syndromes," Blood, May 2008, vol. 111, No. 10, pp. 4841-4851.
Nobumori, Y. et al., B56gamma tumor-associated mutations provide new mechanisms for B56gamma-PP2A tumor suppressor activity. Mol. Cancer Res. 11(9):995-1003 (2013).
Nogami, K. et al., "Mechanisms of Plasmin-catalyzed Inactivation of Factor VIII A crucial role for proteolytic cleavage at arg336 responsible for plasmin-catalyzed factor VIII inactivation," The Journal of Biological Chemistry, vol. 282, (Feb. 2007), pp. 5287-5295.
Olivier, M. et al. (Sep. 2008), "Recent advances in p53 research: an interdisciplinary perspective," Cancer Gene Therapy, vol. 16, pp. 1-12.
Olmos et al., "Targeting polo-like kinase: learning too little too late?," Journal of Clinical Oncology, vol. 26, No. 34, Dec. 2008 (pp. 5497-5499).
Ory, S. et al., Protein phosphatase 2A positively regulates Ras signaling by dephosphorylating KSR1 and Raf-1 on critical 14-3-3 binding sites. Curr Biol 13:1356-1364 (Aug. 2003).
Owonikoko, T. K. et al., "Vorinostat increases carboplatin and paclitaxel activity in non-small cell lung cancer cells," Int. J. Cancer, vol. 126, (2010), pp. 743-755.
Padron, E. et al., "The 5q-Syndrome: Biology and Treatment," Current Treatment Options in Oncology, Dec. 2011, vol. 12, No. 4, pp. 354-368.
Paez, J. G. et al., "PI3K/PTEN/Akt Pathway," Signal Transduction in Cancer, vol. 115, 2006, pp. 145-167.
Pagliarini, R. et al. (2015). Oncogene addiction: pathways of therapeutic response, resistance, and road maps toward a cure. EMBO Reports, 16(3):280-296. https://doi.org/10.15252/embr.201439949.
Park D.M., et al., "N-CoR Pathway Targeting Induces Glioblastoma Derived Cancer Stem Cell Differentiation," Cell Cycle, Feb. 15, 2007, vol. 6 (4), pp. 467-470.
Parsons, R., "Phosphatases and tumorigenesis," Curr. Opin. Oncol. 10:88-91(1998).
Peng, F. et al., Induction of apoptosis by norcantharidin in human colorectal carcinoma cell lines: involvement of the CD95 receptor/ligand. J Cancer Res Clin Oncol 128:223-230 (2002).

(56) References Cited

OTHER PUBLICATIONS

Pepper, C. et al., Bcl-2 antisense oligonucleotides enhance the cytotoxicity of chlorambucil in B-cell chronic lymphocytic leukemia cells. Leukemia & Lymphoma 42(3):491-498 (2001).
Perera, D. et al. (Jul. 2016), "Oncogenic KRAS triggers MAPK-dependent errors in mitosis and MYC-dependent sensitivity to anti-mitotic agents," Scientific Reports, vol. 6:29741, 15 pages. DOI: 10.1038/srep29741.
Perrotti et al., "Protein phosphatases 2A (PP2A), a drugable tumor suppressor in Ph1(+) leukemias," Cancer and Metastasis Reviews, vol. 27, No. 2, Jun. 2008 (pp. 159-168).
Peruzzi, P. et al., MicroRNA-128 coordinately targets Polycomb Repressor Complexes in glioma stem cells. Neuro-Oncology, 15(9):1212-1224 (2013).
Prados et al., "Phase II Study of Erlotinib Plus Temozolomide During and After Radiation Therapy in Patients with Newly Diagnosed Glioblastoma Multiforme or Gliosarcoma," Journal of Clinical Oncology, vol. 27, No. 4, Feb. 2009 (pp. 579-584).
Prendiville, J. et al., "Therapy for small cell lung cancer using carboplatin, ifosfamide, etoposide (without dose reduction), midcycle vincristine with thoracic and cranial irradiation," Eur J Cancer. 1994;30A(14):2085-2090.
Price et al., "Histone deacetylase inhibitors: an analysis of recent patenting activity," Expert Opinion on Therapeutic Patents, vol. 17, No. 7, Aug. 2007 (pp. 745-765).
Quesnel, B. et al., Methylation of the p15INK4b gene in myelodysplastic syndromes is frequent and acquired during disease progression. Blood 91(8):2985-2990 (Apr. 1998).
Quoix, E. et al., Etoposide phosphate with carboplatin in the treatment of elderly patients with small-cell lung cancer: a phase II study. Ann Oncol. 2001;12(7):957-962.
Rabik, C. A. et al., Molecular mechanisms of resistance and toxicity associated with platinating agents. Cancer Treat Rev 33, 9-23 (2007).
Rajapaksa, R. et al., Altered oncoprotein expression and apoptosis in myelodysplastic syndrome marrow cells. Blood 88(11):4275-4287 (Dec. 1996).
Ramanarayanan, J. et al., Pro-apoptotic therapy with the oligonucleotide Genasense (oblimersen sodium) targeting Bcl-2 protein expression enhances the biological anti-tumour activity of rituximab. Br J Haematol 127:519-530 (2004).
Ramezanian et al., "A new super-electrophile: alpha(phenylsulfonyl)maleic anhydride," Journal of Organic Chemistry, vol. 54, No. 12, Jun. 1989 (pp. 2852-2854).
Rautio, J., et al., "Prodrugs: design and clinical applications", Nature Reviews Drug Discovery (Mar. 2008); 7: 255-270.
Reed, J. C., Dysregulation of apoptosis in cancer. J Clin Oncol 17:2941-2953 (1999).
Registry (STN) Online, Nov. 16, 1984, CAS registered No. 57958-23-3, Search Date Jan. 16, 2013, 2 pages.
Reid, M. A. et al., "The B55α subunit of PP2A drives a p53-dependent metabolic adaptation to glutamine deprivation," Molecular Cell, vol. 50, No. 2, Apr. 2013, pp. 200-211.
Reynhout, S. et al. (2019). Physiologic functions of PP2A: Lessons from genetically modified mice. Biochimica et Biophysica Acta—Molecular Cell Research, vol. 1866, Issue 1, pp. 31-50. https://doi.org/10.1016/j.bbamcr.2018.07.010.
Richon, V.M., et al., "A class of hybrid polar inducers of transformed cell differentiation inhibits histone deacetylases," Proceedings of the National Academy of Sciences U.S.A., vol. 95, No. 6, Mar. 1998 (pp. 3003-3007).
Ries, V. et al., "Oncoprotein Akt/PKB induces trophic effects in murine models of Parkinson's disease," PNAS, vol. 103, No. 49, Dec. 2006, pp. 18757-18762.
Riester et al., "Histone deacetylase inhibitors—turning epigenic mechanisms of gene regulation into tools of therapeutic intervention in malignant and other diseases," Applied Microbiology and Biotechnology, vol. 75, Jun. 2007 (pp. 499-514).
Rinkenberger et al., "Mcl-1 deficiency results in peri-implantation embryonic lethality," Genes and Development, vol. 14, No. 1, Jan. 2000 (pp. 23-27).
Riordan, F. A. et al., Okadaic acid-induced apoptosis of HL60 leukemia cells is preceded by destabilization of bd-2 mRNA and downregulation of bd-2 protein. FEBS Lett 435:195-198 (1998).
Roberts, K. G. et al., Essential requirement for PP2A inhibition by the oncogenic receptor c-KIT suggests PP2A reactivation as a strategy to treat c-KIT+ cancers. Cancer Res., 70(13):5438-5447 (2010).
Robertson, M. J. et al., "Norcantharimide analogues possessing terminal phosphate esters and their anti-cancer activity," Bioorg. Med. Chem., vol. 19, Issue 18, Sep. 2011, pp. 5734-5741.
Rodriguez-Acebes, S. et al. (2018). Uncoupling fork speed and origin activity to identify the primary cause of replicative stress phenotypes. Journal of Biological Chemistry, 293(33):12855-12861. https://doi.org/10.1074/jbc.RA118.003740.
Rosenberg, J. E. et al., Atezolizumab in patients with locally advanced and metastatic urothelial carcinoma who have progressed following treatment with platinum-based chemotherapy: a single-arm, multicentre, phase 2 trial. Lancet. 2016;387(10031):1909-1920.
Rubbia-Brandt, L. et al. (2007), "Importance of histological tumor response assessment in predicting the outcome in patients with colorectal liver metastases treated with neo-adjuvant chemotherapy followed by liver surgery," Annals of Oncology, vol. 18, pp. 299-304. 10.1093/annonc/mdl386.
Rubie et al., "Phase II Study of Temozolomide in Relapsed or Refractory high-Risk Neuroblastoma: A Jount Societe Francaise des Cancers del'Enfant and United Kingdom Children Cancer Study Group—New Agents Group Study," Journal of Clinical Oncology, vol. 24, No. 33, Nov. 2006 (pp. 5259-5264).
Rutka et al., "Effect of retinoids on the proliferation, morphology and expression of glial fibrillary acidic protein of an anaplastic astrocytoma cell line," International Journal of Cancer, vol. 42, No. 3, Sep. 1988 (pp. 419-427).
Ruvolo, P. P. et al., A functional role for the B56 alpha-subunit of protein phosphatase 2A in ceramide-mediated regulation of Bcl2 phosphorylation status and function. J. Biol. Chem. 277(25):22847-22852 (Jun. 2002).
Ruvolo, P. P. et al., Phosphorylation of Bcl2 and regulation of apoptosis. Leukemia 15:515-522 (2001).
Sahin, M. et al. (2005), "Retinoic acid isomers protect hippocampal neurons from amyloid-β induced neurodegeneration," Neurotoxicity Research, vol. 7, No. 3, pp. 243-250.
Saito et al., "A synthetic inhibitor of deacetylase, MS-27-275, with marked in vivo antitumor activity against human tumors," Proceedings of the National Academy of Sciences U.S.A., vol. 96, No. 8, Apr. 1999 (pp. 4592-4597).
Sakoff et al., "Anticancer Activity and Protein Phosphatase 1 and 2A Inhibition of a New Generation of Cantharidin Analogues," Investigational New Drugs, vol. 20, No. 1, Feb. 2002 (pp. 1-11).
Sakoff, J. A. et al. (2004), "Protein Phosphatase Inhibition: Structure Based Design. Towards New Therapeutic Agents," Current Pharmaceutical Design, vol. 10, No. 10, pp. 1139-1159.
Salgia, R., "Role of c-Met in cancer: emphasis on lung cancer," Semin Oncol., vol. 36, No. 2, Suppl. 1, pp. S52-S58 (Apr. 2009).
Sanderson et al., "Plasma pharmacokinetics and metabolism of the histone deacetylase inhibitor trichostatin a after intraperitoneal administration to mice," Drug Metabolism and Disposition, vol. 32, No. 10, Jul. 2004, (pp. 1132-1138).
Sandroni, P., Aphrodisiacs past and present: a historical review. Clin Auton Res 11:303-307 (2001).
Schapira, A. H. et al., "Neuroprotection in Parkinson disease: mysteries, myths, and misconceptions," JAMA, vol. 291, No. 3, Feb. 2004, pp. 358-364.
Schmid, P. et al., Atezolizumab and Nab-Paclitaxel in Advanced Triple-Negative Breast Cancer. N Engl J Med. 2018;379(22):2108-2121.
Schmitt, C. A. et al., Genetic analysis of chemoresistance in primary murine lymphomas. Nature Medicine, vol. 6, No. 8, pp. 1029-1035(Sep. 2000).

(56) References Cited

OTHER PUBLICATIONS

Schonthal, A. H., Role of serine/threonine protein phosphatase 2A in cancer. Cancer Letters, 170:1-13 (2001).
Schvartzman, J-M et al., "Mitotic chromosomal instability and cancer: mouse modelling of the human disease," Nature Reviews, Cancer, vol. 10, No. 2, Feb. 2010, pp. 102-115.
Schwind, S. et al., Prognostic significance of expression of a single microRNA, miR-181a, in cytogenetically normal acute myeloid leukemia: a Cancer and Leukemia Group B study. J. Clin. Oncol. 28(36):5257-5264 (Dec. 2010).
Science IP, The CAS Search Service, Structure Search of Thiophenols, Sep. 2007, 375 pages.
Shain, A.H. et al. (Jan. 2013) "The spectrum of SWI/SNF mutations, ubiquitous in human cancers" PLOS One, 8(1): e55119, 11 pages.
Shen, D-W et al., "Cisplatin Resistance: A Cellular Self-Defense Mechanism Resulting from Multiple Epigenetic and Genetic Changes," Pharmacological Reviews, vol. 64, No. 3, pp. 706-721 (2012).
Shen, J. et al., "Skeletal and CNS defects in presenilin-1-deficient mice," Cell, vol. 89, Issue 4, May 1997, pp. 629-639.
Sherrington, R. et al., "Cloning of a gene bearing missense mutations in early-onset familial Alzheimer's disease," Nature, vol. 375, Jun. 1995, pp. 754-760.
Shimi et al., "A new antitumour substance, 7-oxabicyclo (2.2.1)-5-heptene-2,3-dicarboxylic anhydride," European Journal of Cancer, vol. 18, No. 8, Aug. 1982 (pp. 785-793).
Short et al., "DNA repair after irradiation in glioma cells and normal human astrocytes," Neuro-Oncology, vol. 9, No. 4, Oct. 2007 (pp. 404-411).
Shukron, O. et al., Analyzing transformation of myelodysplastic syndrome to secondary acute myeloid leukemia using a large patient database. Am. J. Hematol. 87:853-860 (2012).
Silver, D. P. et al., "Efficacy of neoadjuvant Cisplatin in triple-negative breast cancer," Journal of Clinical Oncology, vol. 28, No. 7, Mar. 2010, pp. 1145-1153.
Simboeck, E. et al., A phosphorylation switch regulates the transcriptional activation of cell cycle regulator p21 by histone deacetylase inhibitors. J Biol Chem 285(52):41062-41073 (2010).
Simizu, S. et al., Dephosphorylation of Bcl-2 by protein phosphatase 2A results in apoptosis resistance. Cancer Sci 95:266-270 (2004).
Singh, et al., "Identification of a cancer stem cell in human brain tumors." Cancer Res. (2003); 63 (18): 5821-5828.
Singh, et al., "Identification of human brain tumour initiating cells." Nature (2004); 432 (7015): 396-401.
Smith et al., "Histone deacetylase inhibitors enhance Candida albicans sensitivity to azoles and related antifungals: correlation with reduction in CDR and ERG upregulation," Antimicrobial Agents and Chemotherapy, vol. 46, No. 11, Nov. 2002 (pp. 3532-3539).
Smith-Cohn, M. A. et al., "Molecularly Targeted Clinical Trials," Feb. 2021, Neurosurgery Clinics, vol. 32, Issue 2, pp. 191-210.
Song et al., Synthesis and Biological Properties of Amino Acid Amide Ligand-Based Pyridinioalkanoyl Thioesters as Anti-HIV Agents, Bioorganic and Medicinal Chemistry, vol. 10, No. 5, May 2002 (pp. 1263-1273).
Sontag, E. et al., "Regulation of the Phosphorylation State and Microtubule-Binding Activity of Tau by Protein Phosphatase 2A," Neuron, vol. 17, Issue 6, Dec. 1996, pp. 1201-1207.
Sorrentino, A. et al., Role of microRNAs in drug-resistant ovarian cancer cells. Gynecol. Oncol., 111:478-486 (2008).
Sotillo, R. et al., "Mad2 overexpression promotes aneuploidy and tumorigenesis in mice," Cancer Cell, vol. 11, No. 1, Jan. 2007, pp. 9-23.
Sotillo, R. et al., "Mad2-induced chromosome instability leads to lung tumour relapse after oncogene withdrawal," Nature, vol. 464, No. 7287, Mar. 2010, pp. 436-440; doi:10.1038/nature08803.
Sridharan et al., "Illuminating the black box of reprogramming," Cell Stem Cell, vol. 2, No. 4, Apr. 2008 (pp. 295-297).
Srivastava, R. K. et al., MS-275 sensitizes Trail-resistant breast cancer cells, inhibits angiogenesis and metastasis, and reverses epithelial-mesenchymal transition in vivo. Mol. Cancer Ther. 9(12):3254-3266 (2010).
Stewart et al., "Synthesis and biological evaluation of norcantharidin analogues: towards PP1 selectivity," Bioorganic and Medicinal Chemistry, vol. 15, No. 23, Dec. 2007 (pp. 7301-7310).
Stoll, V. S. et al., Chapter 6: "Buffers: Principles and Practice," In Methods in Enzymology, Academic Press, 1990, vol. 463, ISSN 0076-6879, pp. 43-56.
Strebhardt et al., "Targeting polo-like kinase 1 for cancer therapy," Nature Reviews: Cancer, vol. 6, Apr. 2006 (11 pages).
Stuart, T. et al. (Jun. 2019), "Comprehensive Integration of Single-Cell Data," Cell, vol. 177, pp. 1888-1902. https://doi.org/10.1016/j.cell.2019.05.031.
Stupp R., et al., "Effects of Radiotherapy With Concomitant and Adjuvant Temozolomide Versus Radiotherapy Alone on Survival in Glioblastoma in a Randomised Phase III study: 5-year Analysis of The EORTC-NCIC Trial," Lancet, Oncology, May 2009, vol. 10 (5), pp. 459-466.
Stupp, R. et al., "Radiotherapy plus Concomitant and Adjuvant Temozolomide for Glioblastoma," N Engl J Med, 352(10):987-996 (2005).
Subbiah, S., et al., "Small Cell Lung Cancer from Traditional to Innovative Therapeutics: Building a Comprehensive Network to Optimize Clinical and Translational Research," Journal of Clinical Medicine, Jul. 30, 2020, vol. 9(8), 19 pages. [Retrieved on Nov. 9, 2021]. Retrieved from the Internet: URL: https://www.mdpi.com/2077-0383/9/8/2433.
Subramanian, A. et al. (Oct. 2005), "Gene set enrichment analysis: A knowledge-based approach for interpreting genome-wide expression profiles," Proc Natl Acad Sci USA, vol. 102, No. 43, pp. 15545-15550. www.pnas.orgcgidoi10.1073pnas.0506580102.
Suganuma, M. et al., "Okadaic acid: an additional non-phorbol-12-tetradecanoate-13-acetate-type tumor promoter," Proceedings of the National Academy of Sciences, USA, vol. 85, No. 6, Mar. 1988, pp. 1768-1771.
Sundstrom, S. et al., "Cisplatin and etoposide regimen is superior to cyclophosphamide, epirubicin, and vincristine regimen in small-cell lung cancer: results from a randomized phase III trial with 5 years' follow-up," Journal of Clinical Oncology, Dec. 2002, vol. 20, No. 24, pp. 4665-4672.
Sunny-Roberts, E. O. et al., "The protective effect of monosodium glutamate on survival of lactobacillus rhamnosus GG and lactobacillus rhamnosus E-97800 (E800) strains during spray-drying and storage in trehalose-containing powders," International Dairy Journal, 2009, vol. 19, pp. 209-214.
Susini, L. et al., "TCTP protects from apoptotic cell death by antagonizing bax function," Cell Death and Differentiation, vol. 15, No. 8, Feb. 2008, pp. 1211-1220.
Suzuki, T., et al., "Synthesis and histone deacetylase inhibitory activity of new derivatives," Journal of Medicinal Chemistry, vol. 42, No. 15, Jul. 1999 (pp. 3001-3003).
Sweatt, "Behavioural Neuroscience: Down Memory Lane," Nature, vol. 447, May 2007 (pp. 151-152).
Szklarczyk, D. et al. (2015). String v10: Protein-protein interaction networks, integrated over the tree of life. Nucleic Acids Research, 43(D1):D447-D452. https://doi.org/10.1093/nar/gku1003.
Tanaka, H. et al., "Studies on sulfur-containing chelating agents. X. Mercapto-acid amides and their metal chelates," Chemical and Pharmaceutical Bulletin (Tokyo), vol. 10, Jul. 1962, pp. 556-562.
Tanaka, K. et al., "Mitotic checkpoint protein hsMAD2 as a marker predicting liver metastasis of human gastric cancers," Japanese Journal of Cancer Research, vol. 92, No. 9, pp. 952-958 (Sep. 2001).
Tefferi and Vardiman, "Myelodysplastic syndromes". Engl J Med. (Nov. 5, 2009); 361(19): 1872-1885.
Testa, B. et al., "The Hydrolysis of Carboxylic Acid Ester Prodrugs," Chapter 8 In: Hydrolysis in Drug and Prodrug Metabolism: Chemistry, Biochemistry, and Enzymology, Helvetica Chimica Acta, Jan. 2003, pp. 419-534.
Thi, T. et al., "Metabolic Reprogramming by c-MET Inhibition as a Targetable Vulnerability in Glioblastoma," Oncoscience, vol. 7(1-2), (Jan. 2020), pp. 14-16.

(56) References Cited

OTHER PUBLICATIONS

Thiel, K.A. (May 2004) "Structure-aided drug design's next generation" Nat Biotechnol, 22(5):513-519.
Thiery, J. P. et al., "Hepatocellular Carcinoma Cell Lines From Diethylnitrosamine Phenobarbital-Treated Rats. Characterization and Sensitivity to Endothall, a Protein Serine/Threonine Phosphatase-2A Inhibitor," Hepatology, May 1999, vol. 29, No. 5, pp. 1406-1417.
Thompson, J. J. et al. (2018). Protein phosphatase 2A in the regulation of wnt signaling, stem cells, and cancer. Genes, vol. 9, Issue 121, 11 pages. https://doi.org/10.3390/genes9030121.
Tian, Q. et al., "Role of Serine/Threonine Protein Phosphatase in Alzheimer's Disease," Neurosignals, vol. 11, No. 5, (2002), pp. 262-269.
Tocris Biosciences, "Retinoic Acid Receptors," Product Data Sheet (2010), 1 page.
Toma et al., "Retinoids and human breast cancer: in vivo effects of an antagonist for RAR-alpha," Cancer Letters, vol. 219, No. 1, Feb. 2005 (pp. 27-31).
Tong, H. et al., P-285, "LB1, Targeting Inhibiting Protein Phosphatase 2A (PP2A), Enhances Daunorubicin Suppression of MDS Cell Line (SKM-1) in Vitro and in Vivo," Leukemia Research, 2013, vol. 37(S1), pp. S150-S151.
Topalian, S. L. et al., "Immunotherapy: The Path to Win The War on Cancer?," Cell, Apr. 2015, vol. 161, No. 2, pp. 185-186.
Touma et al., "Retinoic acid and the histone deacetylase inhibitor trichostatin a inhibit the proliferation of human renal cell carcinoma in a xenograft tumor model," Clinical Cancer Research, vol. 11, No. 9, May 2005 (pp. 3558-3566).
Traag, V. A. et al. (Mar. 2019), "From Louvain to Leiden: guaranteeing well-connected communities," Scientific Reports, vol. 9:5233, 12 pages. https://doi.org/10.1038/s41598-019-41695-z.
Trost et al., "New synthetic reagents, Methylthiomaleic anhydride: a synthon for protected carbomethoxyketene," Journal of the American Chemical Society, vol. 99, No. 21, Oct. 1977 (pp. 7079-7082).
Tsang, A. et al., "Myocardial postconditioning: reperfusion injury revisited," American Journal of Physiology—Heart Circulation Physiology, vol. 289, No. 1, Jul. 2005, pp. H2-H7.
Tsauer W., et al., "The Effects of Cantharidin Analogues on Xanthine Oxidase," Anticancer Research, May-Jun. 1997, vol. 17 (3C), pp. 2095-2098.
Tuynder et al., "Biological models and genes of tumor reversion: cellular reprogramming through tpt1/TCTP and SIAH-1," Proceedings of the National Academy of Sciences U.S.A., vol. 99, No. 23, Nov. 2002 (pp. 14976-14981).
Tuynder et al., "Translationally controlled tumor protein is a target of tumor reversion," Proceedings of the National Academy of Sciences U.S.A., vol. 101, No. 43, Oct. 2004 (pp. 15364-154369).
Uchida, et al., "Direct isolation of human central nervous system stem cells." Proc Natl Acad Sci U S A. (2000); 97 (26): 14720-14725.
Uemura, K. et al., "GSK3β Activity Modifies the Localization and Function of Presenilin 1," The Journal of Biological Chemistry, vol. 282, No. 21, May 2007, pp. 15823-15832.
Ugi, S. et al., Protein phosphatase 2A forms a molecular complex with Shc and regulates Shc tyrosine phosphorylation and downstream mitogenic signaling. Mol Cell Biol 22(7):2375-2387 (Apr. 2002).
Unni, A. M. et al. (2018). Hyperactivation of ERK by multiple mechanisms is toxic to RTK-RAS mutation-driven lung adenocarcinoma cells. ELife, 7, pp. 1-24. https://doi.org/10.7554/eLife.33718.
Unni, A. M. et al. (Jun. 2015). Evidence that synthetic lethality underlies the mutual exclusivity of oncogenic KRAS and EGFR mutations in lung adenocarcinoma. ELife, e06907. http://dx.doi.org/10.7554/eLife.06907, 23 pages.
U.S. Department of Health and Human Services, et al., "Guidance for Industry: Estimating the Maximum Safe Starting Dose in Initial Clinical Trials for Therapeutics in Adult Healthy Volunteers", Pharmacology and Toxicology (Jul. 2005) [online] https://www.fda.gov/media/72309/download"https://www.fda.gov/media/72309/download (Access Date: Jun. 9, 2020); 30 pages.
Vainonen, J. P. et al. (Apr. 2021). Druggable cancer phosphatases. Sci. Transl. Med. vol. 13, eabe2967, 13 pages.
Valdiglesias, V. et al., Okadaic acid: more than a diarrheic toxin. Mar. Drugs 11:4328-4349 (2013).
Valeriote et al., "Synergistic interaction of anticancer agents: a cellular perspective," Cancer Chemotherapy Reports, vol. 59, No. 5, Sep.-Oct. 1975 (pp. 895-900).
Van Deursen, J. M., "Rb loss causes cancer by driving mitosis mad," Cancer Cell, vol. 11, No. 1, Jan. 2007, pp. 1-3.
Van Hoof, C. et al., "PP2A fulfills its promises as tumor suppressor: which subunits are important?" Cancer Cell, vol. 5, No. 5, Feb. 2004, pp. 105-106.
Vardiman, J., "The Classification of MDS: from FAB to WHO and Beyond," Leukemia Research, Dec. 2012, vol. 36, No. 12, pp. 1453-1458.
Vardiman, J. W. et al., "The 2008 revision of the World Health Organization (WHO) classification of myeloid neoplasms and acute leukemia: rationale and important changes," Blood, vol. 114, No. 5, pp. 937-951 (Jul. 2009).
Vardiman, J. W., The World Health Organization (WHO) classification of tumors of the hematopoietic and lymphoid tissues: an overview with emphasis on the myeloid neoplasms. Chem Biol Interact 184:16-20 (2010).
Vazquez A., et al., "The Genetics of the p53 Pathway, Apoptosis and Cancer Therapy," Nature Reviews Drug Discovery, Dec. 2008, vol. 7, pp. 979-987.
Vigneron, S. et al., Greatwall maintains mitosis through regulation of PP2A. The EMBO Journal, 28:2786-2793 (2009).
Virzì, A. R. et al., "Reviving oncogenic addiction to MET bypassed by BRAF (G469A) mutation," Proc Natl Acad Sci USA, vol. 115, No. 40, pp. 10058-10063 (Oct. 2018).
Vitale, I. et al. (2011). Mitotic catastrophe: a mechanism for avoiding genomic instability. Nature Reviews. Molecular Cell Biology, 12(6):385-392. https://doi.org/10.1038/nrm3115.
Walter, M. J. et al., Clonal architecture of secondary acute myeloid leukemia. Engl J Med 366:1090-1098 (2012).
Wang, C-C et al., Cytotoxic effects of cantharidin on the growth of normal and carcinoma cells. Toxicology 147:77-87 (2000).
Wang, G. S. (1983), "Hydrolysis and demethylation of cantharidin on the relief of its urinary irritation," Chin. Pharmac. Bull., vol. 18, No. 7, pp. 18-19.
Wang, G. S. et al. (1986), "Results of clinical trials in 244 cases of primary hepatoma and with norcantharidin," Chinese Pharm. Bull., vol. 21, No. 2. pp. 90-93.
Wang, G. S. et al. (1987), "Effect of norcantharidin on the number of white blood cells," Chinese Pharm. Bull., vol. 22, pp. 517-519.
Wang, J. et al., Inhibiting crosstalk between MET signaling and mitochondrial dynamics and morphology: a novel therapeutic approach for lung cancer and mesothelioma. Cancer Biol Ther 19, 1023-1032 (2018).
Wang, L. et al. (2022). Exploiting senescence for the treatment of cancer. In Nature Reviews Cancer, Nature Research, vol. 22, Issue 6, pp. 340-355. https://doi.org/10.1038/s41568-022-00450-9.
Wang, L. et al., An Acquired Vulnerability of Drug-Resistant Melanoma with Therapeutic Potential. Cell. May 2018, 173(6):1413-1425.
Wang, L. et al., High-Throughput Functional Genetic and Compound Screens Identify Targets for Senescence Induction in Cancer. Cell Rep. Oct. 2017, 21(3):773-783.
Wang, L. et al., "MAD2 as a key component of mitotic checkpoint: A probable prognostic factor for gastric cancer," American Journal of Clinical Pathology, vol. 131, No. 6, Jun. 2009, pp. 793-801.
Wang, R. et al., Okadaic acid inhibits cell multiplication and induces apoptosis in a549 cells, a human lung adenocarcinoma cell line. Int J Clin Exp Med 7(8):2025-2030 (2014).
Wang, X., The expanding role of mitochondria in apoptosis. Genes & Development, 15:2922-2933 (2001).
Wang, Y. et al., "Cross talk between PI3K-AKT-GSK-3beta and PP2A pathways determines tau hyperphosphorylation," Neurobiol Aging. 2015;36(1):188-200.

(56) References Cited

OTHER PUBLICATIONS

Warr, M. R. et al. (2008), "Unique Biology of Mcl-1: Therapeutic opportunities in cancer," Current Molecular Medicine, vol. 8, No. 2, pp. 139-147.
Warrell et al., "Therapeutic Targeting of Transcription in Acute Promyelocytic Leukemia by Use of an Inhibitor of Histone Deacetylase," Journal of the National Cancer Institute, vol. 90, No. 21, Nov. 1998 (pp. 1621-1625).
Warren K., et al., "A phase 2 Study of Pegylated Interferon α-2b (PEG-Intron®) in Children with Diffuse Intrinsic Pontine Glioma," Cancer, Jul. 15, 2012, vol. 118 (14), pp. 3607-3613.
Wassmann, K. et al., "Mad2 phosphorylation regulates its association with Mad1 and the APC/C," The EMBO Journal, vol. 22, No. 4, Feb. 2003, pp. 797-806.
Waters, C. E. et al., "Analysis of Co-Factor Function in a Glucocorticoid-Resistant Small Cell Carcinoma Cell Line," Journal of Endocrinology, 2004, vol. 183, pp. 375-383.
Waters, J. S. et al., Phase I clinical and pharmacokinetic study of bcl-2 antisense oligonucleotide therapy in patients with non-Hodgkin's lymphoma. J Clin Oncol 18:1812-1823 (2000).
Wei, K-C. et al., "Focused Ultrasound-Induced Blood-Brain Barrier Opening to Enhance Temozolomide Delivery for Glioblastoma Treatment: A Preclinical Study," PLoS One, 2013, vol. 8(3), e58995, 10 pages.
Wei, M. C. et al., Proapoptotic BAX and BAK: a requisite gateway to mitochondrial dysfunction and death. Science 292:727-730 (Apr. 2001).
Wei, S. et al., "A critical role for phosphatase haplodeficiency in the selective suppression of deletion 5q MDS by lenalidomide," PNAS, vol. 106, No. 31, pp. 12974-12979 (Aug. 2009); with Correction, PNAS, vol. 110, No. 35 (Aug. 2013), p. 14504.
Wei, S. et al., "Lenalidomide promotes p53 degradation by inhibiting MDM2 auto-ubiquitination in myelodysplastic syndrome with chromosome 5q deletion," Oncogene, 32(9):1110-1120 (Feb. 2013).
Wei, W. et al., "Hypoxia induces a phase transition within a kinase signaling network in cancer cells," Proceedings of the National Academy of Sciences, U.S.A., vol. 110, No. 15, Apr. 2013, pp. E1352-E1360.
Weinmann et al., "Histone deacetylase inhibitors: a survey of recent patents," Expert Opinion on Therapeutic Patents, vol. 15, No. 12, Nov. 2005 (pp. 1677-1690).
Wikipedia, "Platinum-based Antineoplastic," [Online], https://en.wikipedia.org/wiki/platinum-based_antineoplastic, Visited Jan. 2018, 4 pages.
Williams, Lad et al., In vitro anti-proliferation/cytotoxic activity of *Cantharidin* (Spanish Fly) and related derivatives. West Indian Med J., 52(1):10-13 (2003).
Winstanley, K. J. et al., "Ortho-substituted catechol derivatives: The effect of intramolecular hydrogen-bonding pathways on chloride anion recognition," J. Org. Chem., vol. 72, No. 8, 2007, pp. 2803-2815.
Xia, L et al., miR-15b and miR-16 modulate multidrug resistance by targeting BCL2 in human gastric cancer cells. Int. J. Cancer, 123:372-379 (2008).
Xiao, C. et al., MicroRNA control in the immune system: basic principles. Cell, 136:26-36 (Jan. 2009).
Xiao, G. et al., "B-Cell-Specific Diversion of Glucose Carbon Utilization Reveals a Unique Vulnerability in B Cell Malignancies," Cell, Apr. 2018;173(2):470-484.
Xie, Z. et al. (2021), "Gene Set Knowledge Discovery with Enrichr.," Current Protocols, vol. 1, e90, 52 pages. doi: 10.1002/cpz1.90.
Xu, Y. et al., "Structure of the Protein Phosphatase 2A Holoenzyme," Cell, 2006, vol. 127, No. 6, pp. 1239-1251.
Yadav, B. et al. (2015). Searching for Drug Synergy in Complex Dose-Response Landscapes Using an Interaction Potency Model. Computational and Structural Biotechnology Journal, vol. 13, pp. 504-513. https://doi.org/10.1016/j.csbj.2015.09.001.

Yan et al., "Inhibition of protein phosphatase activity induces p53-dependent apoptosis in the absence of p53 transactivation," Journal of Biological Chemistry, vol. 272, No. 24, Jun. 1997 (pp. 15220-15226).
Yanez, A. G., Regulation of microRNA activity by translation initiation factors in melanoma. Doctoral Dissertation, Harvard University (May 2014), 162 pages.
Yang et al., "An N-terminal region of translationally controlled tumor protein is required for its antiapoptotic activity," Oncogene, vol. 24, No. 30, Jul. 2005 (pp. 4778-4788).
Yang, S-H. et al., "Perspectives on the combination of radiotherapy and targeted therapy with DNA repair inhibitors in the treatment of pancreatic cancer," Aug. 2016, World Journal of Gastroenterology, vol. 22, Issue 32, pp. 7275-7288.
Yang, Y. et al., Reactivating PP2A by FTY720 as a novel therapy for AML with C-KIT tyrosine kinase domain mutation. J. Cell. Biochem., 113:1314-1322 (2012).
Yang Y-H., et al., "Enzyme-mediated Hydrolytic Activation of Prodrugs," Acta Pharmaceutica Sinica B, Oct. 2011, vol. 1 (3), pp. 143-159.
Yao, D. et al. (2014). A review of the clinical diagnosis and therapy of cholangiocarcinoma. Journal of International Medical Research, vol. 42, Issue 1, pp. 3-16. https://doi.org/10.1177/0300060513505488.
Yarm, "Plk phosphorylation regulates the microtubule-stabilizing protein TCTP," Molecular and Cellular Biology, vol. 22, No. 17, Sep. 2002 (pp. 6209-6221).
Yellon, D. M. et al., "Realizing the clinical potential of ischemic preconditioning and postconditioning," Nature Clinical Practice Cardiovascular Medicine, vol. 2, No. 11, Nov. 2005, pp. 568-575.
Yi, C. et al., "Determination of malignant disease-associated DNA-binding protein 2 in patients with liver cancer," Hua Xi Vi Ke Da Xue Xue Bao, vol. 31, No. 3, Sep. 2000, pp. 310-311, English Abstract, 1 page.
Yin, X. et al., "Regulation of LC3-dependent protective autophagy in ovarian cancer cells by protein phosphatase 2A," Int J Gynecol Cancer, May 2013; 23(4):630-641. doi: 10.1097/IGC.0b013e3182892cee.
Yoshida et al., "Potent and specific inhibition of mammalian histone deacetylase both in vivo and in vitro by trichostatin A," Journal of Biological Chemistry, vol. 265, No. 28, Oct. 1990 (pp. 17174-17179).
Yoshida, M. et al. (1999), "Trichostatin and leptomycin. Inhibition of histone deacetylation and signal-dependent nuclear export," Annals of the New York Academy of Sciences, vol. 886, pp. 23-26.
Yu, L. et al., "Mitotic arrest defective protein 2 expression abnormality and its clinicopathologic significance in human osteosarcoma," APMIS, vol. 118, No. 3, Mar. 2010, pp. 222-229.
Yu, L. et al., Modeling the Genetic Regulation of Cancer Metabolism: Interplay between Glycolysis and Oxidative Phosphorylation. Cancer Res 77, 1564-1574 (2017).
Yung, W. K. A. et al., "Treatment Of Recurrent Malignant Gliomas With High-Dose 13-cis-Retinoic Acid," Clinical Cancer Research, Dec. 1996, vol. 2, No. 12, pp. 1931-1935.
Zeman, M. K. et al. (Jan. 2014), "Causes and consequences of replication stress," Nat. Cell. Biol., vol. 16, No. 1, 8 pages.
Zhang C., et al., "Inhibition of Protein Phosphatase 2A with The Small Molecule LB100 Overcomes Cell Cycle Arrest in Osteosarcoma After Cisplatin Treatment," Cell Cycle, Jul. 1, 2015, vol. 14 (13), pp. 2100-2108.
Zhang, L. et al., Role of BAX in the apoptotic response to anticancer agents. Science 290:989-992 (Nov. 2000).
Zhang, S-H et al., "Clinicopathologic significance of mitotic arrest defective protein 2 overexpression in hepatocellular carcinoma," Human Pathology, vol. 39, No. 12, Dec. 2008, pp. 1827-1834.
Zhao, X. Z. et al., "2,3-dihydro-6,7-dihydroxy-1 H-isoindol-1-one based HIV-1 integrase inhibitors," J Med Chem, vol. 51, No. 2, (2008) pp. 251-259.
Zhao, Y. et al., Roles of Greatwall kinase in the regulation of cdc25 phosphatase. Mol. Biol. Cell, 19:1317-1327 (Apr. 2008).
Zheng, T. et al., Role of microRNA in anticancer drug resistance. Int. J. Cancer, 126:2-10 (2010).

(56) References Cited

OTHER PUBLICATIONS

Zhou, B. et al., The specificity of extracellular signal-regulated kinase 2 dephosphorylation by protein phosphatases. J Biol Chem 277(35):31818-31825 (Aug. 2002).

Zhu, J. et al. (May 2008), "Activation of PI3K/Akt and MAPK pathways regulates Myc-mediated transcription by phosphorylating and promoting the degradation of Mad1," Proc Natl Acad Sci USA, vol. 105, No. 18, pp. 6584-6589.

Zhu W., et al., "miR-181b Modulates Multidrug Resistance by Targeting BCL2 in Human Cancer Cell Lines," International Journal of Cancer, 2010, vol. 127 (11), pp. 2520-2529.

Zhu, X. N. et al., PP2A-AMPKalpha-HSF1 axis regulates the metal-inducible expression of HSPs and ROS clearance. Cell Signal. 2014;26(4):825-832.

CAS Registry No. 61531-23-5, Nov. 16, 1984, 2 pages.

ClinicalTrials.gov, "Adavosertib, Radiation Therapy, and Temozolomide in Treating Patients With Newly Diagnosed or Recurrent Glioblastoma," [Online], ClinicalTrials.gov Identifier: NCT01849146, First Posted—May 8, 2013, Last update posted—May 3, 2023, Retrieved from the Internet: URL: https://classic.clinicaltrials.gov/ct2/show/NCT01849146, 15 pages.

Enzo Life Sciences, HDAC3/NCOR1 Fluorimetric Drug Discovery Kit Product Manual, Catalog #: BML-AK531 (2010), 24 pages.

Gattinoni, L. et al., "A human memory T cell subset with stem cell-like properties," Nature Medicine, 2012, vol. 17, No. 10, pp. 1290-1297.

HCAPLUS, AN 2012:652703, Wang et al., "Synergistic effect of a novel cantharidin analog LB1 with doxorubicin in chemotherapy against hepatocellular carcinoma cells," HCAPLUS Document No. 158:213321, May 2012, 1 page.

Hinchcliff, E. M. et al., "Loss-of-function mutations in PPP2R1A Correlate with Exceptional Survival in Ovarian Clear Cell Carcinomas Treated with Immune Checkpoint Inhibitors (099)," National oral presentation at SGO Annual Meeting, Abstracts, Gynecologic Oncology, 166:S66, Aug. 2022, 1 page.

Kaartinen, et al., "Low interleukin-2 concentration favors generation of early memory T cells over effector phenotypes during chimeric antigen receptor T-cell expansion", Cytotherapy, Jun. 2017, vol. 19, No. 6, pp. 689-702.

Lixte Biotechnology Holdings, Inc. "Lixte Biotechnology's Lead Compound Reported to be Active Against Hematologic Cancers in Pre-Clinical Studies," [Online], Retrieved from the Internet: https://ir.lixte.com/news-events/press-releases/detail/30/lixte-biotechnologys-lead-compound-reported-to-be-active-against-hematologic-cancers-in-pre-clinical-studies, Feb. 2015, 2 pages.

Lixte Biotechnology Holdings, Inc., "New scientific publication shows LB-100, Lixte's lead clinical compound, can force cancer cells to give up their cancer-causing properties," Mar. 27, 2024, 3 pages.

National Cancer Institute, "CAR T Cells: Engineering Patients' Immune Cells to Treat Their Cancers," [Online], Retrieved from the Internet: https://www.cancer.gov./about-cancer/treatment/research/car-t-cells, Mar. 2022, 13 pages.

Non-Final Office Action for U.S. Appl. No. 17/252,160 mailed Jan. 29, 2024, 28 pages.

Non-Final Office Action for U.S. Appl. No. 18/092,606 mailed Nov. 29, 2023, 29 pages.

Sun, B. et al., Programmed cell death 10 promotes metastasis and epithelial-mesenchymal transition of hepatocellular carcinoma via PP2Ac mediated YAP activation, Cell Death and Disease, Sep. 2021, 14 pages.

\* cited by examiner

Figure 2: Duration on Study (weeks)

Fig. 3
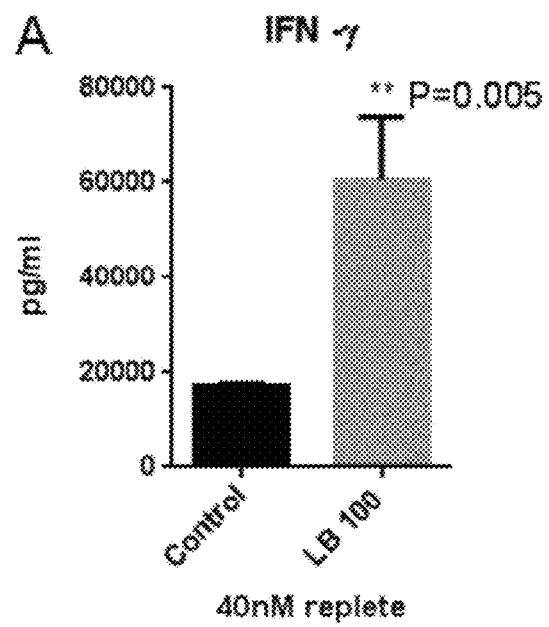
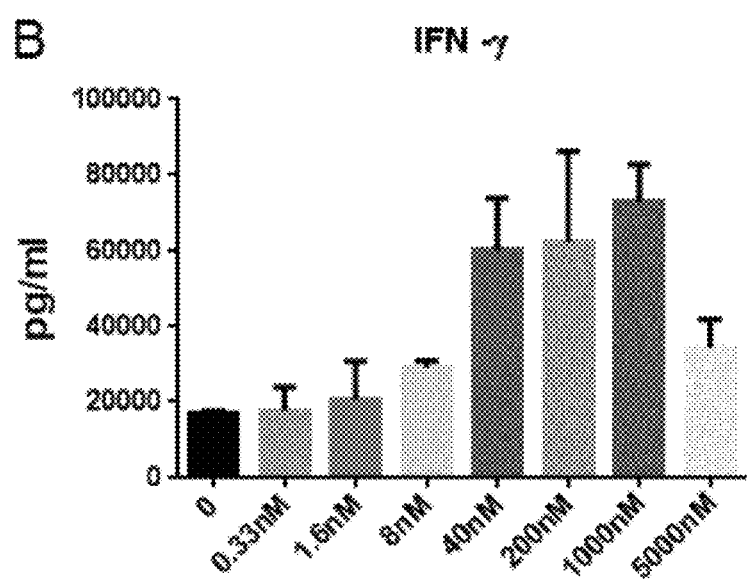

Fig. 4
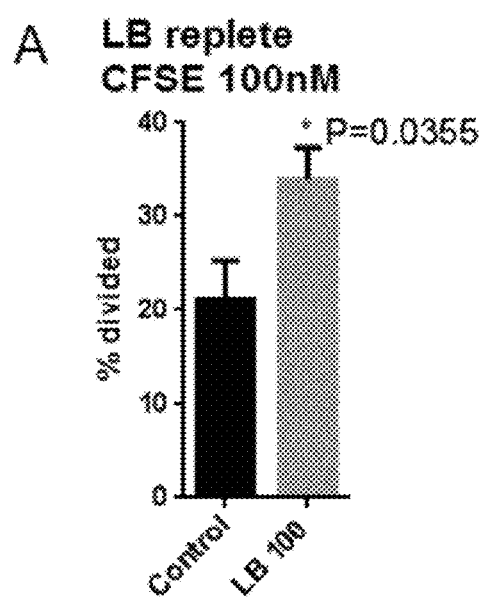
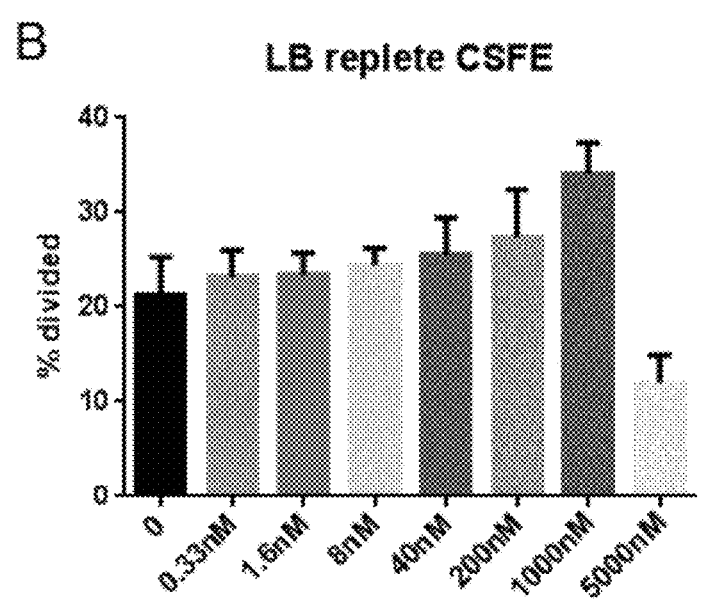

Fig. 5
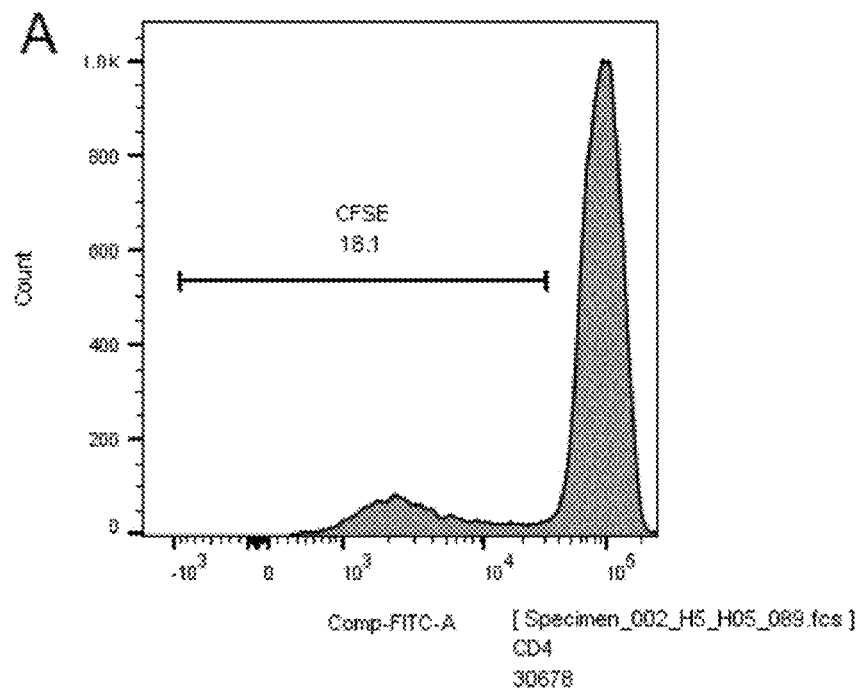
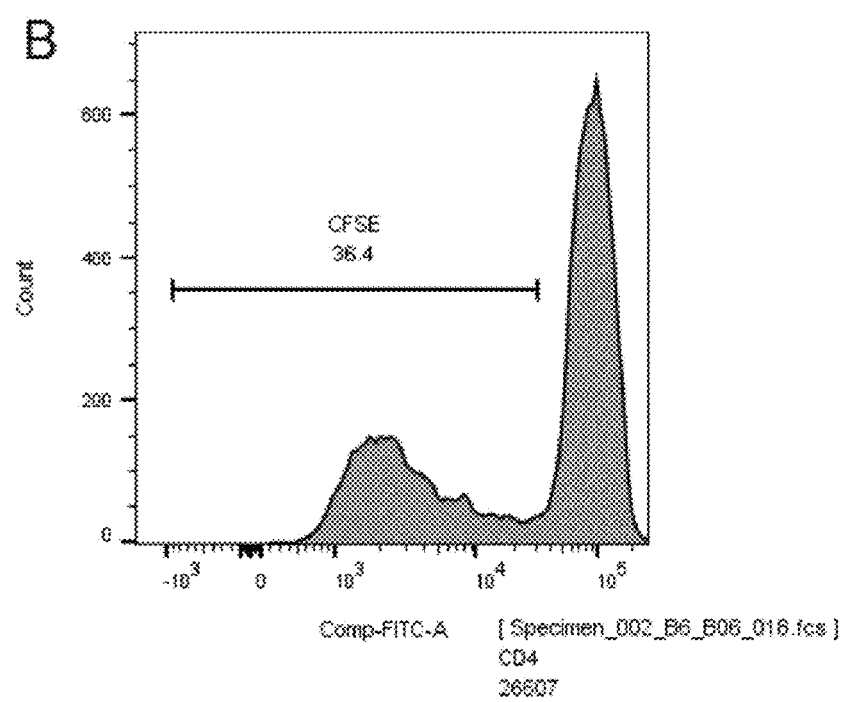

Fig. 8
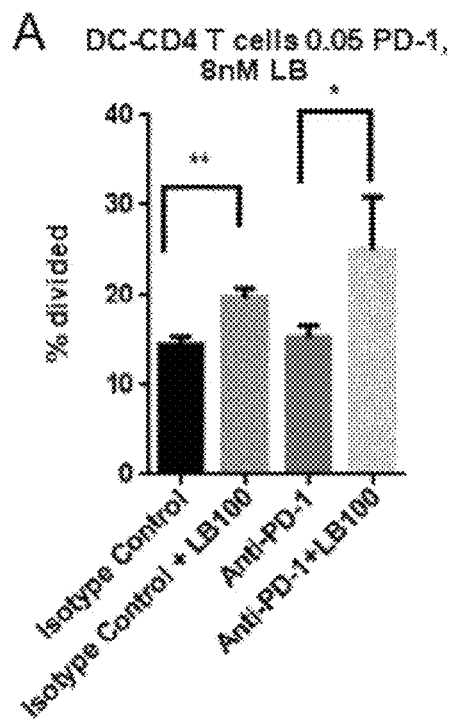
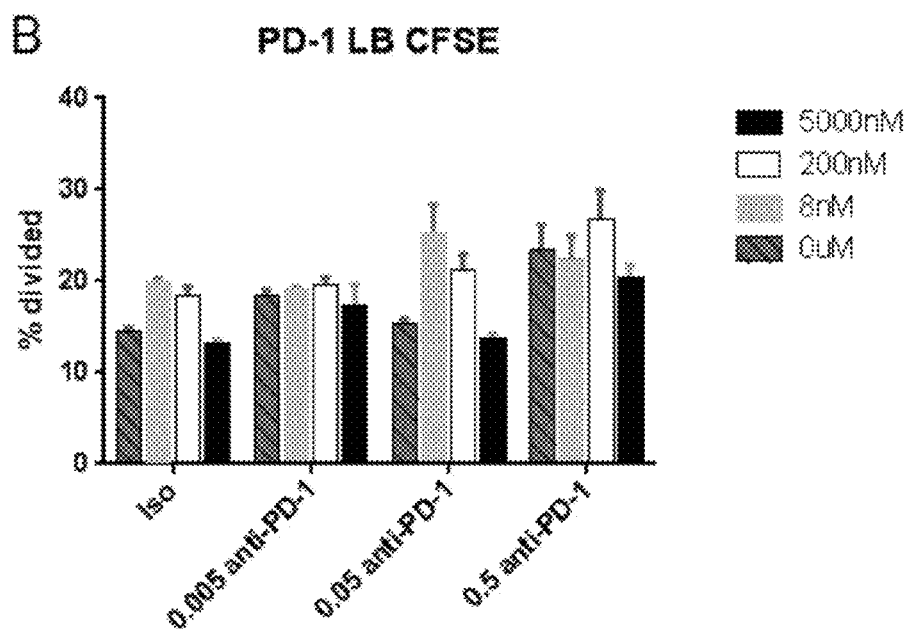

Fig. 17B (continued)
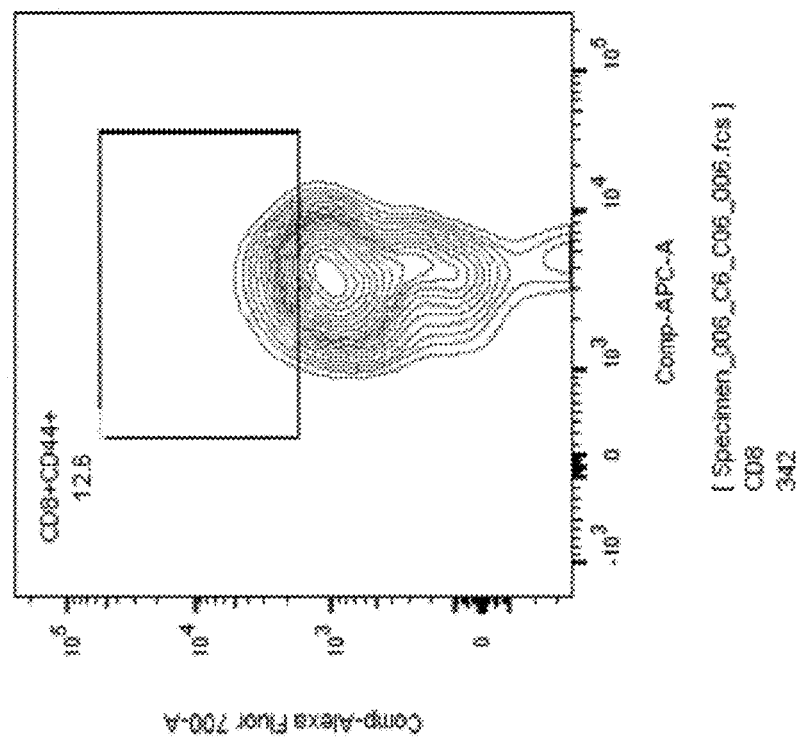
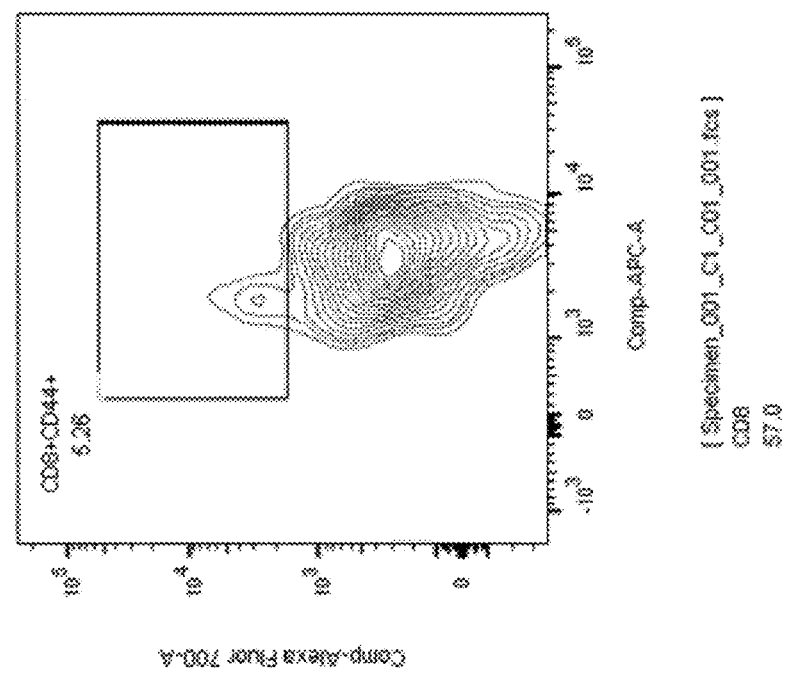

Fig. 19
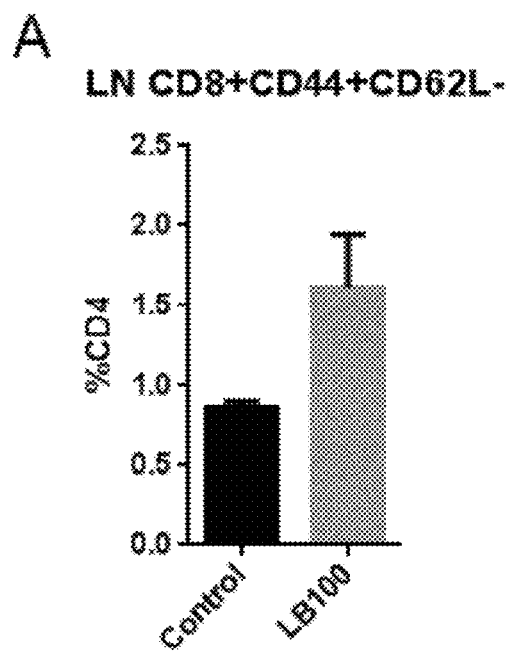
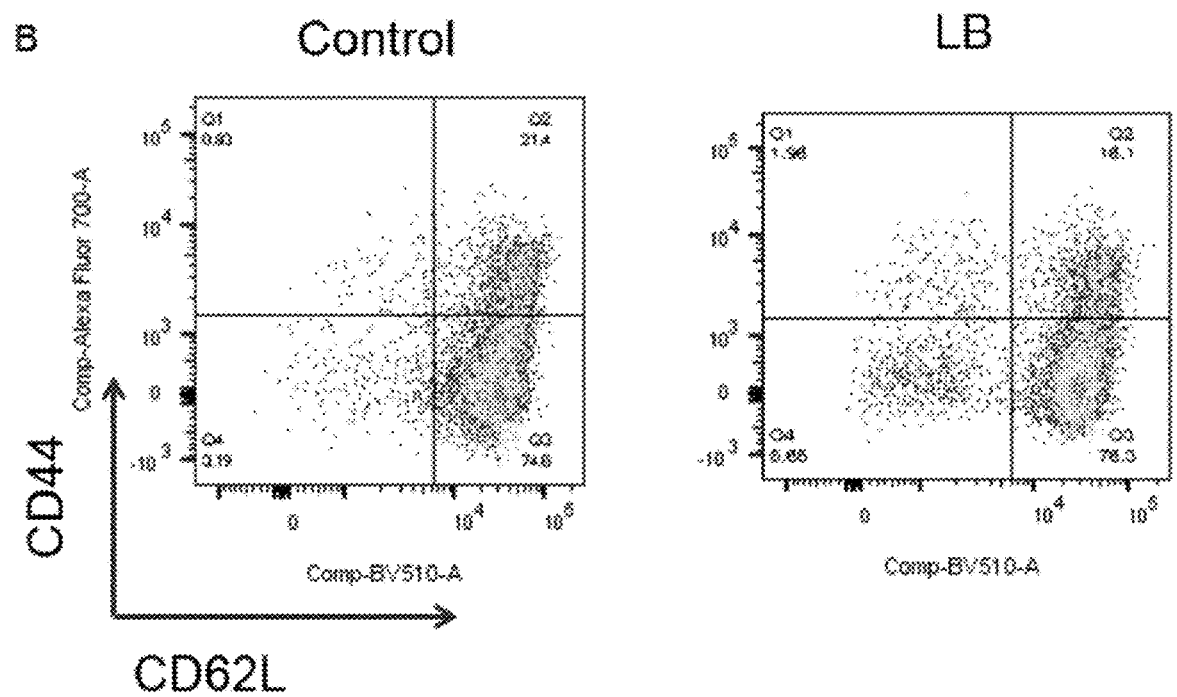

Fig. 24
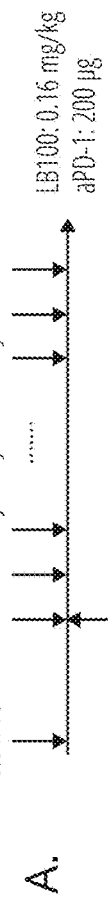
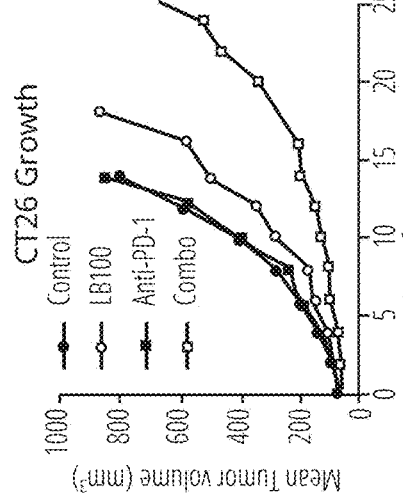
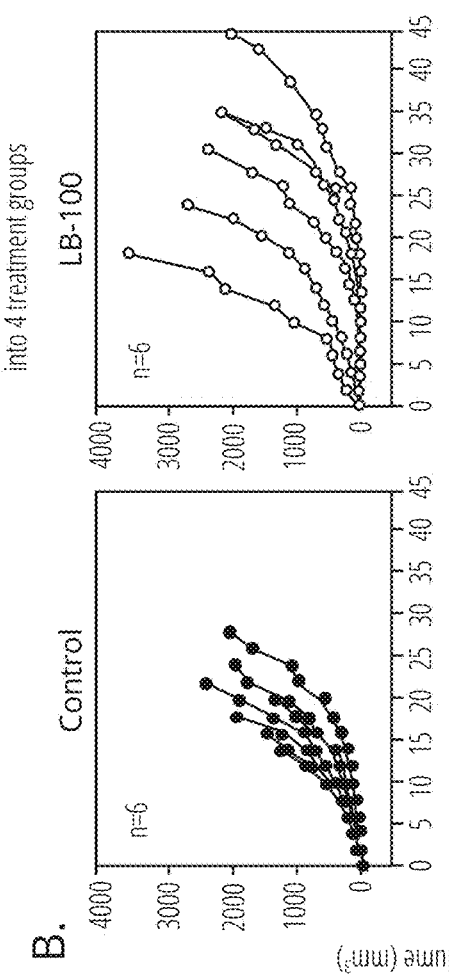
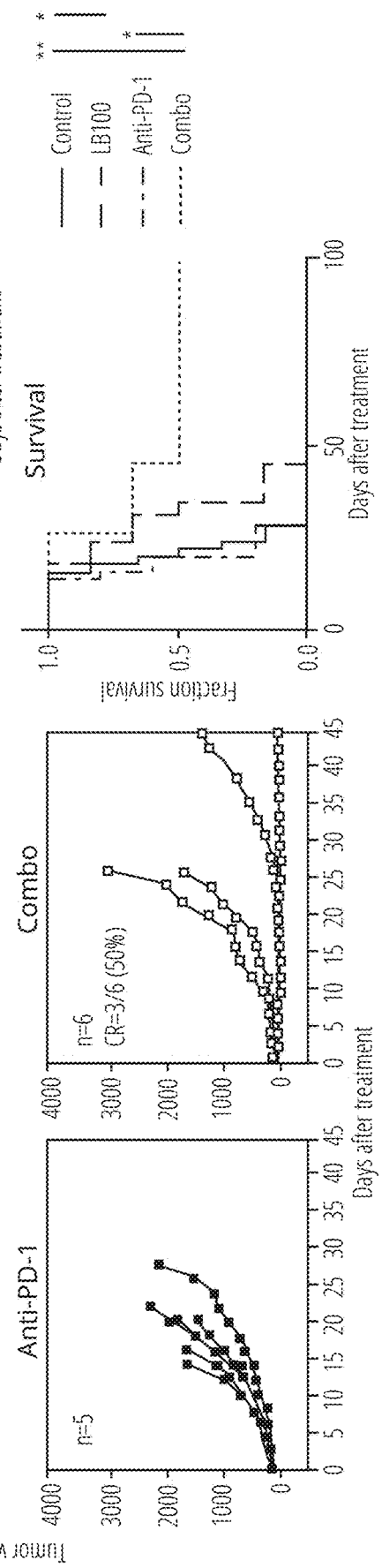

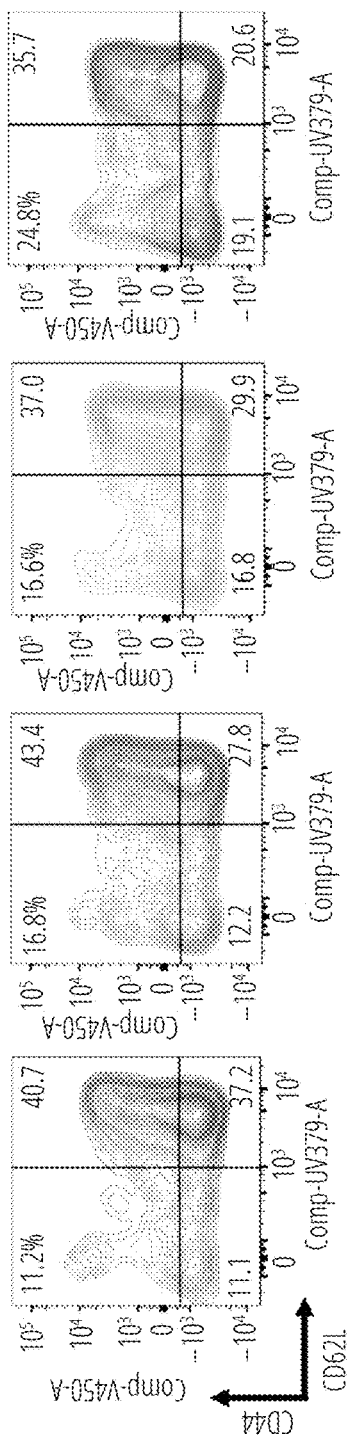
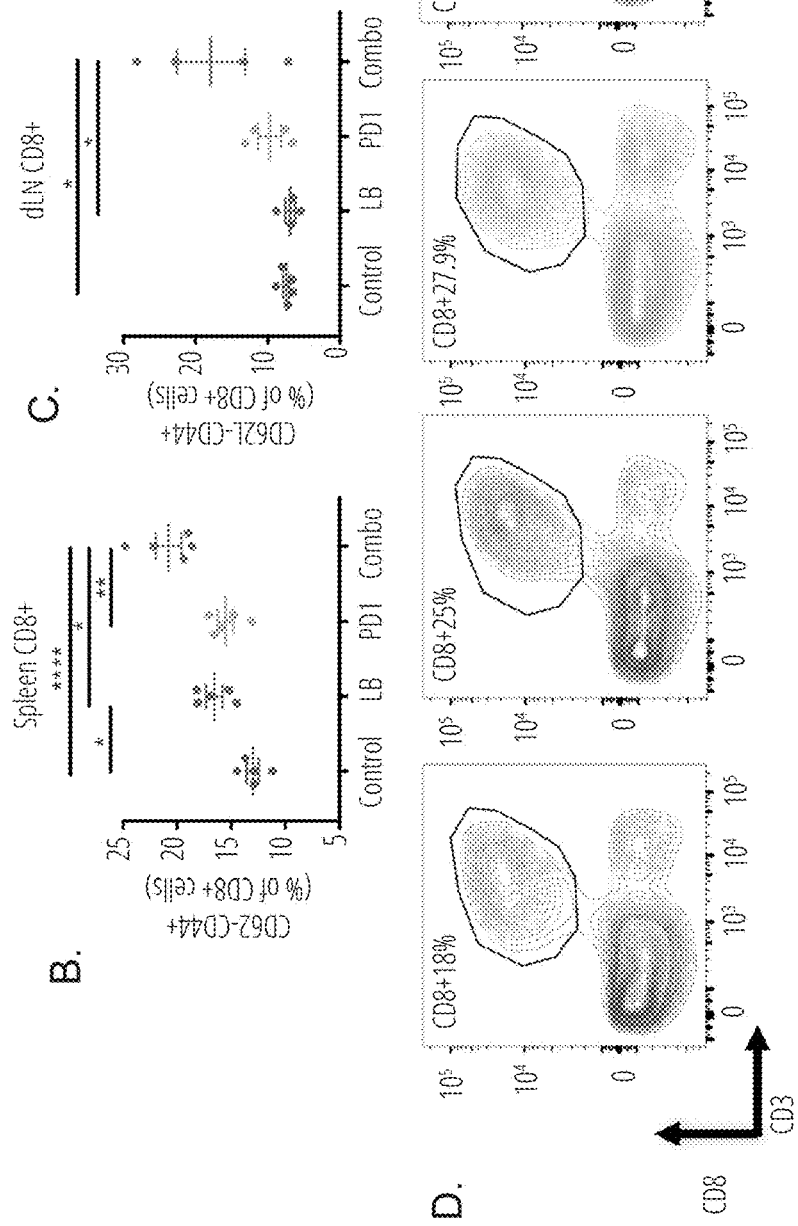
Fig. 26 A.

*(p<0.05) compared to control

OXABICYCLOHEPTANES FOR MODULATION OF IMMUNE RESPONSE

CROSS REFERENCE TO RELATED APPLICATIONS

This application is a U.S. National Phase application, filed under 35 U.S.C. § 371, of International Application No. PCT/US2017/065270, filed Dec. 8, 2017, which claims the benefit of U.S. Provisional Patent Application No. 62/497,949, filed Dec. 8, 2016, U.S. Provisional Patent Application No. 62/465,001, filed Feb. 28, 2017, and U.S. Provisional Patent Application No. 62/545,373, filed Aug. 14, 2017, which are incorporated herein by reference in their entirety.

BACKGROUND OF THE INVENTION

Protein phosphatase 2A (PP2A) is a ubiquitous serine/threonine phosphatase that dephosphorylates numerous proteins of both ATM/ATR-dependent and -independent response pathways (Mumby, M. 2007). Pharmacologic inhibition of PP2A has previously been shown to sensitize cancer cells to radiation-mediated DNA damage via constitutive phosphorylation of various signaling proteins, such as p53, γH2AX, PLK1 and Akt, resulting in cell cycle deregulation, inhibition of DNA repair, and apoptosis (Wei, D. et al. 2013).

Cantharidin, the principle active ingredient of blister beetle extract (Mylabris), is a compound derived from traditional Chinese medicine that has been shown to be a potent inhibitor of PP2A (Efferth, T. et al. 2005). Although cantharidin has previously been used in the treatment of hepatomas and has shown efficacy against multidrug-resistant leukemia cell lines (Efferth, T. et al. 2002), its severe toxicity limits its clinical usefulness. LB-100 is a small molecule derivative of cantharidin with significantly less toxicity. Previous pre-clinical studies have shown that LB-100 can enhance the cytotoxic effects of temozolomide, doxorubicin, and radiation therapy against glioblastoma (GBM), metastatic pheochromocytoma, and pancreatic cancer (Wei, D. et al. 2013; Lu, J. et al. 2009; Zhang, C. et al. 2010; Martiniova, L. et al. 2011). LB-100 is also undergoing a phase 1 study in combination with docetaxel for the treatment of solid tumors (Chung, V. 2013).

SUMMARY OF THE INVENTION

The present invention provides a method of treating a subject afflicted with cancer comprising administering to the subject an effective amount of a PP2A inhibitor in combination with an effective amount of a checkpoint inhibitor, wherein the amounts when taken together are effective to treat the subject.

The present invention also provides a method of treating a subject afflicted with cancer and receiving a checkpoint inhibitor comprising administering to the subject of an amount of PP2A inhibitor effective to enhance treatment relative to the checkpoint inhibitor alone.

The present invention also provides a method of treating a tumor or cancer in a subject comprising administering to the subject an effective amount of a PP2A inhibitor in combination with an effective amount of a checkpoint inhibitor, wherein the amounts when taken together are effective to treat the tumor or cancer.

The present invention also provides a method of increasing a T-cell response to cancer cells in a subject afflicted with cancer comprising administering to the subject an amount of a PP2A inhibitor in combination with an effective amount of a checkpoint inhibitor effective to increase the T-cell response to the cancer cells.

The present invention also provides a method of increasing T cell activation in a subject afflicted with cancer comprising administering to the subject an effective amount of a PP2A inhibitor in combination with an effective amount of a checkpoint inhibitor so as to thereby increase the T cell activation.

The present invention also provides a method of inhibiting the function of CTLA-4 in T cells comprising administering to the T cells a PP2A inhibitor so as to thereby inhibit the function of CTLA-4.

The present invention also provides a method of inhibiting PD-1:PD-L1 interaction in T cells comprising administering to the T cells a PP2A inhibitor so as to thereby inhibit interaction of PD-1:PD-L1.

BRIEF DESCRIPTION OF THE DRAWINGS

FIG. 3A. Inhibition of PP2A significantly enhance IFN-γ production in CD4 T cells. IFN gamma production from activated CD4 T cells with CD3/CD28 beads for 5 days in presence or absence of LB-100 at 40 nM. LB-100 was added or replaced on the $3^{rd}$ day.

FIG. 3B. Inhibition of PP2A significantly enhance IFN-7 production in CD4 T cells. IFN gamma production from activated CD4 T cells with CD3/CD28 beads for 5 days in presence or absence of LB-100 at different concentration. LB-100 was added or replaced on the $3^{rd}$ day.

FIG. 4A. Inhibition of PP2A significantly enhance CD4 T cell proliferation. Percentage of proliferated CD4 T cells with CD3/CD28 beads for 5 days in presence or absence of LB-100 at 1000 nM. LB-100 was added or added or replaced on the $3^{rd}$ day.

FIG. 4B. Inhibition of PP2A significantly enhance CD4 T cell proliferation. Percentage of proliferated CD4 T cells with CD3/CD28 beads for 5 days in presence or absence of LB-100 at different concentration. LB-100 was added or replaced on the $3^{rd}$ day.

FIG. 5A. Inhibition of PP2A significantly enhance CD4 T cell proliferation. Representative flow plot of proliferated CD4 T cells with CD3/CD28 beads for 5 days in the absence of LB-100. LB-100 was added or replaced on the $3^{rd}$ day.

FIG. 5B. Inhibition of PP2A significantly enhance CD4 T cell proliferation. Representative flow plot of proliferated CD4 T cells with CD3/CD28 beads for 5 days in the presence of LB-100 at 1000 nM. LB-100 was added or replaced on the $3^{rd}$ day.

Figure 7:
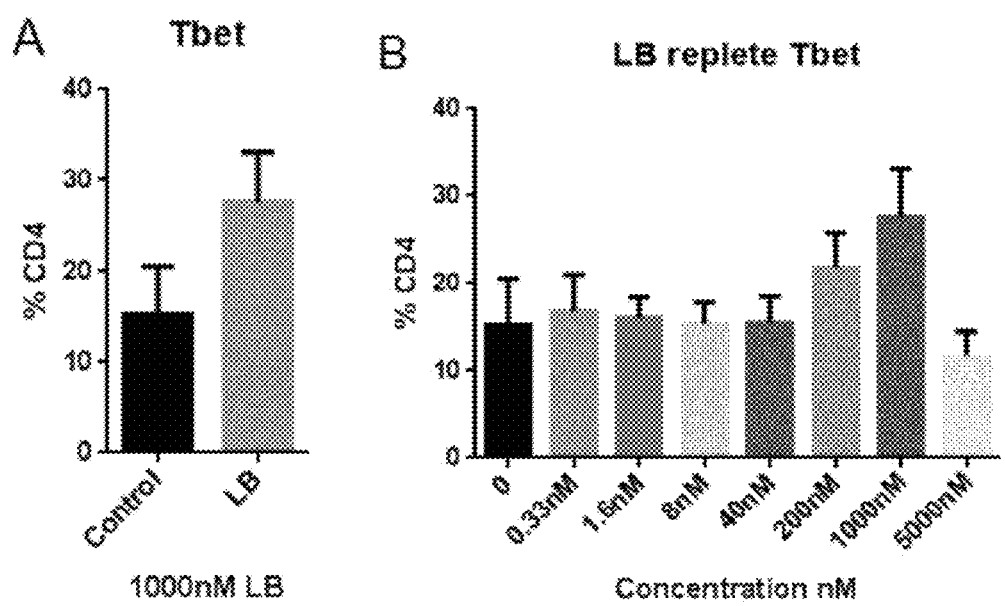
FIG. 7A. Inhibition of PP2A enhances Tbet, a transcription factor to drive IFNγ production in CD4 T cells. Percentage of Tbet expressing CD4 T cells with CD3/Cd28 beads for 5 days in presence or absence of LB-100 at 1000 nM. LB-100 was added or replaced on the $3^{rd}$ day.

FIG. 7B. Inhibition of PP2A enhances Tbet, a transcription factor to drive IFNγ production in CD4 T cells. Percentage of proliferated CD4 T cells co-culture monocyte-derived dendritic cells for 5 days in presence or absence of LB-100 at different concentration with or without anti-PD1 antibody. LB-100 was added or replaced on the $3^{rd}$ day.

FIG. 8A. Enhanced proliferation of CD4 T cells with combination treatment. Percentage of proliferated CD4 T cells co-cultured with monocyte-derived dendritic cells for 5 days in presence or absence of LB-100 at 8 nM with or without anti-PD1 antibody. LB-100 was added or replaced on the $3^{rd}$ day.

FIG. 8B. Enhanced proliferation of CD4 T cells with combination treatment. Percentage of proliferated CD4 T cells co-cultured with monocyte-derived dendritic cells for 5 days in presence or absence of LB-100 at different concentration with or without anti-PD1 antibody. LB-100 was added or replaced on the $3^{rd}$ day.

Figure 9:
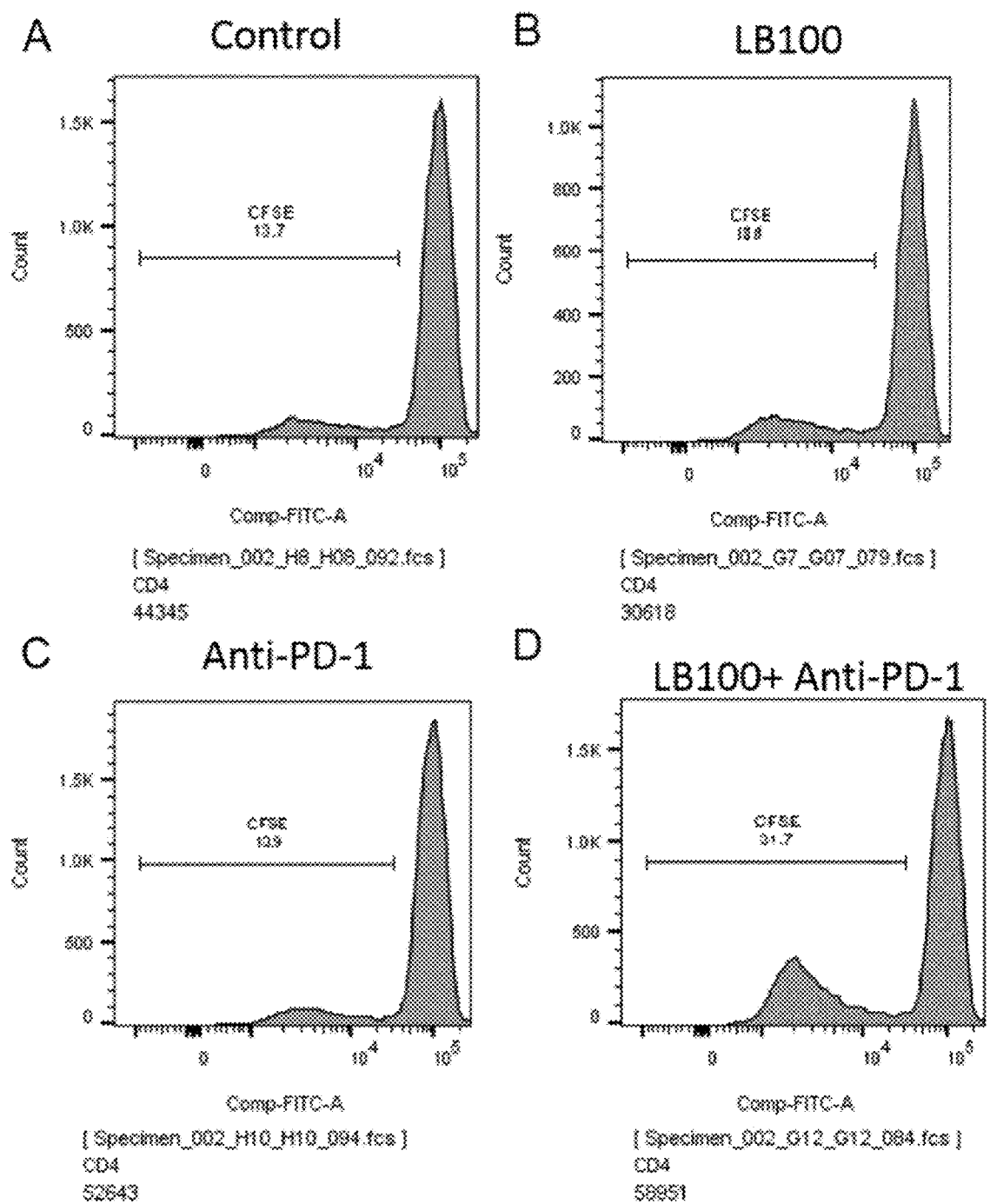

FIG. 9A. Representative flow cytometry plot of CD4 T cell proliferation in control.

FIG. 9B. Representative flow cytometry plot of CD4 T cell proliferation in LB-100.

FIG. 9C. Representative flow cytometry plot of CD4 T cell proliferation in anti-PD-1.

FIG. 9D. Representative flow cytometry plot of CD4 T cell proliferation in LB-100+anti-PD-1.

Figure 10:
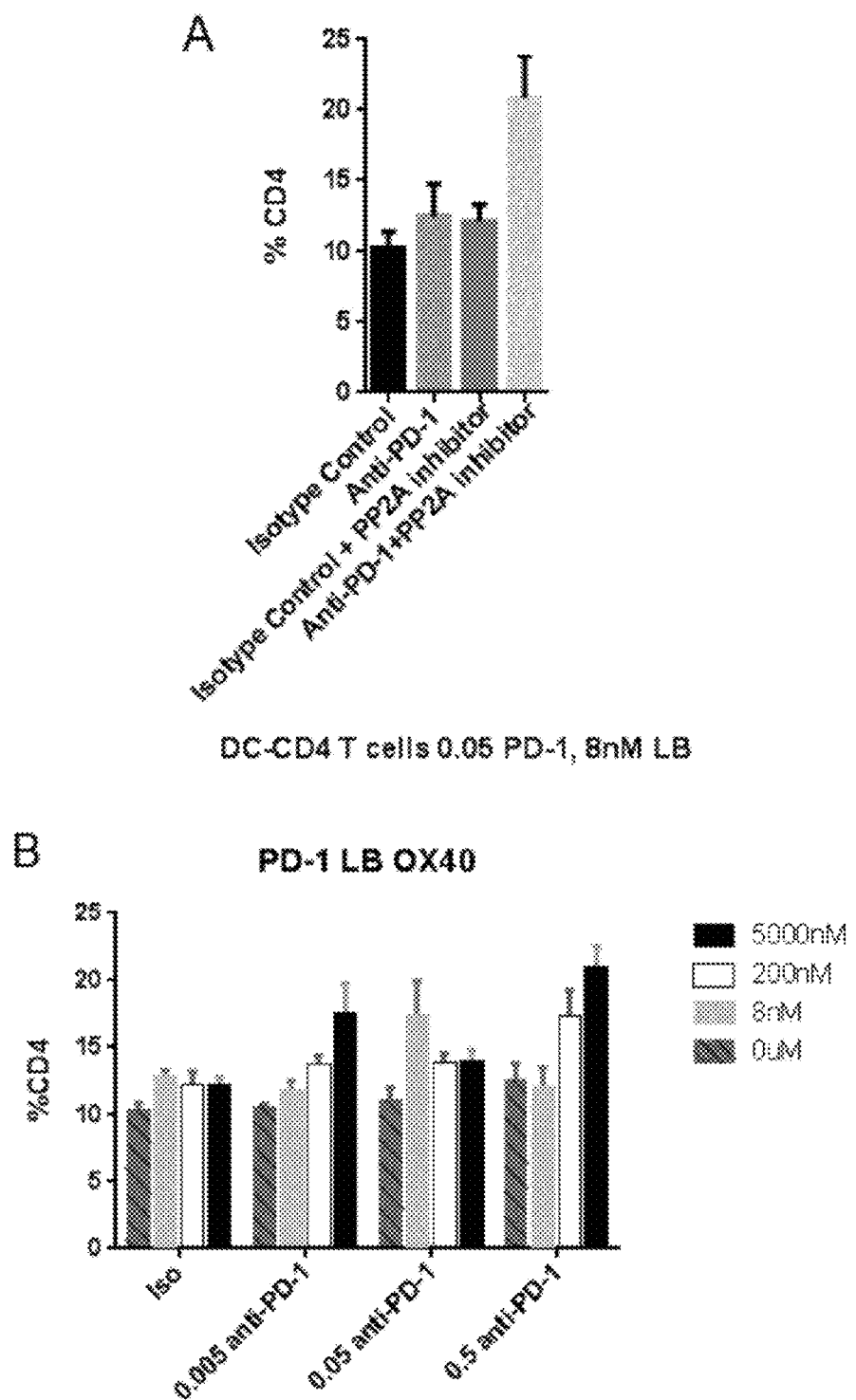

FIG. 10A. Enhanced OX40 expression in CD4 T cells with combination treatment. Percentage of OX40 expressing CD4 T cells co-cultured with monocyte-derived dendritic cells for 5 days in presence or absence of LB-100 at 8 nM with or without anti-PD1 antibody at 0.05 nM. LB-100 was added or replaced on the $3^{rd}$ day.

FIG. 10B. Enhanced OX40 expression in CD4 T cells with combination treatment. Percentage of OX40 expressing CD4 T cells co-cultured with monocyte-derived dendritic cells for 5 days in presence or absence of LB-100 at different concentrations with or without anti-PD1 antibody. LB-100 was added or replaced on the $3^{rd}$ day.

Figure 11:
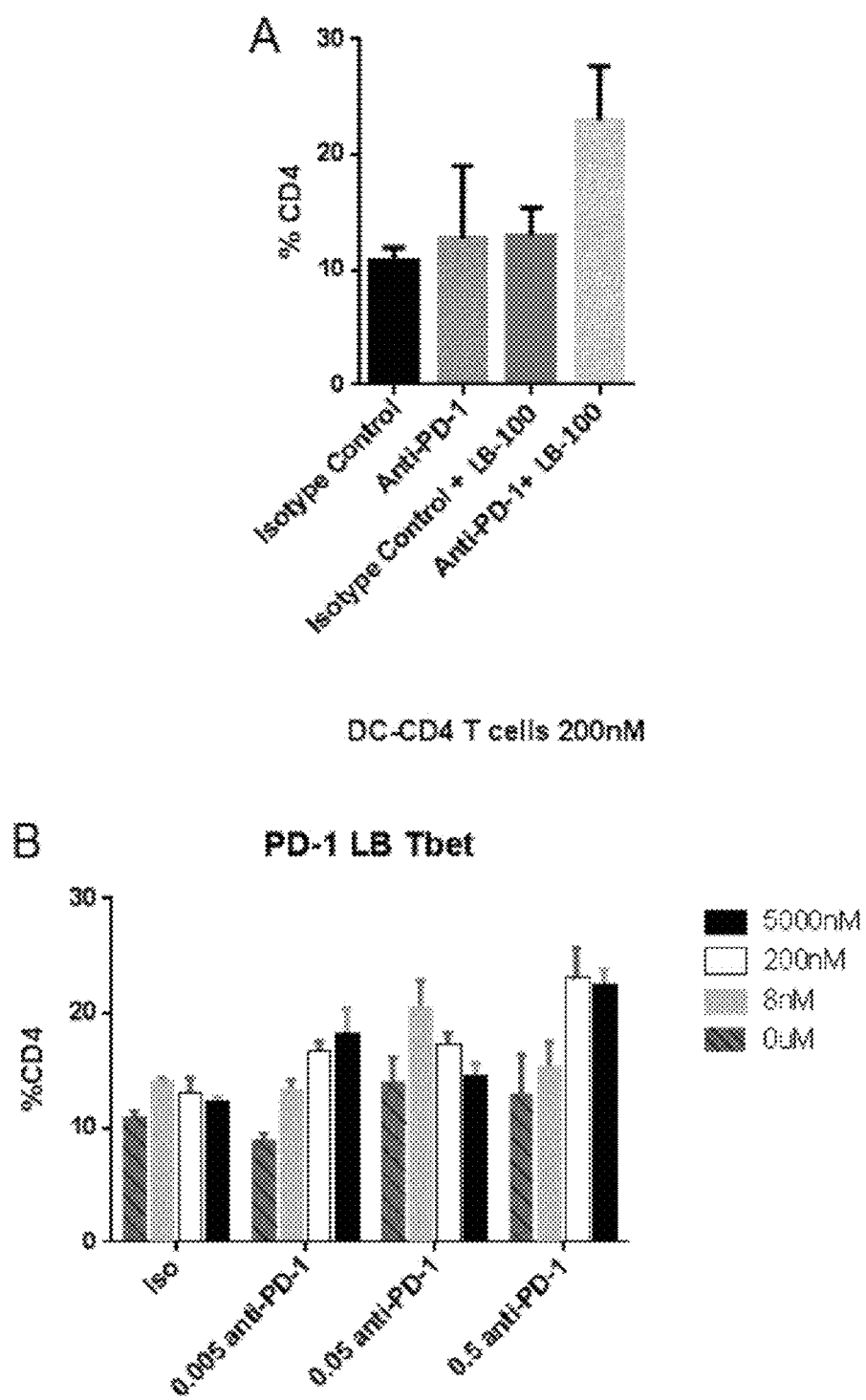

FIG. 11A. Enhanced Tbet expression in CD4 T cells with combination treatment. Percentage of Tbet expressing CD4 T cells co-cultured with monocyte-derived dendritic cells for 5 days in presence or absence of LB-100 at 200 nM with or without anti-PD1 antibody. LB-100 was added or replaced on the $3^{rd}$ day.

FIG. 11B. Enhanced Tbet expression in CD4 T cells with combination treatment. Percentage of Tbet expression in CD4 T cells co-cultured with monocyte-derived dendritic cells for 5 days in presence or absence of LB-100 at different concentrations with or without anti-PD1 antibody. LB-100 was added or replaced on the $3^{rd}$ day.

Figure 12:
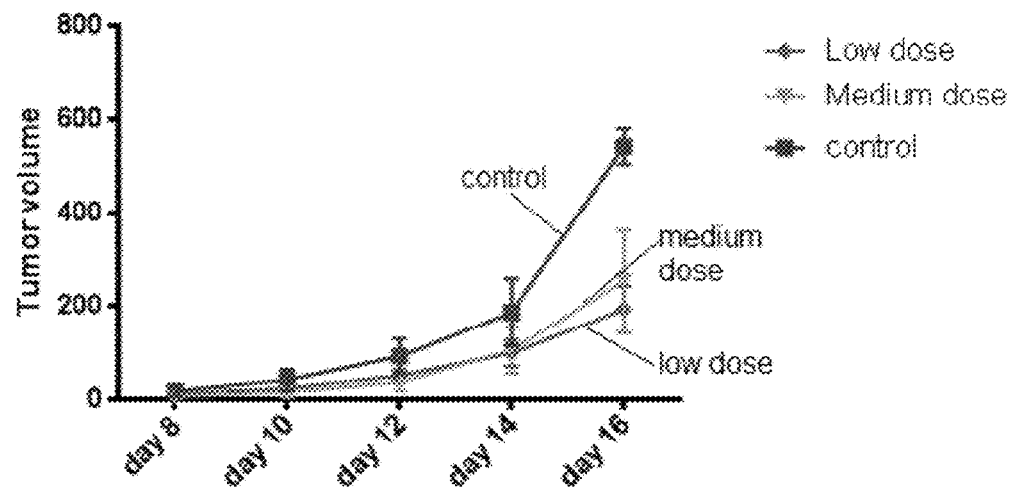

FIG. 12. PP2A inhibitor reduced mouse B16 melanoma tumor growth significantly in mice treated every two days for 8 doses. Treatment was started on the same day of tumor implantation. Control—PBS, Low dose—0.16 mg/kg, Medium dose—0.32 mg/kg.

Figure 13A:
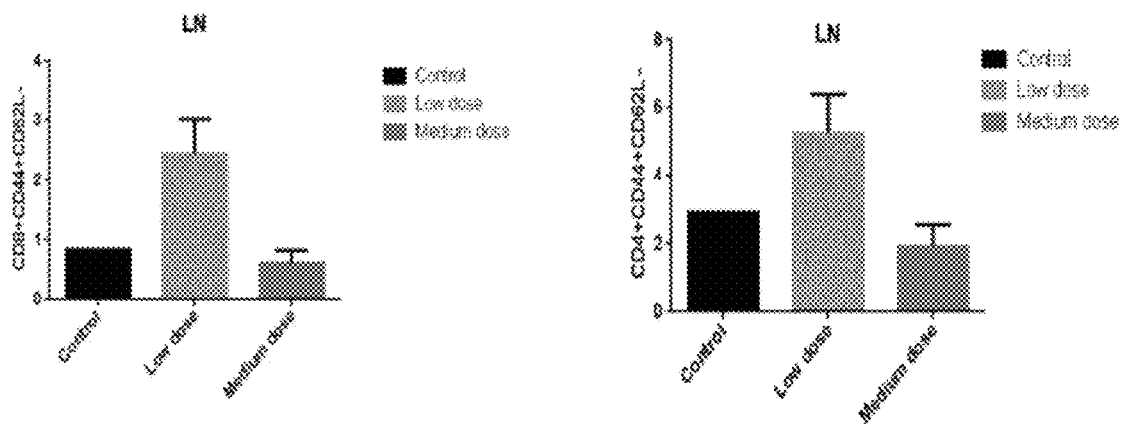
Figure 13:
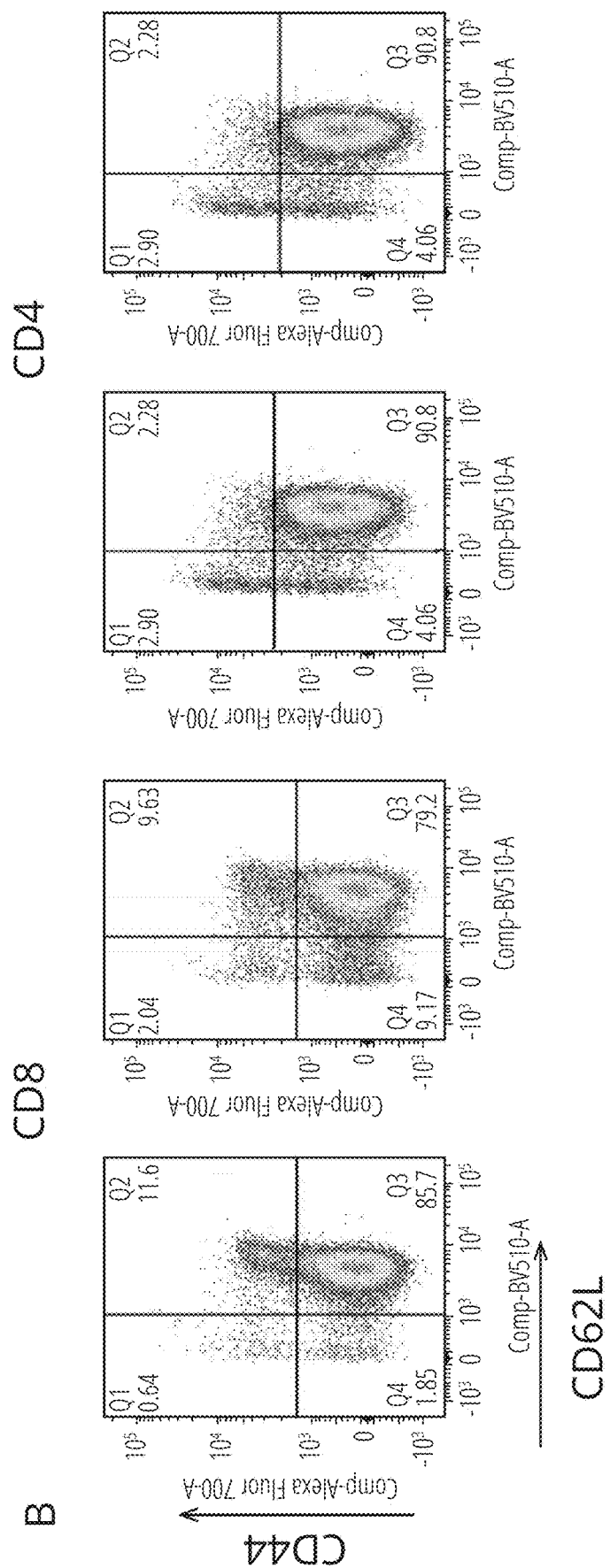

FIG. 13A. PP2A inhibitor increased CD4/8 effector cells in naïve mice. Low dose of LB treatment in vivo induced more CD8 (left) and CD4 (right) effector T cells in lymph node. 5 mice per group. Control—PBS, Low dose—0.16 mg/kg, Medium dose—0.32 mg/kg.

FIG. 13B. PP2A inhibitor increased CD4/8 effector cells in naïve mice. Representative flow cytometry plot of CD44+ CD62L− CD8 (left) and CD4 (right) in FIG. 13A. Control— PBS, Low dose—0.16 mg/kg, Medium dose—0.32 mg/kg.

Figure 14:
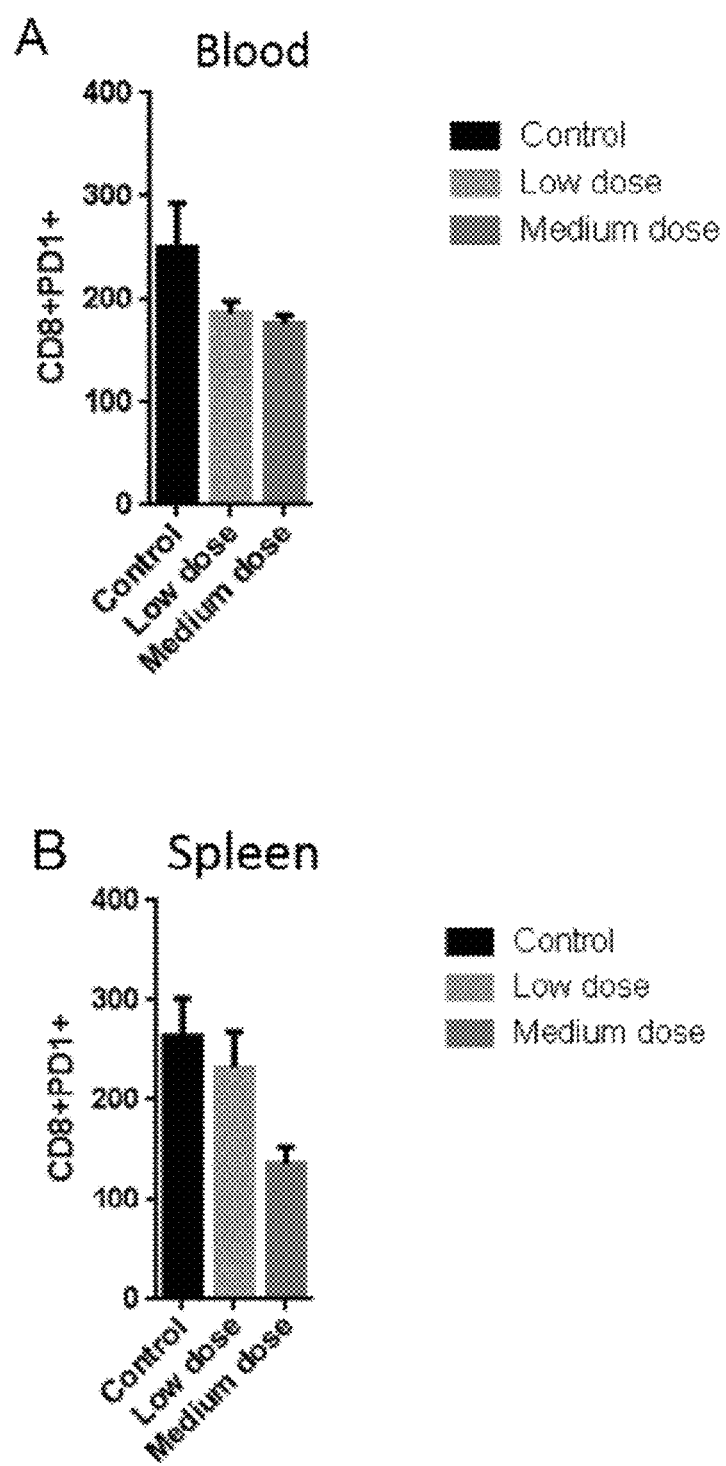

FIG. 14A. PP2A inhibitor reduced PD-1 expression on CD8 T cell in blood and spleen. Low dose of LB treatment in vivo reduced PD-1 expressing CD8+ T cells in blood.

FIG. 14B. PP2A inhibitor reduced PD-1 expression on CD8 T cell in blood and spleen. Medium dose of LB treatment in vivo reduced PD-1 expressing CD8+ T cells in spleen.

Figure 15:
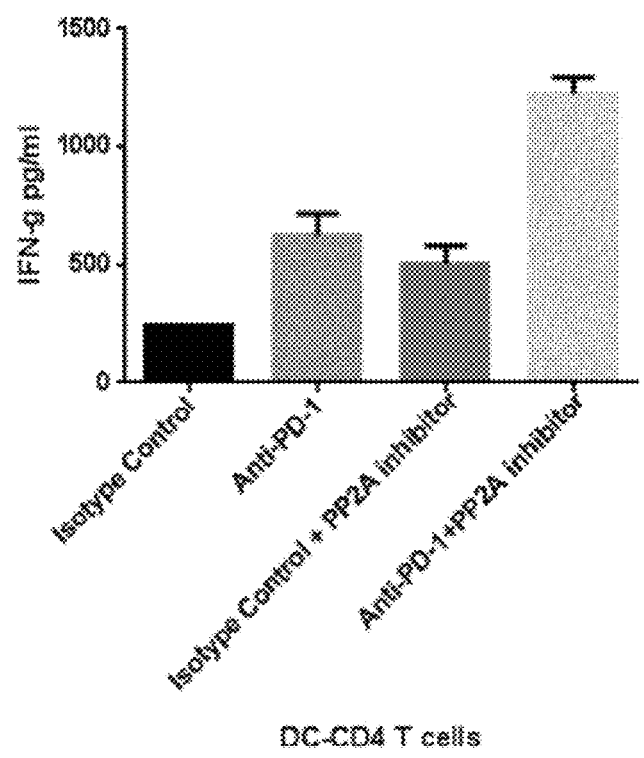

FIG. 15. PP2A inhibitor enhanced IFN-g production from human T cells. IFNγ production in the supernatant from CD4 T cells co-cultured with monocytes derived DC in presence of LB-100, or anti-PD-1 or combination (LB-100 and anti-PD-1).

Figure 16:
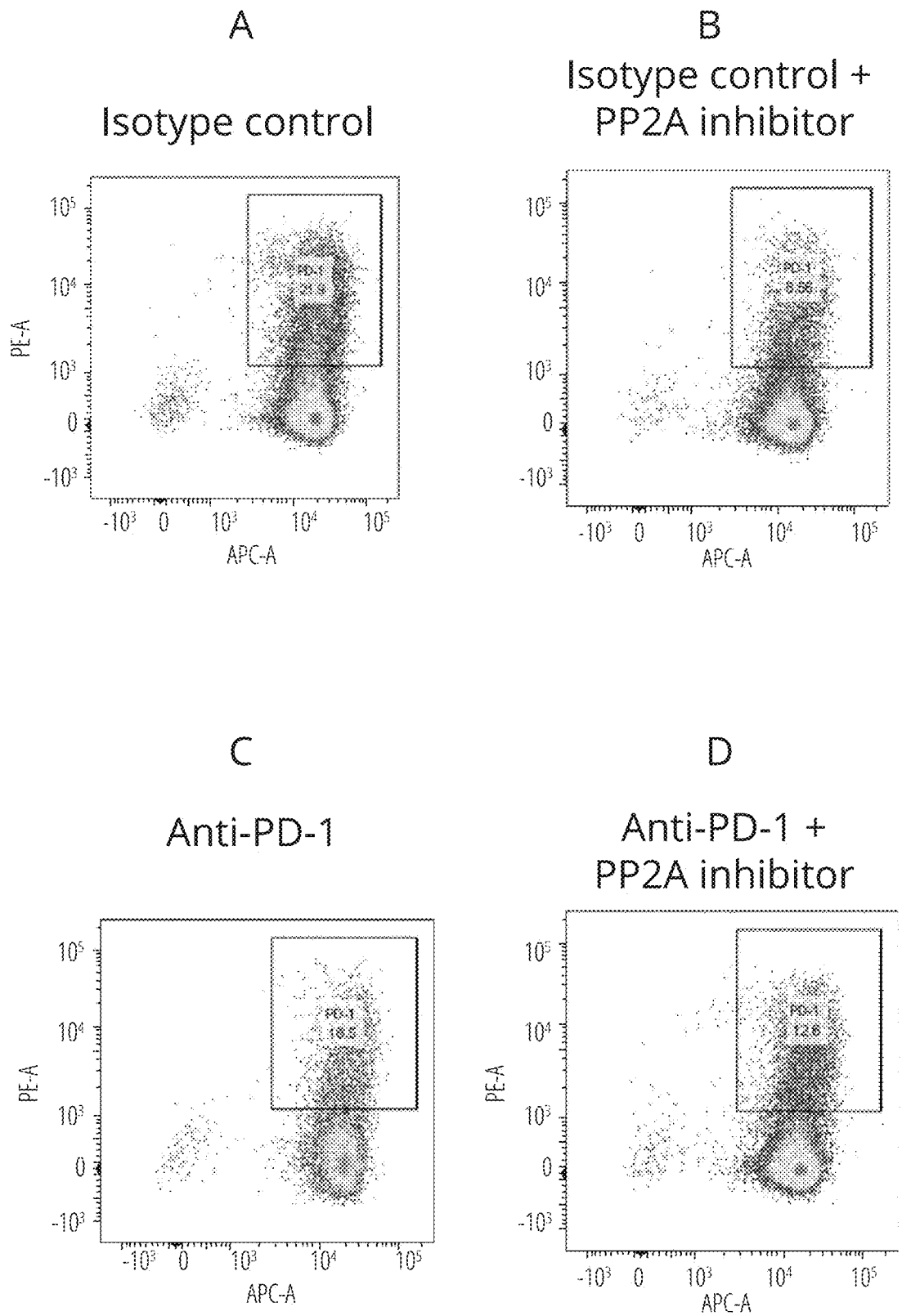

FIG. 16A. PP2A inhibitor reduced PD-1 expression on human CD4 T cells. Percentage of PD-1 expressing CD4 T cells which were co-cultured with monocytes derived DC in presence of isotype control.

FIG. 16B. PP2A inhibitor reduced PD-1 expression on human CD4 T cells. Percentage of PD-1 expressing CD4 T cells which were co-cultured with monocytes derived DC in presence of LB-100.

FIG. 16C. PP2A inhibitor reduced PD-1 expression on human CD4 T cells. Percentage of PD-1 expressing CD4 T cells which were co-cultured with monocytes derived DC in presence of anti-PD-1.

FIG. 16D. PP2A inhibitor reduced PD-1 expression on human CD4 T cells. Percentage of PD-1 expressing CD4 T cells which were co-cultured with monocytes derived DC in presence of combination (LB-100 and anti-PD-1).

Figure 17A:
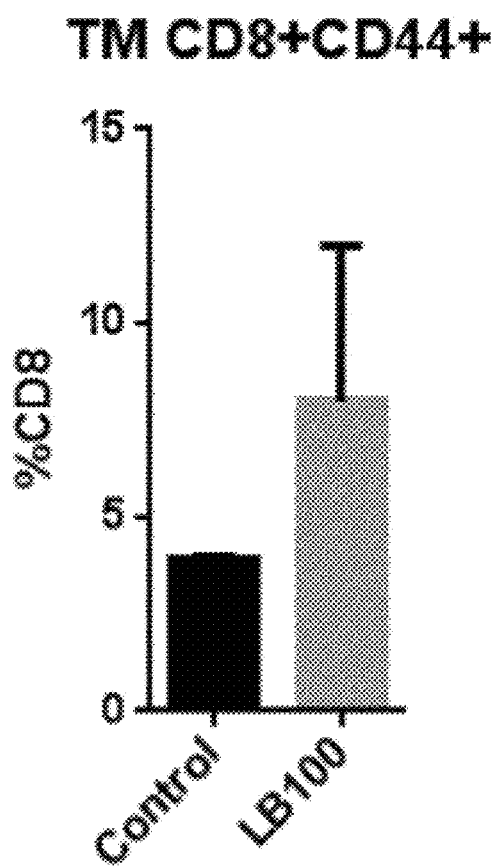

FIG. 17A. CD8+CD44+ effector T cells are increased with PP2A inhibitor LB-100 treatment. Percentage of CD8+ CD44+T effector cells population in tumor draining lymph node from B16 tumor bearing mice treated with LB-100 or PBS. 5 mice per group.

FIG. 17B. CD8+CD44+ effector T cells are increased with PP2A inhibitor LB-100 treatment. Representative flow cytometry plot of data shown in FIG. 17A.

Figure 18:
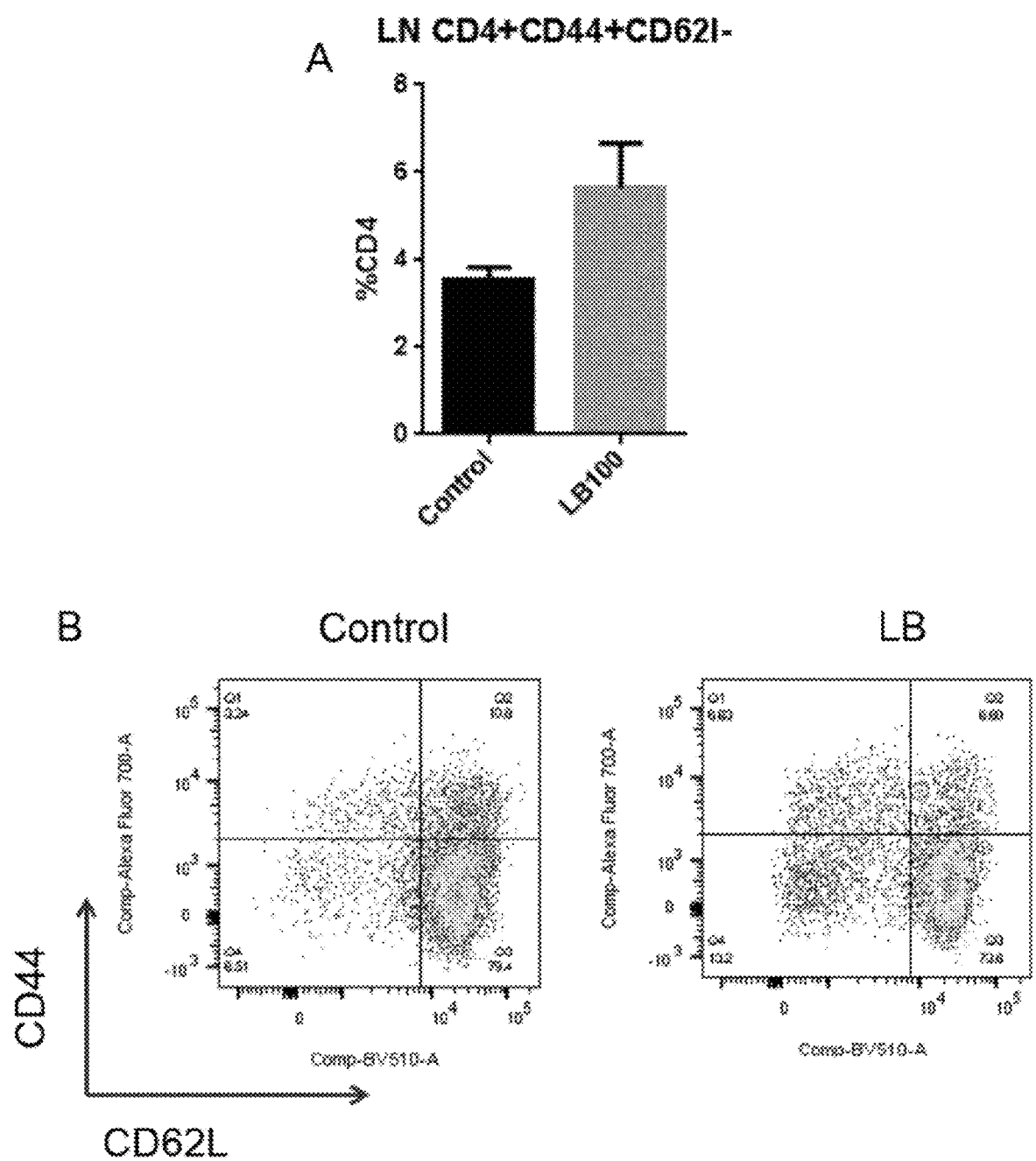

FIG. 18A. Increased CD44+CD62L− CD4 effector T cells in lymph node from B16 tumor bearing mice. Percentage of CD44+CD62L− CD4 effector T cells population in lymph node from B16 tumor-bearing mice treated with LB-100 or PBS. 5 mice per group.

FIG. 18B. Increased CD44+CD62L− CD4 effector T cells in lymph node from B16 tumor bearing mice. Representative flow cytometry plot of data shown in FIG. 18A.

FIG. 19A. Increased CD44+CD62L− CD8 effector T cells in lymph node from B16 tumor bearing mice. Percentage of CD44+CD62L− CD8 effector T cell population in lymph node from B16 tumor-bearing mice treated with LB-100 or PBS. 5 mice per group.

FIG. 19B. Increased CD44+CD62L− CD8 effector T cells in lymph node from B16 tumor bearing mice. Representative flow cytometry plot of data shown in FIG. 19A.

Figure 20:
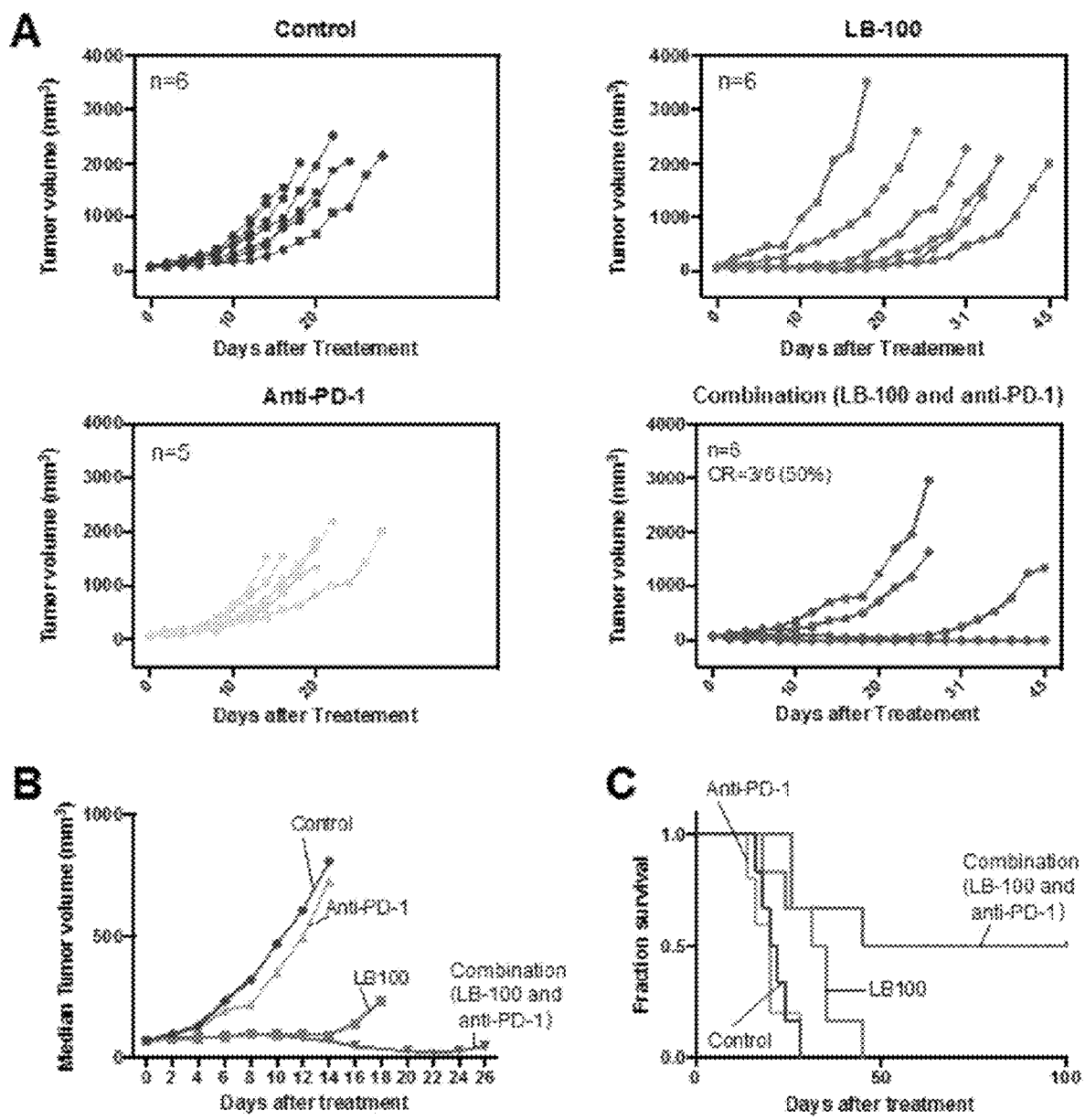

FIG. 20A. BALB/c mice were implanted with CT26 cells in their right thoracic flanks subcutaneously. After 13 days, mice with tumors reaching 30-100 $mm^3$ in size were randomized and treated with PBS control, anti-PD-L1, LB-100, or combination (LB-100 and anti-PD-1) for 28 days. Individual tumor volume over time.

FIG. 20B. BALB/c mice were implanted with CT26 cells in their right thoracic flanks subcutaneously. After 13 days, mice with tumors reaching 30-100 $mm^3$ in size were randomized and treated with PBS control, anti-PD-L1, LB-100, or combination (LB-100 and anti-PD-1) for 28 days. Median tumor volume over time.

FIG. 20C. BALB/c mice were implanted with CT26 cells in their right thoracic flanks subcutaneously. After 13 days, mice with tumors reaching 30-100 $mm^3$ in size were randomized and treated with PBS control, anti-PD-L1, LB-100, or combination (LB-100 and anti-PD-1) for 28 days. Mouse survival over time.

Figure 21:
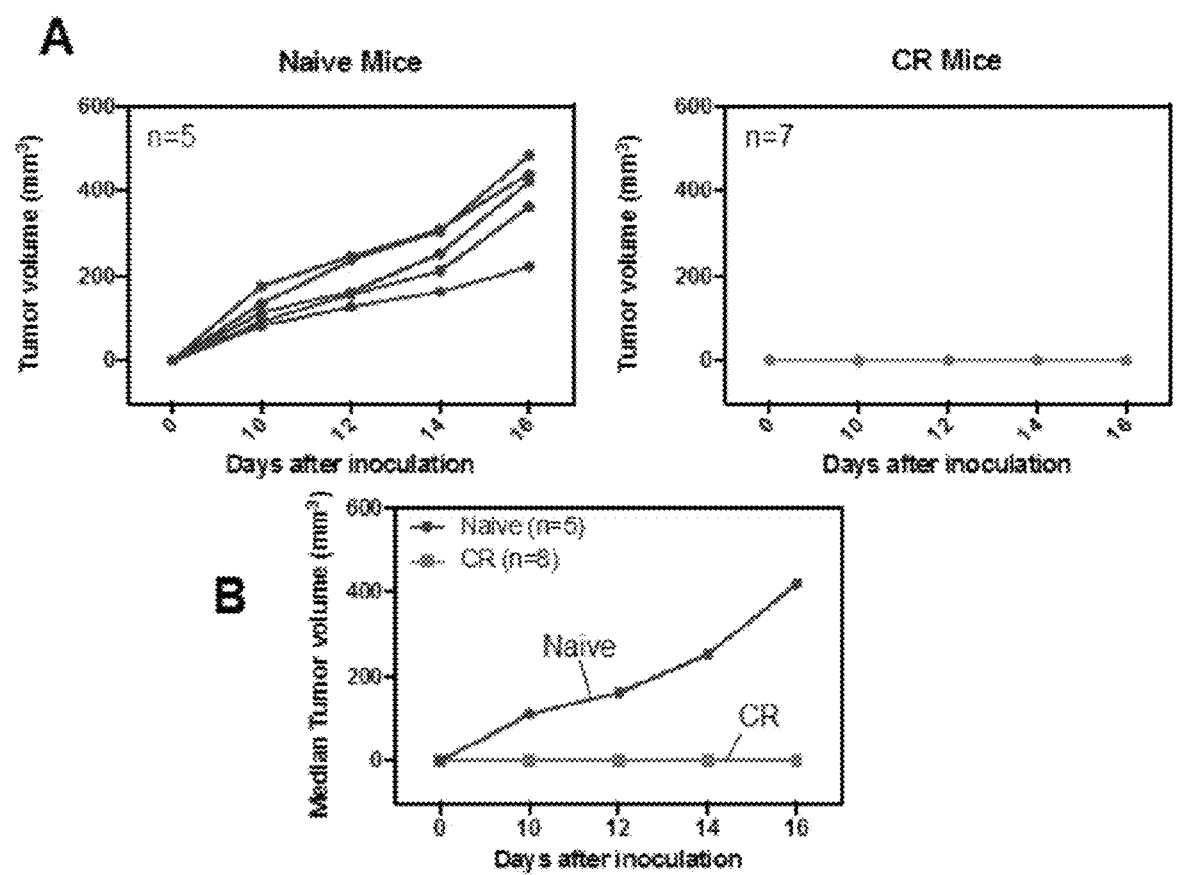

FIG. 21A. About 60 days after initial inoculation, cured mice and CT26-naive control mice, were (re)inoculated with CT26 cells in their left flanks. Individual tumor volumes over time.

FIG. 21B. About 60 days after initial inoculation, cured mice and CT26-naive control mice, were (re)inoculated with CT26 cells in their left flanks. Median tumor volumes over time.

Figure 22:
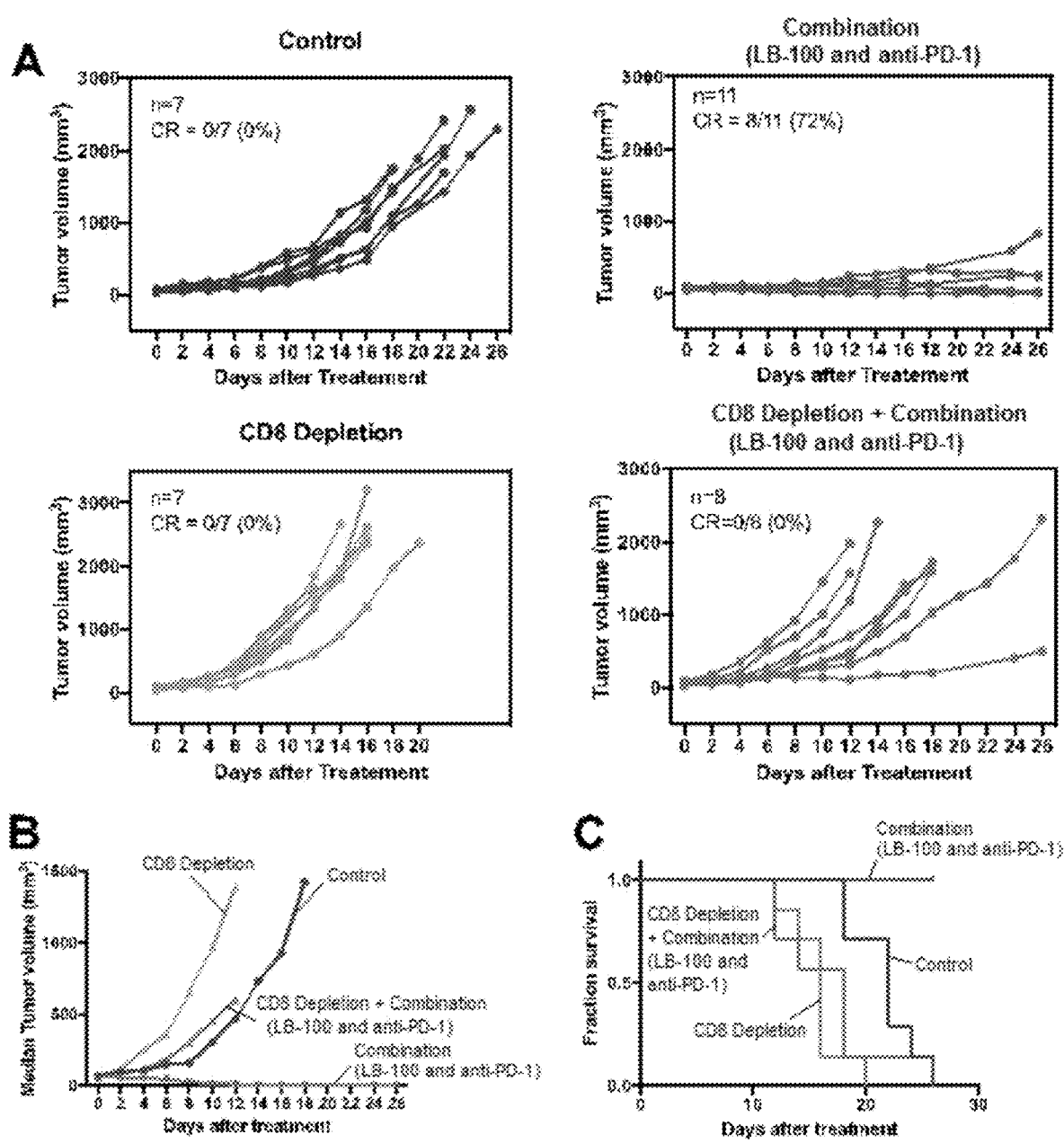

FIG. 22A. BALB/c mice were implanted with CT26 cells in their right thoracic flanks subcutaneously. After 11 days, mice with tumors reaching 30-100 mm³ in size, were randomized into four groups: Control, CD8 depletion, CD8 depletion+Combination (LB-100 and anti-PD-1), or Combination only (LB-100 and anti-PD-1). Mice in the depletion group were then given CD8 depleting antibodies. Two days later mice were then started on respective treatment. Individual tumor volume over time.

FIG. 22B. BALB/c mice were implanted with CT26 cells in their right thoracic flanks subcutaneously. After 11 days, mice with tumors reaching 30-100 mm³ in size, were randomized into four groups: Control, CD8 depletion, CD8 depletion+Combination (LB-100 and anti-PD-1), or Combination only (LB-100 and anti-PD-1). Mice in the depletion group were then given CD8 depleting antibodies. Two days later mice were then started on respective treatment. Median tumor volume over time.

FIG. 22C. BALB/c mice were implanted with CT26 cells in their right thoracic flanks subcutaneously. After 11 days, mice with tumors reaching 30-100 mm³ in size, were randomized into four groups: Control, CD8 depletion, CD8 depletion+Combination (LB-100 and anti-PD-1), or Combination only (LB-100 and anti-PD-1). Mice in the depletion group were then given CD8 depleting antibodies. Two days later mice were then started on respective treatment. Mouse survival over time.

Figure 23:
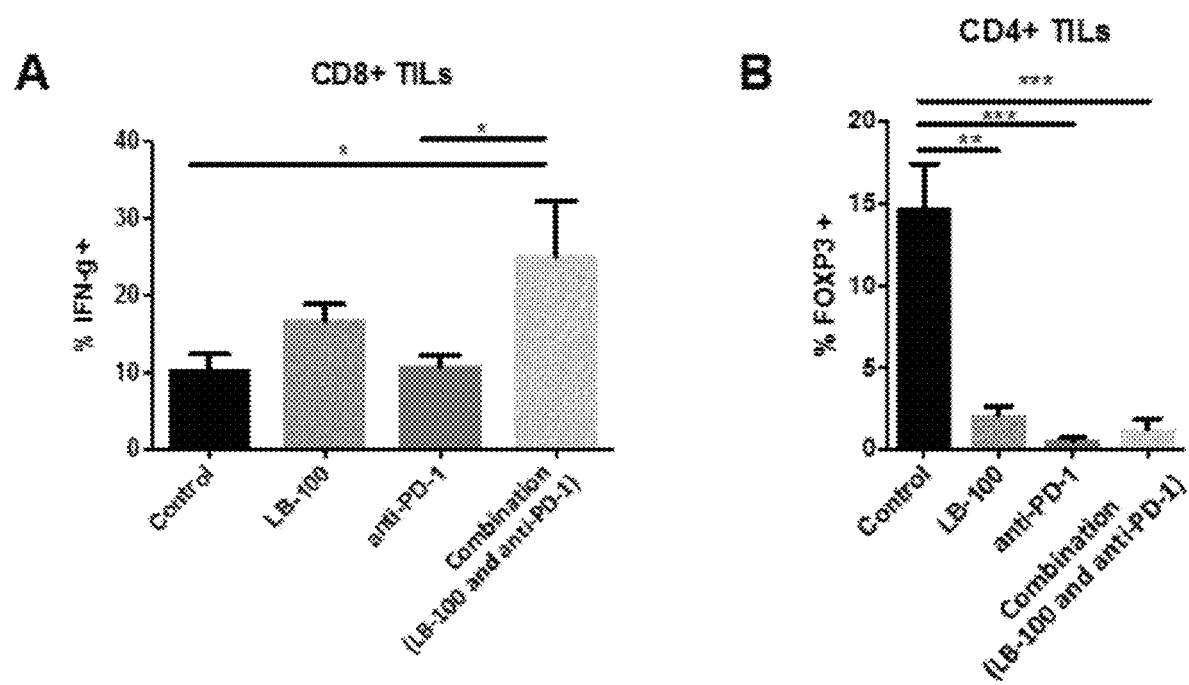

FIG. 23A. BALB/C mice were inoculated subcutaneously with CT26 tumor cells in the right thoracic flanks and treated with control (PBS), LB-100, anti-PD-1, or combination (LB-100 and anti-PD-1), as described in FIGS. 22A-C. Tumor-infiltrating T cells were analyzed by flow cytometry 12 days after the start of treatment. Percentage of CD8+ tumor infiltrating T cells producing IFNg+ after 4 hours of PMA stimulation was increased in the combination group (*p=0.05).

FIG. 23B. BALB/C mice were inoculated subcutaneously with CT26 tumor cells in the right thoracic flanks and treated with control (PBS), LB-100, anti-PD-1, or combination (LB-100 and anti-PD-1), as described in FIGS. 22A-C. Tumor-infiltrating T cells were analyzed by flow cytometry 12 days after the start of treatment. Percentage of CD4+ FoxP3+T-regulatory cells of CD45+ cells in the tumor was decreased in the LB-100 treatment group (**p<0.01).

Figure 24:
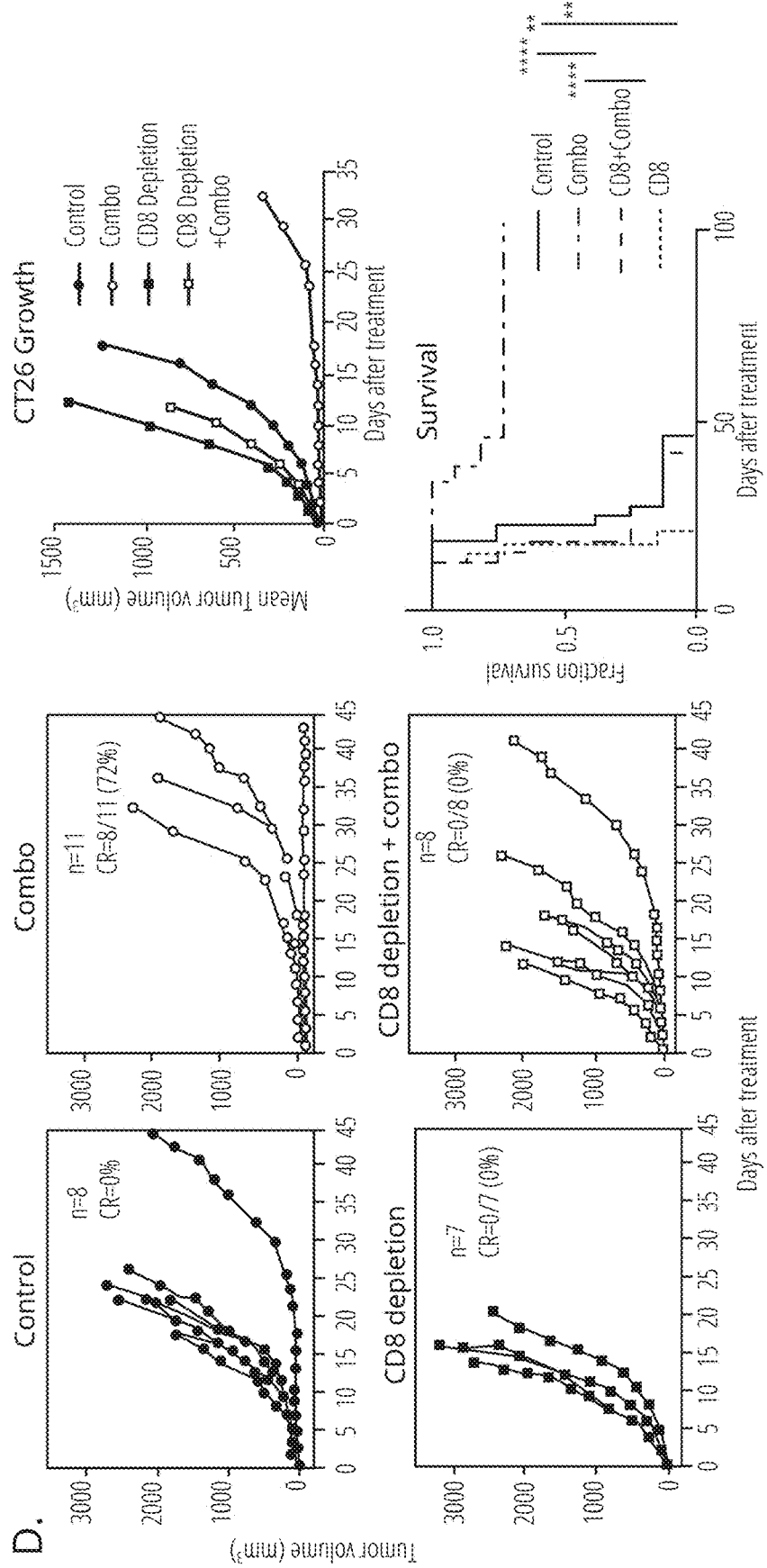

FIG. 24A. BALB/c mice were inoculated with 0.5×10⁶ CT26 cells subcutaneously in the right thoracic flank. When tumors reached between 50-100 mm³ mice were randomized to four treatment groups and treated every 2 days for 4 weeks.

FIG. 24B. Left, individual tumor growth curves: control, LB-100, a-PD-1, and combination. Middle, mean tumor size over time. Right, cumulative survival over time.

FIG. 24C. Efficacy of PP2A inhibition with PD-1 blockade is dependent on CD8+ T cells. BALB/c mice were inoculated as in 24A. When tumors reached 30-100 mm³, mice were temporarily depleted of CD8+ T cells and treated with combination.

FIG. 24D. Left, individual tumor growth curves: control, combination, CD-8 depletion only, and combination with CD8 depletion. Middle, mean tumor size over time. Right, cumulative survival over time. Data are representative of 2 independent experiments. *P<0.05, P<0.01 and **P<0.0001 (log-rank Mantel-Cox test).

Figure 25:
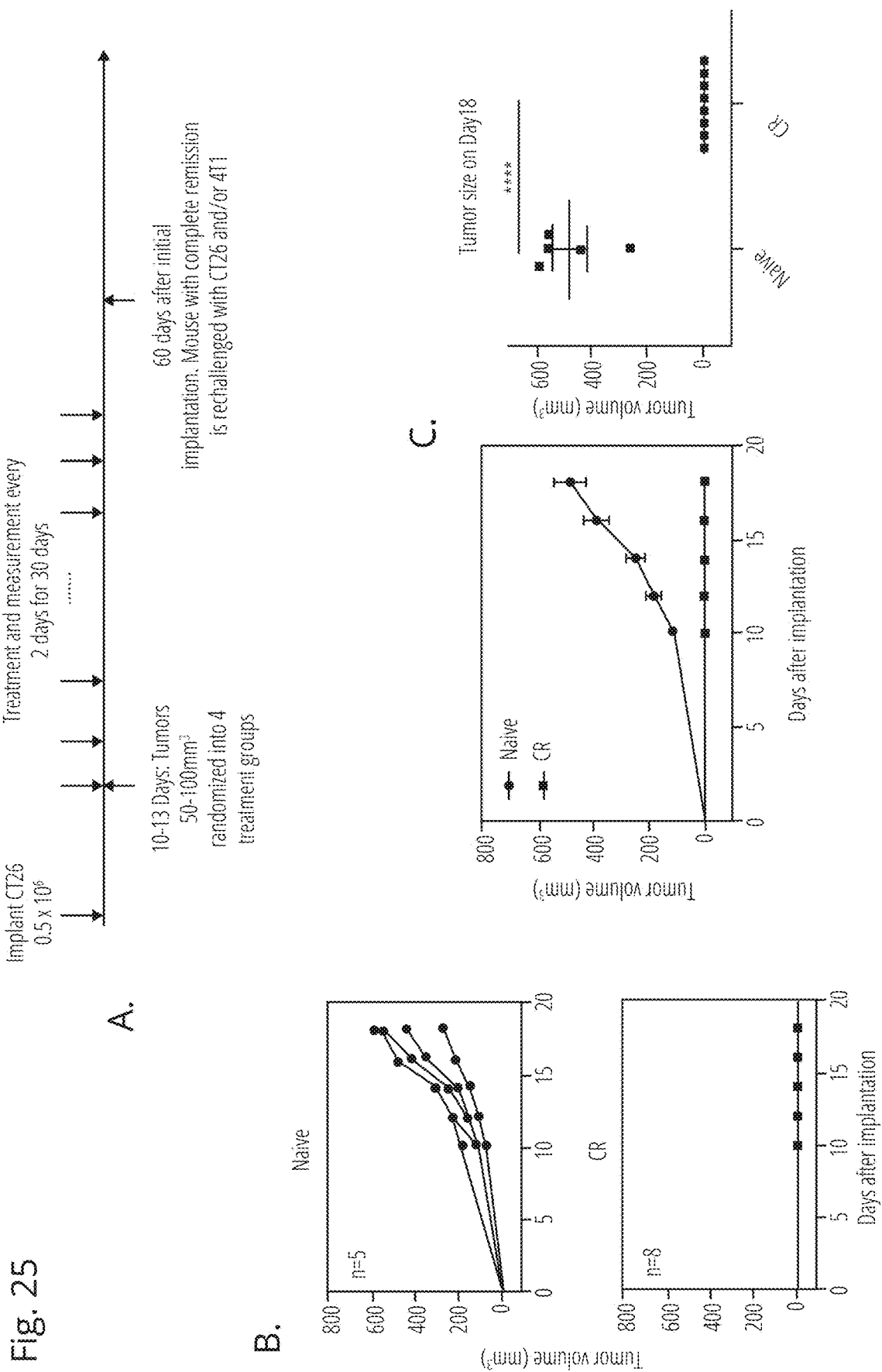
Figure 25:
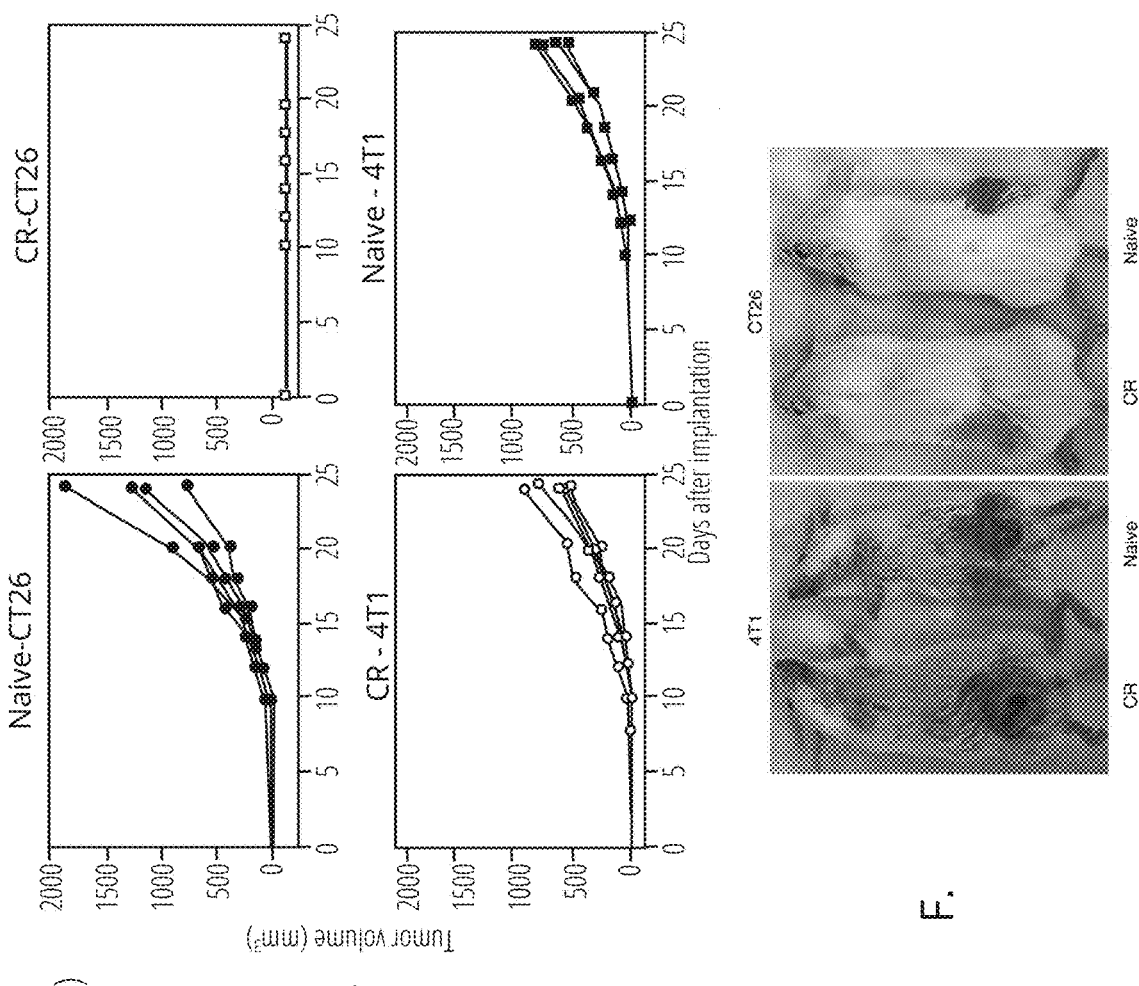

FIG. 25A. BALB/c mice were inoculated with 0.5×10⁶ CT26 cells subcutaneously and treated. CR or naïve control mice were re-challenged about 60-days after initial implantation with 0.5×10⁶ CT26 cells in the left thoracic flank or in combination with 1.25×10⁵ 4T1 breast carcinoma cells in the mammillary fat pad. Mice (re)-challenged with CT26 alone demonstrated no growth of CT 26 tumors.

FIG. 25B. Left, individual tumor growth curves: naive, CR. Right, mean tumor size over time.

FIG. 25C. Quantitation of CT26 tumor volume 18 days after inoculation. (P<0.001, two tailed student t-test).

FIG. 25D. CR and naïve mice were (re)-challenged with CT26 and 4T1 tumor cells: naïve-CT26, CR-CT26, naïve-4T1, CR-4T1. Left, individual tumor growth curves. Right, mean tumor size over time.

FIG. 25E. Quantitation of CT26 and 4T1 tumor volume 18 days after inoculation. (P<0.0001, one way ANOVA with Tukey's multiple comparison test).

FIG. 25F. Picture of representative naïve and CR mouse following inoculation CT26 and 4T1 tumors.

FIG. 26A. Representative FACS plots of CD44 and CD62L in CD8+ T cells in the spleen.

FIG. 26B. Quantification of CD62-CD44+(of CD8+ T cells) in the spleen (n=4-5).

FIG. 26C. Quantification of CD62-CD44+(of CD8+ T cells) in tumor draining lymph nodes (n=4-5).

FIG. 26D. Representative FACS plots of CD8+CD3+ T cells as percentage of CD45+ cells.

FIG. 26E. Immune infiltrate analysis of CD3+ expressed as percentage of CD45+ cells (n=5). Error bars depict SEM. Data represents one of two experiments with five independently analyzed mice/group.

FIG. 26F. Immune infiltrate analysis of CD8+ expressed as percentage of CD45+ cells (n=5). Error bars depict SEM. Data represents one of two experiments with five independently analyzed mice/group.

FIG. 26G. Immune infiltrate analysis of CD4+ expressed as percentage of CD45+ cells (n=5). Error bars depict SEM. Data represents one of two experiments with five independently analyzed mice/group.

FIG. 26H. Ratio of CD8+ to CD4+ cells in tumor. Error bars depict SEM. Data represents one of two experiments with five independently analyzed mice/group.

FIG. 26I. CD8+ and CD44+ expressed as percentage of CD45+ cells in tumor. Error bars depict SEM. Data represents one of two experiments with five independently analyzed mice/group.

FIG. 26J. CD8+ and Ki67+ expressed as percentage of CD45+ cells in tumor. Error bars depict SEM. Data represents one of two experiments with five independently analyzed mice/group.

FIG. 26K. Expression of PD1+ in CD8+ cells in tumor. *P<0.05, (one way ANOVA with Tukey's multiple comparison test).

FIG. 26L. Expression of CD4+ cells in tumor. *P<0.05, (one way ANOVA with Tukey's multiple comparison test).

FIG. 27A. Representative FACS plots of FoxP3+ and CD4+ T cells in tumors.

FIG. 27B. Percentage of CD4+FoxP3+ T cells of total CD3+ cells.

FIG. 27C. Ratio of CD8+ to CD4+FoxP3+ Treg cells in tumor (n=5).

FIG. 27D. Representative FACS plots of CD8+IFNγ+ T cells of CD45+ cells.

FIG. 27E. Percentage of CD8+IFNγ+ T cells of CD45+ cells.

FIG. 27F. Percentage of CD8+TNFα+ T cells of CD45+ cells.

FIG. 27G. Percentage of CD8+ double positive IFNγ+ TNFα+ T cells of CD45+ cells.

FIG. 27H. Percentage of CD8+GranzymeB+ T cells of CD45+ cells.

FIG. 27I. Percentage of CD4+IFNγ+ of CD4+ T cells.

FIG. 27J. Summary of CD45+ immune cell subsets and CD45− cells as determined by FACS. Subsets are depicted as percentage of all acquired live events (right) and CD3+ cells (left); Diagram on the right: Non CD45−, CD3+, Non CD3+CD45 leukocytes; Diagram on the left: CD8, CD4-Treg, CD4-conv. *$P<0.05$, (one way ANOVA with Tukey's multiple comparison test). Error bars depict SEM. Data represents one of two experiments with five independently analyzed mice/group.

FIG. 28A. Flow cytometric analysis of activation and immune checkpoint markers of (A) CD4+ in the spleen of mice receiving LB-100 and/or aPD-1 treatment. In CD4+ T cells, unlike CD8+ T cells, there was no change in expression of CD62L-CD44+ expression. There was also no change in expression of immune check point markers: PD1, CTLA4, TIM3 and Ox40.

FIG. 28B. Flow cytometric analysis of activation and immune checkpoint markers of CD8+ lymphocytes in the spleen of mice receiving LB-100 and/or aPD-1 treatment. In CD8+ T cells, there was no change in expression of immune check point markers: PD1, CTLA4, TIM3 and Ox40.

FIG. 29A. Flow cytometric analysis of activation and immune checkpoint markers of CD4+ in the draining lymph node (dLN) of mice receiving LB-100 and/or aPD-1 treatment. In CD4+ T cells, unlike CD8+ T cells, there was no change in expression of CD62L-CD44+ expression. There was a small, but significant increase in PD-1 expression in aPD-1 treated groups, but LB-100 alone or in combination did not further alter PD-1 expression. There was no change in expression of other immune check point markers: CTLA4, TIM3 and Ox40. *$P<0.05$, **$P<0.01$ (one way ANOVA with Tukey's multiple comparison test). Error bars depict SEM.

FIG. 29B. Flow cytometric analysis of activation and immune checkpoint markers of CD8+ lymphocytes in the draining lymph node (dLN) of mice receiving LB-100 and/or aPD-1 treatment. In CD8+ T cells, there was no change in expression of immune check point markers: PD1, CTLA4, TIM3 and Ox40. *$P<0.05$, **$P<0.01$ (one way ANOVA with Tukey's multiple comparison test). Error bars depict SEM.

Figure 30:
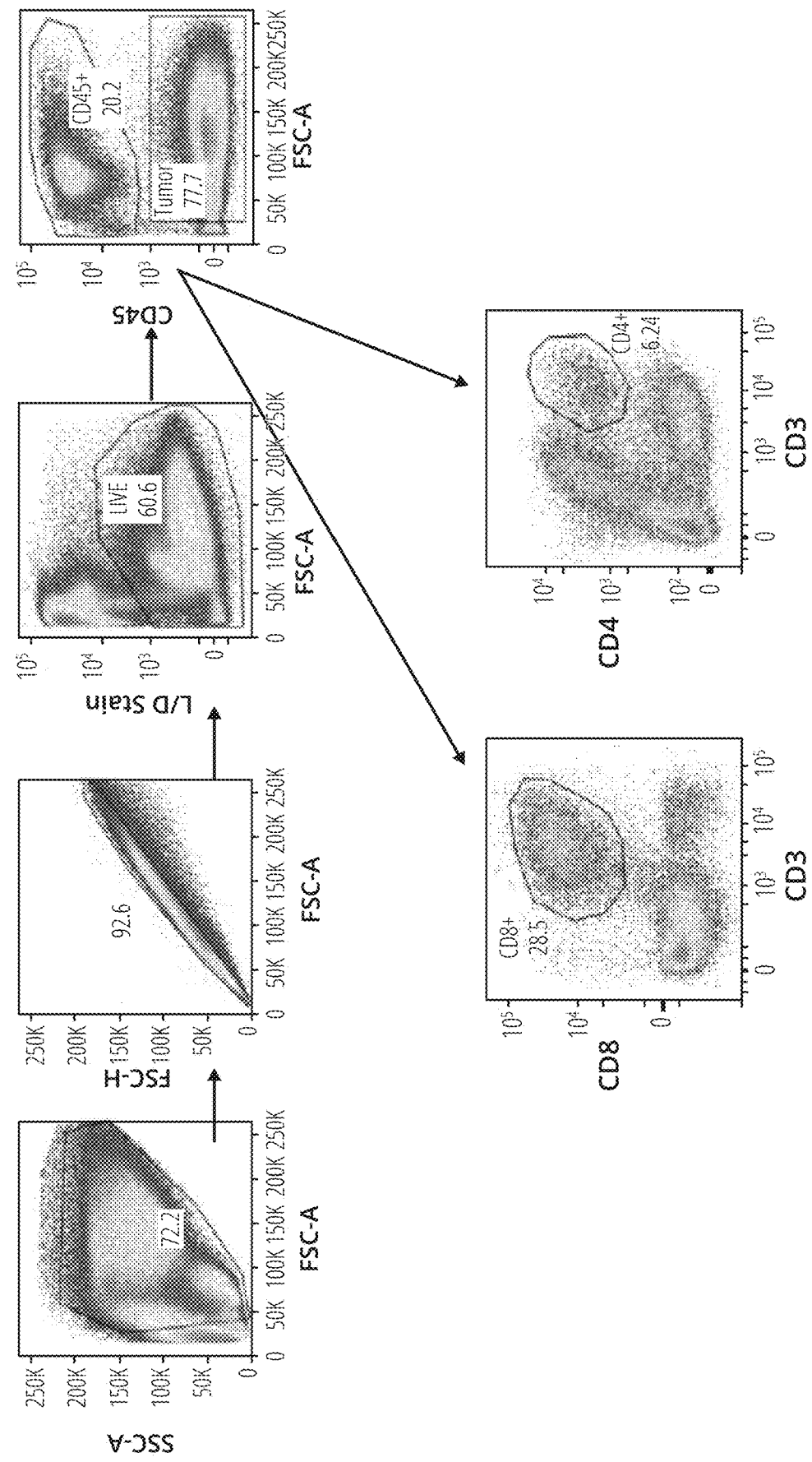

FIG. 30. Gating strategy for flow cytometric analysis of tumor infiltrating lymphocytes. SSC-FSC gate was used to exclude non-cellular debris, followed by exclusion of duplets by FSC-H-FSA-A gate. Fixable live-dead (L/D) stain was used to exclude dead cells. Live cells were then gated based on expression of CD45+ pan leukocyte marker. CD45− cells were considered as tumor cells. CD45+ cells were then phenotyped further based on CD3, CD8, CD4 expression. CD45+CD3+CD8+ cells were gated as CD8+ lymphocytes, while CD45+CD3+CD4+ cells were gated as CD4+ lymphocytes. Further, staining of the CD4+ and CD8+ subsets were then performed as indicated in the text.

FIG. 31A. The ratios of CD3+, CD8+, and CD4+ cells to CD45− tumor-resident cells were shown for each treatment group. There was an increase in CD3/tumor and CD8/tumor ratios in the combination group compared to control, while there was no change in CD4/tumor ratio.

FIG. 31B. The number of CD3+, CD8+ and CD4+ cell per gram of tumor weight were shown for each treatment group. A similar trend was seen as in FIG. 31A, but there were significant differences in CD3+ and CD8+ per gram tumor in aPD-1 treated group alone compared to control. There was a trend of further increase in CD3+ and CD8+/tumor for combination treatment, but there was no statistical significance. *$P<0.05$, ***$P<0.001$ (one way ANOVA with Tukey's multiple comparison test). Error bars depict SEM.

Figure 32:
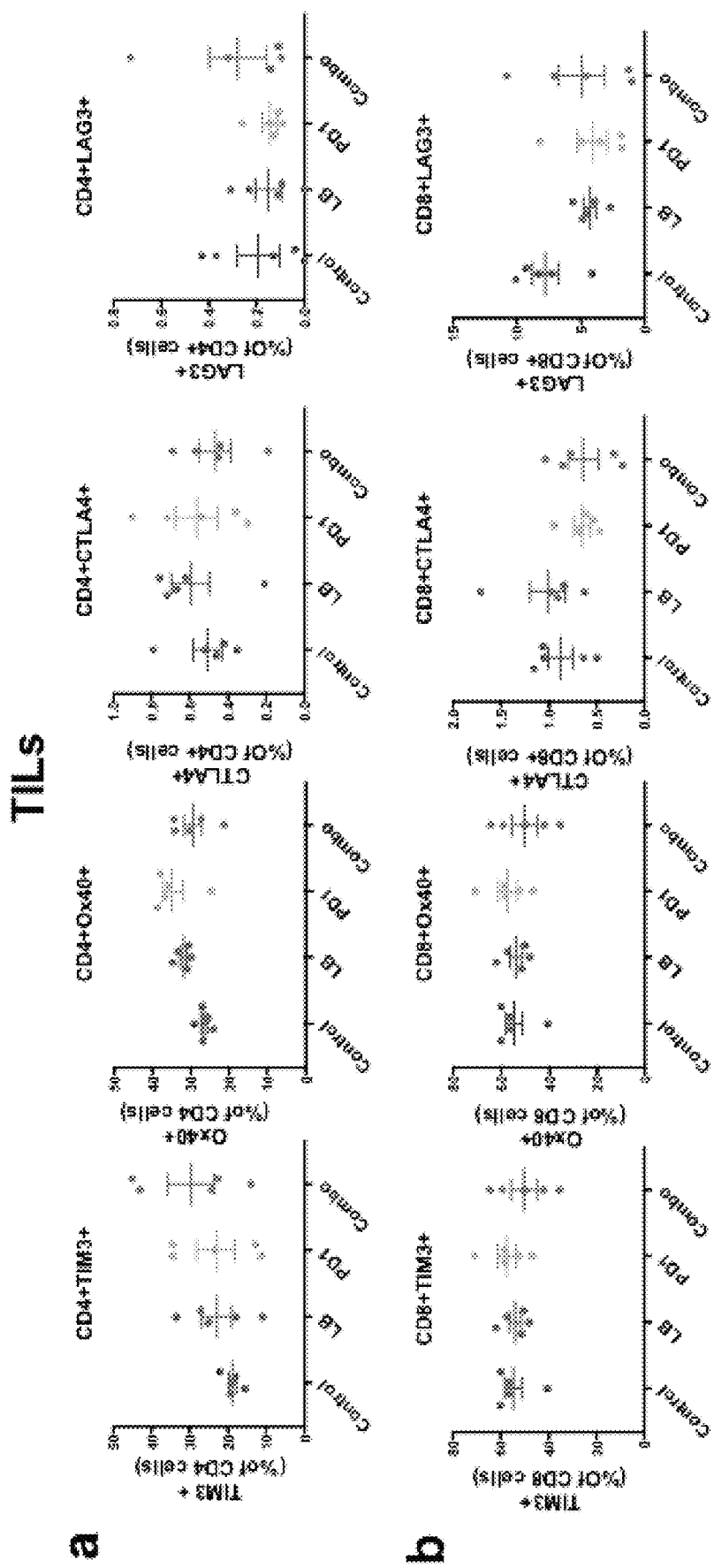

FIG. 32A. Flow cytometric analysis of and immune checkpoint markers of CD4+ lymphocytes in tumors of mice receiving LB-100 and/or aPD-1 treatment. In CD4+ T cells, there was no change in expression of immune check point markers: TIM3, Ox40, CTLA4 and LAG3.

FIG. 32B. Flow cytometric analysis of and immune checkpoint markers of CD8+ lymphocytes in tumors of mice receiving LB-100 and/or aPD-1 treatment. In CD8+ T cells, there was no change in expression of immune check point markers: TIM3, Ox40, CTLA4 and LAG3.

Figure 33:
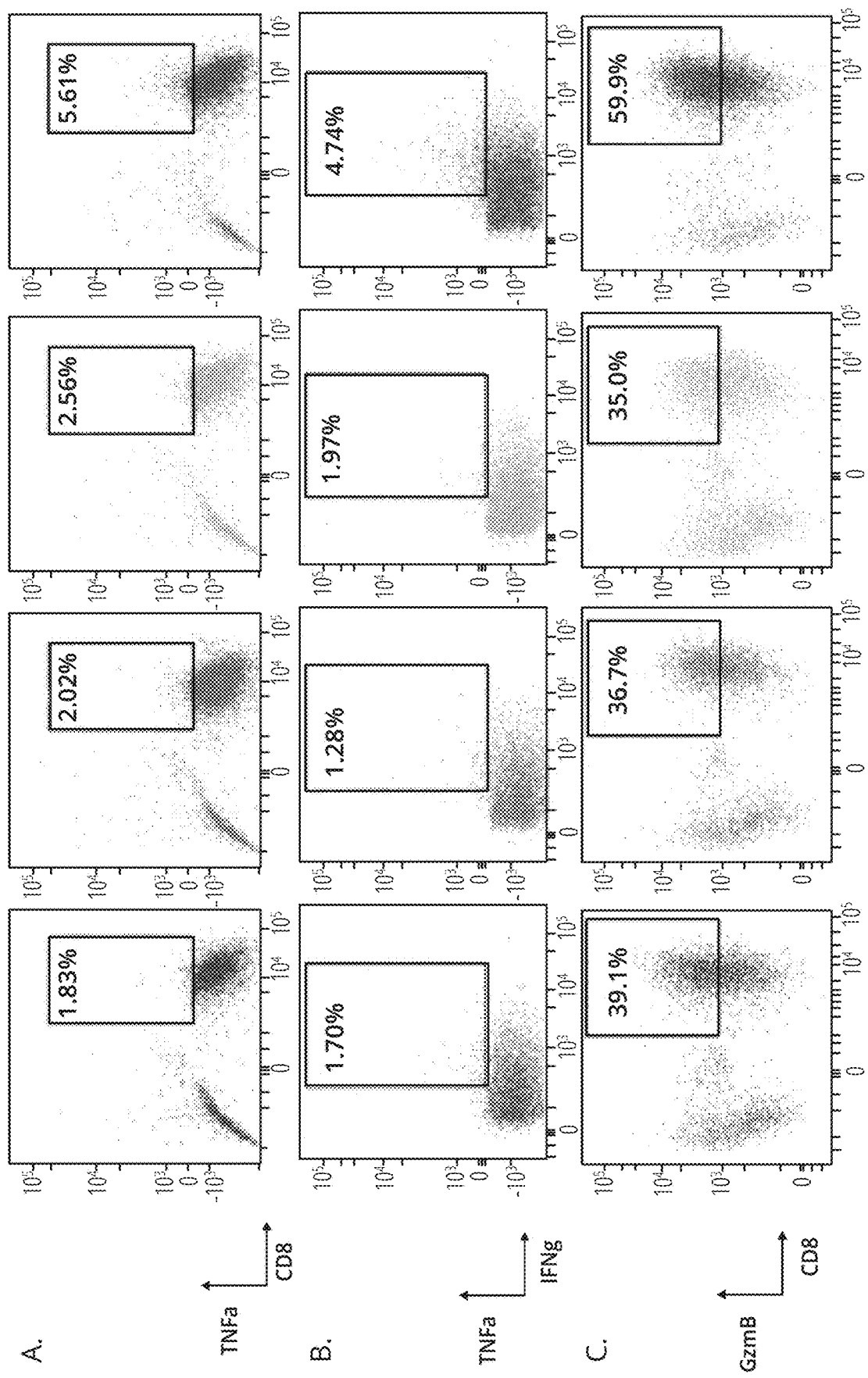

FIG. 33A. Representative flow cytometry plot showing increased TNF-α+. Percentage displayed are of total CD3+.

FIG. 33B. Representative flow cytometry plot showing increased TNF-α+IFN-γ+ double positive. Percentage displayed are of total CD8+.

FIG. 33C. Representative flow cytometry plot showing increased GranzymeB+CD8 tumor infiltrating T-cells. Percentage displayed are of total CD3+ cells.

Figure 34:
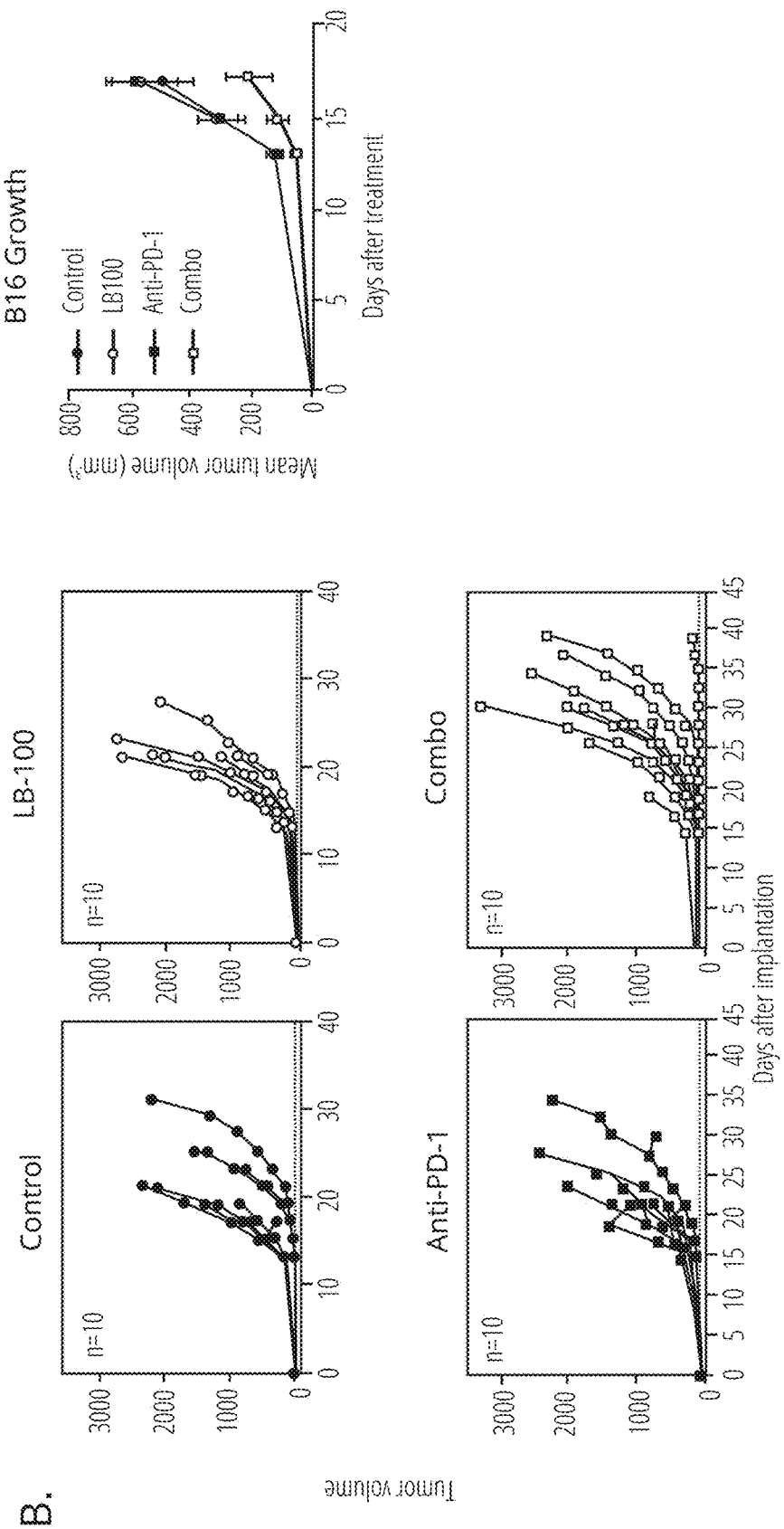
Figure 34:
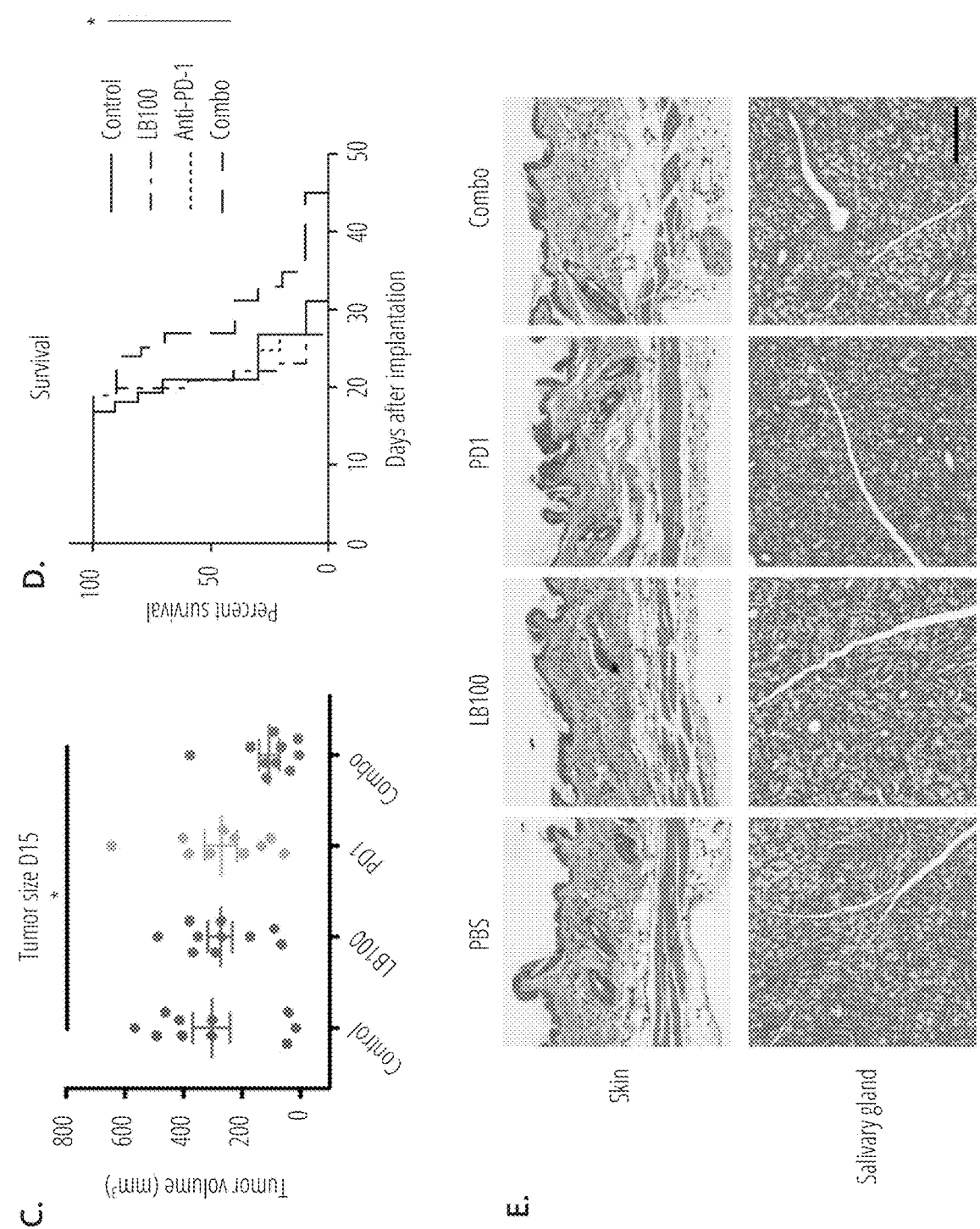

FIG. 34A. C57BL/6 mice were randomized into four treatment groups. $2.5 \times 10^5$ B16F10 cells were inoculated 2 days after initiation of treatment subcutaneously in the right thoracic flank. Mice were treated every two days until survival endpoint.

FIG. 34B. Left, individual tumor growth curves: control, LB-100, a-PD-1, and combination. Right, mean tumor size over time.

FIG. 34C. Quantitation of B16 tumor volume 15 days after inoculation. ($P<0.0001$, one way ANOVA with Tukey's multiple comparison test)

FIG. 34D. Cumulative survival over time. *$P<0.05$, (log-rank Mantel-Cox test) Data are pooled from 2 independent experiments.

FIG. 34E. Representative images of hematoxylin-and-eosin staining of the skin and salivary gland of each treatment group (n=2-3 per group). Scale bars, 100 m.

Figure 35:
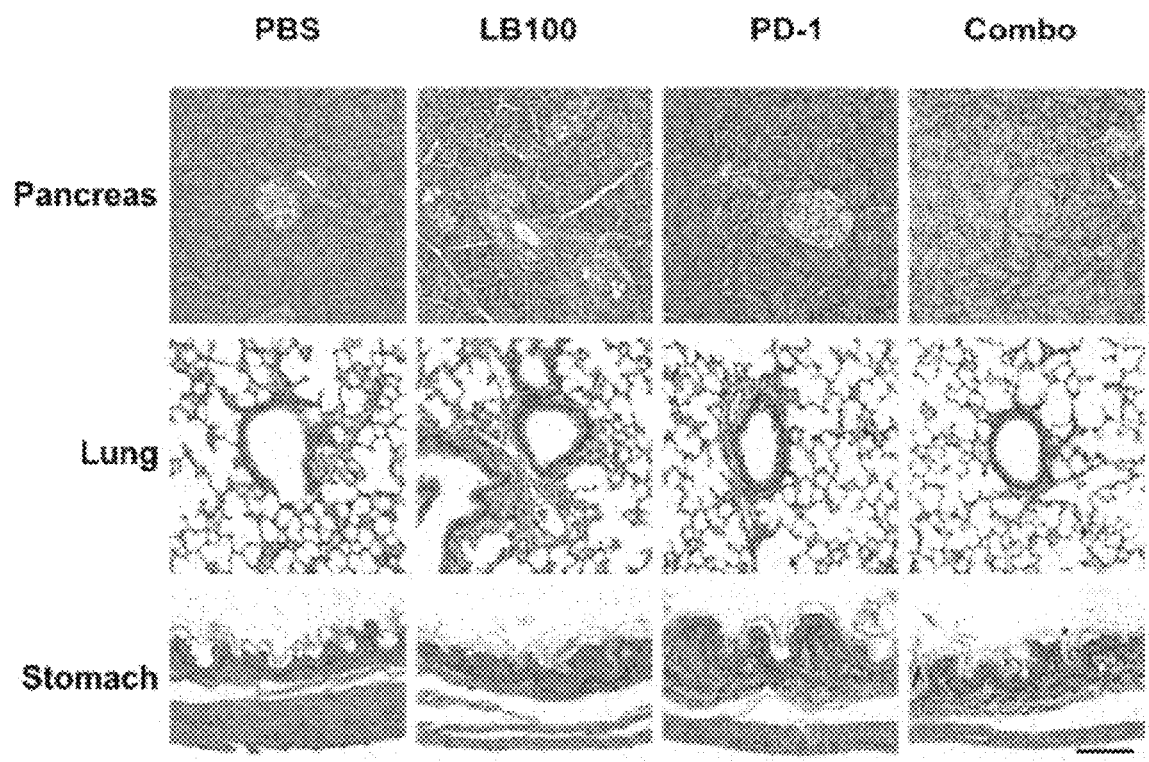

FIG. 35. Representative images of hematoxylin-and-eosin staining of the pancreas, lung and stomach of each treatment group (n=2-3 per group). Scale bars, 100 m.

Figure 36:
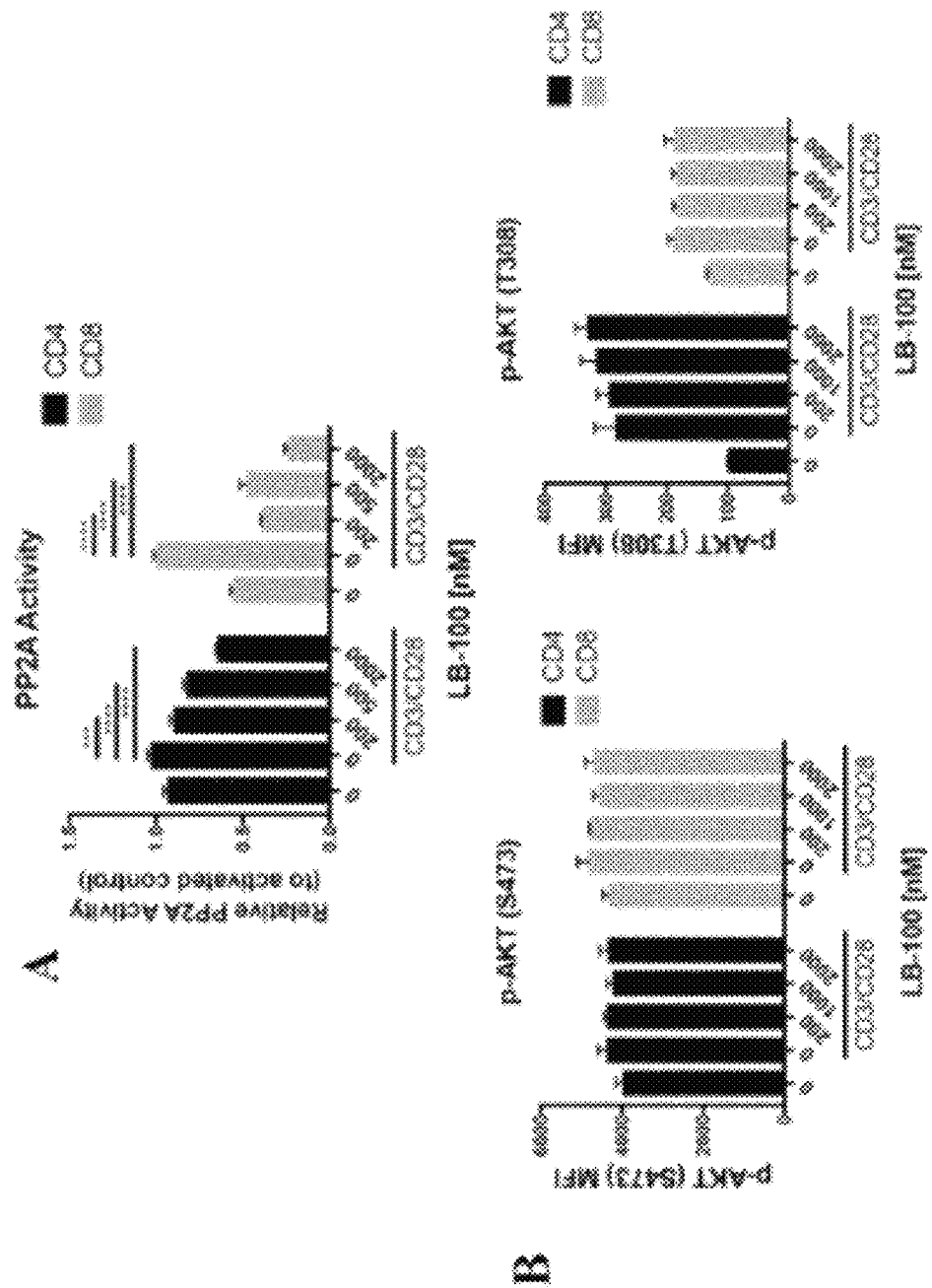
Figure 36:
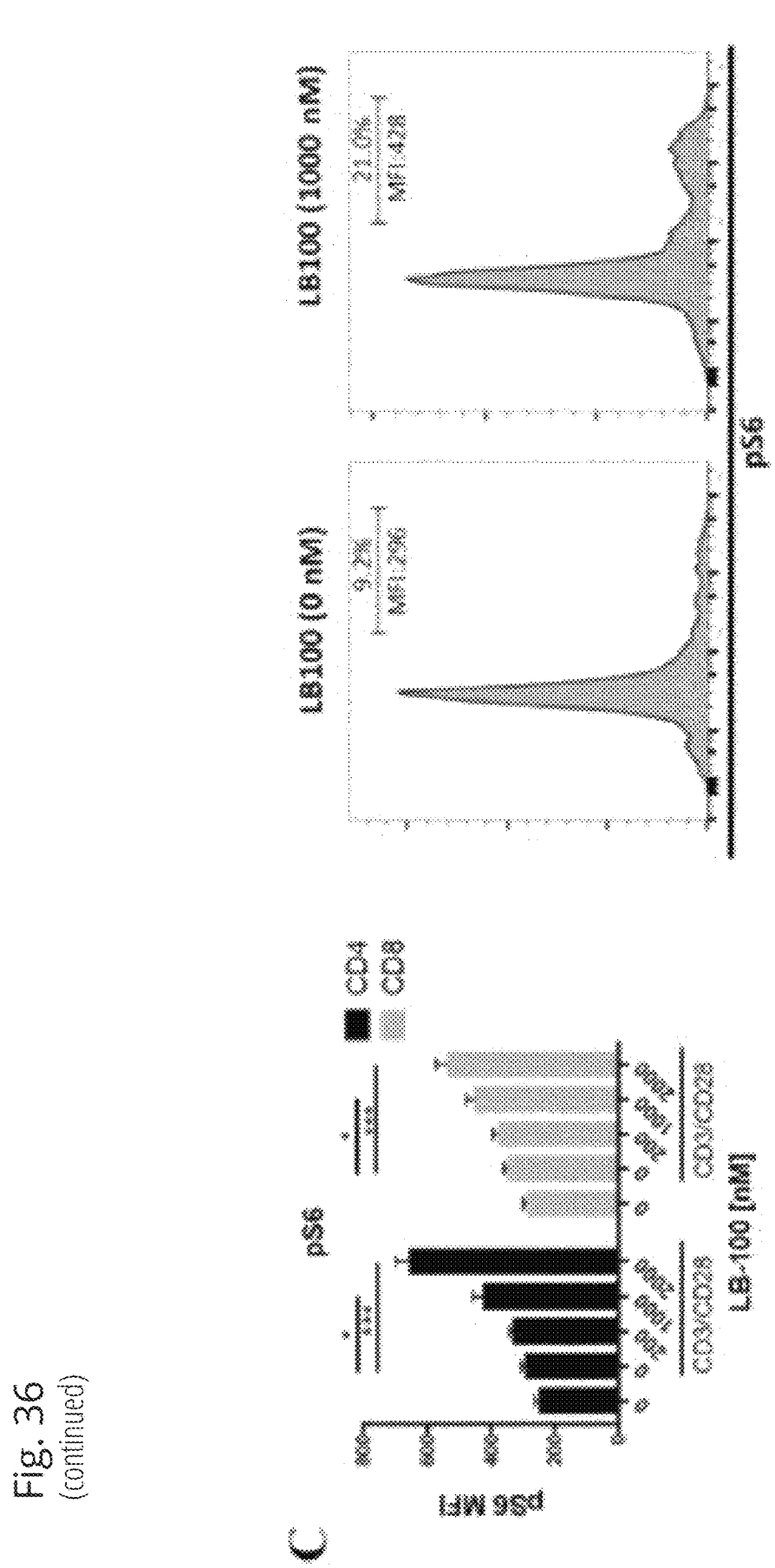

FIG. 36A. CD3 T cells were isolated from mice splenocytes and cultured with or without stimulation using immobilized anti-CD3 (10 .ig/ml) and soluble anti-CD28 (2 .ig/ml). PP2A enzymatic activity was measured after 3 hours of activation. PP2A activity was measured as relative to activated control in presence of LB-100 dose titration.

FIG. 36B. Flow cytometry analyzing AKT phosphorylated at Thr308 (p-AKT(T308)) or Ser473 (p-AKT(5473)) after 3 hours of stimulation in presence of LB-100 dose titration.

FIG. 36C. Flow cytometry analyzing phosphorylated S6 (p-S6) in presence of LB-100 dose titration. *$P<0.05$, ***$P<0.001$, (one way ANOVA with Tukey's multiple comparison test). Data are from one experiment representative of two independent experiments with similar results. Error bars depict SEM.

Figure 37:
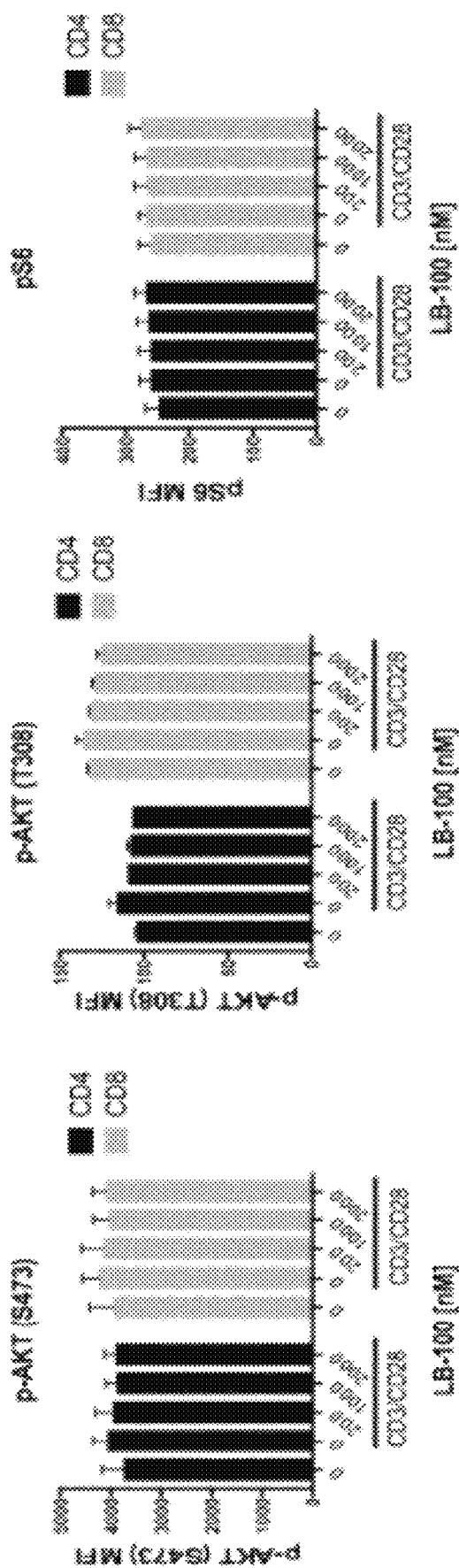

FIG. 37. AKT and mTORC signaling after 30 minutes of stimulation. Flow cytometry analyzing AKT phosphorylated at Thr308 (p-AKT(T308)), Ser473 (p-AKT(5473)) or phosphorylated S6 (p-S6) after 30 minutes of stimulation in presence of LB-100 dose titration. (one way ANOVA with Tukey's multiple comparison test). Data are from one experiment representative of two independent experiments with similar results. Error bars depict SEM.

Figure 38:
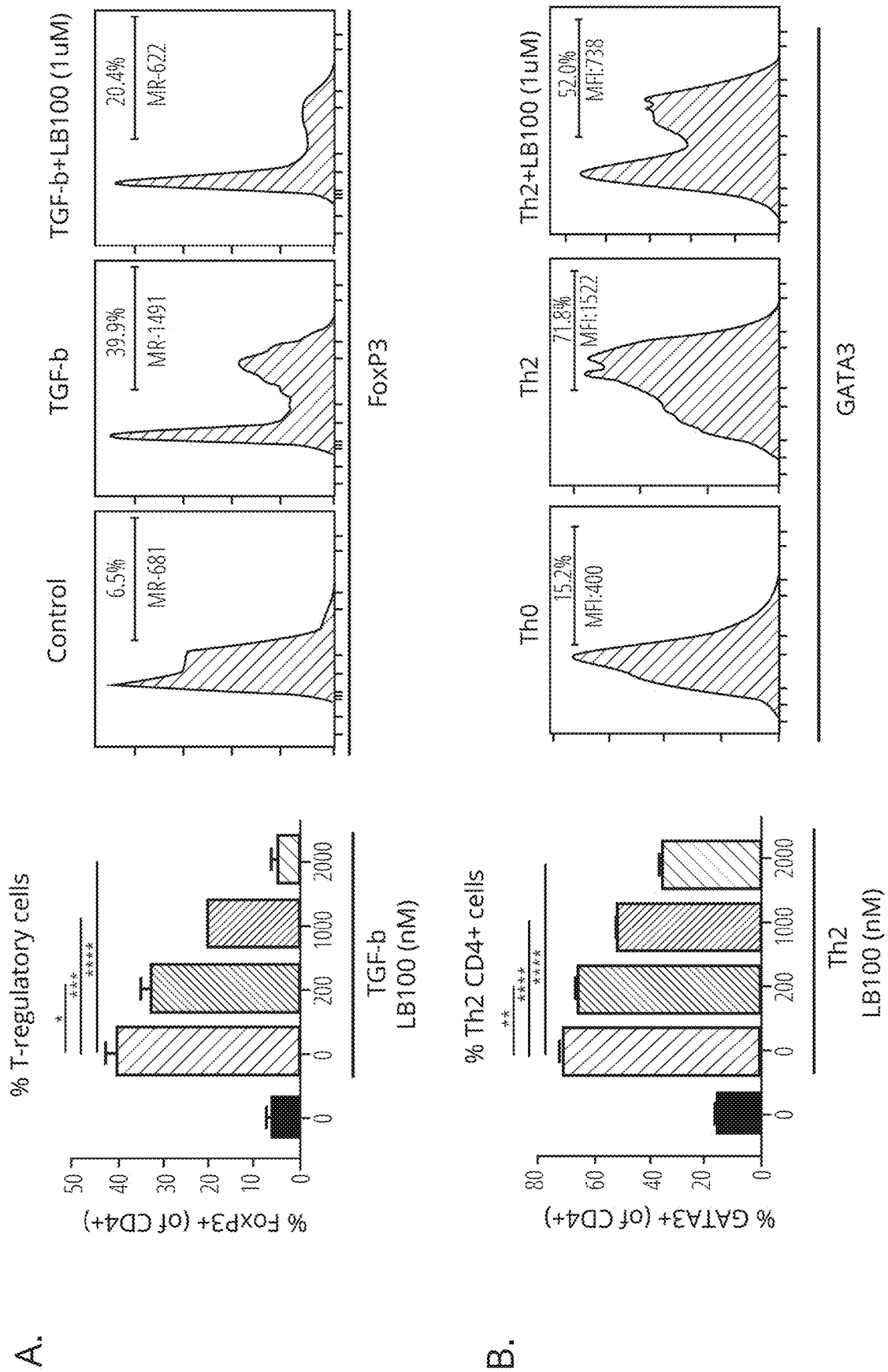
Figure 38:
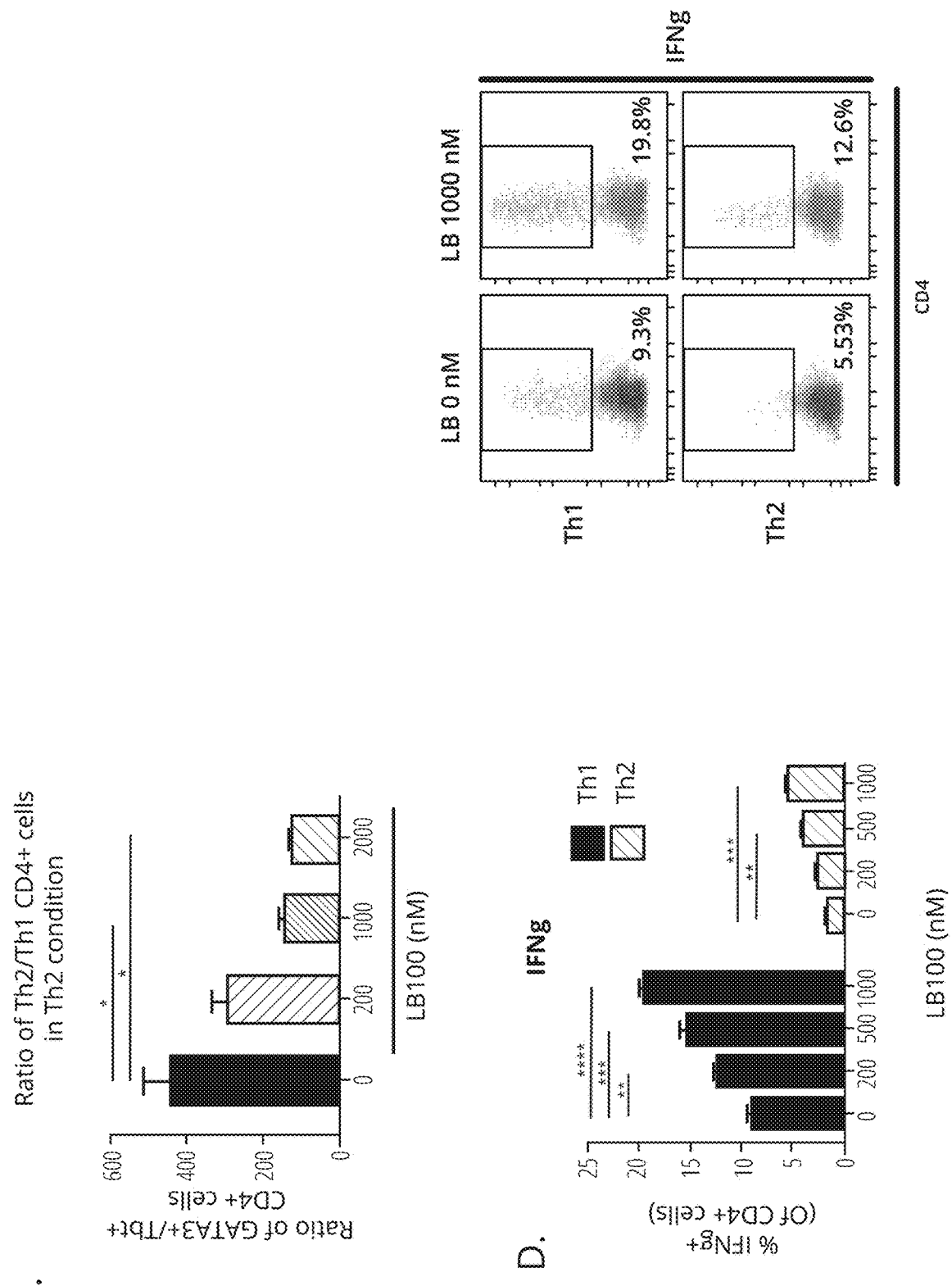
Figure 38:
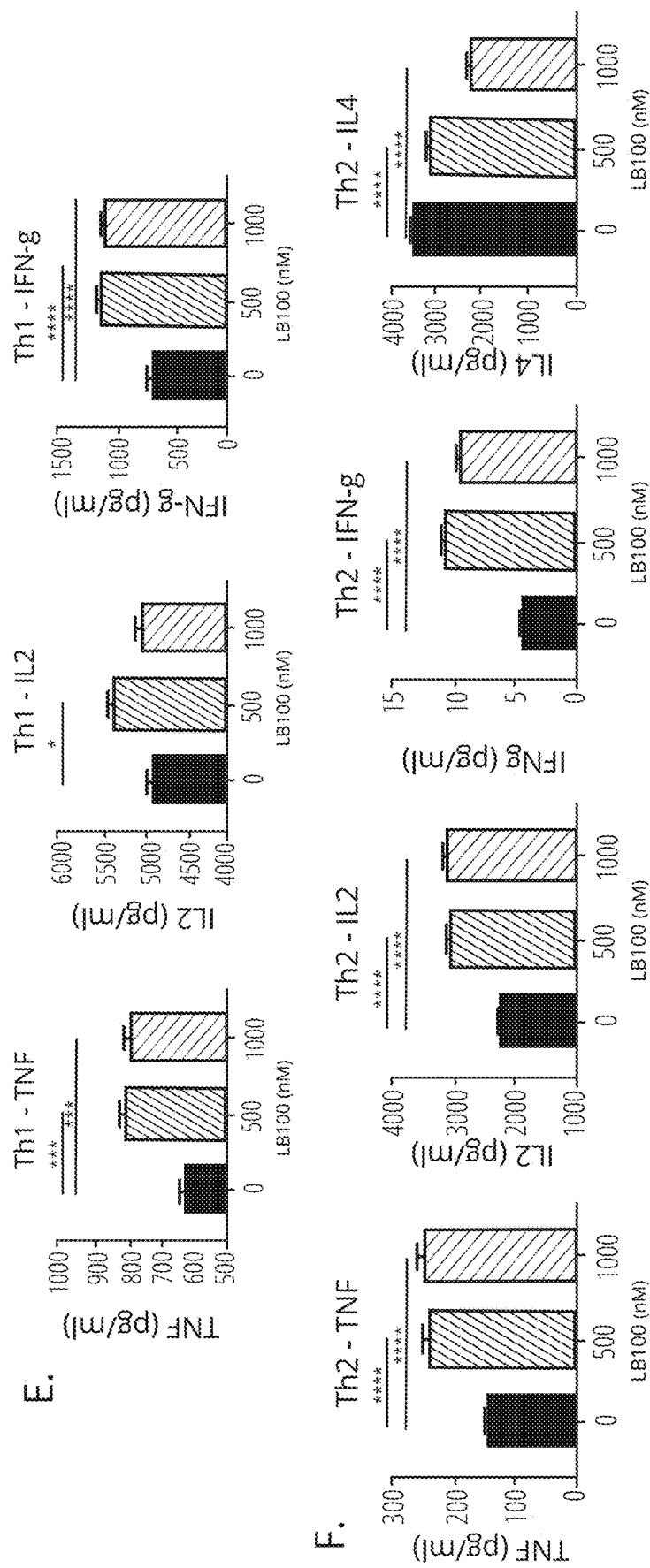

FIG. 38A. Left, the % of CD4 cells positive for Foxp3. Right, representative flow cytometry data demonstrating decreased in % of Foxp3 cells with LB-100. Cells were gated on CD4+ cells.

FIG. 38B. Intracellular levels of GATA3 were measured with flow cytometry. Left, the % of CD4 cells positive for GATA3. Right, representative flow cytometry data demonstrating decreased in % of GATA3 cells with LB-100.

FIG. 38C. Ratio of GATA3+Th2 over Tbet+Th1 CD4 cells.

FIG. 38D. Intracellular production of IFN-7 was measured by flow cytometry. Left, the % of CD4 cells positive for IFN-7 in TH1 and TH2 conditions. Right, representative flow cytometry data demonstrating increased in % of IFN-7 cells with LB-100 in both TH1 and TH2 conditions.

FIG. 38E. TNF, IL2 and IFN-7 production in supernatant of naïve CD4+ T cells activated in TH1 skewing conditions for 3 days.

FIG. 38F. TNF, IL2, IFN-7 and IL4 production in supernatant of naïve CD4+ T cells activated in TH2 skewing conditions for 3 days. Cytokine levels were adjusted to absolute cell number. *P<0.05, P<0.01, *P<0.001, (one way ANOVA with Tukey's multiple comparison test). Data are from one experiment representative of two independent experiments with similar results. Error bars depict SEM.

Figure 39:
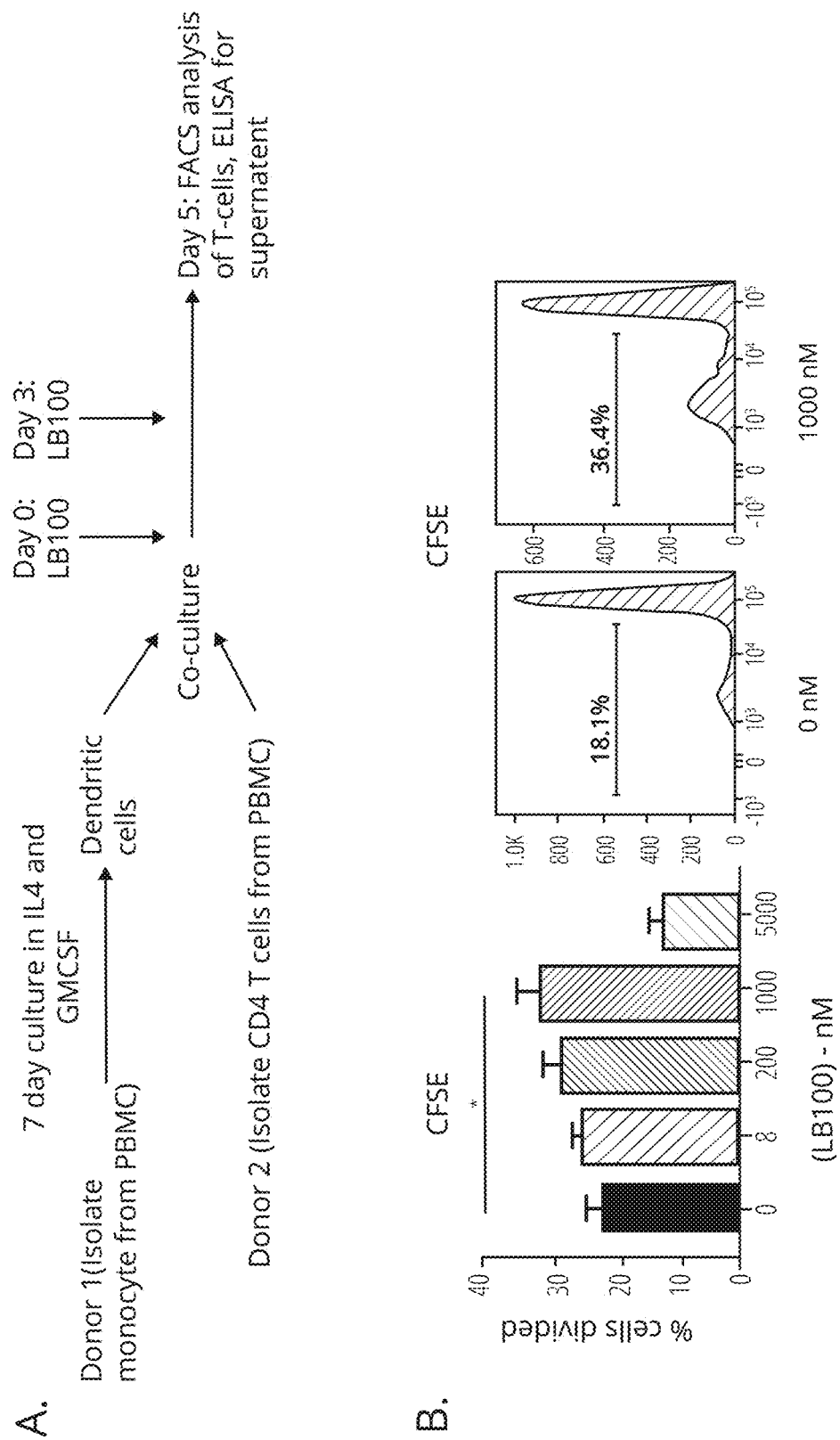
Figure 39:
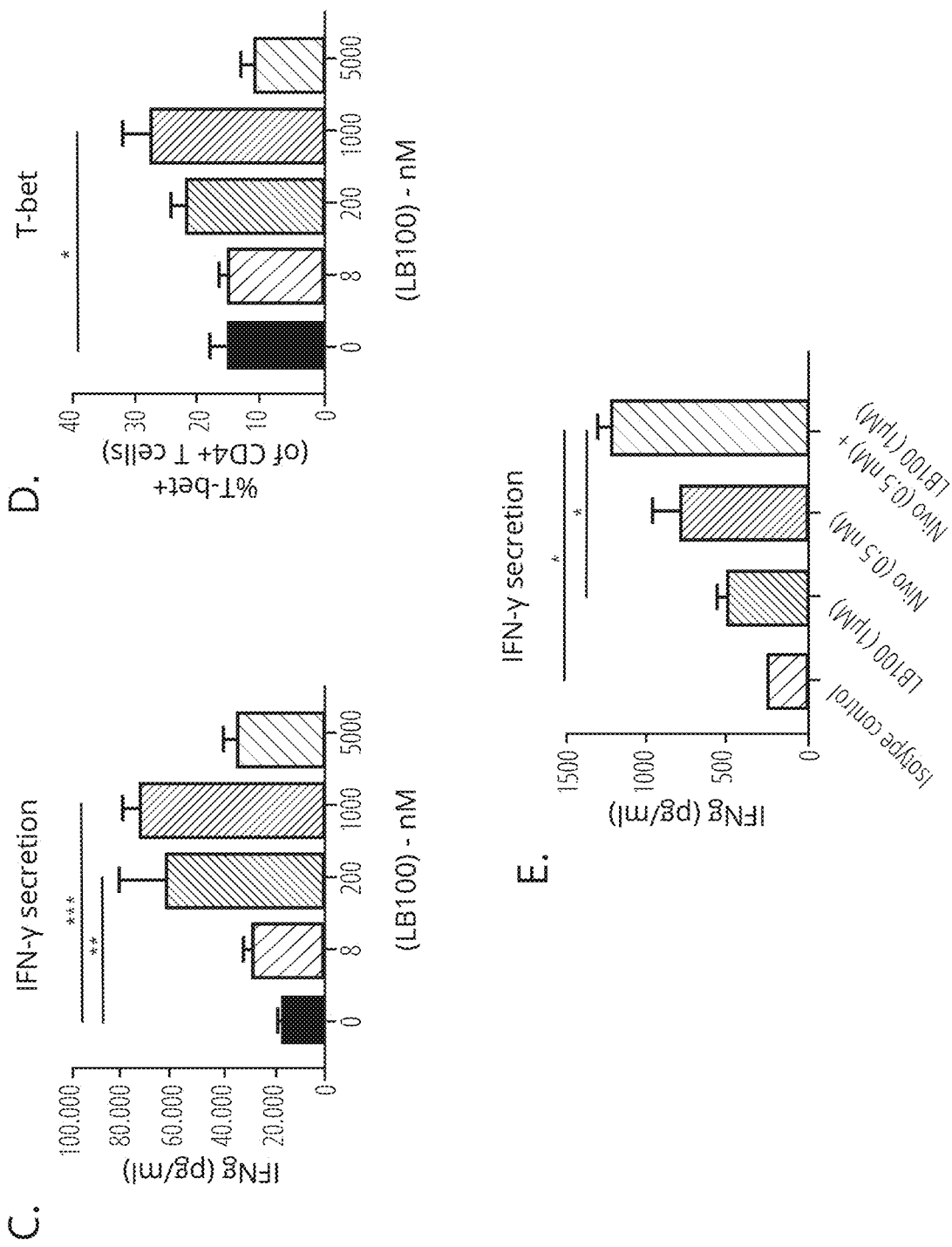

FIG. 39A. DCs were induced from purified monocytes by culturing in IL4 and GM-CSF for 7 days. $10^5$ purified CFSE labelled CD4+ T cells were then co-cultured with $10^4$ allogenic DCs in the presence of a titration of LB-100 in duplicates or triplicates for 5 days. LB-100 was replenished on day 3. Supernatants were collected on day 5 and measured for IFN-γ production. FACS analysis was performed on the cultured cells.

FIG. 39B. In vitro proliferation of CD4+ T cells in presence of LB-100 dose titration, measured by dilution of the cytosolic CFSE. Left, the % of cells divided was plotted against concentration of LB-100. Right, representative flow cytometry data demonstrating increased in % cells divided at 1 uM of LB-100.

FIG. 39C. IFN-α, production was measured at day 5, demonstrating a dose dependent increase in IFN-α secretion with LB-100.

FIG. 39D. Intracellular staining of T-bet was performed in CD4+ T cells after 5 days of co-culture. Percentage of CD4+Tbet+ (of CD4+ cells) against LB-100 concentration.

FIG. 39E. (E) IFN-γ production in cells treated with isotype control, LB-100 and/or Nivolumab, demonstrating a synergistic response to combination treatment. *P<0.05, P<0.01, *P<0.001 (one way ANOVA with Tukey's multiple comparison test). Data are from one experiment representative of two independent experiments with similar results. Error bars depict SEM.

DETAILED DESCRIPTION OF THE INVENTION

The present invention provides a method of treating a subject afflicted with cancer comprising administering to the subject an effective amount of a PP2A inhibitor in combination with an effective amount of a checkpoint inhibitor, wherein the amounts when taken together are effective to treat the subject.

The present invention also provides a method of treating a subject afflicted with cancer and receiving a checkpoint inhibitor comprising administering to the subject of an amount of PP2A inhibitor effective to enhance treatment relative to the checkpoint inhibitor alone.

The present invention also provides a method of treating a tumor or cancer in a subject comprising administering to the subject an effective amount of a PP2A inhibitor in combination with an effective amount of a checkpoint inhibitor, wherein the amounts when taken together are effective to treat the tumor or cancer.

The present invention also provides a method of increasing a T-cell response to cancer cells in a subject afflicted with cancer comprising administering to the subject an amount of a PP2A inhibitor in combination with an effective amount of a checkpoint inhibitor effective to increase the T-cell response to the cancer cells.

The present invention also provides a method of increasing T cell activation in a subject afflicted with cancer comprising administering to the subject an effective amount of a PP2A inhibitor in combination with an effective amount of a checkpoint inhibitor so as to thereby increase the T cell activation.

In some embodiments, the amount of the compound and the amount of the checkpoint inhibitor are each periodically administered to the subject.

In some embodiments, the amount of the compound and the amount of the checkpoint inhibitor are administered simultaneously, separately or sequentially.

In some embodiments, the checkpoint inhibitor is administered concurrently with, prior to, or after the PP2A inhibitor.

In some embodiments, the amount of checkpoint inhibitor and the amount of compound when administered together is more effective to treat the subject than when each agent at the same amount is administered alone.

In some embodiments, the amount of the compound and the amount of the checkpoint inhibitor when taken together is effective to reduce a clinical symptom of the cancer in the subject.

In some embodiments, the compound enhances the immunotherapeutic effect of the checkpoint inhibitor.

In some embodiments, the cancer is susceptible to treatment by an immune response.

In some embodiments, the immune checkpoint inhibitor is a CTLA-4 agent.

In some embodiments, the CTLA-4 checkpoint inhibitor is ipilimumab or tremelimumab.

In some embodiments, the immune checkpoint inhibitor is an Anti-PD-1 or Anti-PD-L1 agent.

In some embodiments, the PD-1 and/or PD-L1 checkpoint inhibitor is atezolizumab, nivolumab or pembrolizumab.

In some embodiments, the cancer is melanoma, renal cell carcinoma, prostate cancer, urothelial carcinoma or ovarian cancer.

In some embodiments, the cancer is melanoma.

In some embodiments, the PP2A inhibitor is administered at a dose of 0.25 mg/m$^2$, 0.5 mg/m$^2$, 0.83 mg/m$^2$, 1.25 mg/m$^2$, 1.75 mg/m$^2$, 2.33 mg/m$^2$, of 3.1 mg/m$^2$.

In some embodiments, the PP2A inhibitor is administered at a dose of 2.33 mg/m$^2$.

In some embodiments, the PP2A inhibitor is administered for 3 days every 3 weeks.

In some embodiments, the ipilimumab is administered intravenously at a dose of 0.5 mg/kg-10 mg/kg or less.

In some embodiments, the ipilimumab is administered intravenously over 90 minutes every 3 weeks or less.

In some embodiments, the atezolizumab is administered intravenously at a dose of 0.1 mg/kg-20 mg/kg or less.

In some embodiments, the atezolizumab is administered intravenously over 60 minutes every 3 weeks or less.

In some embodiments, the nivolumab is administered intravenously at a dose of 0.1 mg/kg-10 mg/kg or less.

In some embodiments, the nivolumab is administered intravenously over 60 minutes every 2 weeks or less.

In some embodiments, the pembrolizumab is administered intravenously at a dose of 1 mg/kg-10 mg/kg or less.

In some embodiments, the pembrolizumab is administered intravenously over 30 minutes every 3 weeks or less.

The present invention also provides a method of inhibiting the function of a CTLA-4 in T cells comprising administering to the T cells a PP2A inhibitor so as to thereby inhibit the function of the CTLA-4.

The present invention also provides a method of inhibiting the PD-1:PD-L1 interaction in T cells comprising administering to the T cells a PP2A inhibitor so as to thereby inhibit the interaction of PD-1:PD-L1.

In some embodiments, the method wherein the PP2A inhibitor has the structure:

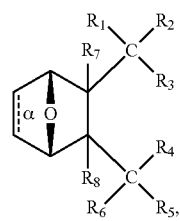

wherein
bond α is present or absent;
$R_1$ and $R_2$ together are =O;
$R_3$ is OH, O$^-$, OR$_9$, O(CH$_2$)$_{1-6}$R$_9$, SH, S$^-$, or SR$_9$,
wherein $R_9$ is H, alkyl, alkenyl, alkynyl or aryl;
$R_4$

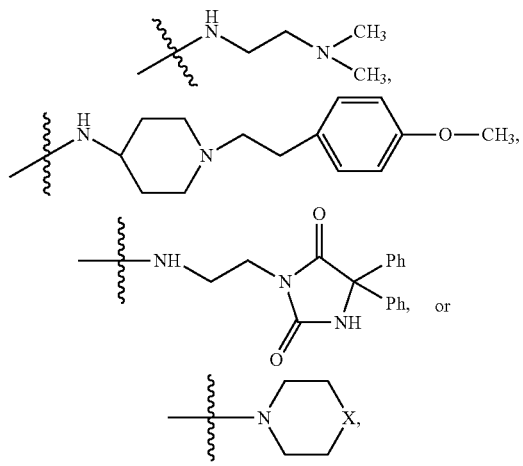

where X is O, S, NR$_{10}$, N$^+$HR$_{10}$ or N$^+$R$_{10}$R$_{10}$,
where each R$_{10}$ is independently H, alkyl, alkenyl, alkynyl, aryl

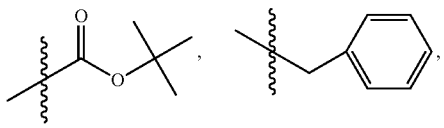

—CH$_2$CO$_2$R$_{11}$, or —CH$_2$COR$_{11}$,
wherein each R$_{11}$ is independently H, alkyl, alkenyl or alkynyl;
$R_5$ and $R_6$ taken together are =O;
$R_7$ and $R_8$ are each H,
or a salt, zwitterion, or ester thereof.

In some embodiments, the compound has the structure:

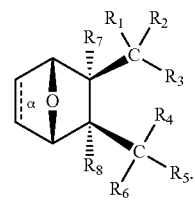

In some embodiments, bond α in the compound is present.

In some embodiments, bond α in the compound is absent.

In some embodiments, $R_3$ is OH, O$^-$, or OR$_9$,
wherein $R_9$ is alkyl, alkenyl, alkynyl or aryl;
$R_4$ is

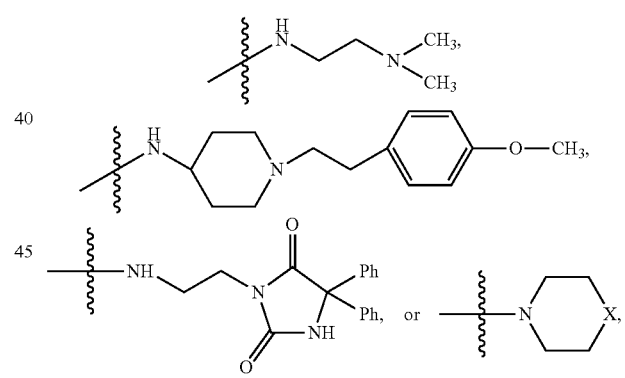

where X is O, S, NR$_{10}$, N$^+$HR$_{10}$ or N$^+$R$_{10}$R$_{10}$,
where each R$_{10}$ is independently H, alkyl, alkenyl, alkynyl, aryl,

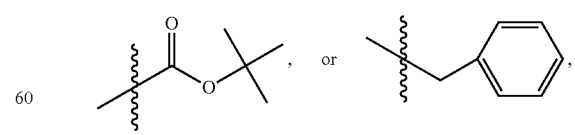

In some embodiments, $R_3$ is OH, O$^-$ or OR$_9$, where R$_9$ is H, methyl, ethyl or phenyl.

In some embodiments, $R_3$ is OH, O$^-$ or OR$_9$, wherein R$_9$ is methyl.

In some embodiments, R₄ is
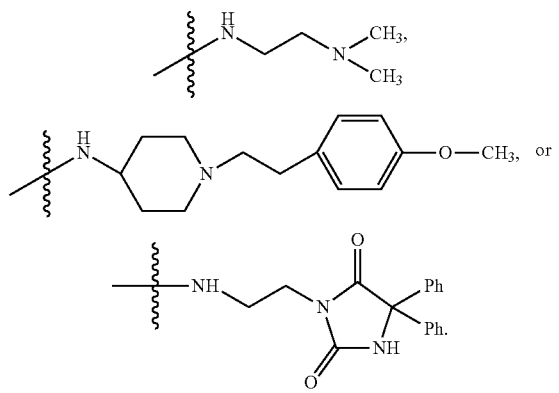
In some embodiments, R₄ is
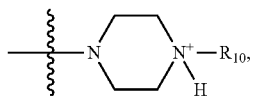
wherein R₁₀ is H, alkyl, alkenyl, alkynyl, aryl, or
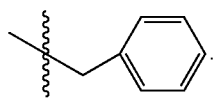
In some embodiments, R₄ is
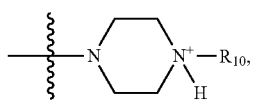
wherein R₁₀ is —H, —CH₃, —CH₂CH₃, or
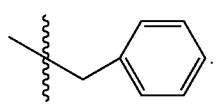
In some embodiments, R₄ is
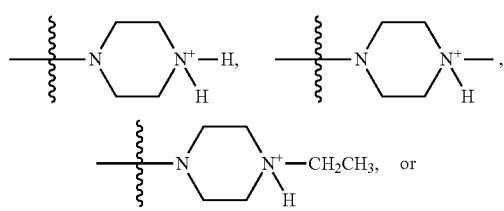
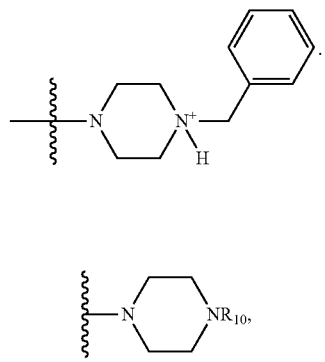
In some embodiments, R₄ is
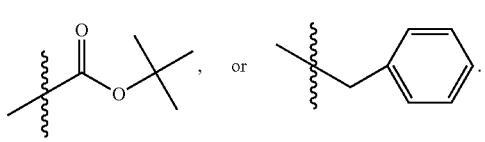
wherein R₁₀ is H, alkyl, alkenyl, alkynyl, aryl,
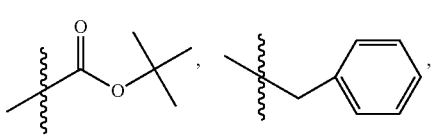
In some embodiments, R₄ is
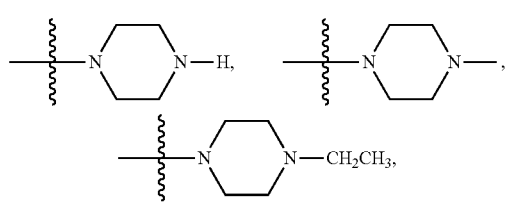
In some embodiments, R₄ is
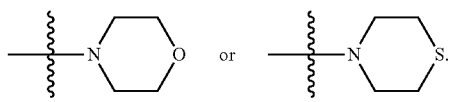

In some embodiments, the compound has the structure

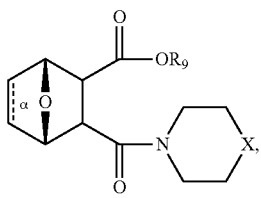

wherein bond α is present or absent;

$R_9$ is present or absent and when present is H, alkyl, alkenyl, alkynyl or phenyl; and X is O, $NR_{10}$, $NH^+R_{10}$ or $N^+R_{10}R_{10}$, where each $R_{10}$ is independently H, alkyl, substituted alkyl, alkenyl, substituted alkenyl, alkynyl, substituted alkynyl, aryl,

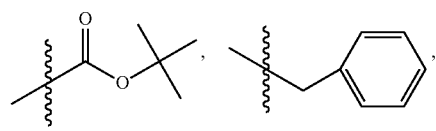

—$CH_2CN$, —$CH_2CO_2R_{12}$, or —$CH_2COR_{12}$, where $R_{12}$ is H or alkyl, or a salt, zwitterion or ester thereof.

In some embodiments, the compound has the structure

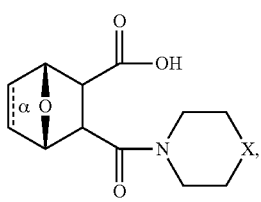

wherein bond α is present or absent;

X is O or $NR_{10}$, where each $R_{10}$ is independently H, alkyl, substituted alkyl, alkenyl, substituted alkenyl, alkynyl, substituted alkynyl, aryl,

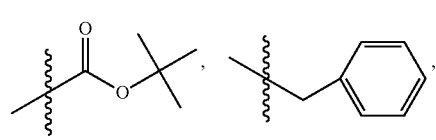

—$CH_2CN$, —$CH_2CO_2R_{12}$, or —$CH_2COR_{12}$, where $R_{12}$ is H or alkyl, or a salt, zwitterion or ester thereof.

In some embodiments, the compound has the structure

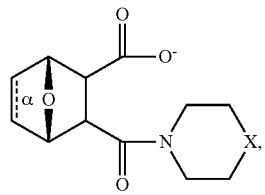

wherein bond α is present or absent;

X is O or $NH^+R_{10}$, where $R_{10}$ is H, alkyl, substituted alkyl, alkenyl, substituted alkenyl, alkynyl, substituted alkynyl, aryl,

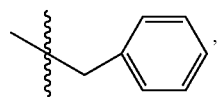

—$CH_2CN$, —$CH_2CO_2R_{12}$, or —$CH_2COR_{12}$, where $R_{12}$ is H or alkyl, or a salt, zwitterion or ester thereof.

In some embodiments, the compound has the structure

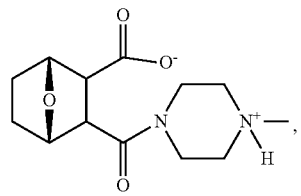 [SMILES: C[NH+]1CCN(C(=O)C2C(C(=O)[O-])[C@H]3CC[C@@H]2O3)CC1]

or a salt or ester thereof.

The present invention provides a method of inhibiting the function of CTLA-4 in T cells comprising administering to the T cells a PP2A inhibitor so as to thereby inhibit the function of CTLA-4.

The present invention also provides a method of inhibiting the function of CTLA-4 in a subject afflicted with cancer comprising administering to the subject a PP2A inhibitor so as to thereby inhibit the function of CTLA-4 in the subject.

The present invention further provides a method of increasing T-cell activation in a subject afflicted with cancer comprising administering to the subject a PP2A inhibitor so as to thereby increase the T-cell activation.

The present invention yet further provides a method of increasing T-cell response to cancers cells in a subject afflicted with cancer comprising administering to the subject a PP2A inhibitor so as to thereby increase the T-cell response to the cancers cells.

The present invention also provides a method of treating a subject afflicted with cancer comprising administering to the subject an effective amount of a CTLA-4 checkpoint inhibitor and an effective amount of a PP2A inhibitor, wherein the amounts when taken together are effective to treat the subject.

In some embodiments, the PP2A inhibitor alters the interaction of PP2A with CTLA-4.

In some embodiments, the PP2A inhibitor decreases the binding of PP2A to CTLA-4.

In some embodiments of any of the above methods, the cancer is susceptible to anti-CTLA-4 immunotherapy.

In some embodiments of any of the above methods, the subject has reduced T-cell activation mediated by CTLA-4.

The present invention also provides a method of treating a subject afflicted with cancer comprising administering to the subject an effective amount of a PP2A inhibitor so as to thereby treat the cancer, wherein the cancer is susceptible to anti-CTLA-4 immunotherapy.

The present invention also provides a method of treating a subject afflicted with cancer comprising administering to the subject an effective amount of a PP2A inhibitor so as to thereby treat the cancer, wherein the cancer is susceptible to immunotherapy.

The present invention also provides a method of treating a subject afflicted with cancer comprising administering to the subject an effective amount of a PP2A inhibitor so as to thereby treat the cancer, wherein the subject has reduced T cell activation mediated by CTLA-4.

In some embodiments of any of the above methods, the cancer is susceptible to anti-CTLA-4 immunotherapy.

In some embodiments of any of the above methods, the subject has reduced T-cell activation mediated by CTLA-4.

In some embodiments of any of the above methods, the cancer is melanoma, renal cell carcinoma, prostate cancer, urothelial carcinoma or ovarian cancer.

In some embodiments of any of the above methods, the cancer is melanoma.

In some embodiments of any of the above methods, the cancer susceptible to anti-CTLA-4 immunotherapy is melanoma.

In some embodiments, the cancer is pancreatic cancer.

In some embodiments, the cancer is pancreatic cancer, and the cancer cells of the pancreatic cancer overexpress Mad2.

In some embodiments, the cancer has abnormalities in PP2A function and/or in the DNA-damage-repair pathway.

In some embodiments, the subject is afflicted with fibrosarcoma, chondrosarcoma, thymoma, atypical carcinoid of lung, or ovarian, testicular, breast, or prostate cancer.

In some embodiments of the above method, the PP2A inhibitor is effective to treat a subject afflicted with a cancer.

In some embodiments, the above method further comprises administering an anti-cancer therapy concurrently with, prior to, or after the PP2A inhibitor.

In some embodiments, the anti-cancer therapy comprises administering a checkpoint inhibitor, for instance a CTLA-4 checkpoint inhibitor. In some embodiments of the above method, the PP2A inhibitor enhances the chemotherapeutic effect of the CTLA-4 checkpoint inhibitor.

In some embodiments of the above method, the CTLA-4 checkpoint inhibitor is an antibody.

In some embodiments of the above method, the PP2A inhibitor alters the interaction of PP2A with CTLA-4.

In some embodiments of the above method, the PP2A inhibitor increases the binding of PP2A to CTLA-4.

Cancers susceptible to anti-CTLA-4 immunotherapy include, but are not limited to, cancers which have been shown to be amenable to anti-CTLA-4 immunotherapy in pre-clinical or clinical trials.

Cancers susceptible to anti-PD-1 or anti-PD-L1 immunotherapy include, but are not limited to, cancers which have been shown to be amenable to anti-PD-1 or anti-PD-L1 immunotherapy in pre-clinical or clinical trials.

In some embodiments, the amount of the compound is effective to reduce a clinical symptom of the cancer in the subject.

In some embodiments, the treatment comprises increasing the amount of cytotoxic T cells in the subject.

In some embodiments, the treatment comprises increasing the amount of cytotoxic T cells that interact with cancer cells in the subject.

In some embodiments, the treatment comprises increasing the amount of cancer cells killed by cytotoxic T cells in the subject.

T cell types include "killer" cytotoxic $CD8^+$ T cells and "helper" $CD4^+$ T cells. The latter encompass subtypes involved in regulating immune responses, such as "$T_{reg}$" cells, and others that stimulate the acquired immune system, including recognition of "non-self" proteins that can stimulate killer T cells or antibody-producing B cells. Specific T cell clones, some of which are maintained after antigen exposure in low levels as "memory" T cells, are activated by particular MHC/epitope combinations, leading to cytokine release, clonal expansion, and acquired immune responses.

In some embodiments, the T cells are CD4+ T cells, CD8+ T cells, and/or CD4+CD8+ T cells.

In some embodiments, the cancer is hepatocellular carcinoma, human osteosarcoma, primary liver cancer, gastric cancer, ovarian cancer, endometrial cancer, colorectal cancer, non-small cell lung cancer, soft-tissue sarcoma, seminoma, breast cancer, lymphoma, fibrosarcoma, neuroblastoma, mucinous ovarian cancer, urothelial bladder cancer, squamous cell carcinoma of the uterine cervix, diffuse large B-cell lymphoma, lung adenoma, hepatoma, intestinal cancer, fibrosarcoma, osteosarcoma, prostate cancer, angiomyolipoma, mammary adenocarcinoma, acute myeloid leukemia, chronic lymphocytic leukemia, and multiple myeloma and other plasma cell neoplasms.

In some embodiments, the cancer is lung adenoma, hepatoma, hepatocellular carcinoma, intestinal cancer, lymphoma, fibrosarcoma, osteosarcoma, prostate cancer, angiomyolipoma, or mammary adenocarcinoma.

In some embodiments, the cancer is acute myeloid leukemia.

In some embodiments, the cancer is breast cancer, colon cancer, large cell lung cancer, adenocarcinoma of the lung, small cell lung cancer, stomach cancer, liver cancer, ovary adenocarcinoma, pancreas carcinoma, prostate carcinoma, promyelocytic leukemia, chronic myelogenous leukemia, acute lymphoblastic leukemia, chronic lymphocytic leukemia, multiple myeloma and plasma cell neoplasms, colorectal cancer, ovarian cancer, lymphoma, non-Hodgkin lymphoma, Hodgkin lymphoma, neuroblastoma, medulloblastoma, glioblastoma, chordoma, meningioma (non-malignant and malignant), diffuse intrinsic pontine glioma, or atypical teratoid/rhabdoid tumor.

In some embodiments of the above method, the cancer is a breast cancer, colon cancer, large cell lung cancer, adenocarcinoma of the lung, small cell lung cancer, stomach cancer, liver cancer, ovary adenocarcinoma, pancreas carcinoma, prostate carcinoma, acute promyelocytic leukemia, chronic myelogenous leukemia, acute lymphoblastic leukemia, chronic lymphocytic leukemia, multiple myeloma and plasma cell neoplasm, colorectal cancer, ovarian cancer, lymphoma, non-Hodgkin lymphoma or Hodgkin lymphoma.

In some embodiments of the above method, the cancer is a brain cancer.

In some embodiments of the above method, the brain cancer is a glioma, pilocytic astrocytoma, low-grade diffuse astrocytoma, anaplastic astrocytoma, glioblastoma multiforme, oligodendroglioma, ependymoma, meningioma, pituitary gland tumor, primary central nervous system lymphoma, medulloblastoma, craniopharyngioma, or diffuse intrinsic pontine glioma.

In some embodiments of the above method, further comprising administering to the subject an anti-cancer agent.

In some embodiments of the above method, the anti-cancer agent is selected from x-radiation or ionizing radiation.

In some embodiments of the above method, the target cell is a cancer cell.

In some embodiments of the above method, the cancer cell is a breast cancer, colon cancer, large cell lung cancer, adenocarcinoma of the lung, small cell lung cancer, stomach cancer, liver cancer, ovary adenocarcinoma, pancreas carcinoma, prostate carcinoma, promyelocytic leukemia, chronic myelogenous leukemia, acute lymphoblastic leukemia, colorectal cancer, ovarian cancer, lymphoma, non-Hodgkin lymphoma or Hodgkin lymphoma cell.

Analogs of LB-100 have analogous activity to LB-100 and exhibit similar effects in the methods described herein. Such analogs include the compounds described in PCT International Application Publication No. WO 2008/097561, published Aug. 14, 2008; PCT International Application Publication No. WO 2010/014254, published Feb. 4, 2010; PCT International Application Publication No. WO 2015/073802, published May 21, 2015; and PCT International Application Publication No. WO 2016/186963, published Nov. 24, 2016, the contents of each of which are hereby incorporated by reference.

Compounds which act as prodrugs for the in vivo delivery of LB-100 and/or endothal have analogous activity to LB-100 and exhibit similar effects in the methods described herein. More specifically, administration of the prodrug provides a similar effect to the administration of LB-100. Pro-drugs of LB-100 and/or endothal include the compounds described in PCT International Application Publication No. WO 2015/073802, published May 21, 2015; and PCT International Application Publication No. WO 2016/186963, published Nov. 24, 2016, the contents of each of which are hereby incorporated by reference.

Except where otherwise specified, when the structure of a compound used in the method of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds in the method disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein. It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein. Isotopically-labeled compounds can generally be prepared by conventional techniques known to those skilled in the art using appropriate isotopically-labeled reagents in place of the non-labeled reagents employed.

In some embodiments, the method wherein the subject is administered a pharmaceutical composition comprising a compound of the present invention and at least one pharmaceutically acceptable carrier for treating the cancer in the subject.

In some embodiments, the pharmaceutical composition wherein the pharmaceutically acceptable carrier comprises a liposome.

In some embodiments, the pharmaceutical composition wherein the compound is contained in a liposome or microsphere.

In some embodiments, the pharmaceutical composition comprises the PP2A inhibitor and the CTLA-4 checkpoint inhibitor.

In some embodiments of any of the above methods or uses, the subject is a human.

In some embodiments of any of the above methods or uses, the compound and/or the CTLA-4 checkpoint inhibitor is orally administered to the subject.

The present invention provides a PP2A inhibitor for use in inhibiting the function of CTLA-4 in T cells.

The present invention provides a PP2A inhibitor for use in inhibiting the function of CTLA-4 in a subject afflicted with cancer.

The present invention provides a PP2A inhibitor for use in increasing T cell activation in a subject afflicted with cancer.

The present invention provides a PP2A inhibitor for use in increasing T cell response to cancers cells in a subject afflicted with cancer.

The present invention provides a PP2A inhibitor for use in treating a subject afflicted with cancer, wherein the cancer is susceptible to anti-CTLA-4 immunotherapy.

The present invention provides a PP2A inhibitor for use in treating a subject afflicted with cancer, wherein the subject has reduced T cell activation mediated by CTLA-4.

The present invention provides a PP2A inhibitor in combination with a CTLA-4 checkpoint inhibitor for use in treating a subject afflicted with cancer.

Use of a PP2A inhibitor for inhibiting the function of CTLA-4 in T cells.

Use of a PP2A inhibitor for inhibiting the function of CTLA-4 in a subject afflicted with cancer.

Use of a PP2A inhibitor for increasing T cell activation in a subject afflicted with cancer.

Use of a PP2A inhibitor for increasing T-cell response to cancers cells in a subject afflicted with cancer.

Use of a PP2A inhibitor for treating a subject afflicted with cancer, wherein the cancer is susceptible to anti-CTLA-4 immunotherapy.

Use of a PP2A inhibitor for treating a subject afflicted with cancer, wherein the subject has reduced T-cell activation mediated by CTLA-4.

Use of a PP2A inhibitor in combination with a CTLA-4 checkpoint inhibitor for treating a subject afflicted with cancer.

The present invention also provides a method of optimizing the concentration of LB-100 in the bloodstream of a subject who has been administered a dosage of LB1-00 comprising:
(a) measuring the plasma concentration of LB-100 in the subject;
(b) determining whether a further LB-100 dose needs to be administered to the subject based on whether the measurement in (a); and
(c) administering a further dosage or dosages of the LB-100 as necessary based on the determination in (b).

In some embodiments, the above step (b) comprises determining whether a further LB-100 dose needs to be administered to the subject based on whether the measurement in (a) is above, below or equal to the Minimum Effective Concentration (MEC) of LB-100.

In some embodiments, the initial dose of LB-100 administered to the subject is an amount of from 0.1 mg/m$^2$ to 5 mg/m$^2$.

In some embodiments, the further dose of LB-100 administered to the subject is an amount of from 0.1 mg/m$^2$ to 5 mg/m$^2$.

In some embodiments, the compound is administered at a dose of 0.25 mg/m$^2$, 0.5 mg/m$^2$, 0.83 mg/m$^2$, 1.25 mg/m$^2$, 1.75 mg/m$^2$, 2.33 mg/m$^2$, or 3.1 mg/m$^2$.

In some embodiments, the compound is administered at a dose of 2.33 mg/m$^2$.

In some embodiments, the compound is administered for 3 days every 3 weeks.

In some embodiments, the further dose of LB-100 administered to the subject is an amount 25% less than the initial dose.

In some embodiments, the further dose of LB-100 administered to the subject is an amount 50% less than the initial dose.

In some embodiments, the further dose of LB-100 administered to the subject is an amount 75% less than the initial dose.

In some embodiments, the further dose of LB-100 administered to the subject is an amount 25% more than the initial dose.

In some embodiments, the further dose of LB-100 administered to the subject is an amount 50% more than the initial dose.

In some embodiments, the further dose of LB-100 administered to the subject is an amount 75% more than the initial dose.

In some embodiments, the subject is further treated with an anti-cancer therapy concurrently with, prior to, or after the administering.

Examples of anti-cancer therapy include radiation therapy or chemotherapy, targeted therapy to promote antigen release, vaccination to promote antigen presentation, agonist for co-stimulatory molecules or blockade of co-inhibitory molecules to amplify T-cell activation, trafficking inhibition of regulatory T cells or myeloid-derived suppressor cells, anti-vascular endothelial growth factor to stimulate intratumoral T-cell infiltration, adoptive cell transfer to increase cancer recognition by T-cell infiltration, or stimulate tumor killing. Further examples may be found in Swart et al. 2016; Topalian et al. 2015; and Tsiatas et al. 2016.

In some embodiments, the anti-cancer therapy comprises immunotherapy. The term "immunotherapy" refers to the treatment of a subject afflicted with a disease by a method comprising inducing, enhancing, suppressing or otherwise modifying an immune response. Immunotherapy agents may include antibody agents targeting one or more of CTLA-4, PD-1, PD-L1, GITR, OC40, LAG-3, KIR, TIM-3, B7-H3, B7-H4, CD28, CD40, and CD137.

In some embodiments, the anti-cancer therapy comprises administering an anti-cancer agent.

In some embodiments, the anti-cancer agent is an immune checkpoint modulator. The term "immune checkpoint modulator" refers to an agent that interacts directly or indirectly with an immune checkpoint. Immune checkpoint modulators may be administered to overcome inhibitory signals and permit and/or augment an immune attach against cancer cells. In some embodiments, an immune checkpoint modulator increases an immune effector response (e.g. cytotoxic T cell response). In some embodiments, an immune checkpoint modulator reduces, removes, or prevents immune tolerance to one or more antigens. For example, immune checkpoint modulators may facilitate immune cell responses by decreasing, inhibiting, or abrogating signaling by negative immune response regulators (e.g. CTLA4), by stimulating or enhancing signaling of positive regulators of immune response (e.g. CD28), or by preventing autoimmune responses and limiting immune cell-mediated tissue damage.

In some embodiments, the anti-cancer agent comprises an antibody or an antigen-binding portion thereof.

In some embodiments, the anti-cancer agent comprises a Programmed Death-Ligand 1 (PD-L1) inhibitor. In some embodiments, the PD-L1 inhibitor is atezolizumab.

Atezolizumab, the active ingredient of Tecentriq™, is a human programmed death ligand-1 (PD-L1) blocking antibody. Atezolizumab is identified by specific antibodies (Tecentriq, Food and Drug Administration Approved Labeling (Reference ID:4000525) [online], Genentech Inc., 2016 [retrieved on Feb. 24, 2017], Retrieved from the Internet: <URL: www.accessdata.fda.gov/drugsatfda_docs/label/2016/761041lbl.pdf>).

The recommended dose and schedule for atezolizumab is 1200 mg administered intravenously over 60 minutes every 3 weeks until disease progression or unacceptable toxicity. Subsequent infusions may be delivered over 30 minutes if the first infusion is tolerated.

In some embodiments, the administration of atezolizumab comprises 1 mg/kg, 2 mg/kg, 3 mg/kg, 4 mg/kg, 5 mg/kg, 10 mg/kg, 15 mg/kg, 20 mg/kg or less of atezolizumab.

In some embodiments, the periodic administration of atezolizumab comprises 1, 2, 3, 4 or less administrations of atezolizumab.

In some embodiments, the administration of nivolumab is every 2 or 3 weeks or less.

In some embodiments, the antibody or antigen-binding portion thereof binds specifically to a Programmed Death-1 (PD-1) receptor and inhibits PD-1 activity ("anti-PD-1 antibody"). In some embodiments, the anti-PD-1 antibody is nivolumab or pembrolizumab.

Nivolumab, the active ingredient of Opdivo™, is a human Programmed Death receptor-1 (PD-1) blocking antibody. Nivolumab is identified by specific antibodies (Opdivo™, Food and Drug Administration Approved Labeling (Reference ID:3677021) [online], Bristol-Myers Squibb, 2014 [retrieved on Feb. 24, 2017], Retrieved from the Internet: <URL: www.accessdata.fda.gov/drugsatfda_docs/label/2014/125554lbl.pdf>).

The recommended dose and schedule for nivolumab is 3 mg/kg administered intravenously over 60 minutes every 2 weeks for 4 doses until disease progression or unacceptable toxicity.

In some embodiments, the administration of nivolumab comprises 0.1 mg/kg, 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg or less of nivolumab.

In some embodiments, the periodic administration of nivolumab comprises 1, 2, 3, 4 or less administrations of nivolumab.

In some embodiments, the administration of nivolumab is every 2 or 3 weeks or less.

Pembrolizumab, the active ingredient of Keytruda™, is a human programmed death receptor-1 (PD-1) blocking antibody. Pembrolizumab is identified by specific antibodies (Keytruda, Food and Drug Administration Approved Labeling (Reference ID:3621876) [online], Merck & Co., 2014 [retrieved on Feb. 24, 2017], Retrieved from the Internet: <URL: www.accessdata.fda.gov/drugsatfda_docs/label/2014/125514lbl.pdf>).

The recommended dose and schedule for pembrolizumab is 2 mg/kg administered intravenously over 30 minutes every 3 weeks until disease progression or unacceptable toxicity.

In some embodiments, the administration of pembrolizumab comprises 1 mg/kg, 2 mg/kg, 3 mg/kg, 4 mg/kg, 5 mg/kg, 6 mg/kg, 7 mg/kg, 8 mg/kg, 9 mg/kg, 10 mg/kg or less of pembrolizumab.

In some embodiments, the periodic administration of pembrolizumab comprises 1, 2, 3, 4, 5, 6, 7, 8, 9, 10, 11, 12, 13, 14, 15, 16, 17, 18 or less administrations of pembrolizumab.

In some embodiments, the administration of pembrolizumab is every 2 or 3 weeks or less.

In some embodiments the antibody or antigen-binding portion thereof binds specifically to Cytotoxic T-Lymphocyte Antigen-4 (CTLA-4) and inhibits CTLA-4) activity ("anti-CTLA-4 antibody"). In another embodiment. In some embodiments, the anti-CTLA-4 antibody is ipilimumab or tremelimumab.

Ipilimumab, the active ingredient of Yervoy™, is a human cytotoxic T-lymphocyte antigen 4 (CTLA-4)-blocking antibody. Ipilimumab is identified by specific antibodies (Yervoy, Food and Drug Administration Approved Labeling (Reference ID: 3839653) [online], Bristol-Myers Squibb, 2015 [retrieved on Feb. 24, 2017], Retrieved from the Internet: <URL: www.accessdata.fda.gov/drugsatfda_docs/label/2015/125377s073lbl.pdf>).

The recommended dose and schedule for ipilimumab for unresectable or metastatic melanoma is 3 mg/kg administered intravenously over 90 minutes every 3 weeks for 4 doses. The recommended dose and schedule for ipilimumab for adjuvant treatment of melanoma is 10 mg/kg administered intravenously over 90 minutes every 3 weeks for 4 doses followed by 10 mg/kg every 12 weeks for up to 3 years.

In some embodiments, the administration of ipilimumab comprises 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg or less of ipilimumab.

In some embodiments, the periodic administration of ipilimumab comprises 1, 2, 3, 4, 5, 6, 7, 8, 9, 10, 11, 12, 13, 14, 15, 16 or less administrations of ipilimumab.

The present invention also provides a method of treating a tumor or cancer in a subject comprising administering to the subject an effective amount of a PP2A inhibitor, wherein the tumor or cancer is susceptible to treatment by an immune response.

The present invention also provides a method of increasing a T-cell response to cancer cells in a subject afflicted with cancer comprising administering to the subject an amount of a PP2A inhibitor effective to increase the T-cell response.

In some embodiments, the PP2A inhibitor has the structure:

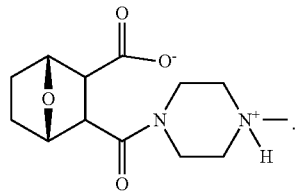 [SMILES: C[NH+]1CCN(C(=O)C2C(C(=O)[O-])[C@H]3CC[C@@H]2O3)CC1]

In some embodiments, the method further comprising administering one or more additional anti-cancer agent.

The present invention also provides a method of treating a subject afflicted with cancer comprising administering to the subject an effective amount of a PP2A inhibitor in combination with an effective amount of an anti-cancer therapy, wherein the amounts when taken together are effective to treat the subject.

The present invention also provides a method of treating a subject afflicted with cancer and receiving anti-cancer therapy comprising administering to the subject an effective amount of PP2A inhibitor effective to enhance treatment relative to the anti-cancer therapy alone.

In some embodiments, the cancer is susceptible to treatment by an immune response.

The compounds used in the method of the present invention are protein phosphatase 2A (PP2A) inhibitors. Methods of preparation may be found in Lu et al., 2009; U.S. Pat. No. 7,998,957 B2; and U.S. Pat. No. 8,426,444 B2. Compound LB-100 is an inhibitor of PP2A in vitro in human cancer cells and in xenografts of human tumor cells in mice when given parenterally in mice. LB-100 inhibits the growth of cancer cells in mouse model systems.

As used herein, a "symptom" associated with reperfusion injury includes any clinical or laboratory manifestation associated with reperfusion injury and is not limited to what the subject can feel or observe.

As used herein, "treatment of the diseases" or "treating", e.g. of reperfusion injury, encompasses inducing prevention, inhibition, regression, or stasis of the disease or a symptom or condition associated with the disease.

As used herein, "inhibition" of disease progression or disease complication in a subject means preventing or reducing the disease progression and/or disease complication in the subject.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{20}$ alkyl, $C_2$-$C_{20}$ alkyl, $C_3$-$C_{20}$ alkyl, $C_4$-$C_{20}$ alkyl and so on. An embodiment can be $C_1$-$C_{30}$ alkyl, $C_2$-$C_{30}$ alkyl, $C_3$-$C_{30}$ alkyl, $C_4$-$C_{30}$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl, $C_3$-$C_{12}$ alkenyl, $C_2$-$C_{20}$ alkenyl, $C_3$-$C_{20}$ alkenyl, $C_2$-$C_{30}$ alkenyl, or $C_3$-$C_{30}$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n−1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_{12}$ alkynyl, $C_2$-$C_{20}$ alkynyl, $C_3$-$C_{20}$ alkynyl, $C_2$-$C_{30}$ alkynyl, or $C_3$-$C_{30}$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynyl, or aryl groups as hereinabove defined.

Each occurrence of alkyl, alkenyl, or alkynyl is branched or unbranched, unsubstituted or substituted.

The alkyl, alkenyl, alkynyl, and aryl substituents may be unsubstituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprolactones and PLGA's).

Other injectable drug delivery systems include solutions, suspensions, gels. Oral delivery systems include tablets and capsules. These can contain excipients such as binders (e.g., hydroxypropylmethylcellulose, polyvinyl pyrrolidone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Implantable systems include rods and discs, and can contain excipients such as PLGA and polycaprolactone.

Oral delivery systems include tablets and capsules. These can contain excipients such as binders (e.g., hydroxypropylmethylcellulose, polyvinyl pyrrolidone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

The compounds used in the method of the present invention may be in a salt form. As used herein, a "salt" is a salt of the instant compounds which has been modified by making acid or base salts of the compounds. In the case of compounds used to treat an infection or disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphtholate, mesylate, glucoheptonate, lactobionate, and laurylsulphonate salts and the like. (See, e.g., Berge et al. (1977) "Pharmaceutical Salts", J. Pharm. Sci. 66:1-19).

The present invention includes esters or pharmaceutically acceptable esters of the compounds of the present method. The term "ester" includes, but is not limited to, a compound containing the R—CO—OR' group. The "R—CO—O" portion may be derived from the parent compound of the present invention. The "R'" portion includes, but is not limited to, alkyl, alkenyl, alkynyl, heteroalkyl, aryl, and carboxy alkyl groups.

The present invention includes pharmaceutically acceptable prodrug esters of the compounds of the present method. Pharmaceutically acceptable prodrug esters of the compounds of the present invention are ester derivatives which are convertible by solvolysis or under physiological conditions to the free carboxylic acids of the parent compound. An example of a pro-drug is an alkyl ester which is cleaved in vivo to yield the compound of interest.

The compound, or salt, zwitterion, or ester thereof, is optionally provided in a pharmaceutically acceptable composition including the appropriate pharmaceutically acceptable carriers.

As used herein, an "amount" or "dose" of an agent measured in milligrams refers to the milligrams of agent present in a drug product, regardless of the form of the drug product.

The National Institutes of Health (NIH) provides a table of Equivalent Surface Area Dosage Conversion Factors below (Table A) which provides conversion factors that account for surface area to weight ratios between species.

TABLE A

Equivalent Surface Area Dosage Conversion Factors

| From | To | | | | |
|---|---|---|---|---|---|
| | Mouse 20 g | Rat 150 g | Monkey 3 kg | Dog 8 kg | Man 60 kg |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 1 2/3 | 1 | 1/2 |
| Man | 12 | 7 | 3 | 2 | 1 |

As used herein, the term "therapeutically effective amount" or "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

Where a range is given in the specification it is understood that the range includes all integers and 0.1 units within that range, and any sub-range thereof. For example, a range of 77 to 90% is a disclosure of 77, 78, 79, 80, and 81% etc.

As used herein, "about" with regard to a stated number encompasses a range of +one percent to −one percent of the stated value. By way of example, about 100 mg/kg therefore includes 99, 99.1, 99.2, 99.3, 99.4, 99.5, 99.6, 99.7, 99.8, 99.9, 100, 100.1, 100.2, 100.3, 100.4, 100.5, 100.6, 100.7, 100.8, 100.9 and 101 mg/kg. Accordingly, about 100 mg/kg includes, in an embodiment, 100 mg/kg.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

For the foregoing embodiments, each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Combination Therapy

The administration of two drugs to treat a given condition, such as melanoma, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug. (Guidance for Industry, 1999) Thus, when two drugs are administered to treat the same condition, it is unpredictable whether each will complement, have no effect on, or interfere with the therapeutic activity of the other in a human subject.

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side effect profile of each drug.

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs. (Guidance for Industry, 1999)

EXPERIMENTAL DETAILS

Example 1. PP2A Inhibition and CTLA-4 Activity

Compound LB-100 and other homologs of LB-100 disclosed herein inhibit the function of CTLA-4 in T cells by altering the interaction of CTLA-4 and PP2A, thereby blocking CTLA-4 mediated inhibition of T-cell activation. Such interaction results in increased T-cell activation.

Example 2. In Vitro Studies: PP2A and CTLA4

Primary human T cells and Jurkat T cells are treated with LB-100 and T-cell activation levels measured. LB-100 increases activation of the T cells.

Primary human T cells and Jurkat T cells are treated with LB-100 and PP2A:CTLA-4 interaction is assessed. LB-100 decreases the interaction of PP2A and CTLA-4.

Primary human T cells and Jurkat T cells are treated with LB-100 and levels of PP2A phosphorylation are measured. LB-100 increases phosphorylation in the T cells.

Example 3. Administration of LB-100 and Analogs

An amount of compound LB-100 is administered to a subject afflicted with cancer. The amount of the compound is effective to treat the cancer by increasing the number of cytotoxic T cells in the subject.

An analog of compound LB-100 disclosed herein is administered to a subject afflicted with cancer. The amount of the compound is effective to treat the cancer by increasing the number of cytotoxic T cells in the subject.

An amount of compound LB-100 is administered to a subject afflicted with melanoma. The amount of the compound is effective to treat the cancer by increasing the number of cytotoxic T cells in the subject.

An analog of compound LB-100 disclosed herein is administered to a subject afflicted with melanoma. The amount of the compound is effective to treat the cancer by increasing the number of cytotoxic T cells in the subject.

Example 4. Administration of LB-100 in Combination with a CTLA-4 Checkpoint Inhibitor An amount of compound LB-100 in combination with a CTLA-4 checkpoint inhibitor is administered to a subject afflicted with cancer. The amount of the compound and inhibitor is effective to treat the subject.

An amount of compound LB-100 in combination with a CTLA-4 checkpoint inhibitor is administered to a subject afflicted with cancer. The amount of the compound is effective to enhance the anti-cancer activity of the CTLA-4 checkpoint inhibitor.

An amount of compound LB-100 in combination with a CTLA-4 checkpoint inhibitor is administered to a subject afflicted with melanoma. The amount of the compound and inhibitor is effective to treat the subject.

An amount of compound LB-100 in combination with a CTLA-4 checkpoint inhibitor is administered to a subject afflicted with melanoma. The amount of the compound is effective to enhance the anti-cancer activity of the CTLA-4 checkpoint inhibitor.

Example 5: Assessment of Efficacy of LB-100 as Add-on Therapy to Ipilimumab or Tremelimumab The add-on therapy provides a synergistic effect, and allows for lower doses with reduced side effects.

Periodic administration of LB-100 as an add-on therapy for a human patient afflicted with melanoma who is already receiving Ipilimumab or Tremelimumab provides a clinically meaningful advantage and is more effective (provides at least an additive effect or more than an additive effect) in treating the patient than when ipilimumab or tremelimumab is administered alone (at the same dose).

Periodic administration Ipilimumab or Tremelimumab as an add-on therapy for a human patient afflicted with melanoma who is already receiving of LB-100 provides a clinically meaningful advantage and is more effective (provides at least an additive effect or more than an additive effect) in treating the patient than when LB-100 is administered alone (at the same dose).

The add-on therapies also provides efficacy (provides at least an additive effect or more than an additive effect) in treating the patient without undue adverse side effects or affecting the safety of the treatment. As compared to when each agent is administered alone:

1. The add-on therapy is more effective (provides an additive effect or more than an additive effect) in increasing the amount of cytotoxic T cells in patients with melanoma;
2. The add-on therapy is more effective (provides an additive effect or more than an additive effect) in slowing the progression of melanoma in patients with melanoma; and/or
3. The add-on therapy is more effective (provides an additive effect or more than an additive effect) in reducing the function of CTLA-4 in the melanoma patients.

Discussion (Examples 1-5)

The importance of the immune system in the context of cancer has increasingly been recognized with the development of cancer immunotherapy. The natural control mechanism of the immune system to prevent autoimmunity is often co-opted by tumors to evade immunosurveillance. Checkpoint molecules, such as programmed death-1 (PD-1) and cytotoxic T lymphocyte-associated protein 4 (CTLA-4), are negative regulators of the immune system that are constitutively activated by tumors to suppress activity of cytotoxic T cells that recognize neo-antigens of tumors (Topalian et al. 2015). Immunosuppressive regulatory T cells (Tregs) are also recruited to the tumor microenvironment (TME) to reduce effectiveness of the CD8 T cells. Monoclonal antibodies blocking PD-1 or CTLA-4 signaling could induce durable long-term responses in some patients with metastatic melanoma. This led to the approval of Ipilimumab (anti-CTLA-4) in 2011 and nivolumab (anti-PD-1) in 2014 by the U.S. Food and Drug Administration for treatment of advanced melanoma. Current clinical trials are underway to expand the use of checkpoint inhibitors to multiple other cancers, ushering a paradigm shift in the approach to cancer therapy. However, only a subset of patients responds to checkpoint inhibition effectively as single agent, highlighting the fact that multiple redundant mechanisms are involved in creating an immunosuppressive TME. Therefore, an active area of research is to identify combination strategies that could augment the effect of checkpoint inhibition.

Cytotoxic T lymphocyte associated antigen-4 (CTLA-4) is an activation-induced glycoprotein of the Immunoglobulin superfamily, whose primary function is to down-regulate T cell responses (Brunet, J. F. et al. 1987). CTLA-4 is expressed on the surface of T cells, where it primarily suppresses their early stages of activation by inducing inhibitory downstream T-cell receptor (TCR) signaling and counteracting activity of the T-cell costimulatory receptor, CD28, thus inhibiting T-cell activation and increasing immune tolerance to certain diseases, e.g. cancer. Several mechanisms, including antagonism of CD28-dependent costimulation and direct negative signaling have been documented to explain the inhibitory capacity of CTLA-4 (Carreno, B. M. et al. 2000). Since the cytoplasmic tail of CTLA-4 lacks intrinsic enzymatic activity, the delivery of such a negative signal is likely provided through the association of CTLA-4 with key signaling molecules (Teft, W. A. Et al. 2006).

Inhibition of CTLA-4 has been targeted for the treatment of cancers by way of an immune-checkpoint blockade. Cellular and murine malignancy models demonstrate that blockade of cytotoxic T lymphocyte antigen-4 (CTLA-4), a negative regulator of T cell responses, augments endogenous responses to tumor cells, thus leading to tumor cell death when utilized on its own or with other therapeutic interventions (Grosso, J. F. et al. 2013). Preclinical findings have translated into clinical development of a fully human, IgG1 monoclonal antibody (mAb), ipilimumab and a fully human, IgG2 mAb, tremelimumab, each of which bind CTLA-4.

Phosphorylation of proteins by kinases and their dephosphorylation by phosphatases are critical components of cellular signaling pathways regulating a multiplicity of processes including cell proliferation and cell death (Shi et al. 2009). Although phosphatases have long been considered potentially important targets for cancer treatment, there has been little effort to develop phosphatase inhibitors due to concern over toxicity (Janssens et al. 2012).

Protein phosphatase 2A (PP2A) is a ubiquitous serine/threonine phosphatase that dephosphorylates numerous proteins of both ATM/ATR-dependent and -independent response pathways (Mumby M. 2007). PP2A is implicated in a diverse set of cellular processes. In the immune system, PP2A has been shown to associate with CTLA-4 and mediates dephosphorylation of Akt leading to inhibition of activated T cells (Parry et al. 2005). Pharmacologic inhibition of PP2A has previously been shown to sensitize cancer cells to radiation-mediated DNA damage via constitutive phosphorylation of various signaling proteins, such as p53, γH2AX, PLK1 and Akt, resulting in cell cycle deregulation, inhibition of DNA repair, and apoptosis (Wei, D. et al. 2013).

Cantharidin, the principle active ingredient of blister beetle extract (Mylabris), is a compound derived from traditional Chinese medicine that has been shown to be a potent inhibitor of PP2A (Efferth, T. et al. 2005). Although cantharidin has previously been used in the treatment of hepatomas and has shown efficacy against multidrug-resistant leukemia cell lines (Efferth, T. et al. 2002), its severe toxicity limits its clinical usefulness. Cantharidin, a naturally occurring toxin, and its demethylated analog, norcantharidin, both potent inhibitors of PP2A (Bertini et al. 2009) were reported to have anti-cancer activity in patients in China with gastrointestinal cancers (Wang et al. 1989) although little clinical detail is available.

Fostriecin, another selective inhibitor of PP2A was evaluated in several US NCI-sponsored phase 1 trials over twenty years ago. In the largest trial, fostriecin was associated with disease stability in 16 (34.8%) of 46 solid tumor patients without dose-limiting toxicity (DLT) (Lê et al. 2004). No trials were completed because of insufficient drug supply.

LB-100 is a small molecule derivative of cantharidin with significantly less toxicity. LB-100 and its lipid-soluble homolog, LB-102, inhibit proliferation of cell lines from a variety of human solid tumors. Both compounds potentiate the activity without significantly increasing the toxicity of cisplatin, doxorubicin, and temozolomide against xenografts of pancreatic and hepatocellular carcinoma; fibrosarcoma; pheochromocytoma; neuroblastoma; and glioblastoma and of focal X-ray against pancreatic, nasopharyngeal and glioblastoma xenografts (Bai et al., 2014a; Bai et al., 2014b; Zhang et al., 2010; Matiniova et al., 2011; Lu et al., 2009; Wei et al., 2013; Lv et al., 2014; Gordon et al., 2015). In addition, LB-100 reversed resistance to cisplatin in ovarian carcinoma and medulloblastoma xenografts (Chang et al., 2015; Ho et al., 2016). Previous pre-clinical studies have shown that LB-100 can enhance the cytotoxic effects of temozolomide, doxorubicin, and radiation therapy against glioblastoma (GBM), metastatic pheochromocytoma, and pancreatic cancer (Wei, D. et al. 2013; Lu, J. et al. 2009; Zhang, C. et al. 2010; Martiniova, L. et al. 2011).

LB-100 is also undergoing a Phase 1 study in combination with docetaxel for the treatment of solid tumors (Chung, V. 2013). LB-100 is a novel, first-in-class, small molecule inhibitor of protein phosphatase 2A (PP2A) recently shown in a Phase 1 trial to be well-tolerated at doses associated with stabilization of progressive solid tumors (Chung et al. 2017). PP2A has been implicated in mediating Akt signaling downstream of CTLA-4 (Parry et al. 2005). In an in vivo pooled short hairpin RNA screen, Ppp2r2d, a regulatory subunit of PP2A, when knocked down was found to increase proliferation of tumor infiltrating lymphocytes to the greatest extent among all genes in the RNA library and identified PP2A as a key regulator in suppressing T-cell proliferation in the tumor microenvironment (Zhou et al. 2014). In addition, PP2A was found to be essential for regulatory-T-cell (Treg) function (Apostolidis et al. 2014).

While multiple pre-clinical studies have shown LB-100 to be an effective chemo- or radio-sensitizer in various tumor models (Hone et al. 2015), none have studied its effect on the immune system.

Impairment of CTLA-4 function allows cancer patients to mount a more effective cytotoxic t-cell attack on their cancers. Unlike the leading clinically used modulator of CTLA-4, the antibody ipilimumab (Yervoy), which is associated with significant toxicity at therapeutically effective doses, compound LB-100 is associated with stability of several different types of cancer in the absence of any significant toxicity or side effects.

There are a number of reports of clinical activity by inhibiting CTLA-4 with ipilimumab, particularly in patients with advanced melanoma. These studies show that single-agent ipilimumab and in combination with a cytotoxic drug such as dacarbazine or with another immune checkpoint inhibitor, nivolumab, cause regression of cancers. Alone or in combination with other agents, ipilimumab is associated with significant toxicity such as in the study by Hodi et al. (2010) in which up to 15% of patients had grade 3 or 4 adverse events including a 2.1% incidence of death. Wolchok et al (2013) studied ipilimumab plus nivolumab in patients with advanced melanoma, but grade 3 or 4 adverse events occurred in 53% of patients. Thus, the availability of a molecule such as LB-100 which has no limiting toxicity at doses associated with stabilization of progressive cancer and has anti CTLA-4 activity is an attractive clinical candidate for the treatment of human cancers. At present, there are no molecular determinants of clinical response to CTLA-4 modulation. Snyder et al (2014) reported a genetic basis for potential benefit from CTLA-4 treatment of melanoma, providing a potential basis for characterizing candidate tumor neoantigens for each patient.

Without being bound by any theory, it is believed that CTLA-4 interacts with PP2A in human T cells and such interaction is essential for the proper function of CTLA-4. When functioning correctly, CTLA-4 inhibits T-cell activation, thus reducing the immunoresponse to cancer cells. Administration of a PP2A inhibitor to a subject with cancer alters the interaction of PP2A with CTLA-4, thereby disrupting the normal function of CTLA-4. The reduction or elimination of CTLA-4 function in T cells leads to increased T-cell activation. Increased T-cell activation results in an increase in cytotoxic T cells in the subject which target and destroy the cancer cells. As with the existing immune checkpoint inhibitors, LB-100 is effective alone and/or in combination with other checkpoint inhibitors.

Example 6. Assessment of LB-100 in Adult Patients with Progressive Solid Tumors

PP2A has long been recognized as a potentially important target for cancer therapy because of its regulatory role in cell division, DNA-damage-response, homologous recombination repair, and mitotic exit but inhibition of this enzyme has been considered likely to be too toxic for clinical use. This study shows the safety, tolerability, and potential anti-cancer activity of an inhibitor of PP2A, LB-100, in patients with refractory solid tumors. PP2A activity is altered by mutation directly or indirectly in many types of cancer. The availability of a clinically safe inhibitor of PP2A opens a promising new avenue for cancer therapy, namely pharmacologic inhibition of PP2A in cancers with mutationally acquired abnormalities in PP2A function and/or in the DNA-damage-repair pathway. The results of this study support further development of LB-100 alone and in combination with other agents for the treatment of cancers.

Purpose: To assess the safety, tolerability, and potential activity of LB-100, a first-in-class small molecule inhibitor of protein phosphatase 2A (PP2A), in adult patients with progressive solid tumors.

Experimental Design: LB-100 was administered intravenously daily for 3 days in 21-day cycles in a 3+3 dose-escalation design. The primary goal was to determine the maximum tolerated dose and recommended phase 2 dose (ClinicalTrials.gov: NCT01837667).

Materials and Methods

Eligible patients were aged 18 years or older with proven progressive solid tumors who had failed standard treatments. Patients had to have a life expectancy of at least 12 weeks, an ECOG performance status of 0 or 1, and be able to give informed consent. Before participation, patients must have recovered to baseline or less than grade 1 toxicity from prior treatments, have adequate bone marrow (an absolute neutrophil count $>1.5 \times 10^9$/L and platelet count $>100 \times 10^9$/L); kidney (serum creatinine <1.2 mg/dL and if >1.2 mg/dL, creatinine clearance [Cockcroft-Gault method]>60 mL/min/ 1.73 $m^2$); and hepatic function (plasma total bilirubin <1.5 mg/dL, alanine transaminase (ALT) and aspartate transaminase (AST)<2.5×upper limit of normal). They must not have any other uncontrolled systemic disease. Women of childbearing potential had to have a negative serum or urine pregnancy test result.

Study Design and Treatment

An open-label, dose-escalation, phase I study was performed to assess the safety, tolerability, and activity of LB-100 administered for 3 consecutive days every 3 weeks. Pharmacokinetic studies were planned at the maximum tolerable dose (MTD). The starting dose, 0.25 mg/$m^2$, $\frac{1}{15}^{th}$ of the highest non-severely toxic dose in dogs, and plan of dose escalation was specified by the FDA. The study was approved by the human investigations committee at each study center and is registered at clinicaltrials.gov: NCT01837667.

LB-100 was supplied as a single use solution. Initially, LB-100 was administered in 50 mL of saline over 15 minutes. Because of a non-limiting reversible increase in serum creatinine at the 2.33 mg/$m^2$ level, LB-100 was subsequently administered in 500 mL normal saline over 2 hours. Dose escalation was prohibited within any cohort. Patients were eligible to receive up to 6 cycles of study therapy, unless unacceptable toxicity, disease progression, or inter-current illness required discontinuation. More than 6 cycles were allowed in the absence of progression and toxicity. Because of cardiac and renal toxicity at high doses in animal toxicology studies, patients had extensive monitoring including ECG, MUGA or echocardiogram, cardiac troponins, and BNP prior to every cycle. Blood chemistries, urinalysis, hematologic profile and vital signs were monitored prior to and on day 1, 3, 8, 15, and 22 of each cycle. Laboratory parameters were tabulated by maximum NCI-CTCAE (Version 4.0) severity grade. A safety review committee assessed all clinical data every 2 weeks and approved dose escalation between cohorts.

Evaluation of Toxicity and Clinical Activity

Doses of LB-100 were escalated in groups of three patients. The first patient at a new dose level was observed for three weeks before treating the next two at that dose. When a potential DLT occurred, three new patients were entered at that dose. If another DLT occurred, three additional patients were treated at the previous non-DLT dose to determine the safety of that level for phase 2 trials.

Response to treatment was assessed using RECIST version 1.1. All patients with measurable disease, who completed 2 cycles of LB-100 and had at least 1 post-baseline tumor assessment, were evaluable for efficacy. Patients receiving any LB-100 were evaluable for safety. The severity of adverse events and laboratory abnormalities is reported according to NCI-CTCAE version 4.0 and coded using Medical Dictionary for Regulatory Activities.

Outcomes

The main objective was to determine the safety, tolerability, and maximum tolerated dose of LB-100 given intravenously daily for three consecutive days every 3 weeks. The secondary objectives were to document any evidence of potential anti-tumor activity and obtain pharmacokinetic data on LB-100 and a metabolite, endothall, in patients receiving LB-100 at the MTD (Quang et al., 2016).

Results:

There were 29 patient entries over 7 dose escalations. One patient stopped treatment after one dose because of an acute infection and was reenrolled after recovery. Both courses were analyzed as separate patient entries. Two patients had dose limiting toxicity (reversible increases in serum creatinine or calculated serum creatinine clearance) at the 3.1 mg/m$^2$ level. Probable or possible study drug related Grade 3 adverse events occurred in 6 (20.7%) patients [anemia (n=2), decreased creatinine clearance, dyspnea, hyponatremia, lymphopenia]. Ten (50%) of 20 response-evaluable patients had stable disease for 4 or more cycles. One patient with pancreatic carcinoma had a partial response noted after 10 cycles that was maintained for 5 additional cycles. The other patients achieving stable disease had one of the following: fibrosarcoma, chondrosarcoma, thymoma, atypical carcinoid of lung, or ovarian, testicular, breast (n=2), and prostate cancer. The recommended phase 2 dose of LB-100 is 2.33 mg/m2 daily for 3 days every 3 weeks.

Patient Characteristics

Twenty-eight patients with advanced solid tumors were enrolled at four clinical sites. Their demographic features are listed in Table 1. Four patients were not evaluable for toxicity. Three of these patients had disease-associated complications prior to completing cycle 1. A fourth patient with atypical carcinoid of the lung was removed from study after one dose of LB-100 because of an acute infection; he was re-entered on study 7 weeks later and achieved stable disease for 5 cycles. Both courses were included in the analyses. None of these adverse events was considered related to drug administration.

TABLE 1

Patient Baseline Clinical and Demographic Characteristics Study population ( n = 28)

| Sex | |
|---|---|
| Male | 14 (50.0%) |
| Female | 14 (50.0%) |
| Ethnic Origin | |
| White | 23 (82.1%) |
| Asian | 3 (10.7%) |
| Not Reported | 1 (3.6%) |
| Other | 1 (3.6%) |
| Age (years) | |
| N | 28 |
| Mean | 62.3 |
| Standard Deviation | 10.66 |
| Median | 64.0 |
| Minimum | 35 |
| Maximum | 79 |
| 8 to 64 | 15 (55.6%) |
| 65+ | 13 (46.4%) |
| Primary Site | |
| LUNG & BRONCHUS | 5 (17.9%) |
| LARGE INTESTINE, (EXCL. APPENDIX) | 5 (17.9%) |
| BREAST | 2 (7.1%) |
| CONNECTIVE & SOFT TISSUE | 2 (7.1%) |
| OVARY | 2 (7.1%) |
| TESTIS | 2 (7.1%) |
| APPENDIX | 1 (3.6%) |
| BONES & JOINTS | 1 (3.6%) |
| CORPUS UTERI | 1 (3.6%) |
| PANCREAS | 1 (3.6%) |
| PROSTATE GLAND | 1 (3.6%) |
| RECTUM | 1 (3.6%) |
| SMALL INTESTINE | 1 (3.6%) |
| THYMUS | 1 (3.6%) |
| UTERUS, NOS | 1 (3.6%) |
| VULVA, NOS | 1 (3.6%) |

Dose Escalation and Toxicity

Twenty-four patients completed at least one 3-day cycle of LB-100. The tested dose levels were 0.25, 0.50, 0.83, 1.25, 1.75, 2.33, and 3.1 mg/m$^2$. There was no DLT during the first 6 dose levels. At the 3.1 mg/m2 dose level, a patient with prostate cancer and one with chondrosarcoma had no DLT during 4 and 9 cycles of treatment, respectively. A third patient with ovarian cancer had a grade 3 increase in calculated creatinine clearance after cycle 1 with a return to normal by day 8 and received 3 more cycles at a reduced dose of 2.33 mg/m2 before tumor progression. A fourth patient with fibrosarcoma had a grade 3 increase in calculated creatinine clearance after the first course. The creatinine returned to pretreatment value by day 21 and a second course at 2.33 mg/m2 resulted in a grade 2 increase in creatinine clearance without other toxicity. The dose was decreased to 1.75 mg/m2 and ten more cycles were administered without toxicity until progression after 36 weeks. Because 2/4 patients at 3.1 mg/m2 had grade 3 increases in creatinine clearance during cycle one, three additional patients were evaluated at the preceding dose level of 2.33 mg/m2. They had no limiting toxicity thereby establishing the MTD at that level. There was no symptomatic toxicity other than reversible mild to moderate fatigue. Adverse events possibly related to drug administration are listed in Table 2.

TABLE 2

Adverse Events in the Safety Population

| MedDRA Preferred Term [1][2] | Grade 1-2 | Grade 3 | Grade 4 | Grade 5 |
|---|---|---|---|---|
| Total Patients with Related Treatment-Emergent Adverse Events [3] | 22 (75.9%) | 6 (20.7%) | 0 | 0 |
| FATIGUE | 8 (27.6%) | 0 | 0 | 0 |
| BLOOD CREATININE INCREASED | 5 (17.2%) | 0 | 0 | 0 |
| ASPARTATE AMINOTRANSFERASE INCREASED | 4 (13.8%) | 0 | 0 | 0 |
| HEADACHE | 3 (10.3%) | 0 | 0 | 0 |
| HYPERNATRAEMIA | 3 (10.3%) | 0 | 0 | 0 |
| HYPOALBUMINAEMLA | 3 (10.3%) | 0 | 0 | 0 |
| NAUSEA | 3 (10.3%) | 0 | 0 | 0 |
| PROTEINURIA | 3 (10.3%) | 0 | 0 | 0 |
| PYREXIA | 3 (10.3%) | 0 | 0 | 0 |
| ALANINE AMINOTRANSFERASE INCREASED | 2 (6.9%) | 0 | 0 | 0 |

TABLE 2-continued

Adverse Events in the Safety Population

| MedDRA Preferred Term [1][2] | Grade 1-2 | Grade 3 | Grade 4 | Grade 5 |
|---|---|---|---|---|
| CONSTIPATION | 2 (6.9%) | 0 | 0 | 0 |
| NEUROPATHY PERIPHERAL | 2 (6.9%) | 0 | 0 | 0 |
| OEDEMA PERIPHERAL | 2 (6.9%) | 0 | 0 | 0 |
| SINUS TACHYCARDIA | 2 (6.9%) | 0 | 0 | 0 |
| ABDOMINAL DISCOMFORT | 1 (3.4%) | 0 | 0 | 0 |
| ABDOMINAL DISTENSION | 1 (3.4%) | 0 | 0 | 0 |
| ACCELERATED HYPERTENSION | 1 (3.4%) | 0 | 0 | 0 |
| ANAEMIA | 1 (3.4%) | 2 (6.9%) | 0 | 0 |
| ARTHRALGIA | 1 (3.4%) | 0 | 0 | 0 |
| BLOOD ALKALINE PHOSPHATASE INCREASED | 1 (3.4%) | 0 | 0 | 0 |
| BLOOD UREA INCREASED | 1 (3.4%) | 0 | 0 | 0 |
| CANDIDIASIS | 1 (3.4%) | 0 | 0 | 0 |
| CHEST PAIN | 1 (3.4%) | 0 | 0 | 0 |
| CHILLS | 1 (3.4%) | 0 | 0 | 0 |
| DECREASED APPETITE | 1 (3.4%) | 0 | 0 | 0 |
| DERMATITIS ACNEIFORM | 1 (3.4%) | 0 | 0 | 0 |
| DIARRHOEA | 1 (3.4%) | 0 | 0 | 0 |
| DIZZINESS | 1 (3.4%) | 0 | 0 | 0 |
| EJECTION FRACTION DECREASED | 1 (3.4%) | 0 | 0 | 0 |
| ELECTROCARDIOGRAM QT PROLONGED | 1 (3.4%) | 0 | 0 | 0 |
| GAIT DISTURBANCE | 1 (3.4%) | 0 | 0 | 0 |
| GASTROINTESTINAL DISORDER | 1 (3.4%) | 0 | 0 | 0 |
| GENERALISED OEDEMA | 1 (3.4%) | 0 | 0 | 0 |
| GINGIVAL PAIN | 1 (3.4%) | 0 | 0 | 0 |
| HYPERCALCAEMIA | 1 (3.4%) | 0 | 0 | 0 |
| HYPERKALAEMIA | 1 (3.4%) | 0 | 0 | 0 |
| HYPERTENSION | 1 (3.4%) | 0 | 0 | 0 |
| HYPOAESTHESIA | 1 (3.4%) | 0 | 0 | 0 |
| HYPOKINESIA | 1 (3.4%) | 0 | 0 | 0 |
| HYPOTENSION | 1 (3.4%) | 0 | 0 | 0 |
| HYPOXIA | 1 (3.4%) | 0 | 0 | 0 |
| INSOMNIA | 1 (3.4%) | 0 | 0 | 0 |
| MUCOSAL INFLAMMATION | 1 (3.4%) | 0 | 0 | 0 |
| MUSCLE TWITCHING | 1 (3.4%) | 0 | 0 | 0 |
| MUSCULAR WEAKNESS | 1 (3.4%) | 0 | 0 | 0 |
| NEUTROPENIA | 1 (3.4%) | 0 | 0 | 0 |
| OEDEMA | 1 (3.4%) | 0 | 0 | 0 |
| PAIN OF SKIN | 1 (3.4%) | 0 | 0 | 0 |
| PERIPHERAL COLDNESS | 1 (3.4%) | 0 | 0 | 0 |
| PERIPHERAL SENSORY NEUROPATHY | 1 (3.4%) | 0 | 0 | 0 |
| PLATELET COUNT DECREASED | 1 (3.4%) | 0 | 0 | 0 |
| PLEURAL EFFUSION | 1 (3.4%) | 0 | 0 | 0 |
| TACHYPNOEA | 1 (3.4%) | 0 | 0 | 0 |
| TREMOR | 1 (3.4%) | 0 | 0 | 0 |
| VOMITING | 1 (3.4%) | 0 | 0 | 0 |
| WEIGHT DECREASED | 1 (3.4%) | 0 | 0 | 0 |
| CREATININE RENAL CLEARANCE | 0 | 1 (3.4%) | 0 | 0 |
| DYSPNOEA | 0 | 1 (3.4%) | 0 | 0 |
| HYPONATRAEMIA | 0 | 1 (3.4%) | 0 | 0 |
| LYMPHOCYTE COUNT DECREASED | 0 | 1 (3.4%) | 0 | 0 |

[1] Number of Patients used as denominator to calculate percentages.

[2] Patients with multiple TEAEs are counted once within a Preferred Term.

[3] Treatment-Emergent Adverse Events (TEAEs) are defined as all AEs that occurred after the first dose of study medication or within 30 days post-treatment period.

Pharmacokinetics

The plasma concentrations of LB-100 and endothall were measured (Quang et al., 2016) prior to and over 4 hours after completion of the 2-hour infusion at the MTD of 2.33 mg/m2 of LB-100 on day 1 in one patient and on day 1 and 3 in two patients. The pharmacokinetics of LB-100 were similar on day 1 and 3 and were characterized by a low clearance, low volume of distribution, and a short half-life. Plasma concentrations of endothall were low throughout the infusion, being below the lower limit of detection (5 ng/mL) in one patient. In the other two patients, the maximal concentration of endothall (34.7 ng/mL) was observed at the last sampling time point (4 h), which precluded determination of its elimination half-life (Table 3).

TABLE 3

Pharmacokinetic parameters for LB-100 and endothall

LB-100

| Subject Group | Day Nominal | Subject | Gender | Dose (mg/m²) | Apparent CL$^a$ (ng*h/mL) | Apparent V$_{ss}$$^b$ (ng*h/mL) | T$_{1/2}$ (h) |
|---|---|---|---|---|---|---|---|
| 1 | 1 | 001-0030 | Male | 2.33 | 2.5 | 0.52 | 1.10 |
|   | 3 |          |      | 2.33 | 5.7 | 1.10 | 0.95 |
| 1 | 1 | 002-0028 | Female | 2.33 | 2.7 | 0.65 | 1.35 |
|   | 3 |          |        | 2.33 | 2.0 | 0.47 | 1.56 |
| 1 | 1 | 003-0029 | Female | 2.33 | 4.7 | 1.06 | 1.58 |

$^a$Clearance value and
$^b$volume of distribution at steady-state represents a close approximation because the plasmaconcentration-time profile was only characterized through 4 hours after completion of the infusion.

Endothall

| Subject Group | Day Nominal | Subject | Gender | Dose (mg/m²) | Cmax (ng/mL) | Tmax (h) | Tin (h) | AUC (ng*h/mL) |
|---|---|---|---|---|---|---|---|---|
| 1 | 1 | 001-0030 | Male | 2.33 | N-D$^a$ | N-D$^a$ | ND$^b$ | N-D$^c$ |
|   | 3 |          |      | 2.33 | N-D$^a$ | N-D$^a$ | ND$^b$ | N-D$^c$ |
| 1 | 1 | 002-0028 | Female | 2.33 | 11.5 | 4 | ND$^d$ | 22 |
|   | 3 |          |        | 2.33 | 34.3 | 4 | ND$^b$ | 143 |
| 1 | 1 | 003-0029 | Female | 2.33 | 14.8 | 4 | ND$^b$ | 28 |

$^a$Plasma concentrations of endothall were below the lower limit of quantification (5 ng/ml)
$^b$Terminal elimination half-life and
$^c$AUC values could not be defined.

Evaluation of Clinical Activity

Figure 1:
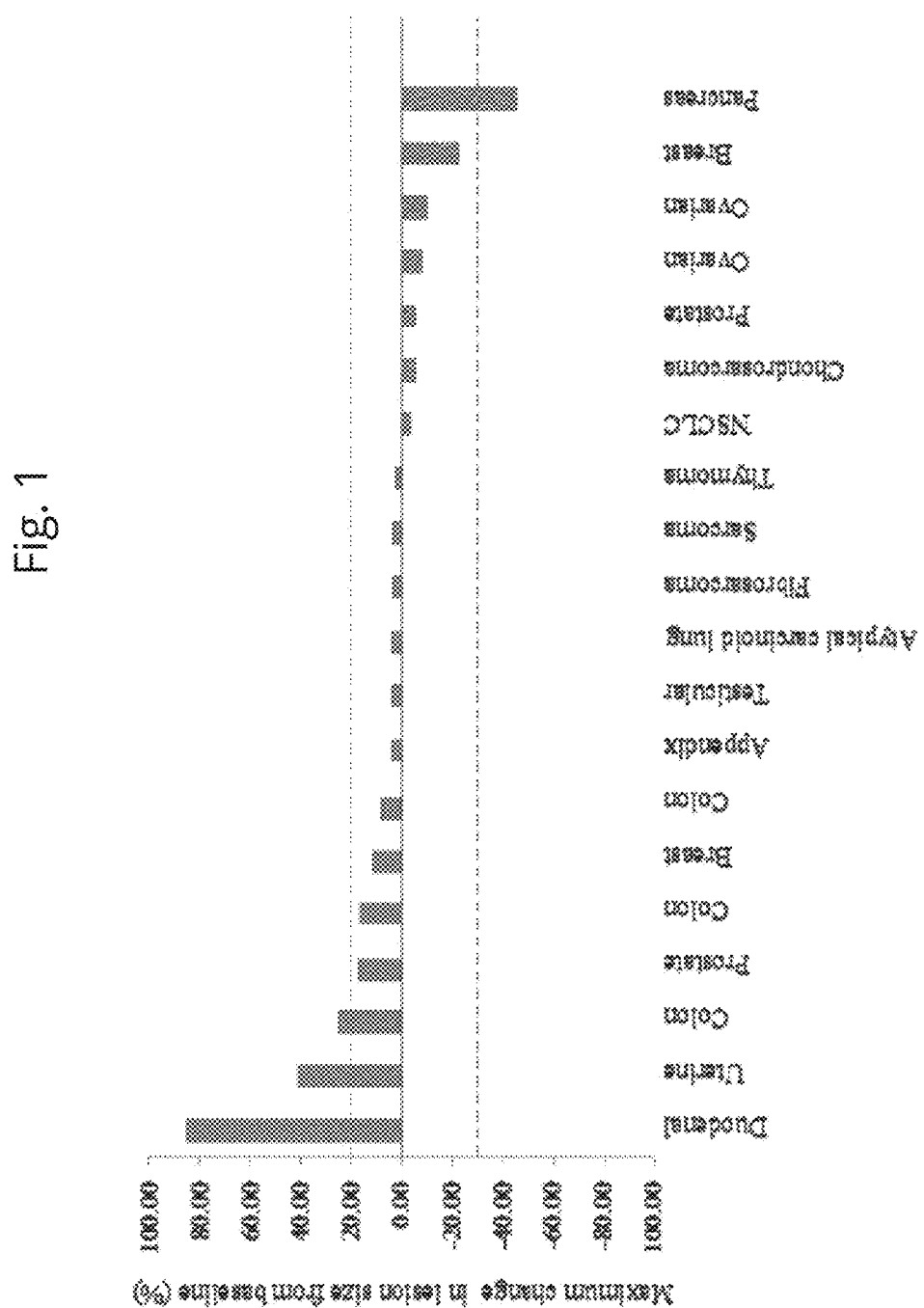
FIG. 1. Greatest change in size of indicator lesion in patients with measurable disease at entry.

Of 20 patients with measurable disease, one patient with pancreatic cancer had a partial response, noted after 10 cycles and lasting for 5 more cycles, and 16 patients had no progression of their indicator lesion(s). They were removed from study for either the appearance of a new lesion or symptoms judged to represent clinical progression. Only 3 patients, one with duodenal and two with colonic adenocarcinomas, had significant increases in the size of their indicator lesion(s) by RECIST criteria (FIG. 1).

Figure 2:
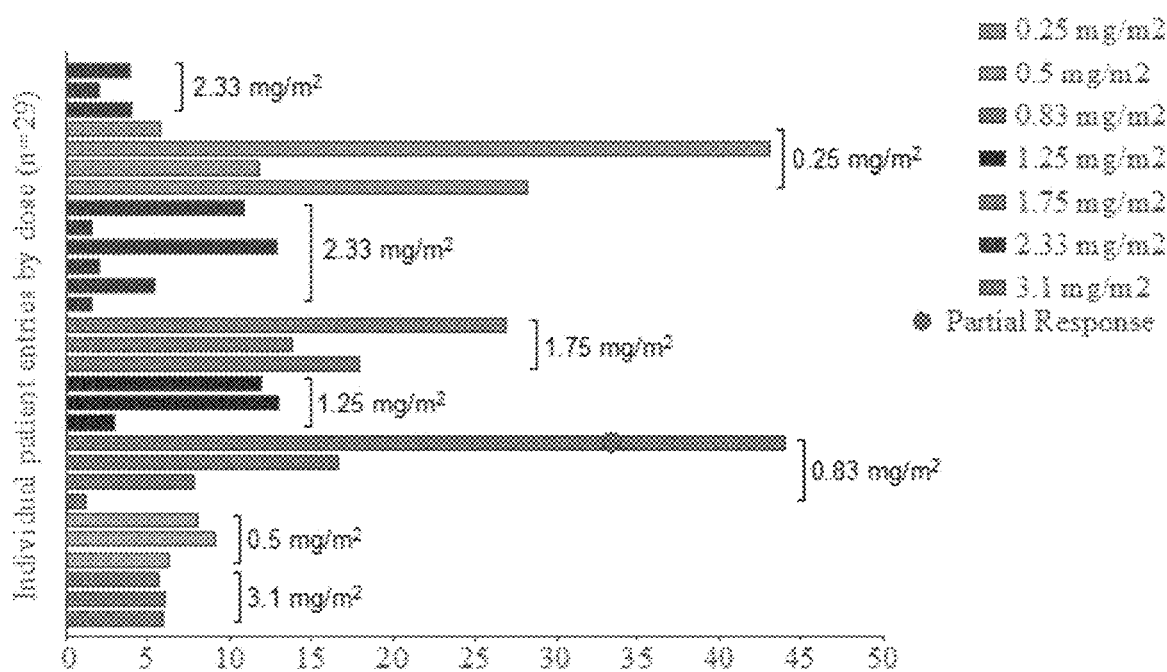
FIG. 2. Duration of stability or partial response (red circle) of disease (number of cycles) for each patient in ascending order of entry onto study.

Achieving partial response or stability of disease was not clearly dose-dependent, occurring at 0.83 mg/m² in pancreatic cancer (15 cycles) and atypical carcinoid of the lung (5 cycles); at 1.25 mg/m² in breast cancer (4 cycles) and testicular cancer (5 cycles); and at 1.75 mg/m² in malignant thymoma (8 cycles) and ovarian cancer (6 cycles). At 3.1 mg/m², a patient with chondrosarcoma was stable for 8 cycles of LB-100 without any alteration in normal renal function whereas a patient with fibrosarcoma started at 3.1 mg/m² was stable for 12 cycles after two dose reductions (FIG. 2).

Conclusions: The safety, tolerability, preliminary evidence of anti-tumor activity, and novel mechanism of action of LB-100, support its continued development alone and in combination with other therapies.

Discussion (Example 6)

The MTD of LB-100, a potent inhibitor of PP2A, was determined in patients with solid tumors. The recommended phase 2 starting dose is 2.33 mg/m² daily for 3 days every 3 weeks with escalation to 3.1 mg/m² in the absence of renal toxicity and de-escalation to 1.75 mg/m² or lower for renal toxicity in the event of stable or regressing disease. As patients had stability of disease and one patient with pancreatic cancer objective regression of pancreatic cancer at doses as low as 0.83 mg/m2 daily for 3 days every 3 weeks, it is possible that optimum anti-cancer activity in humans may be considerable less than the MTD.

Ten (50%) of 20 patients receiving at least 2 cycles of LB-100 had stable disease for up to 15 cycles of therapy without limiting or cumulative toxicity. The mechanism underlying this phenomenon is not clear. PP2A activity is impaired or enhanced in many types of cancer by mutation or by increased expression of one or more of several endogenous PP2A inhibitors (Chang et al., 2015; Perotti et al., 2013; Seshacharyulu et al., 2013; Sangodkar et al; 2016). Since the single patient with pancreatic cancer in the present study had an objective response and otherwise stable disease for over 11 months, it is of special interest that marked overexpression of a regulatory subunit of PP2A associated with PP2A hyperactivity in a majority of human pancreatic cancers has recently been reported (Hein et al., 2016). Knockdown of this subunit, PR55α, in a human pancreatic cell line orthotopically implanted in nude mice, significantly reduced its tumorigenicity and metastatic potency (Hein et al., 2016).

On the other hand, without wishing to be bound to a specific theory, acquired deficits in PP2A activity may render tumors selectively vulnerable to further pharmacologic inhibition of PP2A. For example, in del(5q) myelodysplastic syndrome (MDS), an allele for the catalytic subunit of PP2A is deleted (Sallman et al., 2014). Lenalidomide, the standard agent for the treatment of MDS, was reported to be selectively cytotoxic to these PP2A haploinsufficient del(5q)MDS cells by virtue of its moderate PP2A inhibitory activity (Sallman et al., 2014). PP2A inhibition also results in synthetic lethality of cancer cells that overexpress Mad2 (mitotic arrest deficiency protein 2) occurring in concert with mutations in Rb and/or p53 pathways (Bian et al., 2014; Schvartman et al., 2011). In the present study, the pancreatic cancer of the patient having a partial response markedly overexpressed Mad2.

Another potential mechanism by which single agent LB-100 may inhibit cancer progression is by enhancing cytotoxic T-cell function. Without wishing to be bound to a specific theory, the phosphatase activity of PP2A is important to CTLA-4-mediated T cell activation (Teft et al., 2009) and essential for regulatory T cell function (Apostolidis et al., 2016). In addition, inhibition of Ppp2r2d, a regulatory subunit of PP2A, enhances T-cell proliferation and cytokine production by a mechanism other than those of known negative regulators of T-cell function (Zhou et al., 2014). In the present study, however, no patient experienced toxicities suggestive of autoimmune activity that occurs with the currently approved compounds that induce immune checkpoint blockade.

The availability of a clinically safe inhibitor of PP2A provides an opportunity to exploit a long appreciated but neglected therapeutic target for cancer therapy. The current trial suggests that LB-100 alone has anti-cancer activity. Pharmacologic inhibition of PP2A, however, is likely to be most effective for cancer therapy when combined with cytotoxic drugs, particularly for tumors with acquired abnormalities in PP2A function and/or in the DNA-damage-repair pathway (Zhuang et al., 2009; Hong et al., 2015) and/or with other types of immune checkpoint inhibitors.

Example 7. Administration of LB-100 in a Combination

An amount of compound LB-100 in combination with an anti-cancer therapy is administered to a subject afflicted with cancer. The amount of the compound and anti-cancer therapy is effective to treat the subject.

An amount of compound LB-100 in combination with an anti-cancer therapy is administered to a subject afflicted with cancer. The amount of the compound is effective to enhance the anti-cancer activity relative to the anti-cancer therapy alone.

Example 8. PP2A and PD-1

Pharmacologic inhibition of PP2A could enhance immune activation and cancer immunotherapy. Inhibition of PP2A should enhance the cancer immunotherapy by directly increasing proliferation of conventional CD4 and CD8 T-cells and by impairing the immunosuppressive function of Tregs. It was hypothesized that LB-100 could augment the effect of immune checkpoint blockade. This is the first study demonstrating in a preclinical model, that pharmacologic inhibition of PP2A could synergize with immunotherapy.

Figure 6:
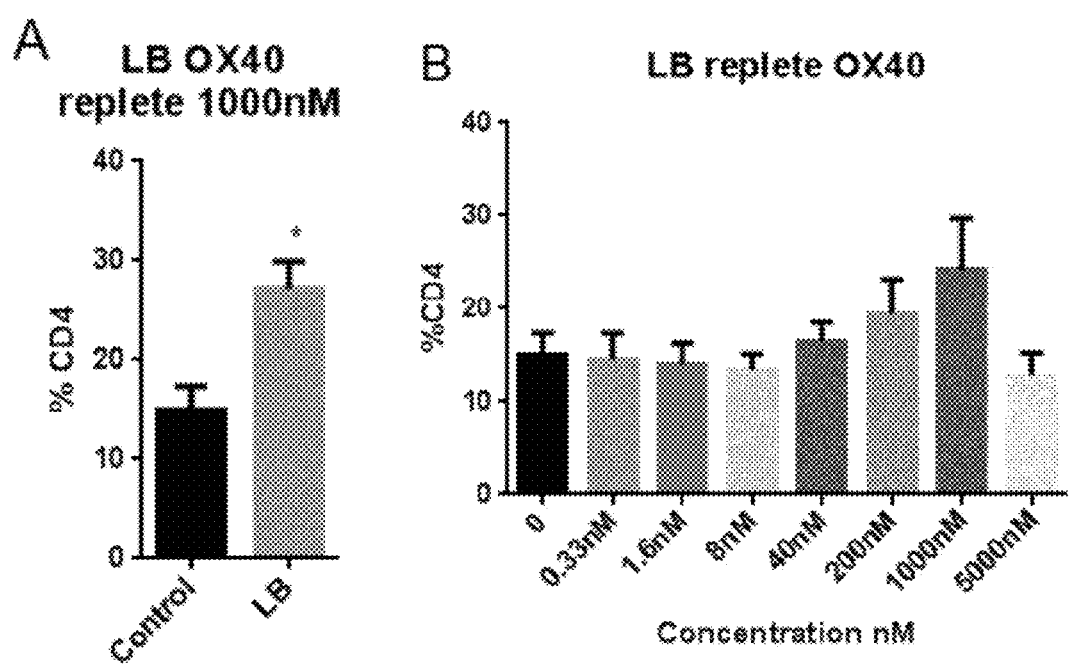
FIG. 6A. Inhibition of PP2A significantly enhance co-stimulatory molecule OX40 expression on T cells. Percentage of OX40 expressing CD4 T cells with CD3/CD28 beads for 5 days in presence or absence of LB-100 at 1000 nM. LB-100 was added or replaced on the $3^{rd}$ day.
FIG. 6B. Inhibition of PP2A significantly enhance co-stimulatory molecule OX40 expression on T cells. Percentage of OX40 expressing CD4 T cells with CD3/CD28 beads for 5 days in presence or absence of LB-100 at different concentration. LB-100 was added or replaced on the $3^{rd}$ day.

The effect of LB-100 on T-cells was assessed in human allogeneic mixed lymphocyte reactions, in which CD8+ or CD4+ T cells were co-cultured with autologous monocyte-derived dendritic cells. A dose dependent increase was found in T cell proliferation in CD8+ and CD4+ cells (FIGS. 4A-B and 5A-B) and an increase in IFNγ secretion in CD4+ T cells (FIGS. 3A-B). A dose dependent increase was found to enhance co-stimulatory molecule OX40 expression on T cells (FIGS. 6A-B) and Tbet, transcription factor to drive IFNγ production in CD4+ T cells (FIGS. 7A-B). The effect of LB-100 plus anti-PD-1 antibody was investigated on CD4+ T cells in the same assay. The combination enhanced proliferation (FIGS. 8A-B, 9A-D), OX40 expression (FIGS. 10A-B), Tbet expression (FIGS. 11A-B), and IFNγ production compared to anti-PD-1 alone (FIG. 15).

Example 9. LB-100 Inhibition and PD-1 Blockades Elicit Durable CD8+ T Cell-Mediated Tumor Rejection To test the hypothesis that inhibition of PP2A with LB-100 can enhance immune-mediated antitumor responses, rice were implanted with CT26 tumor cells. CT26 is a murine colon adenocarcinoma expressing low level of PD-L1 and is resistant to anti-PD1 therapy. After about 13 days, mice with tumor size between 30-100 mm³ were randomized into four treatment groups (PBS control, LB-100 only—0.16 mg/kg, anti-PD-1 only—10 mg/kg, or a combination of both). Treatment was given every 2 days for a total of 28 days. Tumor size was assessed every two days (FIGS. 20A-C). Single agent treatment with anti-PD1 was ineffective in reducing tumor burden or increasing survival. LB-100 alone was able to increase median survival from 21 to 33 days (p=0.02). The combined treatment significantly decreased mean tumor volume by 70% compared to control (p<0.01) on day 14 after treatment. Median survival also increased from 21 to 72 days (p<0.01). More strikingly, 50% of mice achieved complete regression (CR) of tumors with no evidence of disease. This response was durable after completion of treatment.

It was next examined whether mice that achieved CR from combination therapy developed long-term immune memory. About 60 days after initial inoculation, cured mice were re-inoculated with same CT26 cells (FIGS. 21A-B). None of the mice (n=8) developed tumor on re-challenge. CT26 naïve mice were inoculated at the same time to serve as control. This result indicates mice cured by the combination therapy were able to establish long-term memory to tumor specific antigen.

It was then explored whether the synergistic effect of LB-100 with anti-PD-1 that resulted in tumor regression is mediated by CD8 T-cells. Mice bearing CT26 tumors were subjected to CD8 ablation using depleting antibiotics prior to initiation of treatment. CD8+ T cells ablation was confirmed with FACS of splenocytes 3 days after treatment. With CD8 depleted, the combination therapy failed to elicit anti-tumor response. 0% of CD8+ depleted mice receiving combination achieve CR compared to 72% in the CD8+ non-depleted group (FIGS. 22A-C). Taken together, these results demonstrated that the effect of LB-100 is mediated by the immune system rather than a direct cytotoxic effect on the tumor.

Methods

Reagents—LB-100 was provided by Lixte Biotechnology. Anti-mouse PD-1, Clone RMP1-14, antibody was purchased from BioXcell. The following monoclonal antibodies (mAbs) were used for flow cytometry: rat anti-mouse CD4-BV421, rat anti-mouse CD3-PE, rat anti-mouse CD8a-Alexa 647, rat anti-mouse CD45-BV785, rat anti-mouse IFNg-FITC, rat anti-mouse FOXP3-Alexa 647. These antibodies were purchased from Biolegend.

Cell Lines and Mice—CT26.CL25 colon carcinoma line was obtained from ATCC. Tumor cells were cultured in complete medium (RPMI 1640; Cellgro) containing 10% (vol/vol) FBS (Thermofisher), 100 U/mL penicillin, 100 μg/mL streptomycin (Gibco). Six- to 8-week-old female BALB/c were purchased from Charles River. Mice were housed in the Laboratory Animal Facility of the National Institutes of Health (Bethesda, MD). All experiments were approved by the National Institutes of Health Office of Animal Care and Use and conducted in accordance with National Institutes of Health guidelines.

Tumor Inoculation and Animal Studies—CT26 tumor cells ($0.5 \times 10^6$) were injected subcutaneously in the right side of the abdomen. LB-100 and anti-PD-1 was injected by the i.p. route at a dose of 0.16 mg/kg and 10 mg/kg respectively beginning on day 11 after tumor implantation and continued every 2 d for 28 d. Tumor size were monitored with a digital caliper every 2-3 d and expressed as volume (length×width²×0.5). Animals whose tumors became ulcerated/necrotic or a tumor burden exceeding 2,000 mm3 or with a largest diameter greater than 2 cm were euthanized.

Depletion of CD8 T cells. Anti-CD8 (clone 53.6.7) mAbs (BioXcell) were injected 2 d and 1 d before therapy, on the day therapy and at 5 and 8 d after beginning therapy. Dose was 0.1 mg per injection.

Tumor Rechallenge Studies. Naive BALB/c mice and mice previously cured with combination treatment as described above were inoculated with CT26 cells into the left (not previously inoculated) thoracic flank. Tumors were measured two times per week as described above. Animals whose tumors became ulcerated/necrotic or tumor burden exceeded 2,000 mm3 or had a largest diameter greater than 2 cm were euthanized.

Example 10. LB-100 and PD-1 Blockades Regulates Tumor Infiltrating Lymphocytes (TIL)

The treatment effect was assessed on tumor infiltrating lymphocytes (FIGS. 23A-B). CT26 tumor-bearing mice were treated with LB-100 and/or anti-PD-1 antibodies as above. After 12 days of treatment, tumors were analyzed by FACS. Tumor-infiltrating CD8+ T cells from mice treated with the LB-100 and anti-PD-1 antibody combination showed a significant increase in IFNg+CD8+ T cells compared to cells from control animals and animals treated with anti-PD-1 alone (25.3% compared to 11.0% and 10.5% respectively, p=0.05). Since IFNγ is the most critical cytokine mediating anti-tumor response, this result is a functional confirmation that the combination treated mice have enhanced immunity against the implanted tumors. In addition, given the known importance of PP2A in Treg, the effect of LB-100 and/or anti-PD-1 treatment was examined on the amount of Tregs present in the tumor. LB-100 alone significantly depleted Tregs in the tumor environment (2.1% compared to 14.7% in control). This effect is similar in degree to the effect on Tregs depletion by anti-PD-1 or the combination. The fact that LB-100 alone can deplete Tregs suggests a possible mechanism explaining the small but significant survival benefit observed in the LB-100 alone treatment group.

Furthermore, mice achieving CR were resistant to tumor growth when re-inoculated with CT26 cells. Mice subjected to CD8+ T cell ablation using depleting antibodies, were unable to reject CT26 tumors—0/8 (0%) despite treatment with combination therapy, indicating that the anti-tumor effect of LB-100 with anti-PD-1 treatment is CD8+ T cell mediated. In conclusion, in a syngeneic animal model, the PP2A inhibitor, LB-100, has synergistic potential in conjunction with checkpoint blockade supporting investigation of its ability to enhance immunotherapy in the clinic.

In summary, it has been demonstrated in this pre-clinical model that LB-100 when combined with anti-PD-1 has a robust and synergistic effect that results in complete regression of a significant portion of treated mice. This effect is mediated by adaptive immunity through CD8+ T cells. There is also establishment of immune memory associated with regression of tumor. This is the first report of using pharmacologic inhibition of PP2A as a target for enhancing immunotherapy.

Tumors often developed multiple mechanisms to evade the immune system, one of which is expression of PD-1 of T cells, which effectively inhibits T-cells from attacking the tumor. Anti-PD-1 abrogates this inhibitory signal, thereby allowing the T-cell to recognize and eradicate the tumor. LB-100, an inhibitor of Protein Phosphatase 2A (PP2A), was found to have dramatic antitumor effect in a preclinical model of colon cancer. This effect was found to be mediated by enhancement of the immune system.

Example 11. Administration of LB-100 in Combination with a PD-1 and/or PD-L1 Checkpoint Inhibitor An amount of compound LB-100 in combination with a PD-1 and/or PD-L1 checkpoint inhibitor is administered to a subject afflicted with cancer. The amount of the compound and inhibitor is effective to treat the subject.

An amount of compound LB-100 in combination with a PD-1 and/or PD-L1 checkpoint inhibitor is administered to a subject afflicted with cancer. The amount of the compound is effective to enhance the anti-cancer activity of the PD-1 and/or PD-L1 checkpoint inhibitor.

An amount of compound LB-100 in combination with a PD-1 and/or PD-L1 checkpoint inhibitor is administered to a subject afflicted with melanoma. The amount of the compound and inhibitor is effective to treat the subject.

An amount of compound LB-100 in combination with a PD-1 and/or PD-L1 checkpoint inhibitor is administered to a subject afflicted with melanoma. The amount of the compound is effective to enhance the anti-cancer activity of the PD-1 and/or PD-L1 checkpoint inhibitor.

Example 12: Assessment of Efficacy of LB-100 as Add-on Therapy to Atezolizumab, Nivolumab or Pembrolizumab The add-on therapy provides a synergistic effect, and allows for lower doses with reduced side effects.

Periodic administration of LB-100 as an add-on therapy for a human patient afflicted with melanoma who is already receiving Atezolizumab, Nivolumab or Pembrolizumab provides a clinically meaningful advantage and is more effective (provides at least an additive effect or more than an additive effect) in treating the patient than when Atezolizumab, Nivolumab or Pembrolizumab is administered alone (at the same dose).

Periodic administration Atezolizumab, Nivolumab or Pembrolizumab as an add-on therapy for a human patient afflicted with melanoma who is already receiving of LB-100 provides a clinically meaningful advantage and is more effective (provides at least an additive effect or more than an additive effect) in treating the patient than when LB-100 is administered alone (at the same dose).

The add-on therapies also provide efficacy (provides at least an additive effect or more than an additive effect) in treating the patient without undue adverse side effects or affecting the safety of the treatment. As compared to when each agent is administered alone:

1. The add-on therapy is more effective (provides an additive effect or more than an additive effect) in increasing the amount of cytotoxic T cells in patients with melanoma;
2. The add-on therapy is more effective (provides an additive effect or more than an additive effect) in slowing the progression of melanoma in patients with melanoma; and/or
3. The add-on therapy is more effective (provides an additive effect or more than an additive effect) in reducing the function of PD-1 and or PD-L1 in the melanoma patients.

Example 13: Pharmacological Inhibition of Protein Phosphatase-2A with LB-100 Achieves Durable Immune-Mediated Anti-Tumor Activity when Combined with PD-1 Blockade The present example demonstrates, inter alia, that a small molecule PP2A inhibitor, LB-100, when combined with anti-PD1 (aPD-1) blockade synergistically elicits a durable immune-mediated anti-tumor response in the CT26 colon cancer model. This effect was T cell dependent, leading to a striking regression of a significant proportion of tumors. Analysis of tumor lymphocytes demonstrated enhanced infiltration of effector T cells and depletion of suppressive regulatory T cells resulting in a marked increase in effector-to-regulatory T cell ratios. Clearance of tumor established antigen-specific secondary protective immunity. A synergistic effect of LB-100 and aPD-1 blockade was also observed in the B16 melanoma model. In addition, described herein is the finding that LB-100 specifically activated mTORC1 signaling pathway resulting in decreased differentiation of naïve CD4 cells into regulatory T cells. There was also found an increased expression of Th1 and decreased expression of Th2 cytokines. These data highlight the translational potential of PP2A inhibition in combination with checkpoint inhibition.

LB-100 and aPD-1 combination treatment synergistically elicit rejection of CT26 tumors: To test the hypothesis that PP2A inhibition synergizes with aPD-1 therapy in vivo in aPD-1 refractory tumors, a CT26 tumor was used, which is a murine colorectal carcinoma with high PD-L1 expression but limited response to aPD-1 therapy. Mice were inoculated with CT26 tumor cells ($0.25 \times 10^6$). After 10-13 days, mice with tumors reaching 50-100 mm$^3$ in size were randomized into four treatment groups: control (PBS), aPD-1, LB-100 and the combination of aPD-1 and LB-100. Treatments were administered every 2 days for 30 days. Tumor growth was assessed every 2 days (FIG. 24A). In this model, LB-100 alone did not significantly decrease tumor growth, but did extend median survival (33 vs 21 days, p=0.02). Additionally, aPD1 alone had no effect on tumor growth or survival. The combination of LB-100 and aPD1, however, resulted in striking regression of a significant portion of tumors, with 50% achieving complete regression (CR) for the duration of the study. There was a significant difference in tumor size at day 8 after treatment (p<0.05) and significant increase in survival (p<0.005) between the combination and control treatment arms (FIG. 24B).

Effect of LB100 and aPD-1 combination is dependent on CD8 T-cells: Next examined was whether the synergic effect of the LB-100 and aPD-1 combination resulting in durable tumor regression was an immune mediated process. CT26-tumor bearing mice were subjected to CD8+ T cell ablation using depleting antibodies prior to and during treatment with LB-100 and aPD-1 (FIG. 24C). Peripheral CD8+ depletion was confirmed 5 days after treatment by FACS (data not shown). When depleted of CD8+ T-cells, the LB-100 and aPD-1 combination did not elicit tumor rejection (0 vs 72%, p=0.0015) (FIG. 24D). Mean tumor volume was increased 13-fold 10 days after treatment in the combination group with CD8 depletion compared to tumor volume in the non-depleted group (612 vs 46 mm$^3$, p<0.001). Survival was also significantly decreased with CD8 depletion (p<0.0001). CD8 T cell depletion alone had a small deleterious effect compared to control in both tumor growth and survival, suggesting a baseline level of CD8+ T cell mediated immunity served to limit CT26 growth in baseline conditions. These data indicated that LB-100 with aPD-1 synergy is dependent upon CD8+ T cell-mediated adaptive immunity and not a direct effect of PP2A inhibition of tumor growth.

Mice cured by the combination therapy develop antigen-specific long-term memory: The hallmark of a successful adaptive immune response is the establishment of immunologic memory. The following experiment tested mice that experienced a complete response (CR) for their secondary protective anti-tumor response. Mice were re-challenged with CT26 cells about 60 days after initial tumor implantation (FIG. 25A). These mice were completely resistant to CT26 cell re-challenge (FIG. 25B). The average tumor size at day 18 after (re-)implant was 480 mm$^3$ in naïve compared to 0 mm$^3$ in CR mice (p<0.0001) (FIG. 25C).

Next, whether the protective secondary immunologic response was specific to CT26 tumors was tested. After about 60 days from initial implantation, CR mice were re-challenged with both CT26 cells in the flank and 4T1 cells, an unrelated murine breast cancer cell line, in the mammillary fat pad (FIG. 25D). Mice with CR were resistant to CT26 but not to 4T1 cells. Eighteen days after inoculation, there was no difference in 4T1 tumor volume between naïve and CR mice, while CT26 failed to grow in CR mice (FIG. 25E-F). This result indicates that the secondary memory response is specific to CT26-expressed antigens.

Figure 26:
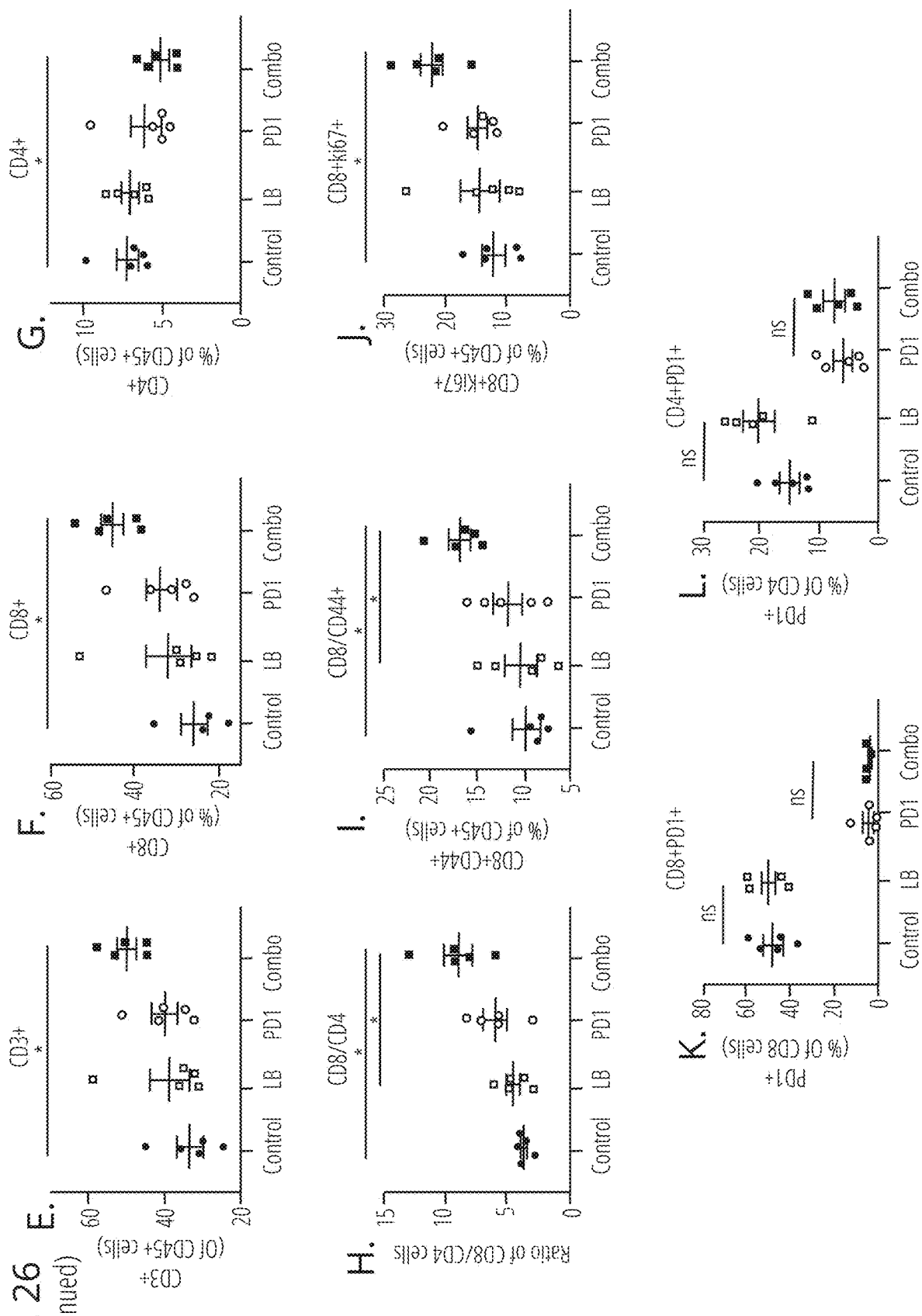
Figure 27:
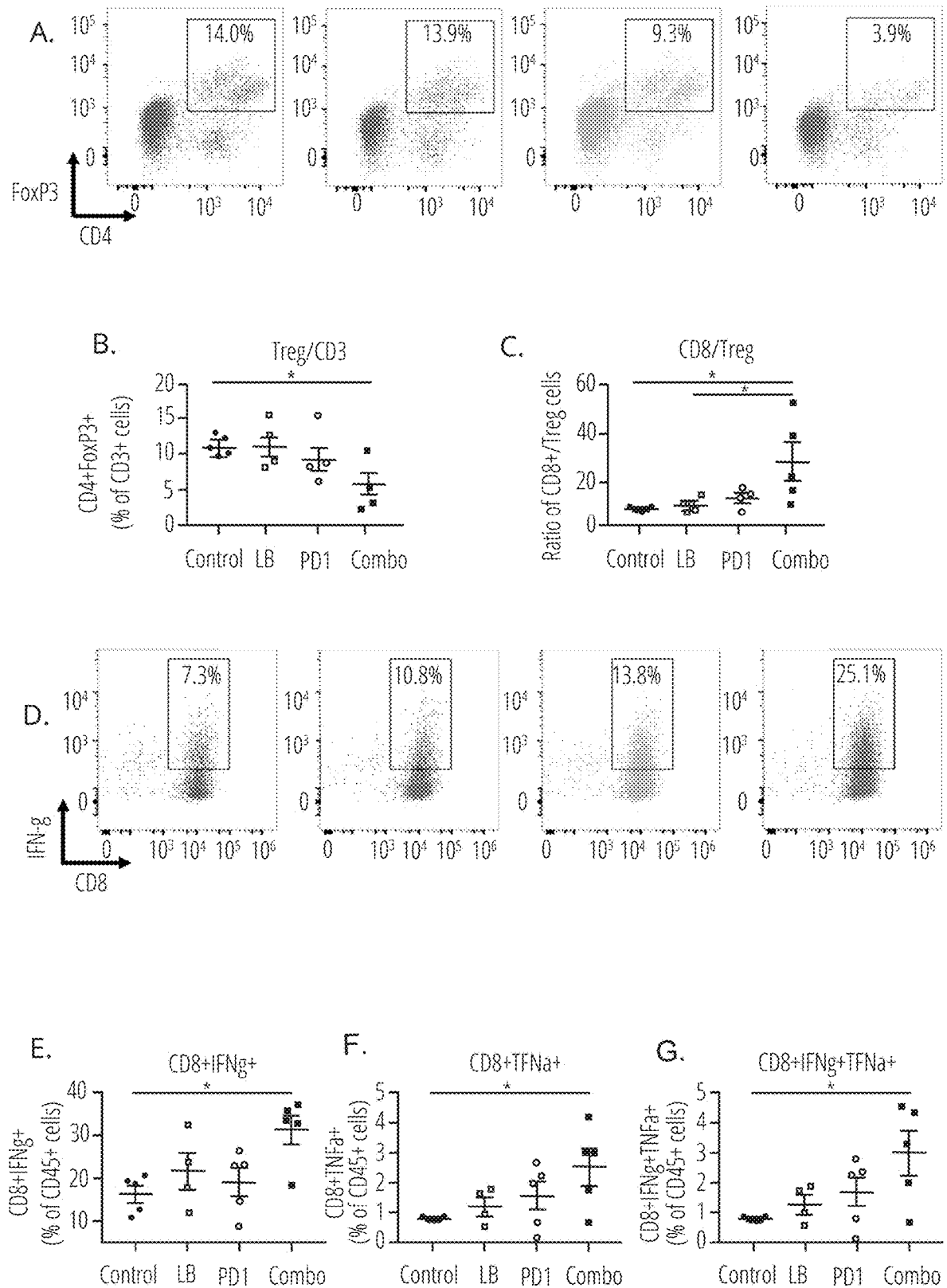
Figure 27:
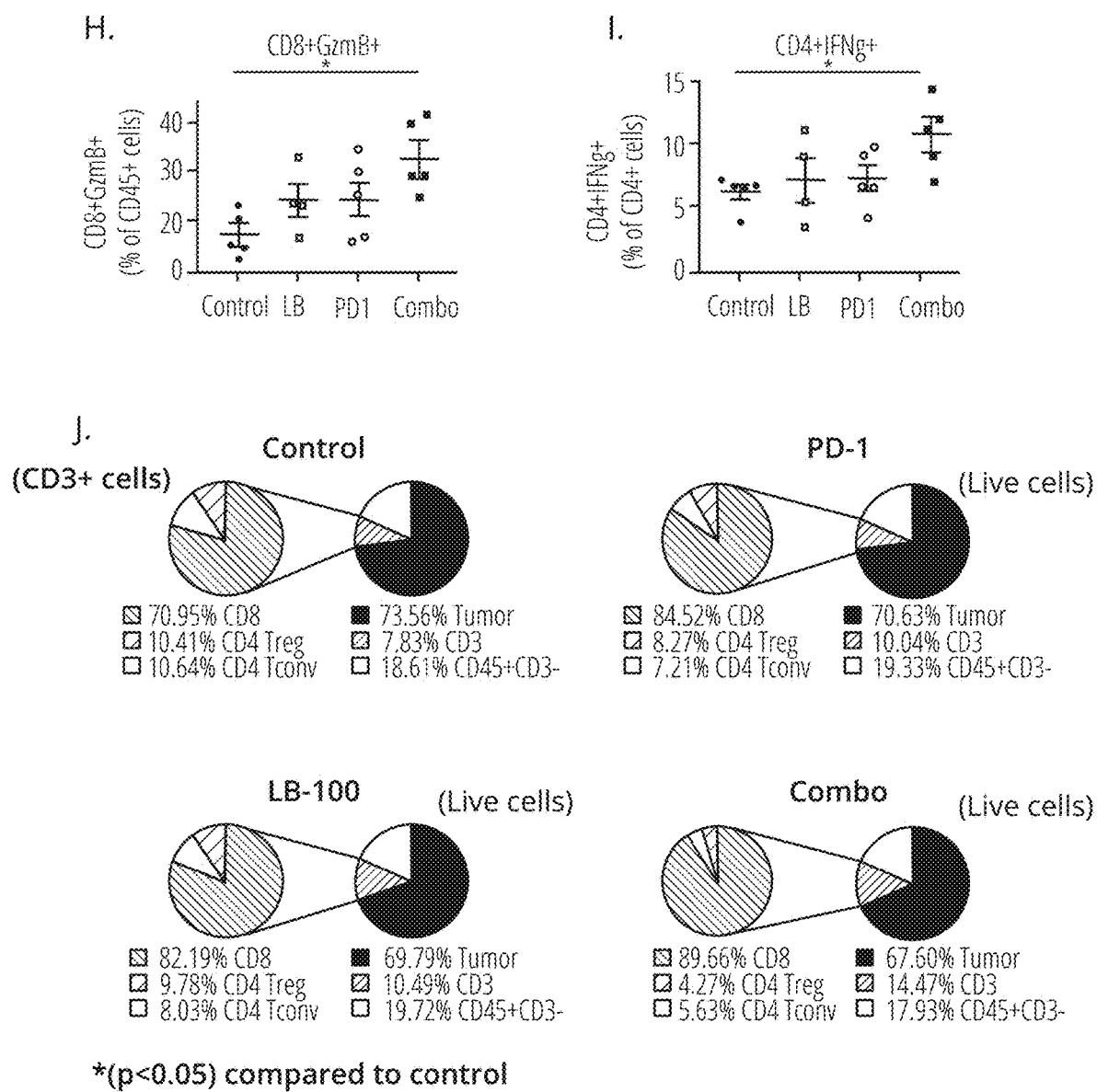
Figure 28:
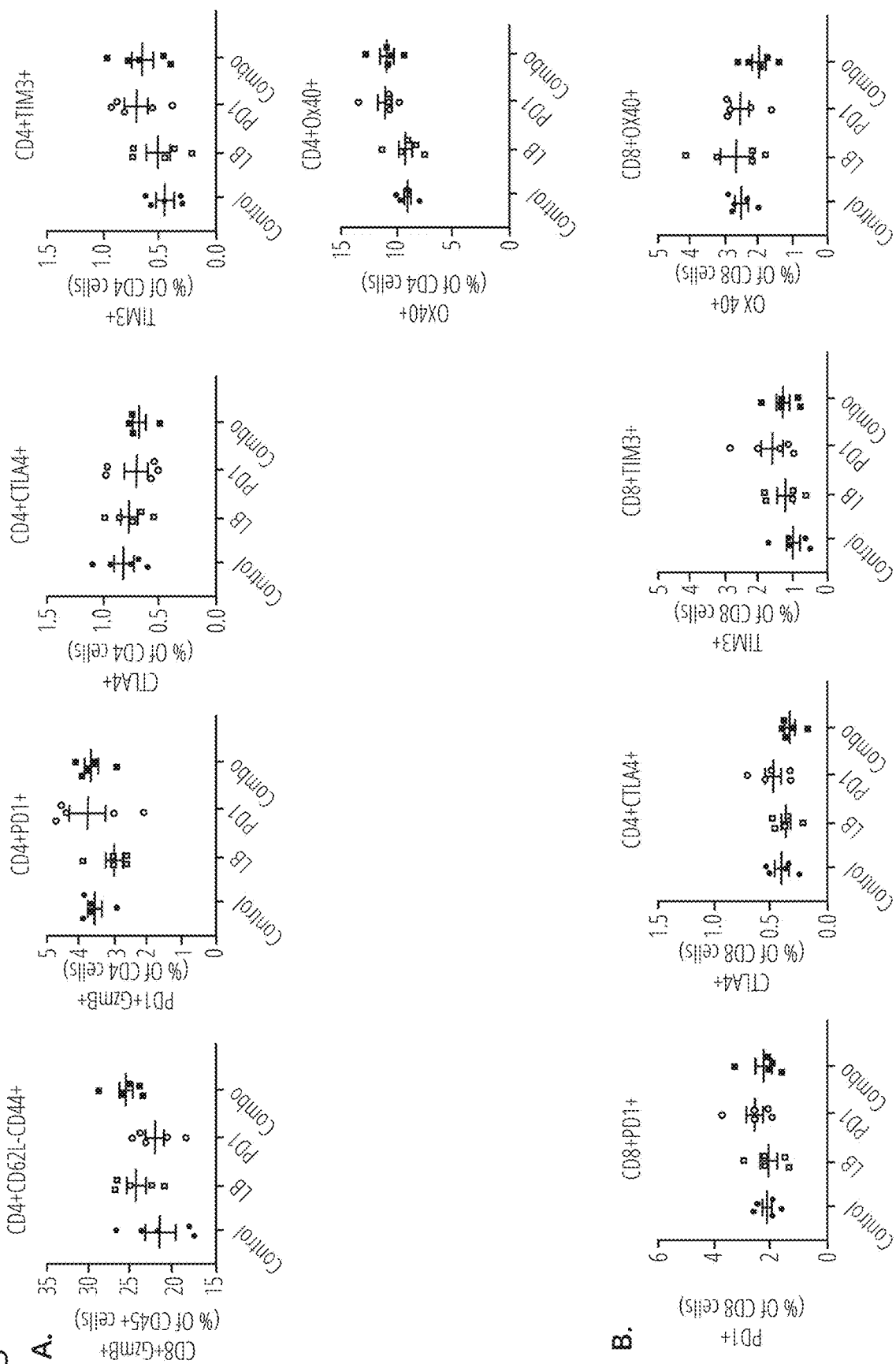
Figure 29:
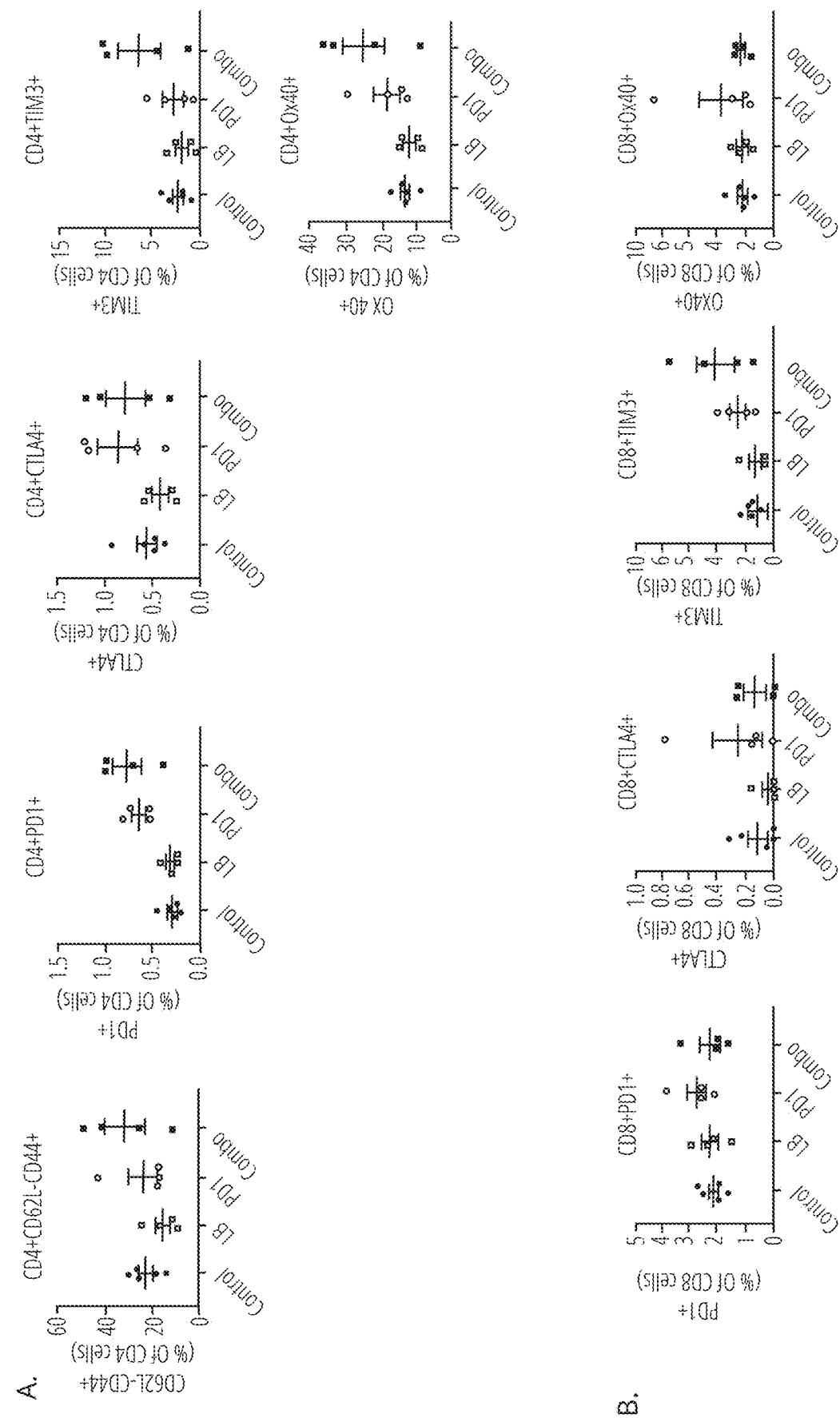

Enhanced activation of lymphocytes with combination treatment: To address the cellular mechanism mediating tumor rejection by the LB-100/aPD-1 combination, the status of the immune system in the secondary lymphoid organs and in the tumor were examined. Mice were implanted with CT26 tumors and treated with LB-100 and/or aPD-1 as described above. On day 3, after two treatments, the spleens, tumor draining lymph nodes (dLN) and tumors were harvested and analyzed by flow cytometry (FIG. 26-27). In the secondary lymphoid tissue, a greater activation of CD8+ T cells in mice treated with the combination regimen compared to controls was observed, as indicated by greater frequency of CD44+CD62L-CD8+ T cells (FIG. 26A-C). In the spleen, treatment with LB-100 alone resulted in a small increase in CD44+CD62L-CD8+ T cells (from 13.0 to 16.6%, p<0.05) but the combination treatment resulted in a greater increase than either LB-100 or aPD1 alone (20.8 compared to 16.6 and 15.5% respectively, p<0.05 and p<0.005) (FIG. 26B). Similarly, CD44+CD62L-CD8+ T cells were increased in the dLN of mice treated with the combination compared to control (from 7.4 to 17.9%, p<0.05) (FIG. 26C). There was no difference in frequency of CD44+CD62L- subset in CD4+ T cells in both the spleen and dLN (FIGS. 28A and 29A). Immune check point markers, including expression of PD-1, CTLA4, TIM3 and Ox40 on CD8+ and CD4+ T cells were examined in the tumor draining lymph node and spleen (FIGS. 28 and 29). There was no difference in the expression of these markers except for a small but significant increase in PD-1 expression in aPD-1 treated CD4+ T cell in the dLN; however, LB-100 alone or in combination did not further alter PD-1 expression (FIG. 29A).

Figure 31:
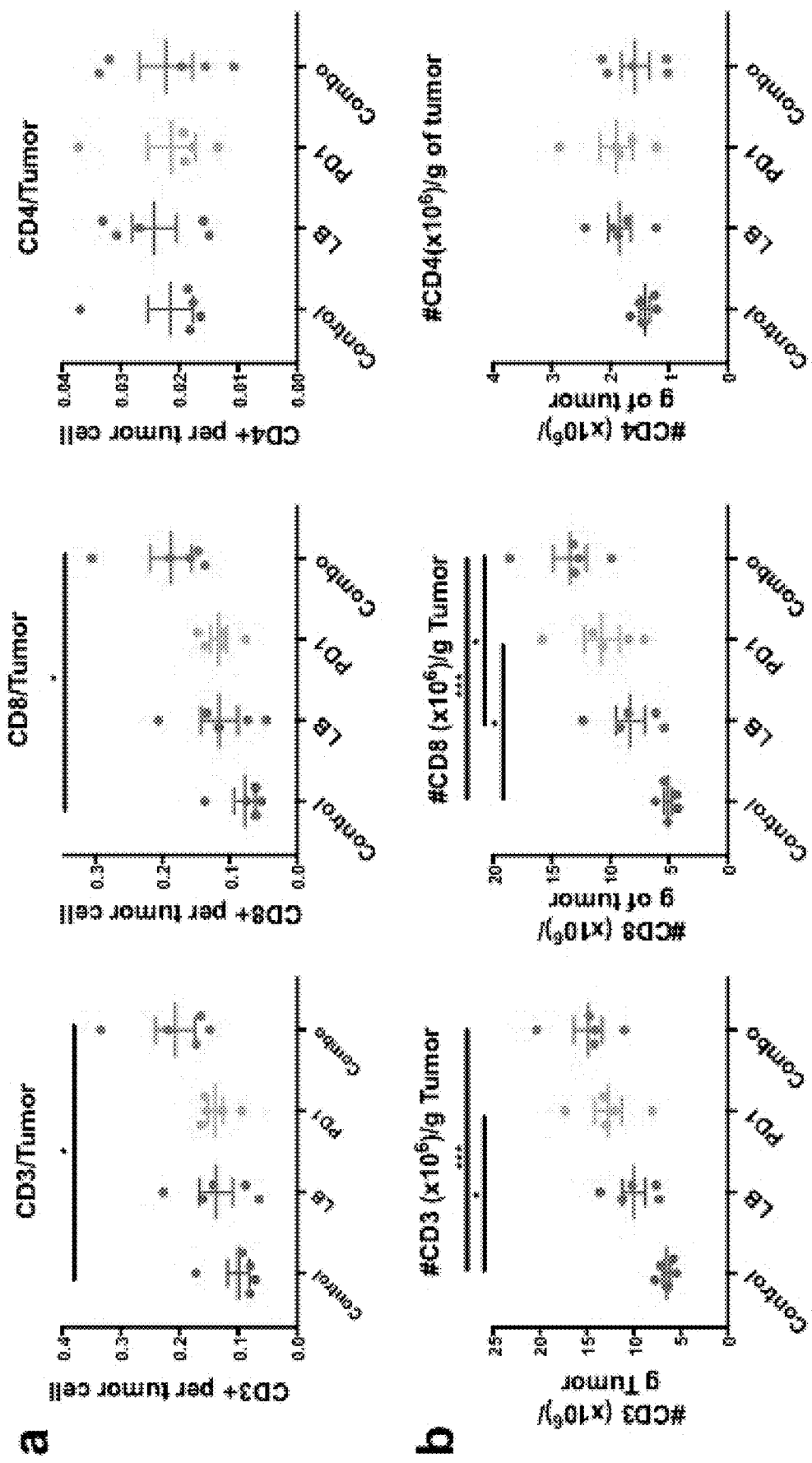

A comprehensive analysis of the tumor infiltrating lymphocytes (FIG. 26-27, 30) was next performed. First, the absolute percentage of CD45+ cells was examined. There was no significant difference among the treatment groups. However, within the CD45+ population, there was a significant increase in CD3+ T cells in the combination treatment compared to control (from 33.3 to 49.9%, p<0.05) (FIG. 26E). More importantly, this increase in CD3+ T cell population was attributed to a significant increase of CD8+ T cells (FIG. 26D), whether normalized to CD45+ cells (from 25.9 to 45.3%, p≤0.01) (FIG. 26F) or number of tumor-resident cells (from 8 to 19%, p<0.05) (FIG. 31A). A similar trend was observed in CD8+ T cells normalized to tumor weight (FIG. 31). Instead, the CD4+ T cell population remained unchanged (FIG. 26G, 31), resulting in a marked increase in CD8/CD4 ratio (from 3.6 to 9.0, p<0.001) (FIG. 27H). This indicated that LB-100/aPD-1 combination resulted in enhanced CD8+ T cells trafficking to the tumor, which has consistently been shown to be one the most important predictors of response to immunotherapy. Further examined was the subpopulation of CD8+ TILs by labeling the effector phenotype marker CD44+. There was a significant increase in CD8+CD44+ T cells in mice treated with the combination relative to control (9.8 to 17.1%, p≤0.01) (FIG. 26I). Also found was increased proliferation of CD8+ TILs, as measured by expression of cell cycle associated protein Ki67 (from 12.3 to 22.5%, p<0.05) (FIG. 26J). Next, the expression of an array of immune checkpoints markers in the TILs, including PD-1, TIM3, Ox40, CTLA4, and LAG3 was examined. Treatment with aPD-1 resulted in an expected decrease in PD-1 expression, but LB-100 alone or in addition to aPD-1 did not further alter PD-1 expression in both CD4+ and CD8+ TILs (FIG. 26K-L). Expression of TIM3, Ox40, CTLA4 and LAG3 were not significantly changed in CD4+ or CD8+ TILs with single or combination treatment (FIG. 32), suggesting that there is potential in combining LB-100 with targeted therapeutics against these check point markers.

Given the previous study demonstrating that PP2A serve an essential role in suppressive Treg, it was then examined whether addition of LB-100 could result in Treg depletion, similar to anti-CTLA4 therapy. aPD-1 is known to act at the level of the tumor and with limited ability to deplete Tregs. However, with addition of LB-100, the combination treatment significantly decreased the percentage of CD4+ FoxP3+ Treg cells among TILs (from 10.3 to 4.9% of CD3+ T cells, p<0.05) (FIG. 27A-B). The concomitant decrease in Treg and increase in CD8+ T cells resulted in a dramatic increase in the CD8+ to Treg ratio by 3.5-fold among the TILs (from 7.5 to 26.4, p<0.05) (FIG. 27C). Subsequently, the functional consequence of LB-100/aPD-1 combination in TILs was assessed. Intracellular expression of IFN-γ in response to in vitro stimulation with PMA/ionomycin was analyzed. Combination treatment significantly enhanced IFN-γ production by CD8+ TILs relative to control (from 16.6 to 31.5% of CD45+, p<0.05) (FIG. 27D-E). In addition, the frequency of tumor necrosis factor alpha (TNF-α)-producing (FIG. 27F, 33A) and IFN-γ/TNF-α dual producing (FIG. 27G, 33B) CD8+ TTLs were significantly increased with the combination treatment. The cytolytic capacity of CD8+ TTLs was also determined by Granzyme B (GzmB) expression, which was also significantly increased with LB-100/a-PD1 treatment (FIG. 27H, 33C). In CD4+ T cells a small, but statistically significant increase in IFN-γ production (from 6.1 to 10.8% of CD4+ cells, p<0.05) was observed (FIG. 27I). This suggests that while there is no overall increase in CD4+ infiltration with LB-100/a-PD1 combination, effector CD4+ T cells present in the tumor were nonetheless more functionally active with enhanced IFN-γ production.

Taken together, combining LB-100 with aPD-1 blockade resulted in a significant change in the composition of TILs (FIG. 27J). While the overall CD45+ population remained relatively stable, there was a marked increase in CD3+ T cell infiltration, driven by a preponderance of CD8+ T cells. At the same time, the Treg population was concomitantly depleted resulting in a dramatic increase in CD8/Treg ratio. In addition, CD8+ T cells were more proliferative and functionally active as indicated by cytokine expressions. These findings are consistent with the observation that LB-100/a-PD1 combination could elicit durable tumor rejection in CT26 in an immune-dependent manner.

LB-100 and aPD-1 enhance anti-tumor activity in B16 melanoma without histologic evidence of autoimmunity: It was next determined whether LB-100/aPD-1 combination was effective against other aPD-1 resistant tumor. In a tumor prevention model, 6-8 weeks old C57BL/6 mice were randomized into four treatment groups: PBS, LB-100, aPD-1 and combination. B16F10 cells ($2.5 \times 10^5$) were inoculated 2 days after initiation of treatment subcutaneously in the right thoracic flank. Treatments were administered every two days following survival (FIG. 34A). By day 15 after tumor implantation, there was no difference between control and the single agent arms. However, tumor size was significantly smaller in the combination group relative to control (from 305.9 to 109.0 mm$^3$, p<0.05) (FIG. 34B-C) and survival was prolonged by the combination treatment (p<0.05) (FIG. 34D).

It is noteworthy that none of the mice in the combination group demonstrated any clinical signs of autoimmune inflammatory events. However, given that the LB-100/aPD-1 combination resulted in increased effector function and Treg depletion, autoimmunity is a concern. We, therefore, examined the histology of multiple organs of treated mice to look for signs of inflammation. C57BL/6 mice that reached survival endpoints were sacrificed and the histology of the skin, salivary gland, pancreas, lung and stomach were examined (FIG. 34E, 35). There was no evidence in any of the treatment group to suggest increased lymphocyte infiltration or signs of autoimmunity.

LB-100 inhibits PP2A activity and enhances mTORC1 activation: PP2A enzymatic activity of isolated CD4 and CD8 cells from mice splenocytes were measured 3 hours after in vitro stimulation with plated CD3 and soluble CD28. There was a dose dependent decrease in PP2A enzymatic activity in both CD4 and CD8 cells, with a greater effect in CD8 than CD4 cells (FIG. 36A).

After 3 hours of in vitro activation of isolated CD3 cells, the activity of mTORC1, mTORC2 and PI(3)K-AKT pathways were assessed by checking the phosphorylation of ribosomal S6 protein (S6), AKT at Thr473 and AKT at Thr308 respectively. It was found that while LB-100 has minimal effect on mTORC2 and PI(3)K-AKT pathways (FIG. 36B), there was a dose dependent increase in activity of mTORC1 as measured by phosphorylation of S6 (FIG. 36c). This difference was not observed in any of the 3 pathways at an early time point of 30 minutes after activation (FIG. 37).

LB-100 inhibits naïve CD4 cells development into regulatory or Th2 CD4 cells:

Naïve CD4 cells were isolated from mice splenocytes and activated in vitro with anti-CD3 and CD28 in the presence of TGF-β or IL4 to induce development of Treg or Th2 CD4+ cells respectively. After 72 hours, intranuclear expressions of Foxp3 or GATA3 were quantitated by flow cytometry to determine percentage of Treg or Th2 cells respectively. LB-100 treatment significantly impaired induction of Foxp3 by TGF-β (FIG. 38A) or GATA3 (FIG. 38B) by IL-4 in a dose dependent manner. In addition, the relative proportion of Th2 and Th1 CD4+ cells was quantified by labeling for T-bet. The frequency of GATA3 expressing cells relative to Tbet expressing cells decreased significantly with LB-100 treatment (FIG. 38C). Next, the functional consequence of Th1 CD4+ cell with LB-100 treatment was explored. Under both Th1 and Th2 skewing conditions, there was a dose dependent increase in IFN-γ expression with PP2A inhibition. This was shown with both intracellular staining (FIG. 38D) and measurement of cytokine secretion (FIG. 38E-F). Other Th1-related cytokines, including TNF-α and TL2 were also increased in both Th1 and Th2 conditions. Secretion of IL4 was expectedly decreased (FIG. 38F). These data suggest that PP2A inhibition decreased Treg formation and skewed CD4 cells differentiation towards Th1 lineage resulting in an overall increase in Th1 cytokine secretion. These in vitro experiments are consistent with the in-vivo TILS findings and potentially suggest that PP2A inhibition enhanced cancer immunity via mTORC1 hyper activation In vitro activity of LB-100 in human mixed lymphocytes reactions: To further confirm the immune-modulating effect of LB-100 has clinical utility, mixed lymphocyte reactions (MLRs) were performed using PBMC from healthy human donors. Monocyte derived dendritic cells were co-cultured with allogenic CD4+ T cells labelled with cytosolic dye CFSE. LB-100 was given on the day of co-culture (Day 0) and again on Day 3. Proliferation and IFN-γ secretion by CD4 T cells were assessed on Day 5 (FIG. 39A). There was a significant increase in CD4 T cell proliferation, as measured by the percentage of dividing cells, with LB-100 treatment at 1 μM (31% compared to 20% in controls) (FIG. 39B). There was also a trend towards increased proliferation at lower LB100 concentrations (in the sub-micromolar range). At the high dose of 5 μM, proliferation was impaired suggesting that there is an optimal window of LB-100 exposure that enhances immunity. A similar pattern was observed with IFN-γ secretion (FIG. 39C). At 0.2 and 1 μM of LB-100, IFN-γ release was significantly enhanced 3.5 to 4-fold respectively. Also examined was the effect of lineage differentiation in CD4 T cells by labeling for T-bet. LB-100 at 1 μM significantly increased T-bet expression (FIG. 39D), confirming our previous finding that LB-100 appears to skew CD4 lineage towards Th1 differentiation. Next tested whether LB-100 could enhance IFN-γ secretion in vitro in combination with PD1 blockade using Nivolumab. A similar MLR assay was performed with LB-100. It was found that LB-100 synergized with anti-PD1 (aPD-1) blockade and enhanced IFN-γ secretion compared to single agents (FIG. 39E).

Materials and Methods

Drugs—Nivolumab was obtained from Bristol-Myers Squibb and LB-100 was obtained from Lixte Biotechnology Holdings, Inc.

Cell lines—CT26.CL25 colon carcinoma, B16 F10 melanoma and 4T1 mammary carcinoma cell lines were obtained from ATCC. Tumor cells were cultured in complete medium (RPMI 1640, Gibco) containing 10% (vol/vol) FBS (Gibco), 100 U/ml penicillin, 100 ug/ml streptomycin (Gibco).

Syngeneic tumor models—Mice were maintained and experiments were conducted with the approval of the NINDS Animal Use and Care Committees. For CT26 tumors: BALB/c (6-8 wk old) were purchased from Charles River Laboratory. CT26 cells ($0.5 \times 10^6$) were injected into the right flank subcutaneously. Once tumors reached a volume of 30-100 mm$^3$ (day 0), mice were randomized and treated with PBS, LB-100 (0.156 mg/kg) and/or anti-mouse PD-1 (10 mg/kg) (RMP1-14; rat IgG2b; Bio X Cell). Treatments were given every 2 days for 30 days. Tumor volume was measured every 2 days using a caliper and tumor volume was calculated according to the formula: Volume (mm$^3$)=L×W$^2$/2, where L is the length and W is the width of the tumor (in millimeters. For B16 tumors: C57BL/6 (6-8 wk old) were purchased from Charles River Laboratory. Mice were randomized into respective treatment groups and 2 days after initial treatment B16F10 cells ($0.5 \times 10^6$) were injected into the right flank subcutaneously. Treatment and measurements were done every 2 days. Survival end-point was defined as when any of the following criteria was reached: 1) tumor volume exceeding 2000 mm$^3$, 2) tumor diameter exceeding 2 cm, 3) severe non-healing skin necrosis over the tumor. When indicated, some mice were depleted for CD8+ T cells by injection of 250 αg of CD8-depleting antibodies (clone 53.6.7; BioXcell). Injections were given 2 d and 1 d before therapy, on the day of therapy initiation, at 5 d and 8 d after start of therapy, and weekly onwards.

Tumor re-challenge studies—Naïve BALB/c mice and previously cured (CR) mice with combination therapy from CT26 tumors were inoculated with $0.5 \times 10^6$ CT26 cells into the left (CR) and right (naïve) thoracic flank. Where indicated, some mice were also inoculated with $1.25 \times 10^5$ 4T1 mammillary carcinoma cells in the mammary fat pad. Tumors volume were then monitored similarly as above.

Isolation of TILs—Mice were injected in the right thoracic flank with $0.5 \times 10^6$ CT26 cells and treated as above after tumors reached between 50-100 mm$^3$. After 2 treatments, mice were sacrificed and tumors excised. Tumors were subjected to mechanical disruption using a GentleMACS Dissociator (Miltenyi Biotec) in presence of enzymatic digestion using Tumor Dissociation Kit (Miltenyi Biotec). Gating strategy used for analysis of TILs is shown in Fig. S3. Intracellular cytokine staining, phosphoflow and flow cytometry—Suspensions containing T cells were stained with a fixable live/dead stain (Invitrogen) in PBS followed by surface antibody staining in FACS buffer (PBS with 0.5% BSA and 0.1% sodium azide). For intracellular staining, cells were stained for surface molecules following by fixation and permeabilization (eBioscience). For cytokine staining, cells were first stimulated with Cell Stimulation Cocktail (eBioscience) containing PMA/Ionomycin and protein transport inhibitor prior to undergoing staining. For phosphostaining, 4% formaldehyde was used for fixation and 100% methanol was used for permeabilization protocols. Cells were analyzed by flow cytometry (LSRII; BD Bioscience). Data analysis was performed using FlowJo software (TreeStar).

PP2A phosphatase assay—Mouse CD4+ and CD8+ T cells were isolated with CD4 and CD8 isolation kit (StemCell) respectively. Cells were activated using immobilized anti-CD3 (10 ug/ml) and soluble anti-CD28 (2 ug/ml) for three hour. PP2A activity was then evaluated after immunoprecipitation using a malachite green phosphatase assay kit as per the manufacturer's instructions (EMD Millipore).

T cell stimulation and skewing—Naïve CD4 cells were isolated from mice splenocytes (StemCell). Cells were activated for 3 days using immobilized anti-CD3 (10 ug/ml) and soluble anti-CD28 (2 ug/ml). Skewing conditions were as follows: T$_H$1, 1 .ig/mL anti-IL4, 5 ng/mL IL2, and 10 ng/mL IL12; T$_H$2, 1 .ig/mL anti-IFN-7, 5 ng/mL IL2, and 10 ng/mL IL4; Treg, 1 .ig/mL anti-IFNγ, and 1 ig/mL anti-IL4, and 2 ng/mL TGFβ1. Bead-based multianalyte flow immunoassays (BD Bioscience) were used to measure cytokine production in the supernatant per manufacturer's instruction. Absolute cell numbers were quantified with flow cytometry using counting beads (Biolegend).

Antibodies for flow cytometry—Anti-mouse: α-CD45 (30-F11, BD), α-CD3 (145-2C11, Biolegend), α-CD4

(GK1.5, Biolegend), α-CD8 (53-6.7, BD), α-PD-1 (J43, ThermoFisher), α-CTLA4 (1B8, abcam), α-TIM-3 (B8.2C12, Biolegend), α-OX-40 (OX-86, Biolegend), α-CD62L (MEL-14, BD), α-CD44 (IM7, Biolegend), α-LAG-3 (C9B7W, Biolegend), α-IFN-7 (XMG1.2, Biolegend), α-TNF-α (MP6-XT22, Biolegend), α-Granzyme B (NGZB, ThermoFisher), α-FOXP3 (MF-14, Biolegend), α-Ki67 (SolA15, ThermoFisher). Anti-human: α-CD4 (A161A1, Biolegend), α-T-bet (4B10, Biolegend), α-Phospho-Akt (Ser473) (D9E, Cell Signaling), α-Phospho-Akt (Thr308) (D25E6, Cell Signaling), α-Phospho-S6 Ribosomal Protein (Ser235/236) (D57.2.2E, Cell Signaling).

Histology—Formalin-fixed tissues were processed, stained with hematoxylin and eosin and evaluated blindly by a board-certified pathologist.

Human mixed lymphocyte reaction—as previously described in 39. Dendritic cells (DCs) were generated by culturing monocytes isolated from PBMC using a monocyte isolation kit (StemCell) in vitro for 7 days with 500U/ml interleukin-4 (IL-4) and 250 U/ml GM-CSF (R&D Systems). CD4+ T cells ($1\times10^5$) isolated with CD4 isolation kit (StemCell) and labeled with CFSE (ThermoFisher) were co-cultured with allogeneic DCs ($1\times10^4$). At the initiation of assay, a titration of LB-100 and/or Nivolumab was added. After 3 days, LB-100 was replenished to the final indicated concentration. After 5 days, culture supernatants were analyzed by ELISA (eBioscience) and cells were analyzed by flow cytometry. At least 3 separate donors were obtained and results of one representative donor were reported.

Statistics—If not stated otherwise in the figure legend, samples were analyzed with GraphPad Prism software using Tukey's multiple comparison test. Scatter dot plots are depicted as means with SEM.

REFERENCES

Apostolidis S, Rodríguez-Rodriguez N, Suárez-Fueyo A et al. Phosphatase PP2A is requisite for the function of regulatory T cells. *Nat Immunol.* 2016, 17:556-64.

Bai X, Zhi X, Zhang Q et al. Inhibition of protein phosphatase 2A sensitizes pancreatic cancer to chemotherapy by increasing drug perfusion via HIF-1α-VEGF mediated angiogenesis. *Cancer Lett.* 2014, 355:281-287.

Bai X L, Zhang Q, Ye L Y, et al. Inhibition of protein phosphatase 2A enhances cytotoxicity and accessibility of chemotherapeutic drugs to hepatocellular carcinomas. *Mol Cancer Ther.* 2014, 13:2062-72.

Baroja, M. L. et al. Inhibition of CTLA-4 Function by the Regulatory Subunit of Serine/Threonine Phosphatase 2A. J Immunol 2002; 168:5070-5078.

Bertini I, Calderone V, Fragai M, Luchinat C, Tallu E. Structural Basis of Serine/Threonine Phosphatase Inhibition by the Archetypal Small Molecules Cantharidin and Norcantharidin *J. Med. Chem.* 2009, 52:4838-4843.

Bian Y, Kitagawa R, KB Parmil, Fujii Y, Stepanov A, and Kitagawa K. Synthetic genetic array screen identifies PP2A as a therapeutic target in Mad2-overexpressing tumors. *Proc Natl Acad Sci USA* 2014, 111:1628-1633

Brahmer J R, et al. Phase I study of single-agent anti-programmed death-1 (MDX-1106) in refractory solid tumors: safety, clinical activity, pharmacodynamics, and immunologic correlates. *J Clin Oncol* 28, 31673175 (2010).

Brunet J F, Denizot F, Luciani M F, Roux-Dosseto M, Suzan M, Mattei M G, Golstein P: A new member of the immunoglobulin superfamily—CTLA-4. Nature 1987, 328:267-270.

Carreno B M, Bennett F, Chau T A, Ling V, Luxenberg D, Jussif J, Baroja M L, Madrenas J: CTLA-4 (CD152) can inhibit T cell activation by two different mechanisms depending on its level of cell surface expression. J Immunol 2000, 165:1352-1356.

Chang K E, Wei B R, Madigan J P et al. The Protein Phosphatase 2A Inhibitor LB-100 Sensitizes Ovarian Carcinoma Cells to Cisplatin-Mediated Cytotoxicity. *Mol Cancer Ther.* 2015, 14:90-100.

Chapman N M, Chi H. mTOR signaling, Tregs and immune modulation. *Immunotherapy* 6, 1295-1311 (2014).

Chen D S, Mellman I. Oncology meets immunology: the cancer-immunity cycle. *Immunity* 39, 1-10 (2013).

Chuang, E. et al. The CD28 and CTLA-4 Receptors Associate with the Serine/Threonine Phosphatase PP2A. 2000, Immunity, Vol. 13, 313-322.

Chung V, Mansfield A S, Braiteh F, Richards D, Durivage H, Ungerleider R S, Johnson F, and Kovach J S. Safety, tolerability, and preliminary activity of LB-100, an inhibitor of protein phosphatase 2A, in patients with relapsed solid tumors. Clin Cancer Res 2017.

Chung, V. Phase I study of LB-100 with docetaxel in solid tumors. 2013: ClinicalTrials.gov.

Delgoffe G M, et al. The kinase mTOR regulates the differentiation of helper T cells through the selective activation of signaling by mTORC1 and mTORC2. *Nat Immunol* 12, 295-303 (2011).

Delgoffe G M. PP2A's restraint of mTOR is critical for T(reg) cell activity. *Nat Immunol* 17, 478-479 (2016).

Ebert P J, et al. MAP Kinase Inhibition Promotes T Cell and Anti-tumor Activity in Combination with PD-L1 Checkpoint Blockade. *Immunity* 44, 609-621 (2016).

Efferth, T. et al. (2005) Molecular modes of action of cantharidin in tumor cells. Biochem Pharmacol. 69(5): p. 811-8.

Efferth, T. et al. (2002) Activity of drugs from traditional Chinese medicine toward sensitive and MDR1- or MRP1-overexpressing multidrug-resistant human CCRF-CEM leukemia cells. Blood Cells Mol Dis. 28(2): p. 160-8.

Eil R, Vodnala S K, Clever D., Klebanoff C A, Sukumar M, Pan J H, Palmar D C, Gros A, Yamamoto T N, Patel S J, Guittard G C, Yu Z, Carbonaro V, Okkenhaug K, Schrump D S, Linehan W M, Roychoudhuri R, Restifo N P. Ionic immune suppression within the tumour microenvironment limits T cell effector function. Nature 2016, 537: 539-543.

Falconer I R, Humpage A R. Preliminary evidence for in vivo tumour initiation by oral administration of extracts of the blue-green alga *Cylindrospermopsis raciborskii* containing the toxin cylindrospermopsin. *Environ Toxicol* 16, 192-195 (2001).

Gehringer M M. Microcystin-LR and okadaic acid-induced cellular effects: a dualistic response. *FEBS Lett* 557, 1-8 (2004).

Gordon I K, Lu J, Graves C A et al. Protein Phosphatase 2A Inhibition with LB-100 Enhances Radiation-Induced Mitotic Catastrophe and Tumor Growth Delay in Glioblastoma. *Mol Cancer Ther.* 2015, 14:1540-47.

Haxhinasto S, Mathis D, Benoist C. The AKT-mTOR axis regulates de novo differentiation of CD4+Foxp3+ cells. *J Exp Med* 205, 565-574 (2008).

Hein A L, Seshacharyulu P, Rachagani S et al. PR55a Subunit of Protein Phosphatase 2A Supports the Tumorigenic and Metastatic Potential of Pancreatic Cancer Cells by Sustaining Hyperactive Oncogenic Signaling. *Cancer Res.* 2016, 8:2243-53

Ho W S, Feldman M J, Maric D et al. PP2A inhibition with LB-100 enhances cisplatin cytotoxicity and overcomes cisplatin resistance in medulloblastoma cells. *Oncotarget.* 2016, 7:12447-63.

Hodi, F. S. et al. Improved Survival with Ipilimumab in Patients with Metastatic Melanoma. 2010, N Engl J Med, 363; 8.

Holmgaard R B, Zamarin D, Munn D H, Wolchok J D, Allison J P. Indoleamine 2,3-dioxygenase is a critical resistance mechanism in antitumor T cell immunotherapy targeting CTLA-4. *J Exp Med* 210, 1389-1402 (2013).

Hong C S, Ho W, Zhang C, Yang C, Elder J B, Zhuang Z. LB-100, a Small Molecule Inhibitor of PP2A with Potent Chemo- and Radio-sensitizing Potential. *Cancer Biol Ther.* 2015, 16:821-33.

Janssens V, Longin S, Goris J. PP2A holoenzyme assembly: in cauda venenum (the sting is in the tail). *Trends Biochem Sci* 33, 113-121 (2008).

Janssens V, Rebollo A. The Role and Therapeutic Potential of Ser/Thr Phosphatase PP2A in Apoptotic Signalling Networks in Human Cancer Cells. *Curr Mol Med.* 2012, 12:268-287.

Joseph F. Grosso and Maria N. Jure-Kunkel. CTLA-4 blockade in tumor models: an overview of preclinical and translational research. Cancer Immun. 2013; 13: 5.

Kiely M, Kiely P A. PP2A: The Wolf in Sheep's Clothing? *Cancers (Basel)* 7, 648-669 (2015).

Kingwell K. Cancer: Live screening of immunotherapy targets. *Nat Rev Drug Discov* 13, 258 (2014).

Kovach J S, Johnson F. (2008) Oxabicycloheptanes and oxabicycloheptenes, their preparation and use. U.S. Pat. No. 7,998,957, Aug. 16, 2011.

Larkin J, et al. Combined Nivolumab and Ipilimumab or Monotherapy in Untreated Melanoma. *N Engl J Med* 373, 23-34 (2015).

Lê L, Erlichman C, Pillon L et al. Phase I and pharmacokinetic study of fostriecin given as an intravenous bolus daily for five consecutive days. *Invest New Drugs* 2004, 22:159-167.

Lecca S, et al. Rescue of GABAB and GIRK function in the lateral habenula by protein phosphatase 2A inhibition ameliorates depression-like phenotypes in mice. *Nat Med* 22, 254-261 (2016).

Lu, J. et al. Inhibition of serine/threonine phosphatase PP2A enhances cancer chemotherapy by blocking DNA damage induced defense mechanisms. Proc Natl Acad Sci USA, 2009. 106(28): p. 11697-702.

Lv Peng, Wang Y, Ma J et al. Inhibition of protein phosphatase 2A with a small molecule LB-100 radiosensitizes nasopharyngeal carcinoma xenografts by inducing mitotic catastrophe and blocking DNA damage repair. *Oncotarget.* 2014, 5:7512-7524.

Martiniova, L. et al. Pharmacologic modulation of serine/threonine phosphorylation highly sensitizes PHEO in a MPC cell and mouse model to conventional chemotherapy. PLoS One, 2011. 6(2): p. e14678.

Melero I, Rouzaut A, Motz G T, Coukos G. T-cell and NK-cell infiltration into solid tumors: a key limiting factor for efficacious cancer immunotherapy. *Cancer Discov* 4, 522-526 (2014).

Mumby M. PP2A: unveiling a reluctant tumor suppressor. Cell 2007; 130:21-4.

Ngiow S F, et al. A Threshold Level of Intratumor CD8+ T-cell PD1 Expression Dictates Therapeutic Response to Anti-PD1. *Cancer Res* 75, 3800-3811 (2015).

Parry, R. V. et al. CTLA-4 and PD-1 Receptors Inhibit T-Cell Activation by Distinct Mechanisms. Molecular and Cellular Biology, 2005, p. 9543-9553 Vol. 25, No. 21.

Perotti D, Neviani P. Targeting A Tumor Suppressor To Suppress Tumor Growth: News and Views on Protein Phosphatase 2A (PP2A) as a Target for Anti-cancer Therapy. *Lancet Oncol.* 2013, 14:e229-e238.

Pico de Coana, Y. et al. Checkpoint blockade for cancer therapy: revitalizing a suppressed immune system Trends in Molecular Medicine (2015) 1-10.

Quang C, Simko J L, Nethero W C, Groeber E A, Kovach J S. LC-MS/MS Method Development and Validation for the Quantification of LB-100 and Endothall Metabolite in Biological Matrices (20). Poster M P 158, American Society for Mass Spectrometry Conference on Mass Spectrometry and Allied Topics, Jun. 6, 2016, San Antonio, TX Robert C, et al. Nivolumab in previously untreated melanoma without BRAF mutation. *N Engl J Med* 372, 320-330 (2015).

Rossini G P, Sgarbi N, Malaguti C. The toxic responses induced by okadaic acid involve processing of multiple caspase isoforms. *Toxicon* 39, 763-770 (2001).

Sagiv-Barfi I, Kohrt H E, Czerwinski D K, Ng P P, Chang B Y, Levy R. Therapeutic antitumor immunity by checkpoint blockade is enhanced by ibrutinib, an inhibitor of both BTK and ITK. *Proc Natl Acad Sci USA* 112, E966-972 (2015).

Sangodkar J, Farrington C C, McClinch K, Galsky M D, Kastrinsky D B, Narla G. All roads lead to PP2A: exploiting the therapeutic potential of this phosphatase. FEBS J 2016, 283:1004-24.

Sallman D, Wei S, List A et al. PP2A: the Achilles heal in MDS with 5q deletion. Front Oncol. 2014, 4:1-7.

Schvartzman J M, Pascal H G D, Sotillo R, Coker C, Benezra R. Mad2 Is a Critical Mediator of the Chromosome Instability Observed upon Rb and p53 Pathway Inhibition. Cancer Cell 2011, 19:701-714.

Seshacharyulu P, Pandey P, Datta K et al. Phosphatase: PP2A structural importance, regulation and its aberrant expression in cancer. Cancer Lett. 2013, 335:9-118.

Shi Y. Serine/Threonine Phosphatases: Mechanism through Structure. Cell 2009, 139: 468-484.

Snyder, A. et al. Genetic Basis for Clinical Response to CTLA-4 Blockade in Melanoma. 2014, *N Engl J Med*, 371; 23.

Sukari A, Nagasaka M, Al-Hadidi A, Lum L G. Cancer Immunology and Immunotherapy. *Anticancer Res* 36, 5593-5606 (2016).

Swart M, Verbrugge I, Beltman. Combination Approaches with Immune-Checkpoint Blockade in Cancer Therapy. Frontiers in Oncology 2016, 6:233.

Taffs R E, Redegeld F A, and Sitkovsky. Modulation of cytolytic T lymphocyte functions by an inhibitor of serine/threonine phosphatase, okadaic acid. Enhancement of cytolytic T lymphocyte-mediated cytotoxicity. *J Immunol.* 1991, 147:722-728.

Teft W A, Kirchhof M G, Madrenas J: A molecular perspective of CTLA-4 function. *Annu Rev Immunol* 2006, 24:65-97.

Teft W A, Kirchhof M G, Madrenas J: Structure-Function analysis of the CTLA-4 interaction with PP2A. *BMC Immunology* 2009, 10:23.

Topalian S L, Drake C G, Pardoll D M. Immune Checkpoint Blockage: A Common Denominator Approach to Cancer Therapy. Cancer Cell 2015, 27:450-461.

Tsiatas M, Mountzios, Curigliano. Future perspective in cancer immunotherapy. Ann Transl Med 2016, 4(14):273.

Wang C, et al. In vitro characterization of the anti-PD-1 antibody nivolumab, BMS-936558, and in vivo toxicology in non-human primates. *Cancer Immunol Res* 2, 846-856 (2014).

Wang G S. Medical uses of mylabris in ancient China and recent studies. *J Ethnopharmacol*. 1989, 2:147-62.

Wei, D. et al. Inhibition of protein phosphatase 2A radiosensitizes pancreatic cancers by modulating CDC25C/CDK1 and homologous recombination repair. Clin Cancer Res, 2013. 19(16): p. 4422-32.

Westermarck J, Hahn W C. Multiple pathways regulated by the tumor suppressor PP2A in transformation. *Trends Mol Med.* 2008, 14:152-160.

Yatsunami J, Komori A, Ohta T, Suganuma M, Yuspa S H, Fujiki H. Hyperphosphorylation of cytokeratins by okadaic acid class tumor promoters in primary human keratinocytes. *Cancer Res* 53, 992-996 (1993).

Zhang, C. et al. A synthetic cantharidin analog for the enhancement of doxorubicin suppression of stem cell-derived aggressive sarcoma. Biomaterials, 2010. 31(36): p. 9535-43.

Zhang M, Yogesha S D, Mayfield J E, Gill G N, Zhang Y. Viewing serine/threonine protein phosphatases through the eyes of drug designers. *FEBS J* 280, 4739-4760 (2013).

Zhou P, Shaffer D R, Alvarez D A et al. In vivo Discovery of Immunotherapy Targets in the Tumor Microenvironment. *Nature* 2014, 506:52-57.

Zhuang Z, Lu J, Lonser R, Kovach J S. Enhancement of cancer chemotherapy by simultaneously altering cell cycle progression and DNA-damage defenses through global modification of the serine/threonine phospho-proteome. *Cell Cycle.* 2009, 8:3303-6.

U.S. Pat. No. 8,697,845 B2, issued Apr. 15, 2014.

What is claimed is:

1. A method of treating a subject afflicted with cancer, comprising administering to the subject a 0.5 mg/m$^2$, 0.83 mg/m$^2$, 1.25 mg/m$^2$, 1.75 mg/m$^2$, or 2.33 mg/m$^2$ dose of LB-100 or a salt thereof and a 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg dose of an anti-programmed cell death protein-1 (anti-PD-1) antibody, wherein the LB-100 or salt thereof and the anti-PD-1 antibody are synergistically effective to treat the subject, wherein the treating is inducing inhibition, regression, or stasis of the cancer, and wherein the cancer is melanoma, colorectal cancer or glioblastoma.

2. A method of treating a subject afflicted with cancer and receiving a 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg dose of an anti-PD-1 antibody, comprising administering to the subject a 0.5 mg/m$^2$, 0.83 mg/m$^2$, 1.25 mg/m$^2$, 1.75 mg/m$^2$, or 2.33 mg/m$^2$ dose of LB-100 or a salt thereof, wherein the LB-100 or salt thereof and the anti-PD-1 antibody are synergistically effective to treat the subject, wherein the treating is inducing inhibition, regression, or stasis of the cancer, and wherein the cancer is melanoma, colorectal cancer or glioblastoma.

3. A method of increasing a T-cell response to cancer cells in a subject afflicted with cancer, comprising administering to the subject a 0.5 mg/m$^2$, 0.83 mg/m$^2$, 1.25 mg/m$^2$, 1.75 mg/m$^2$, or 2.33 mg/m$^2$ dose of LB-100 or a salt thereof and a 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg dose of an anti-PD-1 antibody, wherein the LB-100 or salt thereof and the anti-PD-1 antibody are synergistically effective to increase the T-cell response, and wherein the cancer is melanoma, colorectal cancer or glioblastoma.

4. A method of increasing T-cell activation in a subject afflicted with cancer, comprising administering to the subject a 0.5 mg/m$^2$, 0.83 mg/m$^2$, 1.25 mg/m$^2$, 1.75 mg/m$^2$, or 2.33 mg/m$^2$ dose of LB-100 or a salt thereof and a 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg dose of an anti-PD-1 antibody, wherein the LB-100 or salt thereof and the anti-PD-1 antibody are synergistically effective to increase the T-cell activation, and wherein the cancer is melanoma, colorectal cancer or glioblastoma.

5. The method of any one of claims 1, 3, and 4, wherein the LB-100 or salt thereof and the anti-PD-1 antibody are each periodically administered to the subject.

6. The method of any one of claims 1, 3, and 4, wherein the LB-100 or salt thereof and the anti-PD-1 antibody are administered simultaneously, separately or sequentially.

7. The method of any one of claims 1, 3, and 4, wherein the anti-PD-1 antibody is administered concurrently with, prior to, or after the LB-100 or salt thereof.

8. The method of any one of claims 1, 2, 3 and 4, wherein the LB-100 or salt thereof and the anti-PD-1 antibody are effective to reduce a clinical symptom of the cancer in the subject.

9. The method of any one of claims 1, 2, 3 and 4, wherein the LB-100 or salt thereof enhances the immunotherapeutic effect of the anti-PD-1 antibody.

10. The method of any one of claims 1, 2, 3 and 4, wherein the cancer is susceptible to treatment by an immune response.

11. The method of any one of claims 1, 2, 3 and 4, wherein the anti-PD-1 antibody is nivolumab or pembrolizumab.

12. The method of any one of claims 1, 2, 3, and 4, wherein the LB-100 or salt thereof is administered at a dose of 0.5 mg/m$^2$.

13. The method of any one of claims 1, 2, 3, and 4, wherein the LB-100 or salt thereof is administered for 3 consecutive days every 3 weeks.

14. The method of claim 5, wherein the anti-PD-1 antibody is nivolumab or pembrolizumab.

15. The method of claim 6, wherein the anti-PD-1 antibody is nivolumab or pembrolizumab.

16. The method of claim 7, wherein the anti-PD-1 antibody is nivolumab or pembrolizumab.

17. The method of claim 8, wherein the anti-PD-1 antibody is nivolumab or pembrolizumab.

18. The method of claim 9, wherein the anti-PD-1 antibody is nivolumab or pembrolizumab.

19. The method of claim 10, wherein the anti-PD-1 antibody is nivolumab or pembrolizumab.

20. The method of claim 5, wherein the subject is a human subject.

21. The method of claim 6, wherein the subject is a human subject.

22. The method of claim 7, wherein the subject is a human subject.

23. The method of claim 8, wherein the subject is a human subject.

24. The method of claim 9, wherein the subject is a human subject.

25. The method of claim 10, wherein the subject is a human subject.

26. The method of claim 11, wherein the subject is a human subject.

27. The method of claim 12, wherein the subject is a human subject.

28. The method of claim 13, wherein the subject is a human subject.

29. The method of claim 14, wherein the subject is a human subject.

30. The method of claim 15, wherein the subject is a human subject.

31. The method of claim 16, wherein the subject is a human subject.

32. The method of claim 17, wherein the subject is a human subject.

33. The method of claim 18, wherein the subject is a human subject.

34. The method of claim 19, wherein the subject is a human subject.

35. The method of any one of claims 1, 2, 3, and 4, wherein the anti-PD-1 antibody is administered at a dose of 3 mg/kg every 2 or 3 weeks.

* * * * *